United States Patent
Lo et al.

(10) Patent No.: US 10,633,713 B2
(45) Date of Patent: Apr. 28, 2020

(54) DIAGNOSTIC APPLICATIONS USING NUCLEIC ACID FRAGMENTS

(71) Applicants: The Chinese University of Hong Kong Office of Research and Knowledge Transfer Services, Shatin (HK); GRAIL, Inc., Menlo Park, CA (US)

(72) Inventors: Yuk-Ming Dennis Lo, Homantin (CN); Rossa Wai Kwun Chiu, Shatin (CN); Kwan Chee Chan, Shatin (CN); Peiyong Jiang, Shatin (CN); Wai Kei Lam, Kowloon (CN)

(73) Assignees: The Chinese University of Hong Kong, Shatin, New Territories (HK); GRAIL, Inc., Menlo Park, CA (US)

( * ) Notice: Subject to any disclaimer, the term of this patent is extended or adjusted under 35 U.S.C. 154(b) by 0 days.

(21) Appl. No.: 15/880,403

(22) Filed: Jan. 25, 2018

(65) Prior Publication Data
US 2018/0208999 A1     Jul. 26, 2018

Related U.S. Application Data

(63) Continuation-in-part of application No. PCT/US2017/058099, filed on Oct. 24, 2017.

(60) Provisional application No. 62/507,154, filed on May 16, 2017, provisional application No. 62/450,541, filed on Jan. 25, 2017.

(51) Int. Cl.
| | |
|---|---|
| *C12Q 1/6888* | (2018.01) |
| *C12Q 1/6879* | (2018.01) |
| *C12Q 1/6806* | (2018.01) |
| *C12Q 1/6886* | (2018.01) |
| *C12Q 1/686* | (2018.01) |
| *G16B 20/00* | (2019.01) |
| *G16H 10/40* | (2018.01) |
| *G16H 50/20* | (2018.01) |
| *G16H 50/70* | (2018.01) |
| *G16B 30/10* | (2019.01) |
| *G16H 50/30* | (2018.01) |
| *G16B 40/00* | (2019.01) |

(52) U.S. Cl.
CPC ......... *C12Q 1/6888* (2013.01); *C12Q 1/6806* (2013.01); *C12Q 1/686* (2013.01); *C12Q 1/6879* (2013.01); *C12Q 1/6886* (2013.01); *G16B 20/00* (2019.02); *C12Q 2600/112* (2013.01); *C12Q 2600/118* (2013.01); *C12Q 2600/156* (2013.01); *C12Q 2600/158* (2013.01); *C12Q 2600/166* (2013.01); *G16B 30/10* (2019.02); *G16B 40/00* (2019.02); *G16H 10/40* (2018.01); *G16H 50/20* (2018.01); *G16H 50/30* (2018.01); *G16H 50/70* (2018.01); *Y02A 90/26* (2018.01)

(58) Field of Classification Search
CPC .............................. C12Q 1/6888; G16B 10/00
See application file for complete search history.

(56) References Cited

U.S. PATENT DOCUMENTS

| | | |
|---|---|---|
| 7,704,687 B2 | 4/2010 | Wang et al. |
| 8,620,593 B2 | 12/2013 | Lo et al. |
| 8,741,811 B2 | 6/2014 | Lo et al. |
| 9,892,230 B2 | 2/2018 | Lo et al. |
| 2003/0219765 A1 | 11/2003 | Costa |
| 2005/0164241 A1 | 7/2005 | Hahn et al. |
| 2005/0282196 A1 | 12/2005 | Costa |
| 2007/0122823 A1 | 5/2007 | Bianchi et al. |
| 2007/0202525 A1 | 8/2007 | Quake et al. |
| 2008/0206749 A1 | 8/2008 | Lo et al. |
| 2009/0029377 A1 | 1/2009 | Lo et al. |
| 2009/0087847 A1 | 4/2009 | Lo et al. |
| 2010/0041048 A1 | 2/2010 | Diehl et al. |
| 2010/0136560 A1 | 6/2010 | Vogelstein et al. |
| 2011/0171741 A1* | 7/2011 | Wang ................... C12Q 1/6825 436/94 |
| 2013/0017958 A1 | 1/2013 | Benz et al. |
| 2013/0040824 A1 | 2/2013 | Lo et al. |
| 2013/0237431 A1 | 9/2013 | Lo et al. |
| 2014/0080715 A1 | 3/2014 | Lo et al. |
| 2014/0100121 A1 | 4/2014 | Lo et al. |
| 2014/0274740 A1 | 9/2014 | Srinivasan et al. |

(Continued)

FOREIGN PATENT DOCUMENTS

| | | |
|---|---|---|
| CN | 1790021 | 6/2006 |
| CN | 101622362 | 1/2010 |

(Continued)

OTHER PUBLICATIONS

Torchinsky et al, Sizing femtogram amounts of dsDNA by single-molecule counting, 2016, Nucleic Acids Research, 2016, 42, e17, pp. 1-6. (Year: 201).*

(Continued)

*Primary Examiner* — Narayan K Bhat
(74) *Attorney, Agent, or Firm* — Kilpatrick Townsend & Stockton LLP

(57) ABSTRACT

Various embodiments are directed to applications (e.g., classification of biological samples) of the analysis of the count, the fragmentation patterns, and size of cell-free nucleic acids, e.g., plasma DNA and serum DNA, including nucleic acids from pathogens, such as viruses. Embodiments of one application can determine if a subject has a particular condition. For example, a method of present disclosure can determine if a subject has cancer or a tumor, or other pathology. Embodiments of another application can be used to assess the stage of a condition, or the progression of a condition over time. For example, a method of the present disclosure may be used to determine a stage of cancer in a subject, or the progression of cancer in a subject over time (e.g., using samples obtained from a subject at different times).

51 Claims, 63 Drawing Sheets
(32 of 63 Drawing Sheet(s) Filed in Color)

(56) References Cited

U.S. PATENT DOCUMENTS

| | | |
|---|---|---|
| 2015/0011403 A1 | 1/2015 | Lo et al. |
| 2015/0087529 A1 | 3/2015 | Lo et al. |
| 2015/0368708 A1 | 12/2015 | Talasaz |
| 2016/0002717 A1 | 1/2016 | Lee et al. |
| 2016/0201142 A1 | 7/2016 | Lo et al. |
| 2016/0203260 A1 | 7/2016 | Lo et al. |
| 2016/0217251 A1 | 7/2016 | Lo et al. |
| 2016/0292356 A1 | 10/2016 | Kim et al. |
| 2016/0333416 A1 | 11/2016 | Babiarz et al. |
| 2017/0024513 A1 | 1/2017 | Lo et al. |
| 2017/0073774 A1 | 3/2017 | Lo et al. |
| 2017/0211143 A1 | 7/2017 | Shendure et al. |
| 2017/0260590 A1 | 9/2017 | Eltoukhy et al. |
| 2017/0321284 A1 | 11/2017 | McCarroll et al. |
| 2017/0356053 A1 | 12/2017 | Otto et al. |
| 2018/0119230 A1 | 5/2018 | Velculescu et al. |

FOREIGN PATENT DOCUMENTS

| | | |
|---|---|---|
| CN | 104662168 | 5/2015 |
| CN | 104781421 | 7/2015 |
| CN | 104781422 | 7/2015 |
| CN | 105874068 | 8/2016 |
| EA | 005140 | 12/2004 |
| EA | 010571 | 10/2008 |
| EA | 11608 | 4/2009 |
| EA | 011608 | 4/2009 |
| EA | 018444 | 8/2013 |
| EP | 2426217 | 3/2012 |
| EP | 2864501 | 4/2015 |
| GB | 2485635 | 5/2012 |
| JP | 2005514956 A | 5/2005 |
| JP | 2010534068 | 11/2010 |
| JP | 2010534069 | 11/2010 |
| JP | 2013509884 A | 3/2013 |
| JP | 2014534507 A | 12/2014 |
| WO | 0061612 | 10/2000 |
| WO | 03062441 A1 | 7/2003 |
| WO | 2004078999 | 9/2004 |
| WO | 2004111272 | 12/2004 |
| WO | 2007028155 | 3/2007 |
| WO | 2007100911 | 9/2007 |
| WO | 2008024009 | 2/2008 |
| WO | 2008146309 | 12/2008 |
| WO | 2009013492 | 1/2009 |
| WO | 2009013496 | 1/2009 |
| WO | 2009019455 | 2/2009 |
| WO | 2010112316 | 10/2010 |
| WO | 2011038507 | 4/2011 |
| WO | 2011053790 | 5/2011 |
| WO | 2011054936 | 5/2011 |
| WO | 2011057094 A1 | 5/2011 |
| WO | 2011073665 | 6/2011 |
| WO | 2011090557 | 7/2011 |
| WO | 2011091046 | 7/2011 |
| WO | 2011103236 | 8/2011 |
| WO | 2012071621 | 6/2012 |
| WO | 2013052913 A2 | 4/2013 |
| WO | 2013060762 | 5/2013 |
| WO | 2013086352 | 6/2013 |
| WO | 2013132305 | 9/2013 |
| WO | 2013138510 | 9/2013 |
| WO | 2013190441 | 12/2013 |
| WO | 2014004726 | 1/2014 |
| WO | 2014039556 | 3/2014 |
| WO | 2014043763 | 3/2014 |
| WO | 2014130890 | 8/2014 |
| WO | 2016008451 | 1/2016 |
| WO | 2016015058 | 1/2016 |
| WO | WO 2016/094853 * | 6/2016 |
| WO | 2016116033 | 7/2016 |
| WO | 2016/127944 A1 | 8/2016 |
| WO | 2017012544 | 1/2017 |
| WO | 2017012592 | 1/2017 |
| WO | 2017/019751 A1 | 2/2017 |
| WO | 2017206888 | 12/2017 |
| WO | 2018137685 | 8/2018 |

OTHER PUBLICATIONS

International Search Report and Written Opinion, PCT Application No. PCT/US17/58099, dated Mar. 6, 2018, 25 pages.

Search Report, HK Application No. 18101202.2, dated Feb. 6, 2018, 3 pages.

Chan, et al., "Plasma Epstein-Barr Virus DNA as a Biomarker for Nasopharyngeal Carcinoma," Chinese Journal of Cancer 2014, 33:12, 598-603.

Lam, et al., "Sequencing-Based Counting and Size Profiling of Plasma Epstein-Barr Virus DNA Enhance Population Screening of Nasopharyngeal Carincinoma," Science Translational Medicine Submitted Manuscript; Template Updated Feb. 2012; 50 pages.

Lo, et al., "Quantitative Analysis of Cell-free Epstein-Barr Virus DNA in Plasma of Patients with Nasopharyngeal Carcinoma," Cancer Research 1999, 59, 1188-1191.

Chan, et al., "Analysis of Plasma Epstein-Barr Virus DNA to Screen for Nasopharyngeal Cancer," The New England Journal of Medicine 2107, 377:6, 513-522.

Chan, et al., "Early Detection of Nasopharyngeal Carcinoma by Plasma Epstein-Barr Virus DNA Analysis in a Surveillance Program," Cancer 2013, 119:10, 1838-44.

Hohaus, et al., "The Viral Load of Epstein-Barr Virus (EBV) DNA in Peripheral Blood Predicts for Biological and Clinical Characteristics in Hodgkin Lymphoma," Clinical Cancer Research 2011, 17:9, 2885-2892.

Shoda, et al., "Clinical Utility of Circulating Cell-Free Epstein-Barr Virus DNA in Patients with Gastric Cancer," Oncotarget 2017, 8:17, 28796-28804.

Tan, et al., "Evaluation of Plasma Epstein-Barr Virus DNA Load as a Prognostic Marker for Nasopharyngeal Carcinoma," Singapore Medical Journal 2006, 47:9, 803-807.

TruSeq DNA PCR-Free Sample Preparation Kit, Illumina, Data Sheet: Sequencing, Available online at: http://www.illumina.com/contenUdam/illuminamarketing/documents/products/datasheets/datasheet_truseq_dna_pcr_free_sample_prep.pdf>, 2013, 4 pages.

U.S. Appl. No. 13/801,748, Advisory Action dated Feb. 24, 2017, 3 pages.

U.S. Appl. No. 13/801,748, Final Office Action dated Oct. 3, 2016, 12 pages.

U.S. Appl. No. 13/801,748, Final Office Action dated Apr. 25, 2019, 16 pages.

U.S. Appl. No. 13/801,748, Final Office Action dated Apr. 6, 2018, 17 pages.

U.S. Appl. No. 13/801,748, Non-Final Office Action dated Oct. 19, 2018, 14 pages.

U.S. Appl. No. 13/801,748, Non-Final Office Action dated Aug. 11, 2017, 18 pages.

U.S. Appl. No. 13/801,748, Non-Final Office Action dated Jan. 22, 2016, 9 pages.

U.S. Appl. No. 15/218,497, Non-Final Office Action dated Jan. 11, 2019, 5 pages.

U.S. Appl. No. 15/218,497, Notice of Allowance dated Jun. 12, 2019, 7 pages.

U.S. Appl. No. 15/362,631, Non-Final Office Action dated Jan. 11, 2018, 7 pages.

U.S. Appl. No. 15/362,631, Notice of Allowability dated Aug. 10, 2018, 5 pages.

U.S. Appl. No. 15/362,631, Notice of Allowability dated Oct. 31, 2018, 5 pages.

U.S. Appl. No. 15/362,631, Notice of Allowance dated Jun. 28, 2018, 7 pages.

Aird et al., Analyzing and Minimizing PCR Amplification Bias in Illumina Sequencing Libraries, Genome Biology, vol. 12, No. R18, Available online at: http://genomebiology.com/2011/12/2/R18, Feb. 2011, pp. 1-14.

Australian Application No. 2013278994, First Examination Report dated Aug. 17, 2016, 3 pages.

(56) References Cited

OTHER PUBLICATIONS

Australian Application No. 2013278994, Notice of Acceptance dated Mar. 23, 2017, 3 pages.
Australian Application No. 2017204558, First Examination Report dated Nov. 21, 2018, 11 pages.
Beck et al., Next Generation Sequencing of Serum Circulating Nucleic Acids from Patients with Invasive Ductal Breast Cancer Reveals Differences to Healthy and Nonmalignant Controls, Molecular Cancer Research, vol. 8, Issue 3, Mar. 9, 2010, pp. 335-342.
Beck et al., Profile of the Circulating DNA in Apparently Healthy Individuals, Clinical Chemistry, vol. 55, Issue 4, Apr. 2009, pp. 730-738.
Bianchi et al., Large Amounts of Cell-free Fetal DNA Are Present in Amniotic Fluid, Clinical Chemistry, vol. 47, No. 10, Oct. 2001, pp. 1867-1869.
Canadian Application No. 2,876,327, Office Action dated Feb. 8, 2019, 4 pages.
Canadian Application No. 2,876,327, Office Action dated Jul. 7, 2017, 4 pages.
Canadian Application No. 2,876,327, Office Action dated Mar. 23, 2016, 4 pages.
Chan et al., Cancer Genome Scanning in Plasma: Detection of Tumor-Associated Copy Number Aberrations, Single-Nucleotide Variants, and Tumoral Heterogeneity by Massively Parallel Sequencing, Clinical Chemistry, vol. 59, No. 1, Jan. 2013, pp. 211-224.
Chan et al., Molecular Characterization of Circulating EBV DNA in the Plasma of Nasopharyngeal Carcinoma and Lymphoma Patients, Cancer Research, vol. 63, No. 9, May 1, 2003, pp. 2028-2032.
Chan et al., Noninvasive Detection of Cancer-Associated Genome-Wide Hypomethylation and Copy Number Aberrations by Plasma DNA Bisulfite Sequencing, Proceedings of the National Academy of Sciences, vol. 110, No. 47, Nov. 19, 2013, pp. 18761-18768.
Chan et al., Size Distributions of Maternal and Fetal DNA in Maternal Plasma, Clinical Chemistry, vol. 50, No. 1, Jan. 2004, pp. 88-92.
Chandrananda et al., High-Resolution Characterization of Sequence Signatures due to Non-Random Cleavage of Cell-Free DNA, BMC Medical Genomics, vol. 8, No. 29, Jun. 17, 2015, pp. 1-19.
Chang et al., Assessment of Plasma DNA Levels, Allelic Imbalance and CA 125 as Diagnostic Tests for Cancer, Journal of the National Cancer Institute, vol. 94, No. 22, Nov. 20, 2002, pp. 1697-1703.
Chiu et al., Non-Invasive Prenatal Diagnosis by Single Molecule Counting Technologies, Trends in Genetics, vol. 25, No. 7, Jun. 18, 2009, pp. 324-331.
Chiu et al., Noninvasive Prenatal Diagnosis of Fetal Chromosomal Aneuploidy by Massively Parallel Genomic Sequencing of DNA in Maternal Plasma, Proceedings of the National Academy of Sciences, vol. 105, No. 51, Dec. 23, 2008, pp. 20458-20463.
Cibulskis et al., Sensitive Detection of Somatic Point Mutations in Impure and Heterogeneous Cancer Samples, Nature Biotechnology, vol. 31, No. 3, Mar. 2013, pp. 213-219.
Chinese Application No. CN201380042981.X, Notice of Decision to Grant dated Aug. 21, 2017, 2 pages.
Chinese Application No. CN201380042981.X, Office Action dated Nov. 30, 2016, 5 pages.
Chinese Application No. CN201380042981.X, Office Action dated Apr. 13, 2016, 6 pages.
Chinese Application No. CN201380042981.X, Office Action dated Nov. 2, 2015, 8 pages.
Daniels et al., Whole Genome Sequencing for Lung Cancer, Journal of Thoracic Disease, vol. 4, No. 2, Apr. 1, 2012, pp. 155-163.
Diaz et al., Supplementary Information, Nature, 2012, 25 pages.
Diaz Jr. et al., The Molecular Evolution of Acquired Resistance to Targeted EGFR Blockade in Colorectal Cancers, Nature, vol. 486, No. 7404, Jun. 28, 2012, 10 pages.
Diehl et al., Circulating Mutant DNA to Assess Tumor Dynamics, Nature Medicine, vol. 14, No. 9, Sep. 2008, pp. 985-990.
Diehl et al., Detection and Quantification of Mutations in the Plasma of Patients with Colorectal Tumors, Proceedings of the National Academy of Sciences, vol. 102, No. 45, Nov. 8, 2005, pp. 16368-16373.
Ding et al., MS Analysis of Single-Nucleotide Differences in Circulating Nucleic Acids: Application to Noninvasive Prenatal Diagnosis, Proceedings of the National Academy of Sciences of the United States (PNAS), National Academy of Science US, vol. 101, No. 29, Jul. 20, 2004, pp. 10762-10767.
Eurasian Application No. 201500027, Office Action dated Oct. 22, 2018, 13 pages (8 pages for the original document and 5 pages for the English translation).
Eurasian Application No. 201500027, Office Action dated Mar. 10, 2017, 19 pages (11 pages for the original document and 8 pages for the English translation).
Eurasian Application No. 201500027, Office Action dated Dec. 19, 2017, 21 pages (5 pages for the original document and 16 pages for the English translation).
Eurasian Application No. 201500027, Office Action dated May 23, 2016, 5 pages (3 pages for the original document and 2 pages for the English translation).
Ellinger et al., Cell-Free Circulating DNA: Diagnostic Value in Patients with Testicular Germ Cell Cancer, The Journal of Urology, vol. 181, Issue 1, Jan. 2009, pp. 363-371.
European Application No. 13807105.5, Extended European Search Report dated Feb. 15, 2016, 9 pages.
European Application No. 13807105.5, Notice of Decision to Grant dated Jul. 12, 2018, 3 pages.
European Application No. 13807105.5, Office Action dated Feb. 27, 2017, 10 pages.
European Application No. 16748745.3, Extended European Search Report dated Sep. 18, 2018, 8 pages.
European Application No. 16827283.9, Extended European Search Report dated Dec. 5, 2018, 7 pages.
European Application No. 18185290.6, Extended European Search Report dated Nov. 29, 2018, 17 pages.
Fan et al., Analysis of the Size Distributions of Fetal and Maternal Cell-Free DNA by Paired-End Sequencing, Clinical Chemistry, vol. 56, No. 8, Aug. 2010, pp. 1279-1286.
Fan et al., Detection of Aneuploidy with Digital Polymerase Chain Reaction, Analytical Chemistry, American Chemical Society, vol. 79, No. 19, Oct. 1, 2007, pp. 7576-7579.
Fan et al., Noninvasive Diagnosis of Fetal Aneuploidy by Shotgun Sequencing DNA from Maternal Blood, Proceedings National Academy of Sciences, vol. 105, No. 42, Oct. 21, 2008, pp. 16266-16271.
Fan et al., Whole-Genome Molecular Haplotyping of Single Cells, Nature Biotechnology, vol. 29, No. 1, Jan. 2011, pp. 51-57.
Forshew et al., Noninvasive Identification and Monitoring of Cancer Mutations by Targeted Deep Sequencing of Plasma DNA, Science Translational Medicine. American Association for the Advancement of Science, vol. 4, No. 136, May 30, 2012, pp. 1-12.
Gerlinger et al., Intratumor Heterogeneity and Branched Evolution Revealed by Multiregion Sequencing, The New England Journal of Medicine, vol. 366, No. 10, Available online at: www.nejm.org, Mar. 8, 2012, pp. 883-892.
Goode et al., A Simple Consensus Approach Improves Somatic Mutation Prediction Accuracy, Genome Medicine, vol. 5, No. 90, Sep. 30, 2013, 14 pages.
Hanlon et al., Evaluation of 13q14 Status in Multiple Myeloma by Digital Single Nucleotide Polymorphism Technology, Journal of Molecular Diagnostics; vol. 11, No. 5, Sep. 2009, pp. 450-457.
Heidary et al., The Dynamic Range of Circulating Tumor DNA in Metastatic Breast Cancer, Breast Cancer Research, vol. 16, No. 421, Aug. 9, 2014, pp. 1-10.
Hou et al., Single-Cell Exome Sequencing and Monoclonal Evolution of a JAK2-Negative Myeloproliferative Neoplasm, Cell, vol. 148, Issue 5, Mar. 2, 2012, pp. 873-885.
Israel Application No. 235967, Notice of Allowance dated May 27, 2019, 3 pages.
Israel Application No. 235967, Office Action dated Apr. 10, 2018, 2 pages.
Israel Application No. 235967, Office Action dated Aug. 14, 2017, 2 pages.

(56) References Cited

OTHER PUBLICATIONS

Israel Application No. 235967, Office Action dated Nov. 29, 2018, 4 pages.
Ivanov et al., Non-Random Fragmentation Patterns in Circulating Cell-Free DNA Reflect Epigenetic Regulation, BMC Genomics, vol. 16, Suppl 13, S1, Dec. 16, 2015, 12 pages.
Jacobs et al., Detectable Clonal Mosaicism and its Relationship to Aging and Cancer, Nature Genetics, vol. 44, No. 6, Jun. 2012, 20 pages.
Jahr et al., DNA Fragments in the Blood Plasma of Cancer Patients: Quantitations and Evidence for their Origin from Apoptotic and Necrotic Cells, Cancer Research, vol. 61, No. 4, Feb. 15, 2001, pp. 1659-1665.
Jiang et al., Increased Plasma DNA Integrity Index in Head and Neck Cancer Patients, International Journal of Cancer, vol. 119, No. 11, Dec. 1, 2006, pp. 2673-2676.
Jiang et al., Preferred End Coordinates and Somatic Variants as Signatures of Circulating Tumor DNA Associated with Hepatocellular Carcinoma, Proceedings of the National Academy of Sciences of the United States of America, vol. 115, No. 46, Dec. 5, 2018, pp. E10925-E10933.
Japanese Application No. 2015-517896, Notice of Decision to Grant dated Jun. 12, 2018, 2 pages.
Japanese Application No. 2015-517896, Office Action dated Jul. 26, 2016, 18 pages (7 pages for the original document and 11 pages for the English translation).
Japanese Application No. 2015-517896, Office Action dated Feb. 6, 2018, 7 pages (3 pages for the original document and 4 pages for the English translation).
Japanese Application No. 2015-517896, Office Action dated Jun. 6, 2017, 7 pages (3 pages for the original document and 4 pages for the English translation).
Jung et al., Cell-Free DNA in the Blood as a Solid Tumor Biomarker—A Critical Appraisal of the Literature, Clinica Chimica Acta, vol. 411, Issue 21-22, Nov. 11, 2010, pp. 1611-1624.
Karlsson et al., Amplification-Free Sequencing of Cell-Free DNA for Prenatal Non-Invasive Diagnosis of Chromosomal Aberrations, Genomics, vol. 105, No. 3, Mar. 2015, pp. 150-158.
Kinde et al., Detection and Quantification of Rare Mutations with Massively Parallel Sequencing, Proceedings of the National Academy of Sciences, vol. 108, No. 23, Jun. 7, 2011, pp. 9530-9535.
Kitzman et al., Noninvasive Whole-Genome Sequencing of a Human Fetus, Science Translational Medicine, vol. 4, No. 137-140, Jun. 2012, 11 pages.
Kozarewa et al., Amplification-Free Illumina Sequencing-Library Preparation Facilitates Improved Mapping and Assembly of (GC)-Biased Genomes, Nature Methods, vol. 6, No. 4, Apr. 2009, pp. 291-295.
Korean Application No. 10-2015-7001225, Notice of Decision to Grant dated Apr. 26, 2018, 4 pages (3 pages for the original document and 1 page for the English translation).
Korean Application No. 10-2015-7001225, Office Action dated Oct. 25, 2016, 16 pages (3 pages for the original document and 4 pages for the English translation).
Korean Application No. 10-2015-7001225, Office Action dated Aug. 29, 2017, 9 pages (5 pages for the original document and 4 pages for the English translation).
Korean Application No. 10-2018-7021883, Office Action dated Mar. 22, 2019, 10 pages (4 pages for the original document and 6 pages for the English translation).
Korean Application No. 10-2018-7021883, Office Action dated Sep. 3, 2018, 9 pages (4 pages for the original document and 5 pages for the English translation).
Laframboise et al., Allele-Specific Amplification in Cancer Revealed by SNP Array Analysis, PLoS Computational Biology, vol. 1, Issue 6, Nov. 2005, pp. 0507-0517.
Lapaire et al., Array-CGH Analysis of Cell-Free Fetal DNA in 10 mL of Amniotic Fluid Supernatant, Prenatal Diagnosis, vol. 27, No. 7, Jul. 2007, pp. 616-621.
Lapaire et al., Cell-Free Fetal DNA in Amniotic Fluid: Unique Fragmentation Signatures in Euploid and Aneuploid Fetuses, Clinical Chemistry, vol. 53, No. 3, Mar. 2007, pp. 405-411.
Lapaire et al., Larger Columns and Change of Lysis Buffer Increase the Yield of Cell-Free DNA Extracted from Amniotic Fluid, Clinical Chemistry, vol. 52, No. 1, Jan. 2006, pp. 156-157.
Larkin et al., A Phase II Trial of Nilotinib in the Treatment of Patients with KIT Mutated Advanced Acral and Mucosal Melanoma (NICAM), Journal of Clinical Oncology, vol. 29, No. 15, May 20, 2011, 3 pages.
Larrabee et al., Microarray Analysis of Cell-Free Fetal DNA in Amniotic Fluid: A Prenatal Molecular Karyotype, XP-002413186, The American Society of Human Genetics, vol. 75, No. 3, Sep. 1, 2004, pp. 485-491.
Leary et al., Detection of Chromosomal Alterations in the Circulation of Cancer Patients with Whole-Genome Sequencing, Science Translational Medicine, vol. 4, No. 162, Nov. 28, 2012, 21 pages.
Leary et al., Development of Personalized Tumor Biomarkers Using Massively Parallel Sequencing, Science Translational Medicine, Available Online at: www.ScienceTranslationaiMedicine.org, vol. 2, No. 20, Feb. 24, 2010, 15 pages.
Lecoeur, Nuclear Apoptosis Detection by Flow Cytometry: Influence of Endogenous Endonucleases, Experimental Cell Research, vol. 277, No. 1, Jul. 1, 2002, pp. 1-14.
Li et al., New Hope for Tumor Diagnosis-Detection of Circulating Free DNA, Chinese Journal of Clinical Pathologist, vol. 7, No. 2, Jun. 30, 2015, 14 pages.
Li et al., Size Separation of Circulatory DNA in Maternal Plasma Permits Ready Detection of Fetal DNA Polymorphisms, Clinical Chemistry, Molecular Diagnostics and Genetics, vol. 50, No. 6, Jun. 2004, pp. 1002-1011.
Liao et al., Targeted Massively Parallel Sequencing of Maternal Plasma DNA Permits Efficient and Unbiased Detection of Fetal Alleles, Clinical Chemistry, vol. 57, Issue 1, Jan. 2011, pp. 92-101.
Lo et al., Digital PCR for the Molecular Detection of Fetal Chromosomal Aneuploidy, PNAS, vol. 104, No. 32, Aug. 7, 2007, pp. 13116-13121.
Lo et al., Maternal Plasma DNA Sequencing Reveals the Genome-Wide Genetic and Mutational Profile of the Fetus, Science Translation Medicine, vol. 2, No. 61, Dec. 8, 2010, pp. 1-13.
Longo, Tumor Heterogeneity and Personalized Medicine, The New England Journal of Medicine, vol. 366, No. 10, Available Online at: www.nejm.org, Mar. 8, 2012, pp. 956-957.
Lun et al., Noninvasive Prenatal Diagnosis of Monogenic Diseases by Digital Size Selection and Relative Mutation Dosage on DNA in Maternal Plasma, Proceedings of the National Academy of Sciences of the United States of America, vol. 105, No. 50, Dec. 16, 2008, pp. 19920-19925.
McDermott et al., Genomics and the Continuum of Cancer Care, The New England Journal of Medicine, vol. 364, No. 4, Jan. 27, 2011, pp. 340-350.
Meyerson et al., Advances in Understanding Cancer Genomes through Second-generation Sequencing, Nature Reviews, Genetics, vol. 11, No. 10, Oct. 2010, pp. 685-696.
Miller et al., Genome-Wide Molecular Characterization of Central Nervous System Primitive Neuroectodermal Tumor and Pineoblastoma, Neuro-Oncology, vol. 13, No. 8, Aug. 2011, pp. 866-879.
Mitchell et al., High Sensitivity and Specificity of Chromosomal Pertubations in Human Invasive Breast Cancer (BrCa) Associated with Circulating Nucleic Acids (CNA) Using Concatemers of Short Sequence DNA Tags in Next Generation Sequencing (NGS), Experimental Biology Meeting 2011, The FASEB Journal, vol. 25, No. 1, Apr. 9-13, 2011, 1 page.
Mouliere et al., High Fragmentation Characterizes Tumour-Derived Circulating DNA, PLOS One, Public Library of Science, US, vol. 6, Issue 9, e23418, Sep. 2011, pp. 1-10.
Muller et al., Identification of Loss of Heterozygosity on Circulating Free DNA in Peripheral Blood of Prostate Cancer Patients: Potential and Technical Improvements, Clinical Chemistry, vol. 54, Issue 4, Apr. 2008, pp. 688-696.

(56) References Cited

OTHER PUBLICATIONS

Murtaza et al., Non-Invasive Analysis of Acquired Resistance to Cancer Therapy by Sequencing of Plasma DNA, Nature, vol. 497, No. 7447, May 2, 2013, pp. 108-112.
Mexican Application No. MX/A/2014/016058, Notice of Allowance dated Aug. 27, 2018, 2 pages.
Mexican Application No. MX/A/2014/016058, Office Action dated Mar. 13, 2018, 3 pages.
Mexican Application No. MX/A/2014/016058, Office Action dated Aug. 17, 2017, 4 pages.
Nannya et al., A Robust Algorithm for Copy Number Detection Using High-Density Oligonucleotide Single Nucleotide Polymorphism Genotyping Arrays, Cancer Research, vol. 65, No. 14, Jul. 15, 2005, pp. 6071-6079.
Palomaki et al., DNA Sequencing of Maternal Plasma to Detect Down Syndrome: An International Clinical Validation Study, Genetics in Medicine, vol. 13, No. 11, Nov. 2011, pp. 913-920.
International Application No. PCT/AU2011/001562, International Search Report and Written Opinion dated Feb. 17, 2012, 8 pages.
International Application No. PCT/CN2016/073753, International Preliminary Report on Patentability dated Aug. 24, 2017, 5 pages.
International Application No. PCT/CN2016/073753, International Search Report and Written Opinion dated May 10, 2016, 7 pages.
International Application No. PCT/CN2016/091531, International Preliminary Report on Patentability dated Feb. 1, 2018, 5 pages.
International Application No. PCT/CN2016/091531, International Search Report and Written Opinion dated Sep. 28, 2016, 11 pages.
International Application No. PCT/CN2018/074138, International Search Report and Written Opinion dated Apr. 28, 2018, 10 pages.
International Application No. PCT/CN2018/097072, International Search Report and Written Opinion dated Nov. 5, 2018, 10 pages.
International Application No. PCT/EP2010/066935, International Search Report and Written Opinion dated Feb. 23, 2011, 10 pages.
International Application No. PCT/IB2013/000312, International Search Report and Written Opinion dated Jun. 18, 2013, 13 pages.
International Application No. PCT/IB2013/054898, International Preliminary Report on Patentability dated Dec. 31, 2014, 7 pages.
International Application No. PCT/IB2013/054898, International Search Report and Written Opinion dated Dec. 23, 2013, 16 pages.
International Application No. PCT/US2010/055655, International Search Report and Written Opinion dated Apr. 20, 2011, 20 pages.
International Application No. PCT/US2015/042310, International Search Report and Written Opinion dated Jan. 12, 2016, 17 pages.
Pennisi, Single-Cell Sequencing Tackles Basic and Biomedical Questions, Science, vol. 336, Issue 6084, May 25, 2012, pp. 976-977.
Peter et al., Cell-Free DNA Fragmentation Patterns in Amniotic Fluid Identify Genetic Abnomnalities and Changes Due to Storage, Diagnostic Molecular Pathology, vol. 17, No. 3, Sep. 2008, pp. 185-190.
Prokunina-Olsson et al., Cancer Sequencing Gets a Little More Personal, Available Online at: www.ScienceTranslationalMedicine.org, vol. 2, Issue 20, Feb. 24, 2010, pp. 1-3.
Psifidi et al., Novel Quantitative Real-time LCR for the Sensitive Detection of SNP Frequencies in Pooled DNA: Method Development, Evaluation and Application, PLoS ONE, vol. 6, Issue 1, e14560, Jan. 19, 2011, pp. 1-11.
Qin et al., Studying Copy Number Variations Using a Nanofluidic Platform, Nucleic Acids Research, vol. 36, No. 18, e116, Oct. 2008, pp. 1-8.
Razavi et al., Many Cell-free Dna (CfDNA) Mutations are Derived from Clonal Hematopoiesis: Implications for Interpretation of Liquid Biopsy Tests, GRAIL-MSK WBC Poster, ASCO, vol. 35, No. 15, Available online at: https://grail.com/publication/many-cell-free-dna-cfdna-mutations-are-derived-fromclonal-hematopoiesis-implications-for-interpretation-of-liquid-biopsy-tests/>, Jun. 3, 2017, 41 pages.
Razavi et al., Performance of a High-Intensity 508-Gene Circulating-Tumor DNA (ctDNA) Assay in Patients With Metastatic Breast, Lung, and Prostate Cancer, GRAIL-MSK concordance Poster, ASCOM, vol. 35, No. 18, Available online at: https://grail.com/wpcontenUuploads/2018/05/ASC0_2017 Razavi_Concordance_POS_Final.pdf>, Jun. 2017, 41 pages.
Reed et al., Non-Invasive Determination of the Paternal HLA Haplotype of a Fetus Using Kinetic PCR to Detect Fetal Microchimerism in Maternal Plasma, Bone Marrow Transplantation, vol. 29, No. 6, Mar. 2002, pp. 527-529.
Salani et al., Measurement of Cyclin E Genomic Copy Number and Strand Length in Cell-Free DNA Distinguish Malignant Versus Benign Effusions, Cancer Research, vol. 13, Issue 19, Oct. 1, 2007, pp. 5805-5809.
Schwarzenbach et al., Cell-Free Nucleic Acids as Biomarkers in Cancer Patients, Nature Reviews Cancer, Advance Online Publication, vol. 11, Jun. 2011, pp. 426-437.
Singapore Application No. 11201408113Q, Notice of Decision to Grant dated Jul. 26, 2018, 5 pages.
Singapore Application No. 11201408113Q, Written Opinion dated Aug. 16, 2017, 6 pages.
Singapore Application No. 11201408113Q, Written Opinion dated Aug. 4, 2016, 7 pages.
Singapore Application No. 11201408113Q, Written Opinion dated Dec. 8, 2015, 8 pages.
Singapore Application No. 11201706529T, Notice of Decision to Grant dated May 14, 2019, 5 pages.
Singapore Application No. 11201706529T, Written Opinion dated Jun. 19, 2018, 7 pages.
Shaw et al., Genomic Analysis of Circulating Cell-Free DNA Infers Breast Cancer Dormancy, Genome Research, vol. 22, No. 2, Feb. 2012, pp. 1-12.
Shotelersuk et al., Epstein-Barr Virus DNA in Serum/Plasma as a Tumor Marker for Nasopharyngeal Cancer, Clinical Cancer Research, vol. 6, Mar. 31, 2000, pp. 1046-1051.
Snyder et al., Cell-free DNA Comprises an in Vivo Nucleosome Footprint that Informs its Tissues-of-Origin, Cell, vol. 164, Jan. 14, 2016, pp. 57-68.
Snyder et al., Noninvasive Fetal Genome Sequencing: A Primer, NIH Public Access Author Manuscript in PMC, vol. 33, No. 6, Jun. 2013, pp. 547-554.
Snyder et al., Universal Noninvasive Detection of Solid Organ Transplant Rejection, Proceedings of the National Academy of Sciences, vol. 108, No. 15, Apr. 12, 2011, pp. 6229-6234.
Stratton, Exploring the Genomes of Cancer Cells: Progress and Promise, Science, vol. 331, No. 6024, Mar. 25, 2011, pp. 1553-1558.
Stratton et al., The Cancer Genome, Nature, vol. 458, No. 7239, Apr. 9, 2009, pp. 719-724.
Straver et al., Calculating the Fetal Fraction for Noninvasive Prenatal Testing Based on Genome-Wide Nucleosome Profiles, Prenatal Diagnosis, vol. 36, 2016, pp. 614-621.
Su et al., Inferring Combined CNV/SNP Haplotypes from Genotype Data, Bioinformatics, vol. 26, No. 11, Jun. 1, 2010, pp. 1437-1445.
Sun et al., Research Progress of Circulating DNA and Clinical Tumor, Medical Recapitulate, vol. 16, No. 9, May 31, 2010, pp. 1348-1350.
Taback et al., Prognostic Significance of Circulating Microsatellite Markers in the Plasma of Melanoma Patients, Cancer Research, vol. 61, No. 15, Aug. 1, 2001, pp. 5723-5726.
Tao et al., Rapid Growth of a Hepatocellular Carcinoma and the Driving Mutations Revealed by Cell-Population Genetic Analysis of Whole-Genome Data, Proceedings of the National Academy of Sciences of the United States of America, vol. 108, No. 29, Jul. 19, 2011, pp. 12042-12047.
Thierry et al., Origin and Quantification of Circulating DNA in Mice With Human Colorectal Cancer Xenografts, Nucleic Acids Research, vol. 38, Issue 18, May 21, 2010, pp. 6159-6175.
Tsang et al., Circulating Nucleic Acids in Plasma/Serum, Pathology, vol. 39, No. 2, Apr. 30, 2007, pp. 197-207.
Taiwan Application No. 102122036, Notice of Decision to Grant dated Jul. 18, 2018, 3 pages.
Taiwan Application No. 102122036, Office Action dated Feb. 8, 2017, 8 pages (4 pages for the original document and 4 pages for the English translation).
Van Dijk et al., Library Preparation Methods for Next-Generation Sequencing: Tone Down the Bias, Experimental Cell Research, vol. 322, Issue 1, Mar. 10, 2014, pp. 12-20.

(56) References Cited

OTHER PUBLICATIONS

Wagner, Free DNA—New Potential Analyte in Clinical Laboratory Diagnostics?, Biochemia Medica, vol. 22, No. 1, Feb. 15, 2012, pp. 24-38.

Wang et al., Digital Karyotyping, PNAS, vol. 99, No. 25, Dec. 10, 2002, pp. 16156-16161.

Weber et al., Detection of Human Tumor Cells by Amplicon Fusion Site Polymerase Chain Reaction (AFS-PCR), The Journal of Clinical Investigation, vol. 121, No. 2, Feb. 2011, pp. 545-553.

Welch et al., The Origin and Evolution of Mutations in Acute Myeloid Leukemia, Cell, vol. 150, Issue 2, Jul. 20, 2012, pp. 264-278.

Xie et al., CNV-Seq, A New Method to Detect Copy Number Variation Using High-throughput Sequencing, BMC Bioinformatics, vol. 10, No. 80, Mar. 6, 2009, 9 pages.

Xu et al., Single-Cell Exome Sequencing Reveals Single-Nucleotide Mutation Characteristics of a Kidney Tumor, Cell, vol. 148, Issue 5, Mar. 2, 2012, pp. 886-895.

Yap et al., Intratumor Heterogeneity: Seeing the Wood for the Trees, Science Translational Medicine, vol. 4, Issue 127, Available online at: www.sciencetranslationalmedicine.org, Mar. 28, 2012, pp. 1-4.

Yu et al., Size-Based Molecular Diagnostics Using Plasma DNA for Noninvasive Prenatal Testing, Proc Natl Acad Sci, vol. 111, No. 23, Jun. 10, 2014, pp. 8583-8588.

Yung et al., Single-Molecule Detection of Epidermal Growth Factor Receptor Mutations in Plasma by Microfluidics Digital PCR in Non-Small Cell Lung Cancer Patients, Clin Cancer Res, vol. 15, Issue 6, Mar. 15, 2009, pp. 2076-2084.

South African Application No. 2014/09281, Notice of Acceptance dated Jul. 25, 2017, 1 page.

Zhao et al., Homozygous Deletions and Chromosome Amplifications in Human bLung Carcinomas Revealed by Single Nucleotide Polymorphism Array Analysis, Cancer Research, vol. 65, Issue 13, Jul. 1, 2005, pp. 5561-5570.

Zheng et al., Nonhematopoietically Derived DNA is Shorter than Hematopoietically Derived DNA in Plasma: A Transplantation Model, Clinical Chemistry, vol. 58, No. 3, Mar. 2012, pp. 549-558.

Non-Final Office Action dated Sep. 25, 2019 in U.S. Appl. No. 16/046,795, filed Jul. 26, 2018. 17 pages.

Balakrishnan et al.; "Epigenetic Regulation of Viral Biological Processes"; Viruses; 2017; 9(11); 346; https://doi.org/10.3390/v9110346; 14 pages.

English translation of Office Action dated Jan. 7, 2020 in JP Patent Application No. 2017-559756. 6 pages.

* cited by examiner

Lo, Y. M. Dennis, et al. "Quantitative Analysis of Cell-free Epstein-Barr Virus DNA in Plasma of Patients with Nasopharyngeal Carcinoma." *Cancer Research*, March 1999.

Li, Jing, et al. "A Comparison between the Sixth and Seventh Editions of the UICC/AJCC Staging System for Nasopharyngeal Carcinoma in a Chinese Cohort." *PLoS One*, December 2014

| | Exploratory dataset | | | Validation dataset | | | |
|---|---|---|---|---|---|---|---|
| | Non-cancer subjects with transiently positive plasma EBV DNA | Non-cancer subjects with persistently positive plasma EBV DNA | NPC patients from the screening cohort | Non-cancer subjects with transiently positive plasma EBV DNA | Non-cancer subjects with persistently positive plasma EBV DNA | NPC patients from the screening cohort | NPC patients from an external cohort |
| Number | 20 | 20 | 10 | 159 | 73 | 24 | 31 |
| Sex | | | | | | | |
| M | 20 | 20 | 10 | 159 | 73 | 24 | 24 |
| F | 0 | 0 | 0 | 0 | 0 | 0 | 7 |
| Median age, year (IQR) | 54.5 (50–56) | 55 (50–60.5) | 54 (47–56) | 53 (47–57) | 53 (48–59) | 50 (43–54) | 56 (50–62) |
| Tumor stage | | | | | | | |
| I | | | 5 | | | 11 | 3 |
| II | | | 2 | | | 6 | 2 |
| III | | | 2 | | | 6 | 20 |
| IV | | | 1 | | | 1 | 6 |

*FIG. 12*

HPV DNA fragments in patients with Ca cervix

| Type | Sample | Stage | Mapped Fragments | Fragments mapped to HPV16 | %reads mapped to HPV16 | Fragments mapped to HPV18 | Fragments mapped to HPV33 | Fragments mapped to HPV35 | Fragments mapped to HPV52 | Fragments mapped to HPV58 | %reads mapped to HPV58 |
|---|---|---|---|---|---|---|---|---|---|---|---|
| Ca cervix | C.768 | N/A | 13137672 | 7992 | 0.06083 | 0 | 0 | 0 | 0 | 0 | 0 |
| Ca cervix | C.801 | N/A | 4660998 | 2127 | 0.04563 | 0 | 0 | 0 | 0 | 0 | 0 |
| Ca cervix | C.803 | N/A | 8747442 | 1316 | 0.01504 | 0 | 0 | 0 | 0 | 0 | 0 |
| Ca cervix | C.819 | N/A | 20372000 | 1489 | 0.00731 | 0 | 0 | 0 | 0 | 0 | 0 |
| Ca cervix | C.822 | N/A | 13026820 | 1720 | 0.0132 | 0 | 0 | 0 | 0 | 0 | 0 |
| Ca cervix | C.877 | N/A | 21316598 | 6773 | 0.03177 | 0 | 0 | 0 | 0 | 0 | 0 |
| Ca cervix | CaCx 3276 | IIIB | 53407769 | 31 | 5.80E-05 | 1375 | 0.0026 | 0 | 0 | 0 | 0 |
| Ca cervix | CaCx 3485 | IIB | 64175765 | 143525 | 0.2236 | 1 | 1.56E-06 | 0 | 0 | 0 | 0 |
| Ca cervix | CaCx 3499 | IIB | 41596564 | 36 | 8.65E-05 | 0 | 0 | 0 | 0 | 0 | 0 |
| Ca cervix | CaCx 3542 | IIIA | 60523865 | 24 | 3.96E-05 | 0 | 0.000012 | 7 | 0 | 0 | 0 |
| Ca cervix | CaCx 3581 | IIB | 46051601 | 39 | 8.46E-05 | 0 | 0 | 0 | 1 | 2.17E-06 | 152 | 0.00033 |

FIG. 17

HPV DNA fragments in patients with CIN

| Type | Sample | Stage | Mapped to human genome | Fragments mapped to HPV16 | Fragments mapped to HPV18 | Fragments mapped to HPV31 | Fragments mapped to HPV33 | Fragments mapped to HPV45 | Fragments mapped to HPV52 | Fragments mapped to HPV58 | Proportion mapped to HPV16 | Proportion mapped to HPV18 | Proportion mapped to HPV31 | Proportion mapped to HPV33 |
|---|---|---|---|---|---|---|---|---|---|---|---|---|---|---|
| CIN | CIN264 | III | 90267591 | 0 | 0 | 0 | 19 | 0 | 1 | 1 | 0.000021 | 1.11E-06 | 1 | 1.11E-06 |
| CIN | CIN266 | III | 69164406 | 2 | 2.96E-06 | 0 | 7 | 0 | 0 | 0 | 0.000031 | 0 | 0 | 0 |
| CIN | CIN270 | III | 25521018 | 0 | 0 | 0 | 0 | 0 | 0 | 0 | 0 | 0 | 0 | 0 |
| CIN | CIN272 | III | 52110586 | 0 | 0 | 0 | 0 | 0 | 0 | 0 | 0 | 0 | 0 | 0 |
| CIN | CIN306 | III | 79970503 | 0 | 0 | 0 | 0 | 0 | 0 | 0 | 0 | 0 | 0 | 0 |
| CIN | CIN323 | III | 49674122 | 1 | 0 | 0 | 0 | 0 | 0 | 0 | 0 | 0 | 0 | 0 |
| CIN | CIN346 | III | 47867453 | 0 | 2.10E-06 | 0 | 0 | 0 | 0 | 0 | 0 | 0 | 0 | 0 |
| CIN | CIN347 | III | 62446833 | 0 | 0 | 0 | 0 | 0 | 0 | 0 | 0 | 0 | 0 | 0 |
| CIN | CIN351 | III | 65724902 | 0 | 0 | 0 | 0 | 0 | 0 | 0 | 0 | 0 | 0 | 0 |
| CIN | CIN362 | III | 47016678 | 0 | 0 | 0 | 0 | 0 | 0 | 0 | 0 | 0 | 0 | 0 |
| CIN | CIN_1501 | N/A | 14094368 | 0 | 0 | 0 | 0 | 0 | 0 | 0 | 0 | 0 | 0 | 0 |
| CIN | CIN_1502 | N/A | 13689492 | 0 | 0 | 0 | 0 | 0 | 0 | 0 | 0 | 0 | 0 | 0 |
| CIN | CIN_1503 | N/A | 14975461 | 0 | 0 | 0 | 0 | 0 | 0 | 0 | 0 | 0 | 0 | 0 |
| CIN | CIN_1504 | N/A | 19560726 | 0 | 0 | 0 | 0 | 0 | 0 | 0 | 0 | 0 | 0 | 0 |
| CIN | CIN_1506 | N/A | 14089988 | 0 | 0 | 0 | 0 | 0 | 0 | 0 | 0 | 0 | 0 | 0 |
| CIN | CIN_1507 | N/A | 9179781 | 0 | 0 | 0 | 0 | 0 | 0 | 0 | 0 | 0 | 0 | 0 |

FIG. 18

HPV DNA fragments in patients with HPV+ve HNSCC

| Type | Sample | Stage | Mapped fragments | Fragments mapped to HPV16 | Reads mapped to HPV16 | Fragments mapped to HPV18 | Fragments mapped to HPV31 | Fragments mapped to HPV33 | Fragments mapped to HPV35 | Fragments mapped to HPV52 | Fragments mapped to HPV58 | Reads mapped to HPV58 |
|---|---|---|---|---|---|---|---|---|---|---|---|---|
| HNSCC | TBR1019 | II | 51218387 | 3287 | 0.006418 | 0 | 0 | 0 | 0 | 0 | 0 | 0 |
| HNSCC | TBR1067 | III | 57211291 | 53 | 9.26E-05 | 0 | 0 | 0 | 0 | 0 | 0 | 0 |
| HNSCC | TBR1245 | I | 63709771 | 1715 | 0.002692 | 0 | 0 | 0 | 0 | 0 | 0 | 0 |
| HNSCC | TBR1988 | I | 76586806 | 1159 | 0.001513 | 0 | 0 | 0 | 0 | 0 | 0 | 0 |
| HNSCC | TBR1989 | III | 60576165 | 484920 | 0.800513 | 0 | 0 | 0 | 0 | 0 | 0 | 0 |
| HNSCC | TBR2002 | I | 78175247 | 1949 | 0.002493 | 0 | 0 | 0 | 0 | 0 | 0 | 0 |
| HNSCC | TBR2175 | II | 60128334 | 4022 | 0.006689 | 0 | 0 | 0 | 0 | 0 | 0 | 0 |

FIG. 19

HPV detection in healthy control

| Sample type | Sample number | No. of sample with detectable HPV reads by sequencing | Proportion(%) |
|---|---|---|---|
| Healthy control | 270 | 9 | 3.3 |

| Type | Sample | HPV type | Number of HPV fragment(s) |
|---|---|---|---|
| Healthy controls | AB155 | HPV39 | 1 |
| Healthy controls | AC135 | HPV45 | 1 |
| Healthy controls | AF121 | HPV16 | 4 |
| Healthy controls | CK018 | HPV56 | 1 |
| Healthy controls | GG017 | HPV16 | 125 |
| Healthy controls | GT023 | HPV58 | 2 |
| Healthy controls | HK074 | HPV16 | 2 |
| Healthy controls | AE011 | HPV16 | 2 |
| Healthy controls | DZ071 | HPV16 | 1 |

FIG. 20

The mean proportion of HBV DNA fragments below 150bp in plasma.

Carcinoma of cervix

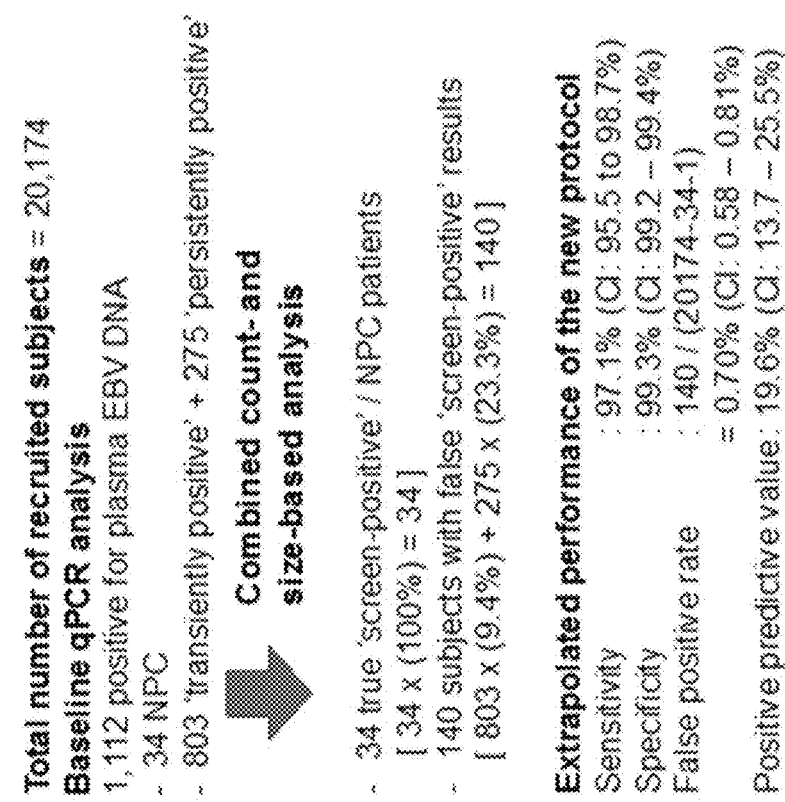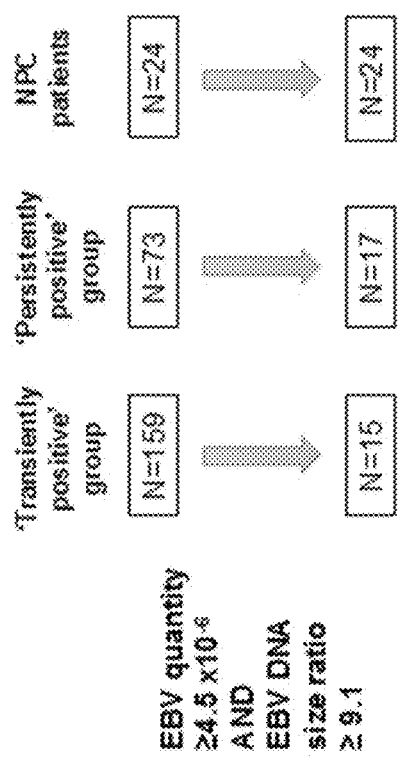
FIG. 57

US 10,633,713 B2

DIAGNOSTIC APPLICATIONS USING NUCLEIC ACID FRAGMENTS

CROSS-REFERENCES TO RELATED APPLICATIONS

The present application claims priority from and is a non-provisional of U.S. Provisional Application No. 62/450,541, entitled "Diagnostic Applications Using Nucleic Acid Fragments" filed Jan. 25, 2017, and 62/507,154, entitled "Diagnostic Applications Using Nucleic Acid Fragments" filed May 16, 2017; and is a continuation-in-part of PCT application No. PCT/US2017/058099, entitled "Methods And Systems For Tumor Detection," filed Oct. 24, 2017, the entire contents of which are herein incorporated by reference for all purposes.

BACKGROUND

The discovery that tumor cells release tumor-derived DNA into the blood stream has sparked the development of non-invasive methods capable of determining the presence, location and/or type of tumor in a subject using cell-free samples (e.g., plasma). Many tumors can be treatable if detected early in their development. However, current methods can lack the sensitivity and/or specificity to detect a tumor at an early stage and can return a large number of false positive or false negative results. The sensitivity of a test can refer to the likelihood that a subject that is positive for a condition tests positive for the condition. The specificity of a test can refer to the likelihood that a subject that is negative for a condition tests negative for that condition. The problems of sensitivity and specificity can be exaggerated in assays for the early detection of tumors, e.g., because samples on which such tumor detection methods are performed can have relatively small amounts of tumor-derived DNA and because the condition itself can have a relatively low prevalence among individuals tested in the early stage. Accordingly, there is a clinical need for methods having higher sensitivity and/or specificity for the detection of tumors.

SUMMARY

Various embodiments are directed to applications (e.g., classification of biological samples) of the analysis of the count, the fragmentation patterns, and size of cell-free nucleic acids, e.g., plasma DNA and serum DNA, including nucleic acids from pathogens, such as viruses. Embodiments of one application can determine if a subject has a particular condition. For example, a method of present disclosure can determine if a subject has cancer or a tumor, or other pathology. Embodiments of another application can be used to assess the stage of a condition, or the progression of a condition over time. For example, a method of the present disclosure may be used to determine a stage of cancer in a subject, or the progression of cancer in a subject over time (e.g., using samples obtained from a subject at different times).

According to one embodiment, sequence reads obtained from a sequencing of the mixture of cell free nucleic acid molecules can be used to determine an amount of the sequence reads aligning to a reference genome corresponding to the virus. The amount of sequence reads aligning to the reference genome can be compared to a cutoff value to screen for the pathology.

According to another embodiment, sizes of viral nucleic acid molecules (e.g., those aligning to a reference genome corresponding to the virus) can be used. A statistical value of a size distribution of the nucleic acid molecules from the virus can be determined. A level of pathology in the subject can be determined by processing the statistical value against a cutoff value.

According to another embodiment, a first amount of cell-free nucleic acid molecules that end within one or more first windows of a reference genome corresponding to the virus is determined. Each first window comprising at least one of a first set of genomic positions at which ends of cell-free nucleic acid molecules are present at a rate above a first threshold in subjects with a cancer (or other pathology) associated with the virus. A relative abundance can be computed by normalizing the first amount using a second amount of cell-free nucleic acid molecules, which includes cell-free nucleic acid molecules ending at a second set of genomic positions outside of the one or more first windows including the first set of genomic positions. A level of cancer in the subject can be determined by processing the relative abundance against a cutoff value.

Embodiments can combine various techniques. For example, a first assay can be count-based, size-based, or fragmentation-based. A second assay can be one of the other techniques. As examples a majority voting can be used, or cutoff values can be determined for both techniques, thereby determining a set of data points from the two techniques that correspond to a particular level of pathology.

Other embodiments are directed to systems, portable consumer devices, and computer readable media associated with methods described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 12 is a table showing subject characteristics in the exploratory and validation sample sets.

FIG. 17 shows the numbers and proportions of reads uniquely mapped to the HPV genome of different HPV serotypes for each clinical case of carcinoma of cervix.

FIG. 18 shows the numbers and proportions of reads uniquely mapped to the HPV genome of different HPV serotypes for each clinical case of cervical intraepithelial neoplasia (CIN).

FIG. 19 shows the numbers and proportions of reads uniquely mapped to the HPV genome of different HPV serotypes for each clinical case of HPV positive-head and neck squamous cell carcinoma (HPV+ve HNSCC).

FIG. 20 shows the number of plasma HPV fragments and the corresponding HPV serotypes in the plasma samples of the 9 healthy subjects with at least one plasma HPV DNA.

FIG. 57 shows modeling the performance of count-based analysis and size-based analysis of plasma EBV DNA in the entire 20,174-subject screening cohort using the cutoffs from FIG. 56A.

TERMS

Figure 1:
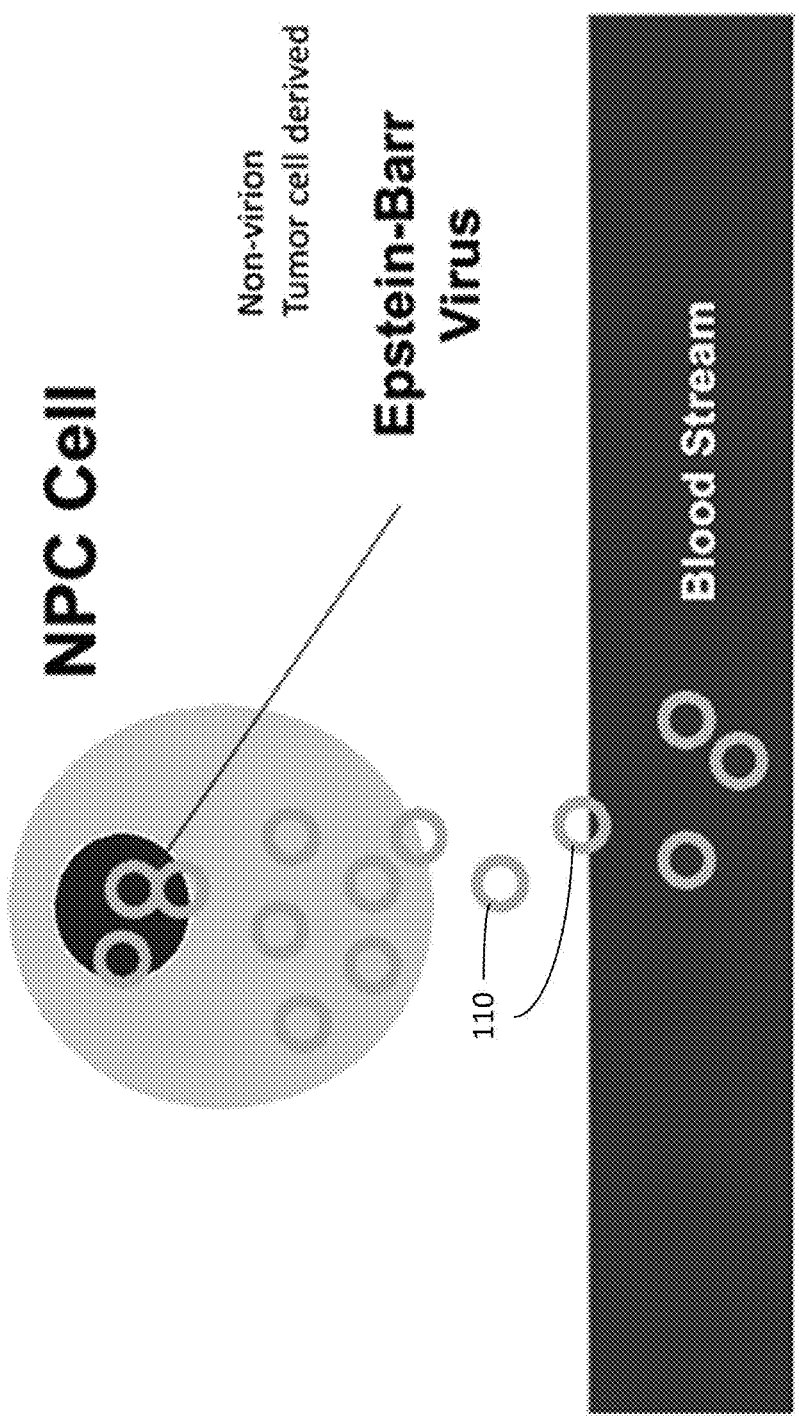
FIG. 1 depicts a schematic showing Epstein-Barr virus (EBV) DNA fragments from a nasopharyngeal cancer (NPC) cell being deposited into the bloodstream of a subject.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (host vs. virus) or to healthy cells vs.

tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" may be used to refer to a tissue from which a cell-free nucleic acid originates. In one example, viral nucleic acid fragments may be derived from blood tissue, e.g., for Epstein-Barr Virus (EBV). In another example, viral nucleic acid fragments may be derived from tumor tissue, e.g., EBV or Human papillomavirus infection (HPV).

The term "sample", "biological sample" or "patient sample" is meant to include any tissue or material derived from a living or dead subject. A biological sample may be a cell-free sample, which may include a mixture of nucleic acid molecules from the subject and potentially nucleic acid molecules from a pathogen, e.g., a virus. A biological sample generally comprises a nucleic acid (e.g., DNA or RNA) or a fragment thereof. The term "nucleic acid" may generally refer to deoxyribonucleic acid (DNA), ribonucleic acid (RNA) or any hybrid or fragment thereof. The nucleic acid in the sample may be a cell-free nucleic acid. A sample may be a liquid sample or a solid sample (e.g., a cell or tissue sample). The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). The biological sample may be treated to physically disrupt tissue or cell structure (e.g., centrifugation and/or cell lysis), thus releasing intracellular components into a solution which may further contain enzymes, buffers, salts, detergents, and the like which are used to prepare the sample for analysis.

The terms "control", "control sample", "reference", "reference sample", "normal", and "normal sample" may be interchangeably used to generally describe a sample that does not have a particular condition, or is otherwise healthy. In an example, a method as disclosed herein may be performed on a subject having a tumor, where the reference sample is a sample taken from a healthy tissue of the subject. In another example, the reference sample is a sample taken from a subject with the disease, e.g. cancer or a particular stage of cancer. A reference sample may be obtained from the subject, or from a database. The reference generally refers to a reference genome that is used to map sequence reads obtained from sequencing a sample from the subject. A reference genome generally refers to a haploid or diploid genome to which sequence reads from the biological sample and the constitutional sample can be aligned and compared. For a haploid genome, there is only one nucleotide at each locus. For a diploid genome, heterozygous loci can be identified, with such a locus having two alleles, where either allele can allow a match for alignment to the locus. A reference genome may correspond to a virus, e.g., by including one or more viral genomes.

The phrase "healthy," as used herein, generally refers to a subject possessing good health. Such a subject demonstrates an absence of any malignant or non-malignant disease. A "healthy individual" may have other diseases or conditions, unrelated to the condition being assayed, that may normally not be considered "healthy".

The terms "cancer" or "tumor" may be used interchangeably and generally refer to an abnormal mass of tissue wherein the growth of the mass surpasses and is not coordinated with the growth of normal tissue. A cancer or tumor may be defined as "benign" or "malignant" depending on the following characteristics: degree of cellular differentiation including morphology and functionality, rate of growth, local invasion, and metastasis. A "benign" tumor is generally well differentiated, has characteristically slower growth than a malignant tumor, and remains localized to the site of origin. In addition, a benign tumor does not have the capacity to infiltrate, invade, or metastasize to distant sites. A "malignant" tumor is generally poorly differentiated (anaplasia), has characteristically rapid growth accompanied by progressive infiltration, invasion, and destruction of the surrounding tissue. Furthermore, a malignant tumor has the capacity to metastasize to distant sites. "Stage" can be used to describe how advance a malignant tumor is. Early stage cancer or malignancy is associated with less tumor burden in the body, generally with less symptoms, with better prognosis, and with better treatment outcome than a late stage malignancy. Late or advanced stage cancer or malignancy is often associated with distant metastases and/or lymphatic spread.

The term "level of cancer" can generally refer to whether cancer exists (i.e., presence or absence), a stage of a cancer, a size of tumor, whether there is metastasis, the total tumor burden of the body, and/or other measure of a severity of a cancer (e.g., recurrence of cancer). The level of cancer may be a number or other indicia, such as symbols, alphabet letters, and colors. The level may be zero. The level of cancer also includes premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can mean 'screening' or can mean checking if someone, with suggestive features of cancer (e.g., symptoms or other positive tests), has cancer. A "level of pathology" can refer to level of pathology associated with a pathogen, where the level can be as described above for cancer. When the cancer is associated with a pathogen, a level of cancer can be a type of a level of pathology.

The term "fragment" (e.g., a DNA fragment), as used herein, can refer to a portion of a polynucleotide or polypeptide sequence that comprises at least 3 consecutive nucleotides. A nucleic acid fragment can retain the biological activity and/or some characteristics of the parent polypeptide. A nucleic acid fragment can be double-stranded or single-stranded, methylated or unmethylated, intact or nicked, complexed or not complexed with other macromolecules, e.g. lipid particles, proteins. In an example, nasopharyngeal cancer cells can release fragments of Epstein-Barr Virus (EBV) DNA into the blood stream of a subject, e.g., a patient. These fragments can comprise one or more BamHI-W sequence fragments, which can be used to detect the level of tumor-derived DNA in the plasma. The BamHI-W sequence fragment corresponds to a sequence that can be recognized and/or digested using the Bam-HI restriction enzyme. The BamHI-W sequence can refer to the sequence 5'-GGATCC-3'.

A tumor-derived nucleic acid can refer to any nucleic acid released from a tumor cell, including pathogen nucleic acids from pathogens in a tumor cell. For example, Epstein-Barr virus (EBV) DNA can be released from a cancer cell of a subject with nasopharyngeal carcinoma (NPC).

The term "assay" generally refers to a technique for determining a property of a nucleic acid. An assay (e.g., a first assay or a second assay) generally refers to a technique for determining the quantity of nucleic acids in a sample, genomic identity of nucleic acids in a sample, the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art may be used to detect any of the properties of nucleic acids mentioned herein. Properties of nucleic acids include a sequence, quantity, genomic identity, copy number, a methylation state at one or more nucleotide positions, a size of the nucleic acid, a mutation in the nucleic acid at one or more nucleotide positions, and the pattern of fragmentation of a nucleic acid (e.g., the nucleotide position(s) at which a nucleic acid fragments). The term "assay" may be used interchangeably with the term "method". An assay or method can have a particular sensitivity and/or specificity, and their relative usefulness as a diagnostic tool can be measured using ROC-AUC statistics.

The term "random sequencing," as used herein, generally refers to sequencing whereby the nucleic acid fragments sequenced have not been specifically identified or predetermined before the sequencing procedure. Sequence-specific primers to target specific gene loci are not required. In some embodiments, adapters are added to the end of a fragment, and the primers for sequencing attached to the adapters. Thus, any fragment can be sequenced with the same primer that attaches to a same universal adapter, and thus the sequencing can be random. Massively parallel sequencing may be performed using random sequencing.

A "sequence read" (or sequencing reads), as used herein, generally refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

The term "sequencing depth," as used herein, generally refers to the number of times a locus is covered by a sequence read aligned to the locus. The locus may be as small as a nucleotide, or as large as a chromosome arm, or as large as the entire genome. Sequencing depth can be expressed as 50×, 100×, etc., where "×" refers to the number of times a locus is covered with a sequence read. Sequencing depth can also be applied to multiple loci, or the whole genome, in which case x can refer to the mean number of times the loci or the haploid genome, or the whole genome, respectively, is sequenced. When a mean depth is quoted, the actual depth for different loci included in the dataset spans over a range of values. Ultra-deep sequencing can refer to at least 100× in sequencing depth.

The terms "size profile" and "size distribution" generally relate to the sizes of DNA fragments in a biological sample. A size profile may be a histogram that provides a distribution of an amount of DNA fragments at a variety of sizes. Various statistical parameters (also referred to as size parameters or just parameter) can distinguish one size profile to another. One parameter is the percentage of DNA fragment of a particular size or range of sizes relative to all DNA fragments or relative to DNA fragments of another size or range.

An "ending position" or "end position" (or just "end") can refer to the genomic coordinate or genomic identity or nucleotide identity of the outermost base, i.e., at the extremities, of a cell-free DNA molecule, e.g., plasma DNA molecule. The end position can correspond to either end of a DNA molecule. In this manner, if one refers to a start and end of a DNA molecule, both may correspond to an ending position. In practice, one end position is the genomic coordinate or the nucleotide identity of the outermost base on one extremity of a cell-free DNA molecule that is detected or determined by an analytical method, such as but not limited to massively parallel sequencing or next-generation sequencing, single molecule sequencing, double- or single-stranded DNA sequencing library preparation protocols, polymerase chain reaction (PCR), or microarray. Such in vitro techniques may alter the true in vivo physical end(s) of the cell-free DNA molecules. Thus, each detectable end may represent the biologically true end or the end is one or more nucleotides inwards or one or more nucleotides extended from the original end of the molecule e.g., 5' blunting and 3' filling of overhangs of non-blunt-ended double stranded DNA molecules by the Klenow fragment. The genomic identity or genomic coordinate of the end position may be derived from results of alignment of sequence reads to a human reference genome, e.g., hg19. It may be derived from a catalog of indices or codes that represent the original coordinates of the human genome. It may refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment). The term "genomic position" is not limited to nucleotide positions within a genome (e.g., the haploid set of chromosomes in a gamete or microorganism, or in each cell of a multicellular organism).

A "preferred end" (or "recurrent ending position") may refer to an end that is more highly represented or prevalent (e.g., as measured by a rate) in a biological sample having a physiological or pathological (disease) state (e.g., cancer) than a biological sample not having such a state or than at different time points or stages of the same pathological or physiological state, e.g., before or after treatment. A preferred end therefore has an increased likelihood or probability for being detected in the relevant physiological or pathological state relative to other states. The increased probability can be compared between the pathological state and a non-pathological state, for example in patients with and without a cancer and quantified as likelihood ratio or relative probability. The likelihood ratio can be determined based on the probability of detecting at least a threshold number of preferred ends in the tested sample or based on the probability of detecting the preferred ends in patients with such a condition than patients without such a condition. Examples for the thresholds of likelihood ratios include but not limited to 1.1, 1.2, 1.3, 1.4, 1.5, 1.6, 1.8, 2.0, 2.5, 3.0, 3.5, 4.0, 4.5, 5, 6, 8, 10, 20, 40, 60, 80 and 100. Such likelihood ratios can be measured by comparing relative abundance values of samples with and without the relevant state. Because the probability of detecting a preferred end in a relevant physiological or disease state is higher, such preferred ending positions may be seen in more than one individual with that same physiological or disease state. With the increased probability, more than one cell-free DNA molecule can be detected as ending on a same preferred ending position, even when the number of cell-free DNA molecules analyzed is far less than the size of the genome. Thus, the preferred or recurrent ending positions are also referred to as the "frequent ending positions." A quantitative threshold generally requires that ends be detected at least multiple times (e.g., 3, 4, 5, 6, 7, 8, 9, 10, 15, 20, or 50) within the same sample or same sample aliquot to be considered as a preferred end. A relevant physiological state may include a state when a person is healthy, disease-free, or free from a disease of interest. Similarly, a "preferred ending window" corresponds to a contiguous set of preferred ending positions.

A "relative abundance" may generally refer to a ratio of a first amount of nucleic acid fragments having a particular characteristic (e.g., a specified length, ending at one or more specified coordinates/ending positions, or aligning to a particular region of the genome) to a second amount nucleic acid fragments having a particular characteristic (e.g., a specified length, ending at one or more specified coordinates/ending positions, or aligning to a particular region of the genome). In one example, relative abundance may refer to a ratio of the number of DNA fragments ending at a first set of genomic positions to the number of DNA fragments ending at a second set of genomic positions. In some aspects, "relative abundance" may correspond to a type of separation value that relates an amount (one value) of cell-free DNA molecules ending within one window of genomic positions to an amount (other value) of cell-free DNA molecules ending within another window of genomic positions. The two windows may overlap, but may be of different sizes. In other implementations, the two windows may not overlap. Further, the windows may be of a width of one nucleotide, and therefore be equivalent to one genomic position.

A "rate" of nucleic acid molecules (e.g., DNA or RNA) ending on a position relates to how frequently a nucleic acid molecule ends on the position. For example, the rate may be based on a number of nucleic acid molecules that end on the position normalized against a number of nucleic acid molecules analyzed. As another example, the rate may be based on a number of nucleic acid molecules that end on the position normalized against a number of nucleic acid molecules that end on a different position. As yet another example, the rate may be based on a number of nucleic acid molecules from a first sample that end on the position normalized against a number of nucleic acid molecules from a second sample (e.g., a reference sample) that end on the position. As yet another example, the rate may be based on a number of nucleic acid molecules from a first sample that end on a first set of positions (e.g., genomic positions within one or more first windows) normalized against a number of nucleic acid molecules from a second sample (e.g., a reference sample) that end on a second set of positions.

The term "classification" can refer to any number(s) or other characters(s) that are associated with a particular property of a sample. For example, a "+" symbol (or the word "positive") could signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts.

The term "true positive" (TP) can refer to subjects having a condition. True positive generally refers to subjects that have a tumor, a cancer, a pre-cancerous condition (e.g., a precancerous lesion), a localized or a metastasized cancer, or a non-malignant disease. True positive generally refers to subjects having a condition, and are identified as having the condition by an assay or method of the present disclosure.

The term "true negative" (TN) can refer to subjects that do not have a condition or do not have a detectable condition. True negative generally refers to subjects that do not have a disease or a detectable disease, such as a tumor, a cancer, a pre-cancerous condition (e.g., a precancerous lesion), a localized or a metastasized cancer, a non-malignant disease, or subjects that are otherwise healthy. True negative generally refers to subjects that do not have a condition or do not have a detectable condition, or are identified as not having the condition by an assay or method of the present disclosure.

The term "false positive" (FP) can refer to subjects not having a condition. False positive generally refers to subjects not having a tumor, a cancer, a pre-cancerous condition (e.g., a precancerous lesion), a localized or a metastasized cancer, a non-malignant disease, or are otherwise healthy. The term false positive generally refers to subjects not having a condition, but are identified as having the condition by an assay or method of the present disclosure.

The term "false negative" (FN) can refer to subjects that have a condition. False negative generally refers to subjects that have a tumor, a cancer, a pre-cancerous condition (e.g., a precancerous lesion), a localized or a metastasized cancer, or a non-malignant disease. The term false negative generally refers to subjects that have a condition, but are identified as not having the condition by an assay or method of the present disclosure.

The terms "sensitivity" or "true positive rate" (TPR) can refer to the number of true positives divided by the sum of the number of true positives and false negatives. Sensitivity may characterize the ability of an assay or method to correctly identify a proportion of the population that truly has a condition. For example, sensitivity may characterize the ability of a method to correctly identify the number of subjects within a population having cancer. In another example, sensitivity may characterize the ability of a method to correctly identify one or more markers indicative of cancer.

The terms "specificity" or "true negative rate" (TNR) can refer to the number of true negatives divided by the sum of the number of true negatives and false positives. Specificity may characterize the ability of an assay or method to correctly identify a proportion of the population that truly does not have a condition. For example, specificity may characterize the ability of a method to correctly identify the number of subjects within a population not having cancer. In another example, specificity may characterize the ability of a method to correctly identify one or more markers indicative of cancer.

The term "ROC" or "ROC curve" can refer to the receiver operator characteristic curve. The ROC curve can be a graphical representation of the performance of a binary classifier system. For any given method, an ROC curve may be generated by plotting the sensitivity against the specificity at various threshold settings. The sensitivity and specificity of a method for detecting the presence of a tumor in a subject may be determined at various concentrations of tumor-derived nucleic acid in the plasma sample of the subject. Furthermore, provided at least one of the three parameters (e.g., sensitivity, specificity, and the threshold setting), and ROC curve may determine the value or expected value for any unknown parameter. The unknown parameter may be determined using a curve fitted to the ROC curve. The term "AUC" or "ROC-AUC" generally refers to the area under a receiver operator characteristic curve. This metric can provide a measure of diagnostic utility of a method, taking into account both the sensitivity and specificity of the method. Generally, ROC-AUC ranges from 0.5 to 1.0, where a value closer to 0.5 indicates the method has limited diagnostic utility (e.g., lower sensitivity and/or specificity) and a value closer to 1.0 indicates the method has greater diagnostic utility (e.g., higher sensitivity and/or specificity). See, e.g., Pepe et al, "Limitations of the Odds Ratio in Gauging the Performance of a Diagnostic, Prognostic, or Screening Marker," Am. J. Epidemiol 2004, 159 (9): 882-890, which is entirely incorporated herein by reference. Additional approaches for characterizing diagnostic utility using likelihood functions, odds ratios, information theory, predictive values, calibration (including goodness-of-fit), and reclassification measurements are summarized according to Cook, "Use and Misuse of the Receiver Operating Characteristic Curve in Risk Prediction," Circulation 2007, 115: 928-935, which is entirely incorporated herein by reference.

"Negative predictive value" or "NPV" may be calculated by TN/(TN+FN) or the true negative fraction of all negative test results. Negative predictive value is inherently impacted by the prevalence of a condition in a population and pre-test probability of the population intended to be tested. "Positive predictive value" or "PPV" may be calculated by TP/(TP+FP) or the true positive fraction of all positive test results. It is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which is entirely incorporated herein by reference.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

DETAILED DESCRIPTION

Circulating cell-free DNA analysis has been shown to be of value in noninvasive monitoring of cancer treatment response (1-3) and for the detection of cancer recurrence (4-6). To extend the application of circulating cell-free DNA to cancer screening, researchers have to face the challenge of developing assays that are sufficiently sensitive for detecting the expectedly low concentrations of circulating tumor DNA in early stages of cancer.

Extending beyond studies on plasma DNA molecules of human origin, this disclosure proposes that there might be differences in the molecular characteristics between viral DNA molecules present in the plasma of persons with or without cancer, e.g., between Epstein-Barr virus (EBV) and nasopharyngeal cancer (NPC). Differences among plasma viral DNA molecules, if exist, would allow one to better differentiate NPC patients, thus reducing the false positive rate and enhancing the positive predictive value (PPV) of a plasma EBV DNA-based screening test.

Circulating cell-free EBV DNA is a blood-based biomarker for EBV-related malignancies (8-10). Its clinical utility in prognostication and surveillance of recurrence of NPC has been validated (11, 12) using real-time PCR for late stage cases of NPC. But, while such techniques have identified late stage cases of NPC, current techniques have low PPV for screening for early stage cases of NPC. The accurate screening of early stage cancer provides the most benefit for treatment, and thus it is desirable to increase the accuracy for such early stage screening.

In this disclosure, we describe differentiating NPC subjects from non-NPC subjects with detectable EBV DNA based on the analysis of properties of EBV DNA in a sample (e.g., a cell-free sample, such as plasma or serum). Such properties can include a proportion of sequence reads of nucleic acids from the sample that align to a reference NPC genome; a size distribution of nucleic acids from the reference NPC genome (e.g., a proportion of nucleic acid fragments that are below a size threshold); and fragmentation patterns of the nucleic acid fragments (e.g., an amount of nucleic acid fragments that end on certain positions relative to an amount of NPC fragments that end on other positions). Embodiments can also be applied for the analysis of other types of cancers associated with viral infection.

To demonstrate the use of plasma EBV DNA for NPC screening, we conducted a large-scale prospective screening study which involved 20,174 asymptomatic participants identified from the community. A significantly higher proportion of early-stage NPC cases (stage I or II) were identified in the screened cohort than in a historical unscreened cohort. The NPC cases identified by screening had longer progression-free survival. These promising results, together with the noninvasive nature of a blood-based test, would potentially contribute to widespread use of plasma EBV DNA as a screening tool for NPC.

I. VIRAL DNA IN CELL-FREE SAMPLES

Pathogens can invade a cell. For example, viruses such as EBV can exist within cells. These pathogens can release their nucleic acids (e.g., DNA or RNA). The nucleic acids are often released from cells in which the pathogen has caused some pathology, e.g., cancer.

FIG. 1 shows an NPC cell that includes EBV. An NPC cell may include many copies of the virus, e.g., 50. FIG. 1 shows nucleic acid fragments 110 of the EBV genome being released (e.g., when the cell dies) into the blood stream. Although nucleic acid fragments 110 are depicted as circular (e.g., as the EBV genome is circular), the fragments would just be part of the EBV genome. Thus, an NPC cell can deposit fragments of the EBV DNA into the bloodstream of a subject. This tumor marker can be useful for the monitoring (Lo et al. Cancer Res 1999; 59: 5452-5455) and prognostication (Lo et al. Cancer Res 2000; 60: 6878-6881) of NPC.

A. Relation of Certain Viruses to Various Cancers

Viral infections are implicated in a number of pathological conditions. For example, EBV infection is closely associated with NPC and natural killer (NK) T-cell lymphoma, Hodgkin lymphoma, gastric cancer, and infectious mononucleosis. Hepatitis B virus (HBV) infection and hepatitis C virus (HCV) infection are associated with increased risks of developing hepatocellular carcinoma (HCC). Human papillomavirus infection (HPV) are associated with increased risks of developing cervical cancer (CC) and head and neck squamous cell carcinoma (HNSCC).

However, not all subjects that have such an infection will get an associated cancer. The source of the plasma EBV DNA must be different in persons without NPC. Unlike the persistent release of EBV DNA into the circulation from NPC cells, the source of EBV DNA only contributes such DNA transiently in the persons without NPC.

B. Detecting Viral DNA in Cell-Free Samples

Embodiments can provide methods for detecting and differentiating different conditions associated with viral infections by analyzing the levels and molecular features of circulating viral DNA. This may advantageously provide for the detection or screening of various pathological conditions using a cell-free sample from a subject, in some cases even when the subject is not displaying a given pathological condition. This may also enable monitoring of a progression or regression of the given pathological condition with time, in some cases during or following treatment. As examples, the nucleic acids of the pathogen found in the sample (e.g., plasma or serum) may be: (1) released from tumor tissues; (2) released from a non-cancer cell, e.g. rest B cells carrying EBV; and (3) contained in a virion.

The pathogenesis of NPC is closely associated with EBV infection. In endemic areas of NPC, e.g. South China, almost all NPC tumor tissues harbor EBV genomes. In this regard, plasma EBV DNA has been established as a biomarker for NPC (Lo et al. Cancer Res 1999; 59:1188-91). It has been shown that plasma EBV DNA is useful for detecting residual disease in NPC subjects after curative-intent treatment (Lo et al. Cancer Res 1999; 59:5452-5 and Chan et al. J Natl Cancer Inst 2002; 94:1614-9). The plasma EBV DNA in NPC subjects has been shown to be short DNA fragments of less than 200 bp and is thus unlikely to have derived from intact virion particles (Chan et al. Cancer Res 2003, 63:2028-32).

1. qPCR Assay for Late Stage

A real-time quantitative PCR assay can detect late stage NPC using specific regions of the EBV genome, specifically two regions of the EBV genome, the BamHI-W and the EBNA-1 regions. There can be about six to twelve repeats of the BamHI-W fragments in each EBV genome and there can be approximately 50 EBV genomes in each NPC tumor cell (Longnecker et al. Fields Virology, 5th Edition, Chapter 61 "Epstein-Barr virus"; Tierney et al. J Virol. 2011; 85: 12362-12375). In other words, there can be on the order of 300-600 (e.g., about 500) copies of the PCR target in each NPC tumor cell.

Figure 2:
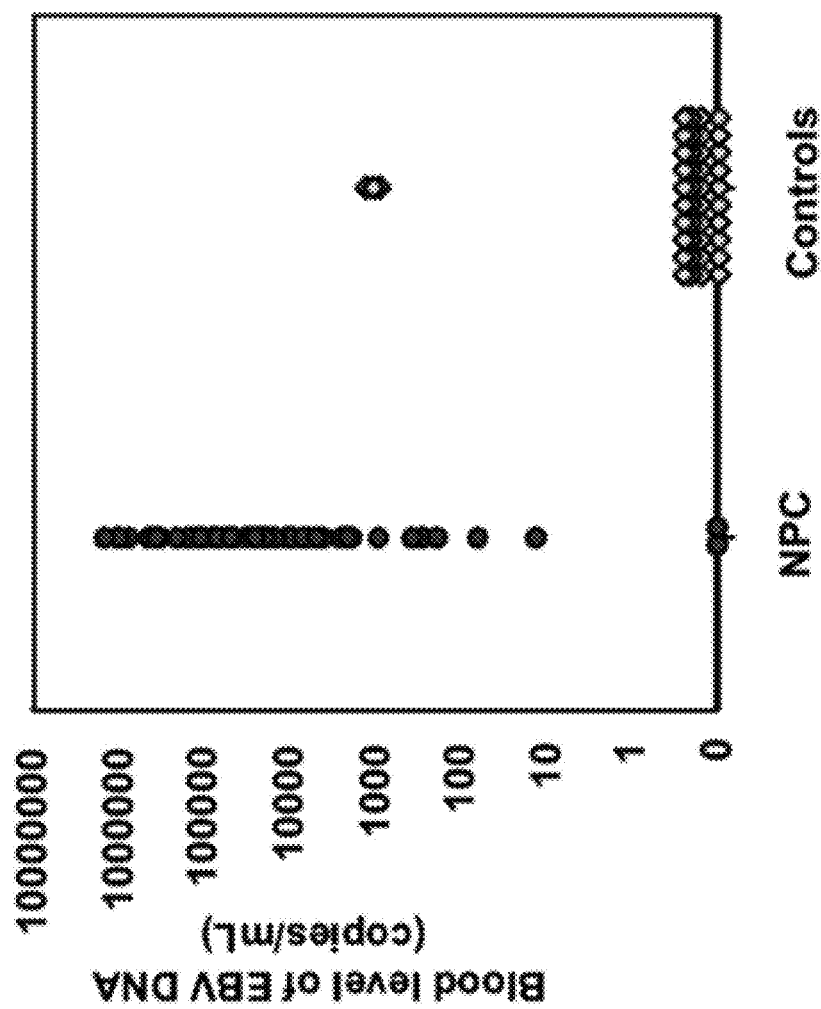
FIG. 2 depicts the concentration of plasma EBV DNA (copies/mL of plasma) in subjects with NPC and control subjects.

FIG. 2 shows a comparison of plasma cell-free EBV DNA in NPC and control subjects. The categories (NPC and control subjects) are plotted on the X axis. The Y axis denotes the concentration of cell-free EBV DNA (copies of EBV DNA/ml of plasma) detected by the BamHI-W region PCR system. Similar results were obtained using the EBNA-1 PCR that showed a strong correlation with the BamHI-W region PCR data (Spearman rank order correlation, correlation coefficient 5 0.918; P, 0.0005).

As shown in FIG. 2, cell-free EBV DNA was detectable in the plasma of 96% (55 of 57) of nasopharyngeal carcinoma (NPC) patients (median concentration, 21058 copies/ml) and 7% (3 of 43) of controls (median concentration, 0 copies/ml).

In a further analysis, Table 1 shows the number of different types of samples analyzed. In the initial analysis (cohort 1), six subjects presenting with symptoms compatible with NPC, including neck lumps, hearing loss and epistaxis were recruited from the ear-nose and throat (ENT) clinic. The NPC subjects in cohort 1 have advanced disease (late stage) than those examined in other cohorts that did not present with symptoms. Historical data from the Hong Kong Cancer Registry shows that 80% of individuals presenting with symptoms and later confirmed to have NPC had advanced stage NPC at the time of presentation for medical care. We determined if the concentration of plasma EBV DNA determined by real-time PCR and massively parallel sequencing would be useful for differentiating NPC subjects and those with false-positive plasma EBV DNA without a cancer.

TABLE 1

| Type of samples | Number of samples |
|---|---|
| Non-NPC subjects with detectable plasma EBV DNA at enrollment to the study but undetectable plasma EBV DNA approximately four weeks later. For these subjects, the samples collected at enrollment were analyzed. These subjects are denoted as "transiently positive". | 5 |
| Non-NPC subjects with persistently detectable plasma EBV DNA at enrollment and approximately four weeks later. For these subjects, the samples collected at enrollment were analyzed. These subjects are denoted as "persistently positive". | 9 |
| NPC subjects | 6 |
| EBV-positive lymphoma subjects (two with NK T-cell lymphoma and one with Hodgkin lymphoma) | 3 |
| Subject with infectious mononucleosis | 1 |

Figure 3B:
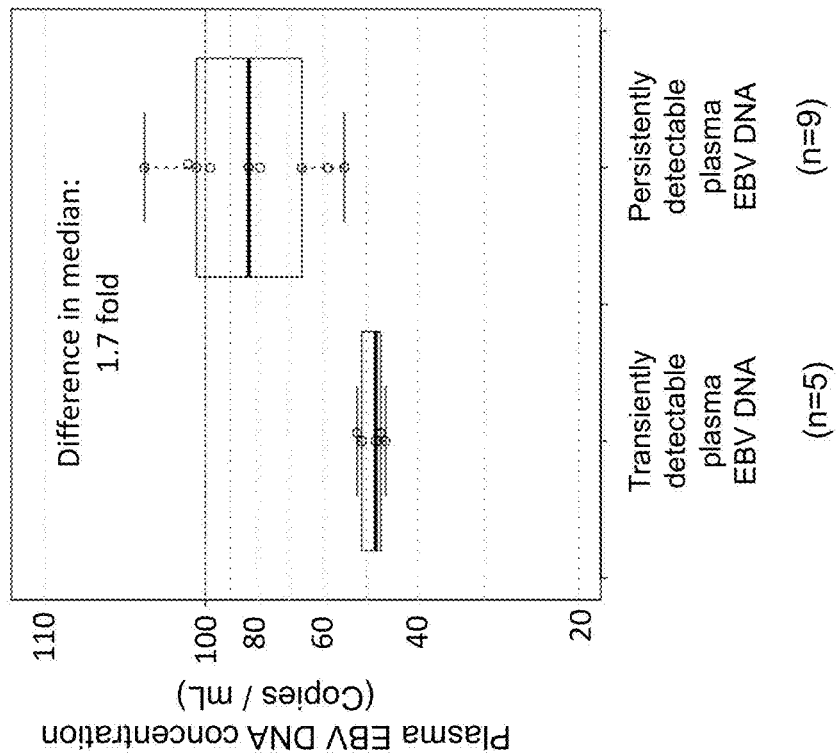
FIGS. 3A and 3B show plasma EBV DNA concentrations measured by real-time PCR for different groups of subjects.
Figure 3A:
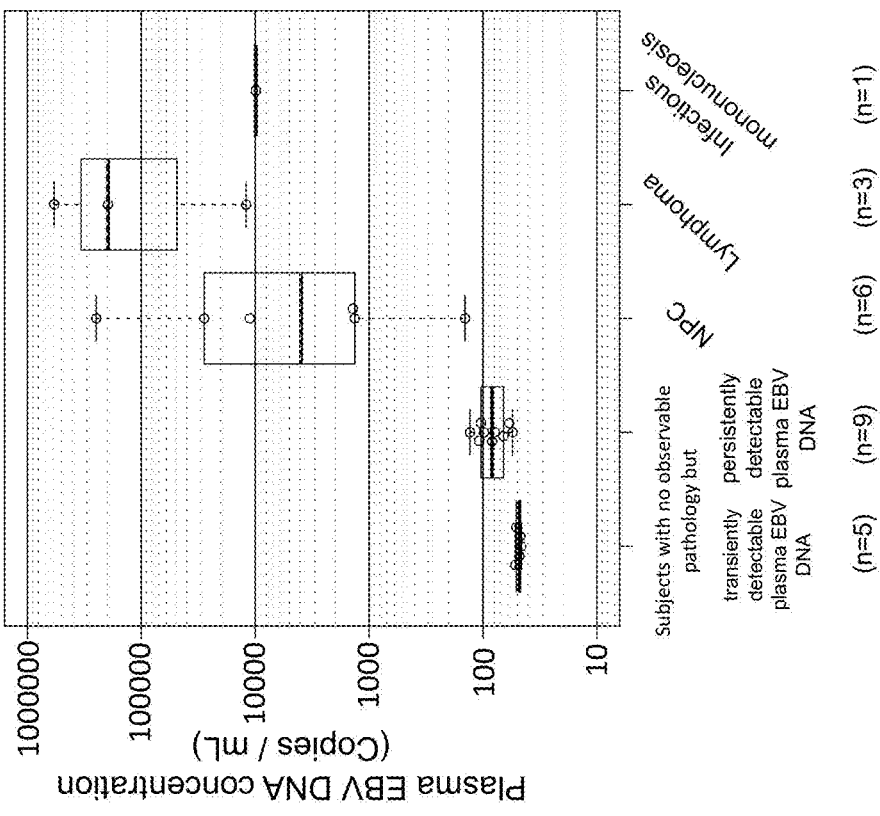

FIGS. 3A and 3B show plasma EBV DNA concentrations measured by real-time PCR for different groups of subjects. As shown in FIG. 3A, plasma EBV DNA concentrations were higher in subjects with NPC, lymphoma, and infectious mononucleosis compared with those with detectable plasma EBV DNA, but without any observable pathology. As shown in FIG. 3B, for those subjects with detectable plasma EBV DNA at enrollment but without any observable pathology, the plasma EBV DNA concentration measured at enrollment was higher in the subjects with persistently positive results compared with those who would become negative in the follow-up test (i.e. with transiently detectable plasma EBV DNA) (p=0.002, Mann-Whitney test).

2. qPCR Results for Early Stage

Figure 4:
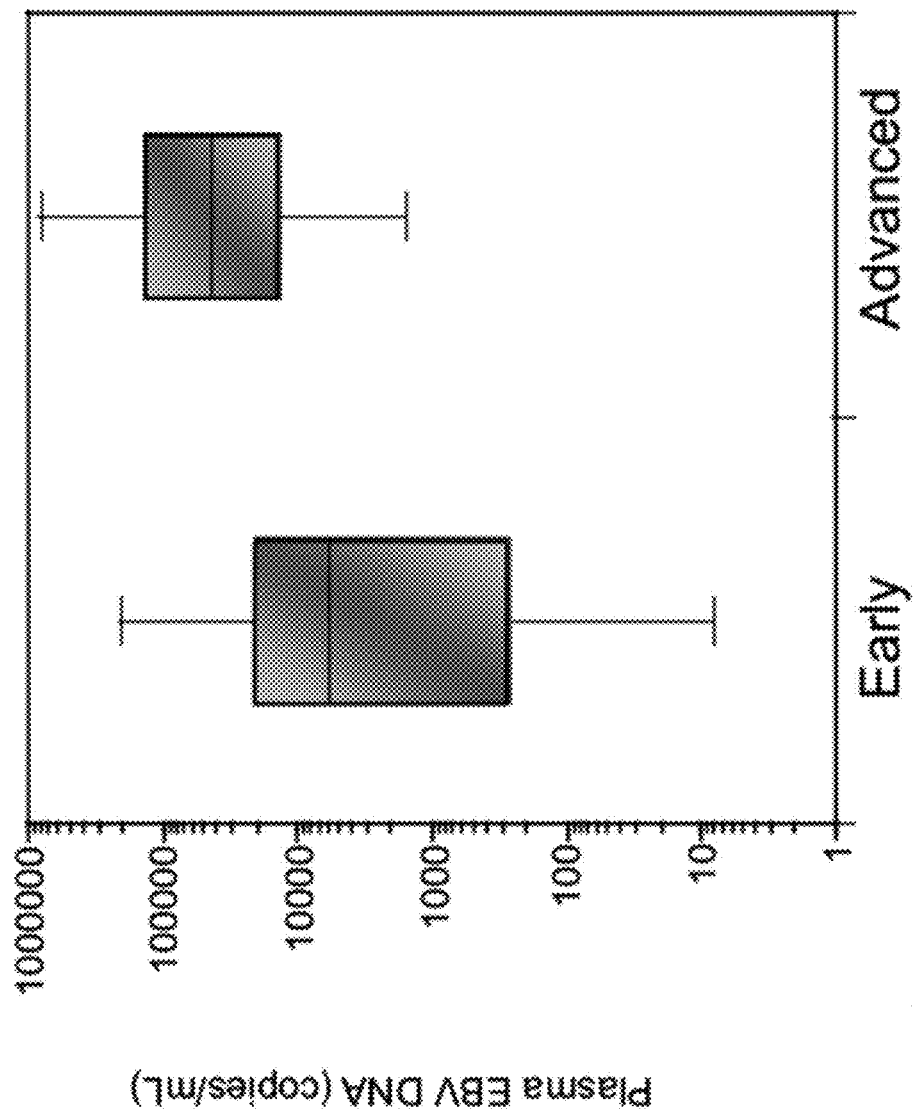
FIG. 4 depicts the concentration of plasma EBV DNA (copies/mL of plasma) in subjects with early stage NPC and advanced stage NPC.

FIG. 4 depicts the concentration of plasma EBV DNA (copies/mL of plasma) in subjects with early stage NPC and advanced stage NPC. As shown in FIG. 4, this test plasma cell-free EBV DNA levels in advanced NPC cases (median, 47,047 copies/ml; interquartile range, 17,314-133,766 copies/ml) were significantly higher than those in early-stage NPC cases (median, 5,918 copies/ml; interquartile range, 279-20,452 copies/ml; Mann-Whitney rank-sum test, P<0.001).

As mentioned herein, the detection of late stage NPC is not as useful as an early stage detection. The utility of a plasma EBV DNA analysis using real-time PCR for BamHI-W fragments was investigated for the detection of early NPC in asymptomatic subjects. (Chan et al. Cancer 2013; 119:1838-1844). In a population study with 1,318 participants, plasma EBV DNA levels were measured to investigate whether EBV DNA copy number can be useful for NPC surveillance. 69 participants (5.2%) had detectable levels of plasma EBV DNA, of 3 participants ultimately were clinically diagnosed, using nasal endoscopy and magnetic resonance imaging, as having NPC. Thus, the positive predictive value (PPV) of a single plasma EBV DNA test in this study is about 4%, calculated as the number of patients truly having NPC (n=3) divided by the sum of number of patients truly having NPC and the number of patients falsely identified as having NPC (n=66).

A larger study of 20,174 asymptomatic Chinese males aged between 40 to 62 years was performed. Out of the recruited 20,174, there were 1,112 subjects (5.5%) who had detectable plasma EBV DNA from baseline PCR tests. Among them, 34 subjects were later confirmed to have NPC. For the remaining 1,078 non-cancer subjects, 803 subjects had 'transiently positive' plasma EBV DNA results (i.e., positive at baseline but negative at follow-up) and 275 had 'persistently positive' plasma EBV DNA results (i.e., positive at both baseline and follow-up). A validation analysis was first performed with a subset of the data.

Figure 5:
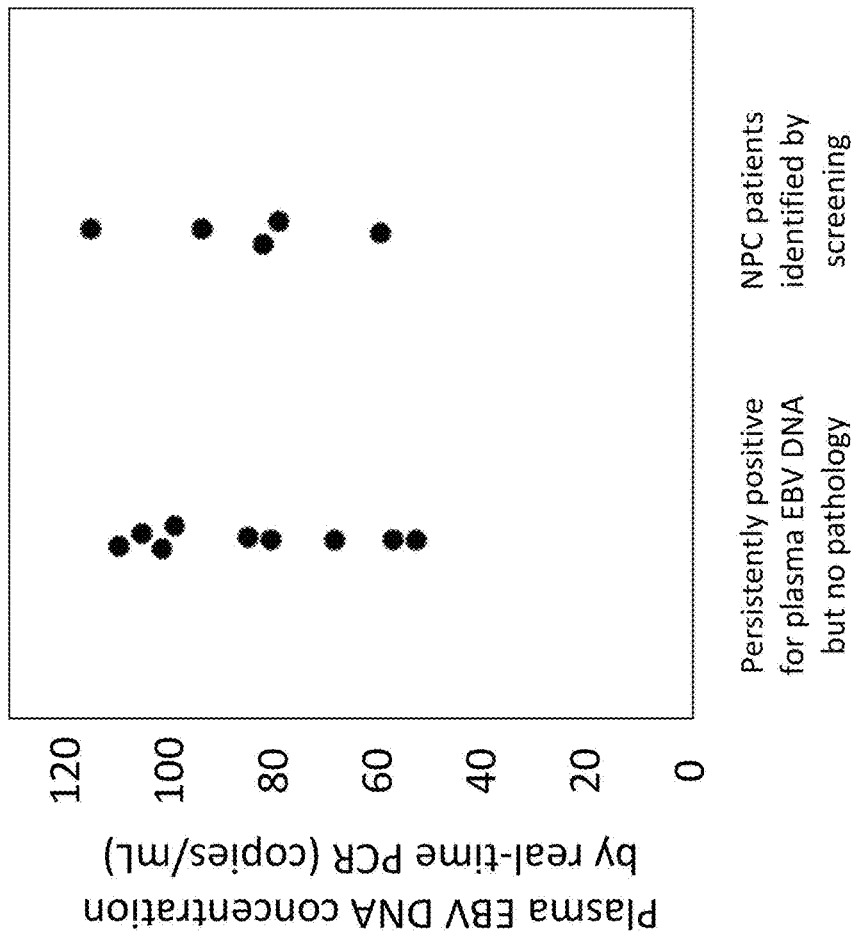
FIG. 5 shows plasma EBV DNA concentrations measured by real-time PCR for (left) subjects persistently positive for plasma EBV DNA but having no observable pathology, and (right) early-stage NPC patients identified by screening, as part of a validation analysis.

FIG. 5 shows plasma EBV DNA concentrations measured by real-time PCR for (left) subjects persistently positive for plasma EBV DNA but having no observable pathology, and (right) early-stage NPC patients identified by screening, as part of a validation analysis. Five of the 34 NPC subjects who were identified through the screening of 20,174 asymptomatic subjects were included in this validation analysis. These 5 subjects were asymptomatic when they joined the study. The plasma samples of these 5 subjects in cohort 2 were persistently positive for EBV DNA, and NPC was subsequently confirmed by endoscopy and MRI. These 5 asymptomatic NPC cases were of early stage unlike the 6 NPC subjects in cohort 1 who presented to ENT clinics with symptoms and were diagnosed with advanced stage NPC.

Figure 6:
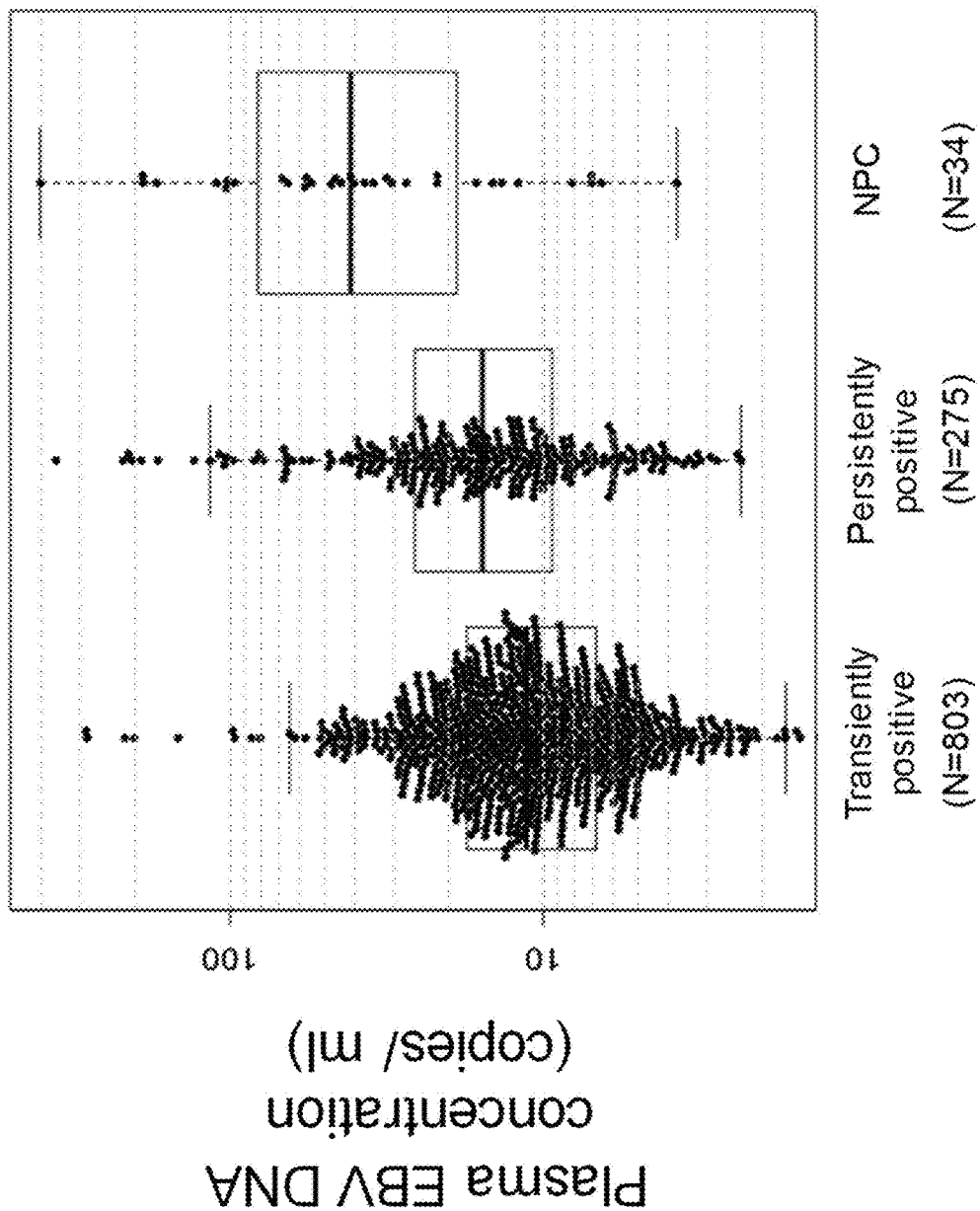
FIG. 6 shows plasma EBV DNA concentrations (copies/milliliter) measured by real-time PCR in subjects that are transiently positive or persistently positive for plasma EBV DNA (left or middle, respectively) but have no observable pathology, and subjects identified as having NPC.

FIG. 6 shows a box and whiskers plot of the concentration of EBV DNA fragments (copies per milliliter) from the plasma of subjects that are transiently positive (n=803) or persistently positive (n=275) for plasma EBV DNA (left or middle, respectively) but have no observable pathology, and subjects identified as having NPC (n=34). FIG. 6 shows results for all of the subjects of the 1,112 subjects who had detectable plasma EBV DNA from baseline PCR tests. The concentration of EBV DNA fragments (copies per milliliter) was measured by real-time PCR analysis.

Plasma EBV DNA results were expressed as 'positive' or 'negative'. Here we reviewed the quantitative levels of the plasma EBV DNA concentrations between the groups as measured by real-time PCR (FIG. 6). The mean plasma EBV DNA concentration of the NPC group (942 copies/mL; interquartile range (IQR), 18 to 68 copies/mL) was significantly higher than those of the 'transiently positive' group (16 copies/mL; IQR, 7 to 18 copies/mL) and 'persistently positive' group (30 copies/mL; IQR, 9 to 26 copies/mL) (P<0.0001, Kruskal-Wallis test). However, there is much overlap in the plasma EBV DNA concentrations among the three groups (FIG. 6).

Figure 7:
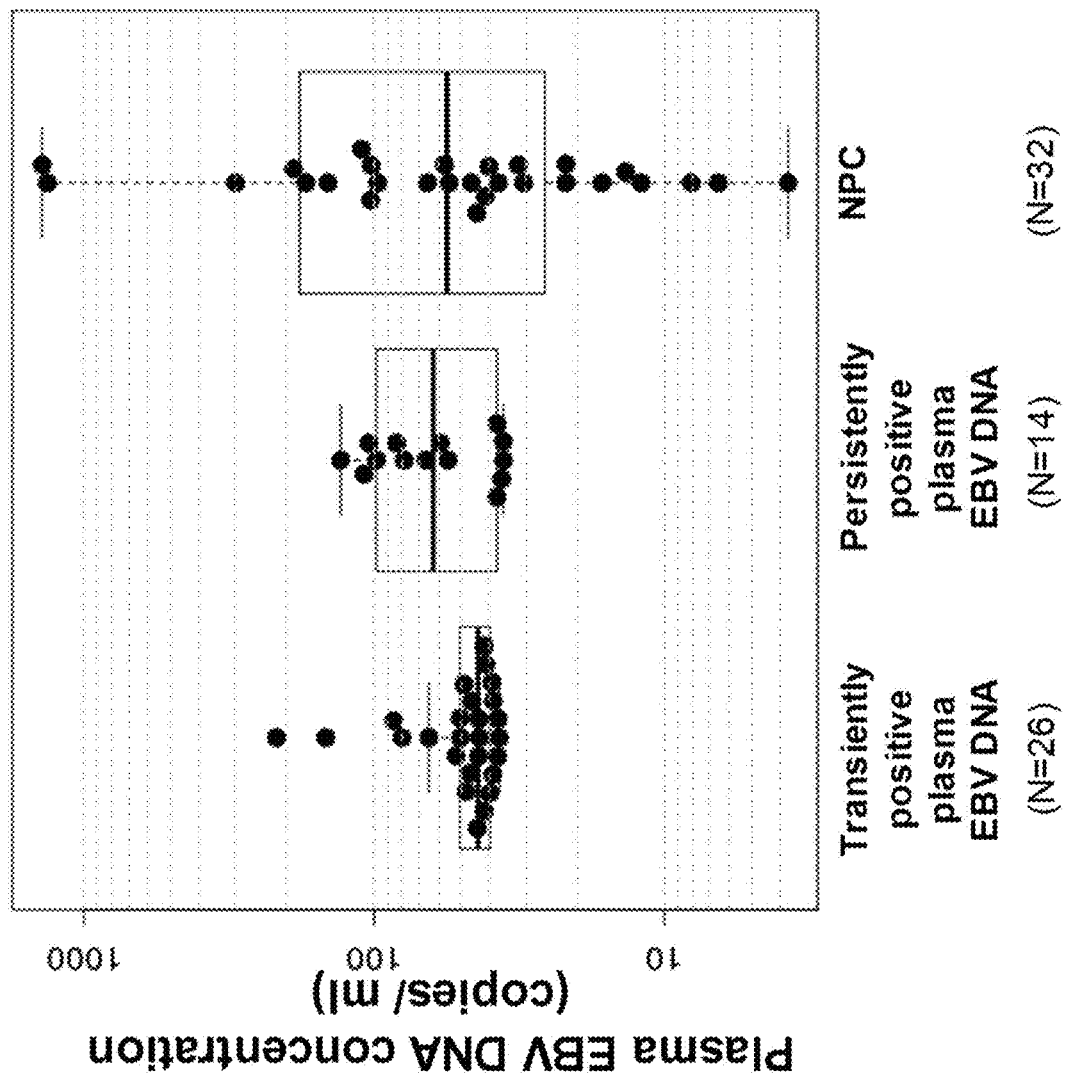
FIG. 7 shows plasma EBV DNA concentrations (copies/milliliter) measured by real-time PCR in subjects that are transiently positive or persistently positive for plasma EBV DNA (left or middle, respectively) but have no observable pathology, and subjects identified as having NPC.

FIG. 7 shows plasma EBV DNA concentrations (copies/milliliter) measured by real-time PCR in subjects that are transiently positive or persistently positive for plasma EBV DNA (left or middle, respectively) but have no observable pathology, and subjects identified as having NPC. In this cohort of 72 subjects, there was no statistically significant difference in the plasma EBV DNA concentrations measured by real-time PCR among different groups of subjects (p-value=0.19; Kruskal-Wallis test).

3. Two Assay Analysis for Early Stage

The real-time polymerase chain reaction (PCR) assay used in the prospective screening study was shown to be highly sensitive to the detection of plasma EBV DNA even from small tumors. However, there is room for improvement with respect to the test specificity. The peak age-specific incidence of NPC in Hong Kong is 40 per 100,000 persons (13) but approximately 5% of healthy population has detectable levels of EBV DNA in plasma (8, 14). The screening study yielded a positive predictive value (PPV) of 3.1% when plasma EBV DNA assessment by the real-time PCR assay was performed on one occasion per participant (7).

Given the low PPV of the real-time PCR assay, the utility of two assays at two times was investigated. For example, the above previous study showed that EBV DNA tended to be persistently detectable in the plasma of NPC subjects, but appeared transiently in the plasma of non-cancer subjects.

To investigate if plasma EBV DNA is useful for the screening of early NPC in asymptomatic individuals, we have screened 20,174 subjects without symptoms of NPC using plasma EBV DNA analysis. Subjects with detectable plasma EBV DNA were retested in approximately 4 weeks later with a follow-up plasma EBV DNA analysis. Subjects with persistently positive results on the two serial analyses were further investigated with nasal endoscopic examination and magnetic resonance imaging (MRI) of the nasopharynx. Out of the 20,174 subjects recruited, 1,112 were positive for plasma EBV DNA at enrollment. Among them, 309 were persistently positive on the follow-up test. Within the cohort of subjects who were persistently positive for EBV DNA in plasma, 34 were subsequently confirmed of having NPC after being investigated with nasal endoscopic examination and MRI.

The two time-point testing approach indeed reduced the false-positive rate from 5.4% to 1.4% with a resultant PPV of 11.0%. These results showed that the retesting of the subjects with initial positive plasma EBV DNA results could differentiate NPC subjects from those with transiently positive results and substantially reduce the proportion of subjects requiring the more invasive and costly investigations, namely endoscopy and MRI. However, the sequential testing of plasma EBV DNA requires the collection of an additional blood sample from subjects with initial positive results, which can present logistical challenges.

While the PPV of testing on two occasions fared well in comparison with population screening modalities for other cancers (16), in this study we asked if there might be strategies for further enhancing the PPV for NPC screening by plasma EBV DNA analysis, e.g., by developing new assays that can be used as a standalone test. These improvements might allow us to replace the two time-point testing protocol with one based on testing at a single time-point.

C. Initial Sequencing Analysis of Early Stage and Late Stage Cancers Using Viral DNA In some cases, an assay to screen for a condition (e.g., tumor, e.g., NPC) after an initial assay (e.g., qPCR assay) or instead of qPCR can comprise using massively parallel sequencing to assess proportion of sequence reads from a sample that map to an EBV reference genome.

To analyze the cell-free viral DNA in plasma, targeted sequencing with capture enrichment with specifically designed capture probes was used. These capture probes covered the whole EBV genome, the whole HBV genome, the whole HPV genome and multiple genomic regions in the human genome (including regions on chr1, chr2, chr3, chr5, chr8, chr15 and chr22). For each plasma sample analyzed, DNA was extracted from 4 mL plasma using the QIAamp DSP DNA blood mini kit. For each case, all extracted DNA was used for the preparation of the sequencing library using the KAPA library preparation kit. Twelve cycles of PCR amplification were performed on the sequencing library using the KAPA PCR amplification kit. The amplification products were captured using the SEQCAP-EZ kit (Nimblegen) using the custom-designed probes covering the viral and human genomic regions stated above. After target capturing, 14 cycles of PCR amplification were performed and the products were sequenced using the Illumina NextSeq platform. For each sequencing run, four to six samples with unique sample barcodes were sequenced using the paired-end mode. Each DNA fragments would be sequenced 75 nucleotides from each of the two ends. After sequencing, the sequenced reads would be mapped to an artificially combined reference sequence which consists of the whole human genome (hg19), the whole EBV genome, the whole HBV genome and the whole HPV genome. Sequenced reads mapping to unique position in the combined genomic sequence would be used for downstream analysis. The median number of uniquely mapped reads is 53 million (range: 15~141 million).

1. Late Stage

Figure 8B:
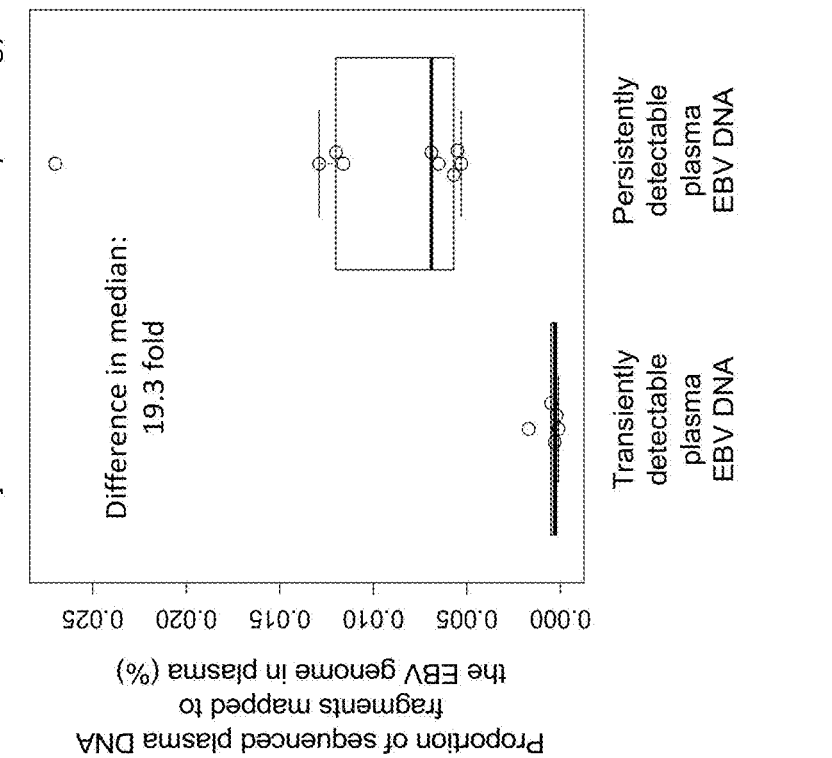
FIGS. 8A and 8B show the proportion of sequenced plasma DNA fragments mapped to the EBV genome for different groups of subjects.
Figure 8A:
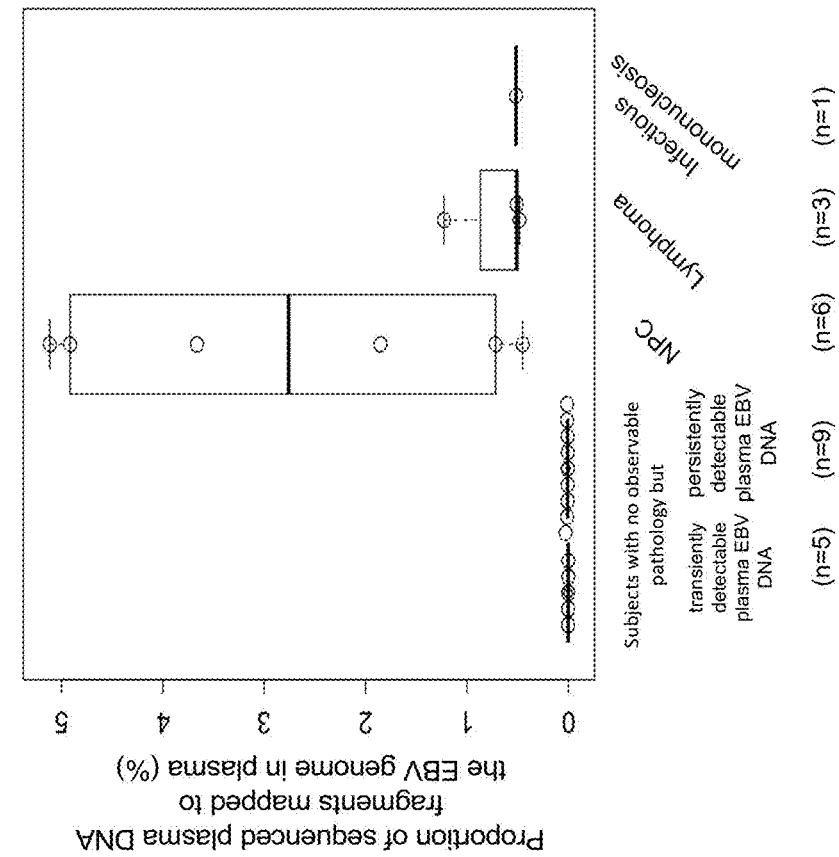

FIGS. 8A and 8B show the proportion of sequenced plasma DNA fragments mapped to the EBV genome in plasma for different groups of subjects. The subjects correspond to cohort 1, same as FIGS. 3A and 3B.

As shown in FIG. 8A, using massively parallel sequencing following target capture, the proportions of reads uniquely mapped to the EBV genome were higher in subjects with NPC, lymphoma and infectious mononucleosis compared with those with detectable plasma EBV DNA at enrollment but without any observable pathology. As shown in panel B, for those subjects with detectable plasma EBV DNA at enrollment but without any observable pathology, the proportion of reads mapped to the EBV genome measured at enrollment was higher in the subjects with persistently positive results compared with those who would become negative in the follow-up test (i.e. with transiently detectable plasma EBV DNA) (p=0.002, Mann-Whitney test). The difference between subjects with transiently and persistently positive results is greater using the measurement of the proportion of reads uniquely mapped to the EBV genome compared with the concentration of plasma EBV DNA measured using real-time PCR (19.3 folds vs 1.7 folds).

Elevated plasma EBV DNA is associated with NPC. Previous studies compared NPC cases and healthy controls who are mostly negative for plasma EBV DNA. FIGS. 3A, 3B, 8A, and 8B provide a quantitative comparison between NPC cases and the non-NPC cases who are false-positive for plasma EBV DNA. Techniques described below allow for increased accuracy in discriminating between subjects with a pathology and those without, thereby reducing false-positives. In the context of EBV DNA, the term "false-positive" can mean that the subject has detectable plasma EBV DNA but the subject does not have NPC (an example of a pathology associated with the pathogen). The presence of plasma EBV DNA is true, but the identification of the associated pathology (e.g., NPC) may be false.

2. Early Stage

Figure 9:
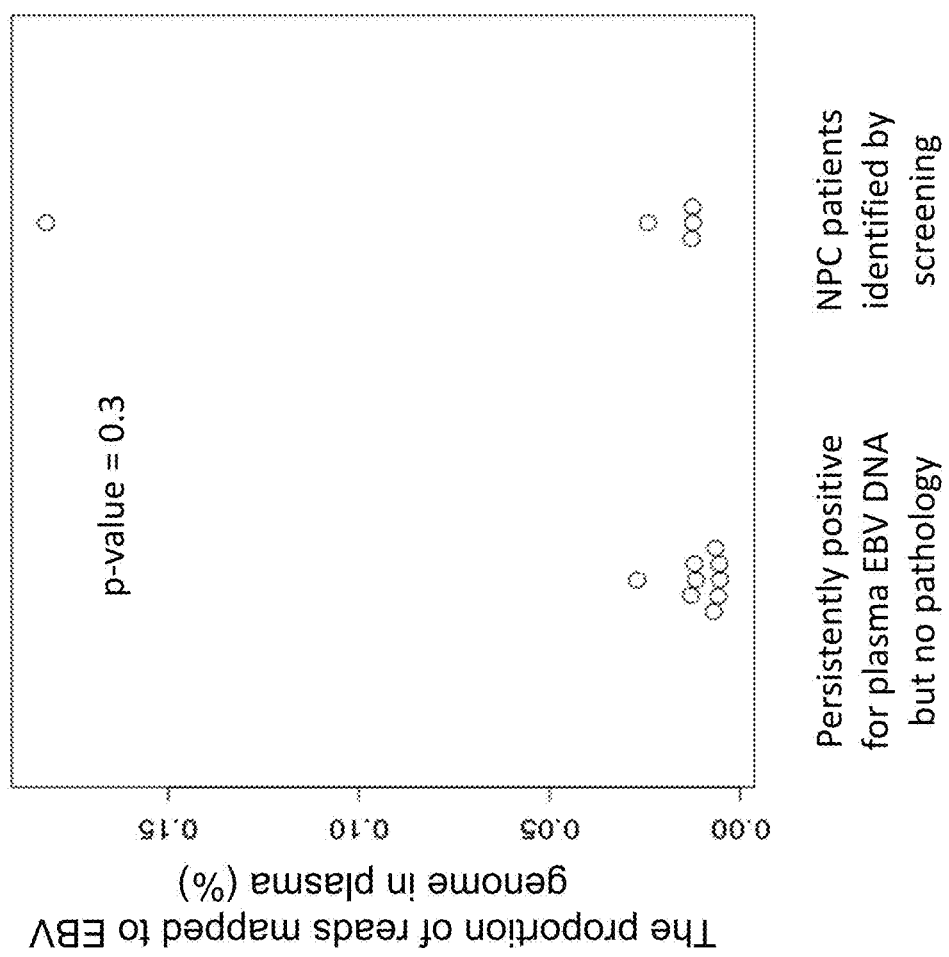
FIG. 9 shows the proportion of reads mapped to the EBV genome in plasma for (left) subjects persistently positive for plasma EBV DNA but having no observable pathology, and (right) early-stage NPC patients identified by screening.

FIG. 9 shows the proportion of reads mapped to the EBV genome in plasma for (left) subjects persistently positive for plasma EBV DNA but having no observable pathology, and (right) early stage NPC subjects. The subjects correspond to cohort 2, same as FIG. 5.

The plasma samples were sequenced after target enrichment as described above. For the five NPC subjects in cohort 2, while their plasma samples were persistently positive for EBV DNA, the EBV DNA concentration did not show significant difference compared with the 9 subjects with false-positive plasma EBV DNA results based on real-time PCR analysis (P=0.7, Mann-Whitney test). Plasma EBV DNA concentration is known to correlate with the stage of NPC. Thus, it is not unexpected that the early stage NPC subjects had lower levels of plasma EBV DNA.

The proportion of sequenced plasma DNA reads mapped to the EBV genome were not significantly different between the false-positive cases and the cohort 2 NPC cases. These initial data suggest that the approaches shown in FIGS. 5 and 9 may not work well in differentiating false-positives from the early stage NPCs. But, this was for a small sample size. Further results for sequencing are discussed in the next section.

D. Benefits of Early Stage Diagnosis

Figure 10:
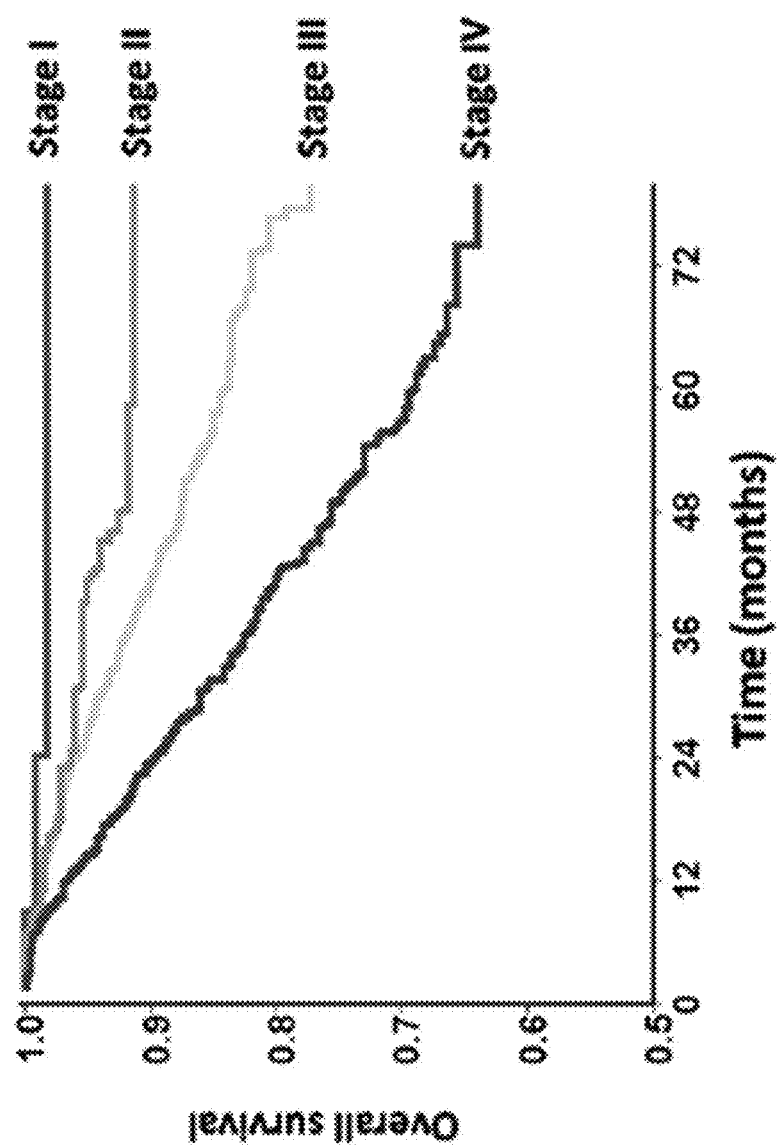
FIG. 10 depicts overall survival of subjects with various stages of NPC over time.

FIG. 10 depicts the overall survival of NPC patients at various stages of cancer, and the stage distribution of NPC in Hong Kong, respectively. In some embodiments, methods of the present disclosure can be useful in reducing the number of patients that reach a higher stage of cancer, thereby increasing their overall survival probability.

II. COUNT-BASED ANALYSIS OF VIRAL DNA

As shown in our prospective large scale screening study of 20,174 asymptomatic individuals, the presence or absence of detectable plasma EBV DNA sequences as determined by real-time PCR could detect 97.1% of the asymptomatic NPC cases with a false-positive rate of 5.4% if testing was performed on just one occasion. 71% of the asymptomatic NPC cases were confirmed by nasal endoscopy and/or magnetic resonance imaging to be of early stage (stages I and II). To further improve the PPV for detecting early stage NPC or to reduce the false-positive rate, we investigated if plasma EBV DNA quantification by real-time PCR would be of value. The real-time PCR analysis of plasma EBV DNA quantification for early stage detection of NPC (FIGS. 5-7) shows that real-time PCR provides limited ability differentiate between screened subjects that are asymptomatic and are true positives for NPC from those who are false-positives. A small sample size for targeted sequencing (FIG. 9) also suggested that a proportion of sequence reads mapped to EBV genome in plasma would likely not provide sufficient differentiation as a standalone test. However, we now have the validated PPV, sensitivity and specificity values for the sequencing quantification and show that it is effective even on its own. For count-based analysis alone, sensitivity is 97.1%, specificity is 97.4% and PPV is 6.1% (Table 4).

We used targeted sequencing to capture and measure the abundance of EBV DNA in plasma of subjects with and without NPC using the samples of the 20,174 subjects identified above. An aim is to identify plasma EBV DNA molecular characteristics that would ideally maintain the sensitivity but offer enhanced specificity in differentiating persons with NPC from the ~5% of the population who do not have NPC but have positive plasma EBV DNA (8, 14).

A. Proportion of Sequence Reads—Exploration and Validation

This large set of samples from the screening study of 20,174 subjects was used to determine whether a proportion of sequence reads from a sample could provide accurate results. An initial set of samples was used in an exploration mode to determine a model (e.g., a cutoff value) for initially identifying whether a subject has cancer. A second set of samples is used in a validation mode to determine an accuracy of the results of the model (e.g., cutoff value) determined from the discovery mode. Although this section focuses on EBV and its association to NPC, the discussion applies to other associations between a virus and a cancer.

Figure 11:
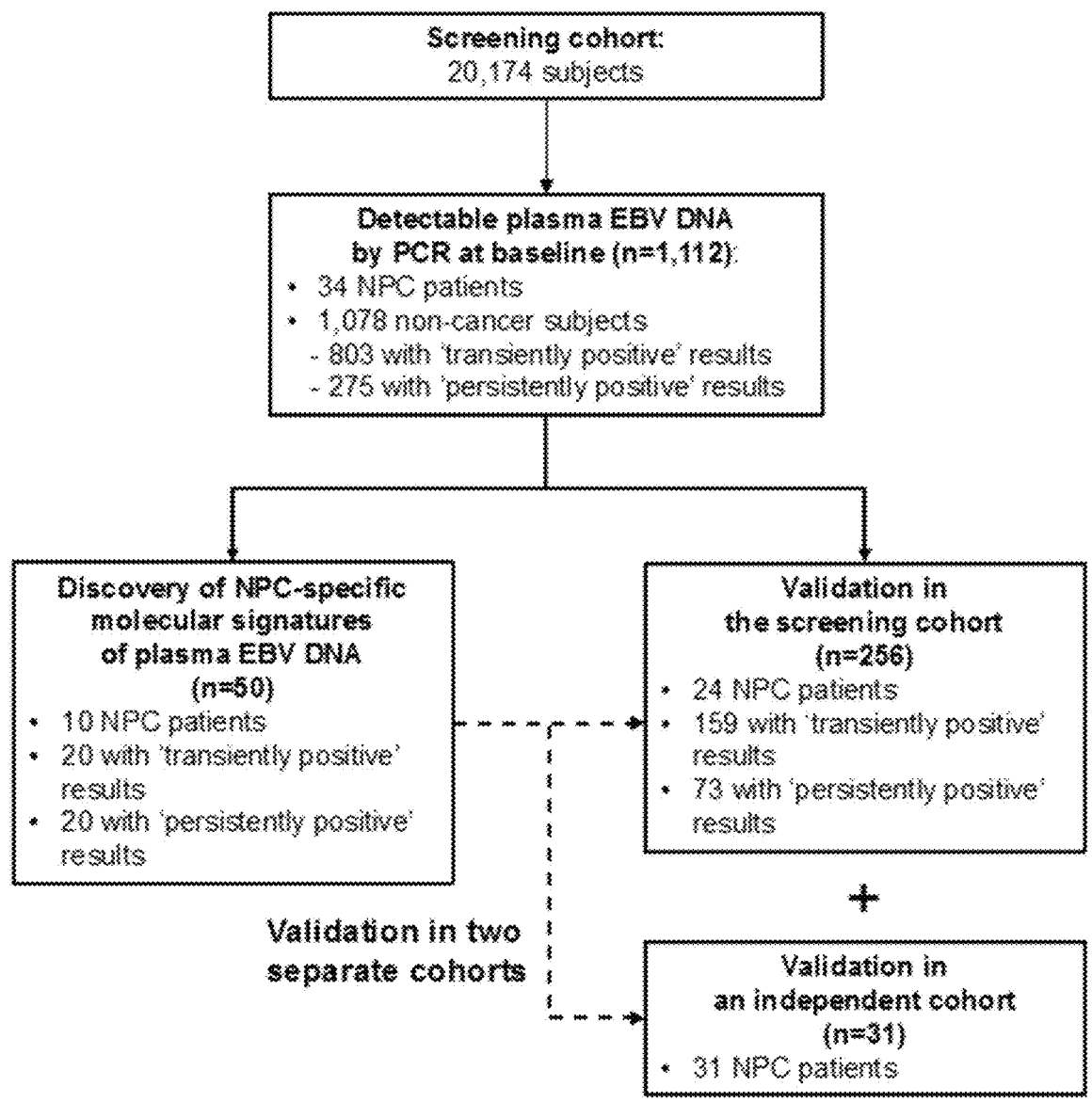
FIG. 11 illustrates the cohorts used to explore and validate use of a proportion of sequence reads that align to an EBV genome for screening NPC.

FIG. 11 illustrates the cohorts used to explore and validate use of a proportion of sequence reads that align to an EBV genome for screening NPC. In the screening study, 20,174 subjects were recruited and all received a baseline test for plasma EBV DNA by real-time PCR. 1,112 subjects had detectable plasma EBV DNA at baseline. Among them, 34 subjects were confirmed to have NPC. For the remaining 1,078 non-cancer subjects, 803 subjects had 'transiently positive' plasma EBV DNA results (i.e., positive at baseline but negative at follow-up) and 275 had 'persistently positive' plasma EBV DNA results (i.e., positive at both baseline and follow-up).

We randomly selected plasma samples of cancer and non-cancer subjects and distributed them into the exploratory and validation sample sets for the current study. Samples in the two sets did not overlap. All the 34 NPC cases from the screening study had been analyzed either as part of the exploratory or validation sample sets. An additional 31 NPC patients from an independent cohort were included in the validation sample set.

Specifically, we randomly selected 10 NPC patients and 40 non-cancer subjects (20 with transiently positive and 20 with persistently positive EBV DNA results) from the screening study to be included in the exploratory sample set. Among the 10 randomly selected NPC subjects, 5 had stage I, 2 had stage II, 2 had stage III and 1 had stage IV diseases.

In the validation sample set, we included the remaining 24 patients with NPC and randomly selected 232 non-cancer subjects. These 232 non-cancer subjects included 159 subjects with transiently positive and 73 with persistently positive plasma EBV DNA results. The ratio of the 'transiently positive' group to the 'persistently positive' group is similar to the actual ratio observed in the screening study requiring two assays. Subjects in the validation group did not overlap with those in the exploratory group.

We have also included 31 other NPC patients from an external unscreened population in the validation sample set. Among the 24 NPC patients from the screening cohort, 11 had stage I, 6 had stage II, 6 had stage III and 1 had stage IV diseases. There is no statistically significant difference in the distribution of NPC patients with early (stages I and II) and late (stages III and IV) stage disease from the screening cohort between the exploratory and validation sample sets (P=1.0, Fisher's exact test). Among the 31 NPC patients from the external cohort, there were 3 patients with stage I, 2 with stage II, 20 with stage III and 6 with stage IV diseases.

FIG. 12 is a table showing subject characteristics in the exploratory and validation sample sets. There is no statistically significant difference in the plasma EBV DNA concentrations measured by real-time PCR among the selected NPC patients in the exploratory set and those in the validation set from the screening cohort (P=0.2, t-test). There is no statistically significant difference in the plasma EBV DNA concentrations measured by real-time PCR between these selected 232 non-cancer subjects and all non-cancer subjects in the screening cohort (P=0.07, t-test).

The sequencing analyses were performed on the baseline (first time-point) sample collected at the time of enrollment into the prospective screening study. For all the samples in the exploratory and validation sample sets, the median number of mapped reads per sample was 70 million (interquartile range (IQR), 61 million to 85 million).

Plasma DNA molecules were captured by probes covering the entire EBV genome and portions of human chromosomes 1, 2, 3, 5, 8, 15 and 22, and then sequenced. Plasma EBV DNA reads refer to plasma DNA fragments that were sequenced and mapped to the EBV genome. We measured the proportion of EBV DNA reads among the total number of aligned DNA reads after removal of PCR duplicates (e.g., as determined by same start and end coordinates). Such a technique may be referred to as the count-based analysis.

Figure 13A:
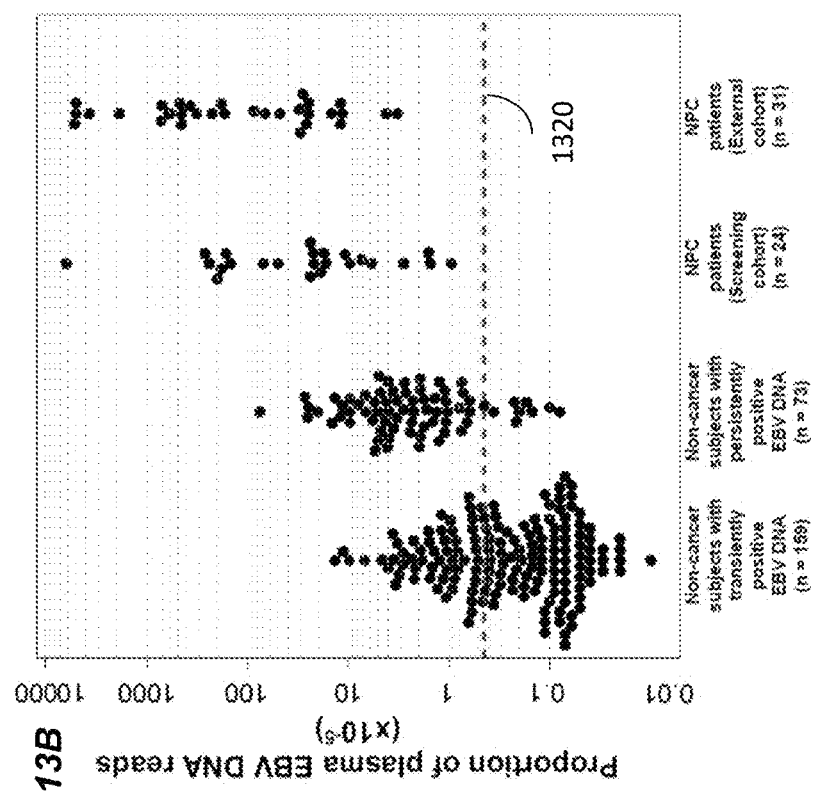
FIG. 13A shows the proportions of plasma EBV DNA reads among the total number of sequenced plasma DNA reads of the NPC patients and non-cancer subjects with transiently positive and persistently positive results in the exploratory dataset.

FIG. 13A shows the proportions of plasma EBV DNA reads among the total number of sequenced plasma DNA reads of the NPC patients and non-cancer subjects with transiently positive and persistently positive results in the exploratory dataset. Using the data derived from the exploratory sample set, cutoff values in the count-based and size-based analyses were defined to achieve 100% sensitivity for capturing all the NPC cases. In the count-based analysis, a cutoff value was defined at 3 standard deviations below the mean of the logarithmic values of portion of EBV DNA reads of these 10 NPC patients in exploratory dataset. The cutoff value of $4.5 \times 10^{-6}$ is denoted by the red dotted line 1310.

Using this cutoff value, 13 of the 20 subjects with transiently positive and 15 of the 20 subjects with persistently positive EBV DNA results passed the cutoff in the count-based analysis. Patients with NPC (median, $7.6 \times 10^{-5}$; IQR, $6.2 \times 10^{-5}$ to $1.1 \times 10^{-4}$) had a statistically significantly higher proportion of EBV DNA reads than non-cancer subjects with transiently positive (median, $6.9 \times 10^{-6}$; IQR, $1.1 \times 10^{-6}$ to $1.9 \times 10^{-5}$, P=0.0005, Kruskal-Wallis test) and persistently positive results (median, $3.0 \times 10^{-5}$; IQR, $4.5 \times 10^{-6}$ to $5.8 \times 10^{-5}$, P=0.04, Kruskal-Wallis test).

Figure 13B:
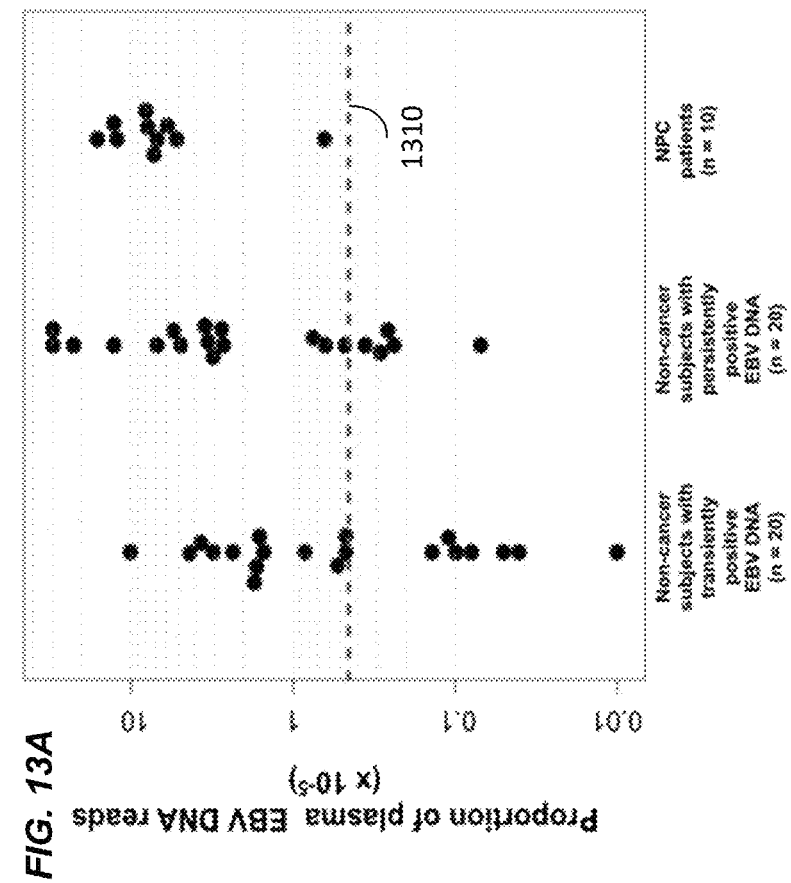
FIG. 13B shows the proportions of plasma EBV DNA reads of the NPC patients and non-cancer subjects with transiently positive and persistently positive results in the validation sample set.

FIG. 13B shows the proportions of plasma EBV DNA reads of the NPC patients and non-cancer subjects with transiently positive and persistently positive results in the validation sample set. The same cutoff value of $4.5 \times 10^{-6}$ defined in exploratory dataset is denoted by the red dotted line 1320.

We analyzed the proportions of EBV DNA reads in all the samples from the validation sample set. There were significantly higher proportions of EBV DNA reads from samples of NPC patients from both the screening cohort (median, $2.2\times10^{-4}$; IQR, $8.9\times10^{-5}$ to $1.5\times10^{-3}$) and the external cohort (median, $1.7\times10^{-3}$; IQR, $2.5\times10^{-4}$ to $5.4\times10^{-3}$) than samples of non-cancer subjects with transiently (median, $2.1\times10^{-6}$; IQR, $6.5\times10^{-7}$ to $8.0\times10^{-6}$; P<0.0001) and persistently positive results (median, $2.4\times10^{-5}$; IQR, $1.1\times10^{-5}$ to $5.0\times10^{-5}$; P=0.0044). With the cutoff value of $4.5\times10^{-6}$ defined in the exploratory dataset, all the samples of NPC patients from both cohorts could be captured and had proportions of EBV DNA reads higher than the defined cutoff value. There were 56 (out of 159) subjects with transiently positive results and 64 (out of 73) subjects with persistently positive results who passed the cutoff in the count-based analysis.

B. Further Results

The analysis above illustrates that a proportion of sequence reads in a cell-free sample that align to the EBV genome can provide a useful standalone test to screen early stages of NPC. Further results are provided for EBV, HBV, and HPV.

1. EBV

Figure 14:
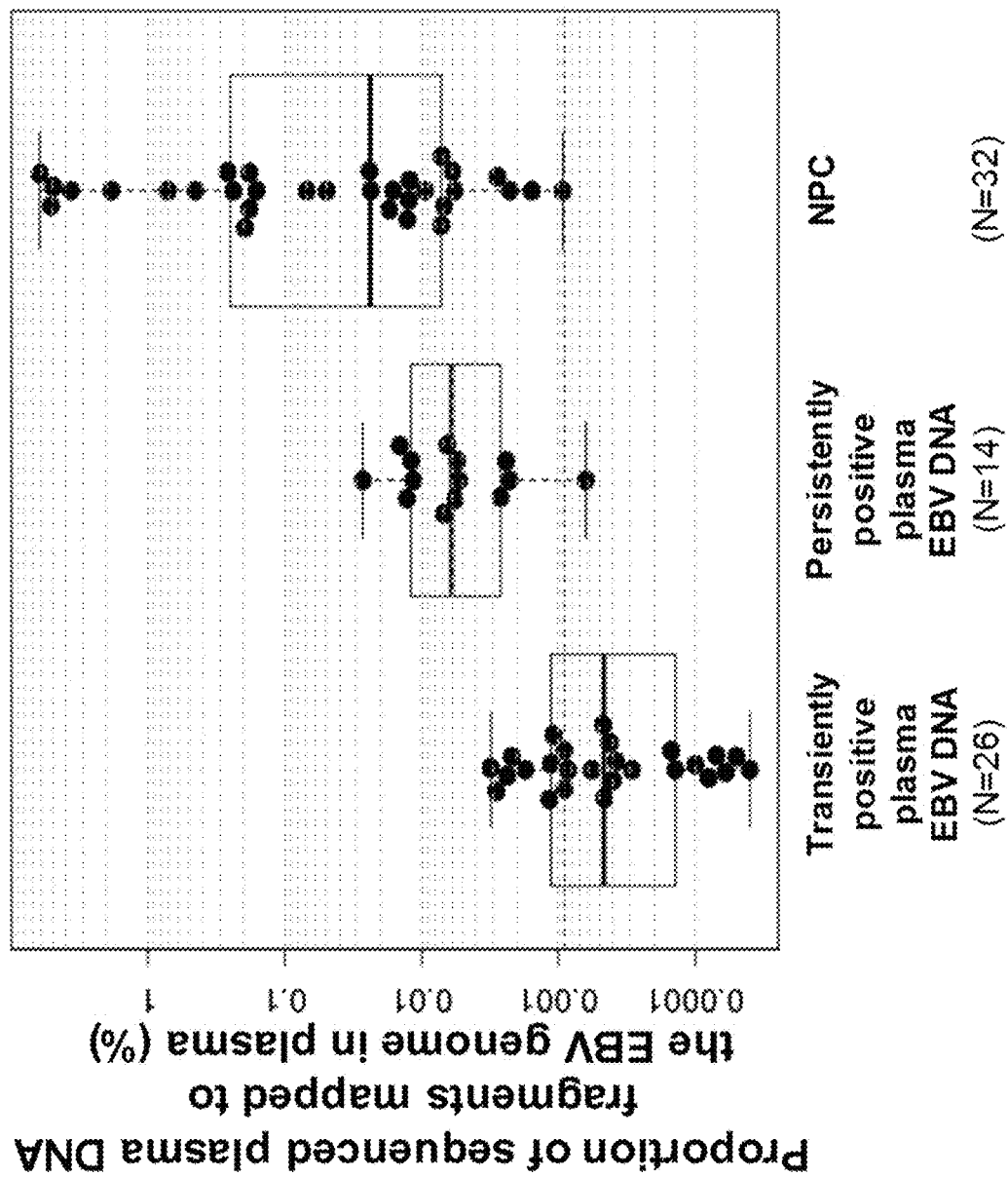
FIG. 14 shows the proportion of plasma DNA fragments (%) mapped to the EBV genome in subjects that are transiently positive or persistently positive for plasma EBV DNA (left or middle, respectively) but have no observable pathology, and subjects identified as having NPC.

FIG. 14 shows the proportion of plasma DNA fragments (%) mapped to the EBV genome in subjects that are transiently positive or persistently positive for plasma EBV DNA (left or middle, respectively) but have no observable pathology, and subjects identified as having NPC. The cohort used for FIG. 14 is the same cohort used for FIG. 7. The separation between NPC and the persistently positive subjects is clearly better for the sequencing results in FIG. 14 than the real-time PCR quantitative results in FIG. 7.

Using massively parallel sequencing following targeted capture and sequencing of DNA fragments, there was a statistically significant difference in the EBV quantity as deduced from the proportion of reads uniquely mapped to the EBV genome among all sequenced reads (p-value=0.01; Kruskal-Wallis test). By applying a cutoff value of 0.0009% ($9\times10^{-6}$ in units of FIG. 13A) for the proportion of plasma EBV DNA fragments among all the sequenced reads, subjects with NPC and persistently positive plasma EBV DNA from the majority of subjects with transiently positive plasma EBV DNA results were able to be differentiated. The proportion of EBV reads in plasma was highest in the group of subjects having NPC. The proportion of plasma EBV DNA fragments measured at enrollment was higher in the subjects with persistently positive results compared with those who would become negative in the follow-up test (i.e. with transiently detectable plasma EBV DNA).

Figure 15A:
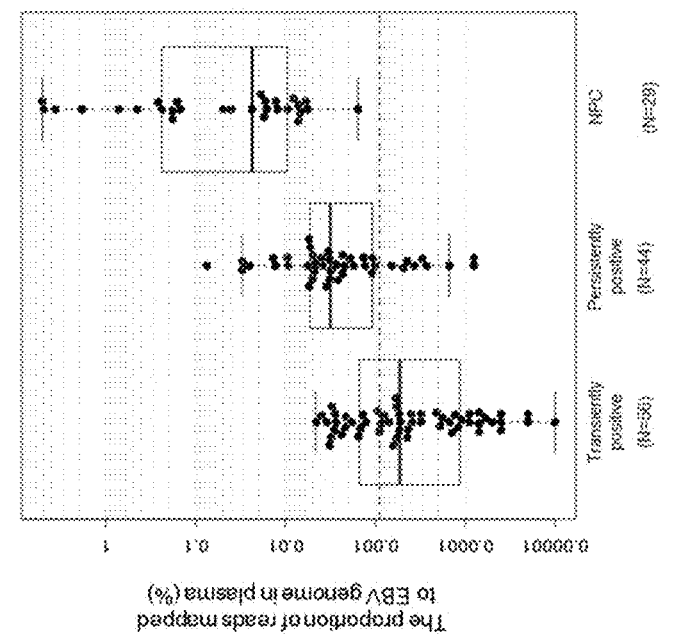
FIG. 15A shows a proportion of reads mapped to EBV genome in plasma (%) for a training set of 15 transiently positive samples, 20 persistently positive samples, and 10 samples from confirmed NPC subjects.

FIG. 15A shows a proportion of reads mapped to EBV genome in plasma (%) for a training set of 15 transiently positive samples, 20 persistently positive samples, and 10 samples from confirmed NPC subjects. There was a statistically significant difference in the EBV quantity as deduced from the proportion of reads uniquely mapped to the EBV genome among all sequenced reads (p-value<0.0001; Kruskal-Wallis test).

In the example shown in FIG. 15A, a cutoff value of 0.0009% was set to capture all the NPC patients. By applying a cutoff value of 0.0009% for the proportion of plasma EBV DNA fragments among all the sequenced reads, subjects with NPC and persistently positive plasma EBV DNA from the majority of subjects with transiently positive plasma EBV DNA results were differentiated. The proportion of EBV reads in plasma was highest in the group of subjects having NPC. The proportion of plasma EBV DNA fragments was higher in the subjects with persistently positive results compared with those with transiently detectable plasma EBV DNA. In some embodiments, those samples with values above the 0.0009% cutoff value (5 transiently positive samples; 13 persistently positive samples, and 10 NPC samples) could be evaluated using a size analysis, as described in section V.A.

Figure 15B:
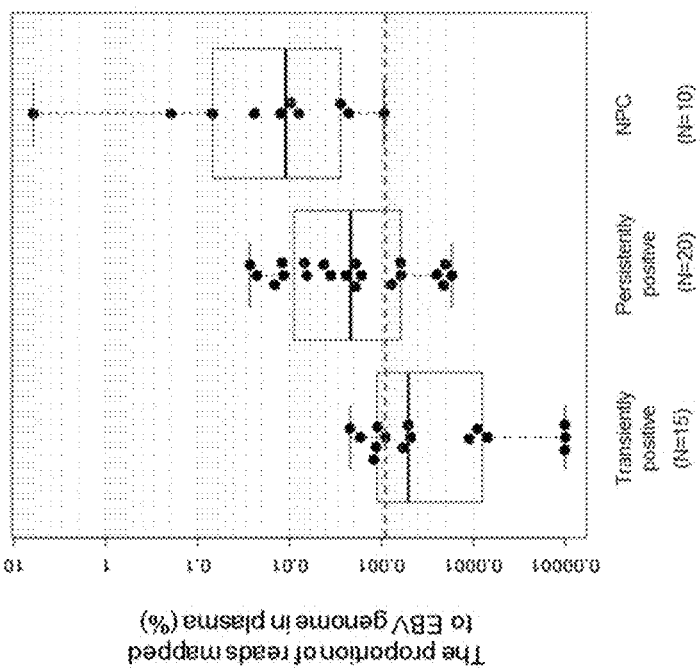
FIG. 15B shows a proportion of reads mapped to EBV genome in plasma (%) for a validation set of 56 transiently positive samples, 44 persistently positive samples, and 29 samples from confirmed NPC subjects.

FIG. 15B shows a proportion of reads mapped to EBV genome in plasma (%) for a validation set of 56 transiently positive samples, 44 persistently positive samples, and 29 samples from confirmed NPC subjects. There was a statistically significant difference in the EBV quantity as deduced from the proportion of reads uniquely mapped to the EBV genome among all sequenced reads (p-value<0.0001; Kruskal-Wallis test). By applying a cutoff value of 0.0009% for the proportion of plasma EBV DNA fragments among all the sequenced reads, subjects with NPC and persistently positive plasma EBV DNA from the majority of subjects with transiently positive plasma EBV DNA results were able to be differentiated. The proportion of EBV reads in plasma was highest in the group of subjects having NPC. The proportion of plasma EBV DNA fragments was higher in the subjects with persistently positive results compared with those with transiently detectable plasma EBV DNA. The samples above the cutoff value were: 18 transiently positive samples; 35 persistently positive samples, and 29 NPC samples.

2. HBV

Figure 16:
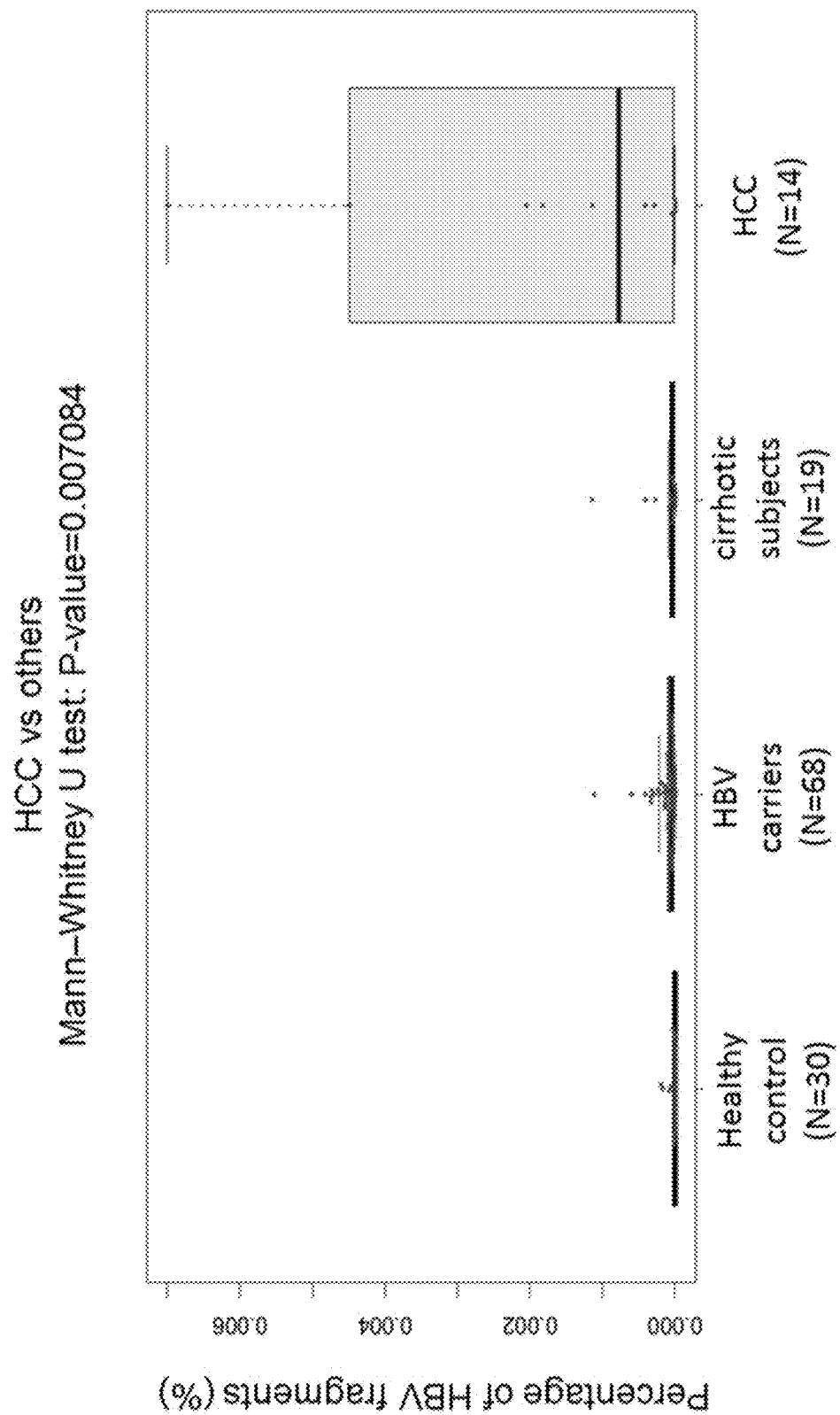
FIG. 16 shows the abundance of hepatitis B virus (HBV) DNA fragments in plasma of HCC group (mean: 0.00047%) is significantly higher than non-HCC groups (mean: 0.021%) including healthy control subjects, HBV carriers, cirrhotic subjects.

FIG. 16 shows the abundance of hepatitis B virus (HBV) DNA fragments in plasma of HCC group (mean: 0.00047%) is significantly higher than non-HCC groups (mean: 0.021%) including healthy control subjects, HBV carriers, cirrhotic subjects. The percentage of HBV DNA fragments in HCC was 45 times higher than that of non-HCC subjects. These data show that the quantitative assessment of plasma HBV DNA molecules would offer high sensitivity and specificity for the detection of HCC.

3. HPV

A sequencing assay can be used in a way similar to that described herein for EBV to measure an amount of tumor-associated HPV DNA in a sample. Such analysis can be especially useful for screening of cervical cancer (CC) and head and neck squamous cell carcinoma (HNSCC). In one example, a targeted sequencing assay targets a region (e.g., 200 nucleotides) within the polymorphic L1 region of the HPV genome. More specifically, capture probes can be used that selectively hybridize to sequences that encode one or more hypervariable surface loops in the L1 region.

Table 2 below illustrates that HPV DNA in plasma is detectable by sequencing.

TABLE 2

| Groups | Sample IDs | Fragment mapped to HPV genomes | Percentage or fragments mapped to HPV genomes (%) |
|---|---|---|---|
| Healthy controls | EN088 | 0 | 0 |
|  | GC038 | 0 | 0 |
|  | ER022 | 0 | 0 |
|  | BP065 | 0 | 0 |
|  | FF159 | 0 | 0 |
| Nasopharyngeal carcinoma (NPC) patients | TBR1358 | 0 | 0 |
|  | TBR1390 | 0 | 0 |
|  | TBR1379 | 0 | 0 |
|  | TBR1376 | 0 | 0 |
| Chronic hepatitis B virus (HBV) carriers | GM2192F | 0 | 0 |
|  | GM2910F | 0 | 0 |
|  | GM6421F | 0 | 0 |

TABLE 2-continued

| Groups | Sample IDs | Fragment mapped to HPV genomes | Percentage or fragments mapped to HPV genomes (%) |
|---|---|---|---|
| Hepatocellular carcinoma (HCC) patients | TBR_1330 | 0 | 0 |
| | TBR_1386 | 0 | 0 |
| | TBR_1428 | 0 | 0 |
| Cervical cancer (CC) patients | C-189 | 1489 | 0.00731 |
| | C-822 | 1720 | 0.0132 |
| | C-877 | 6773 | 0.03177 |
| | C-788 | 7992 | 0.06083 |
| | C-801 | 2127 | 0.04563 |
| | C-803 | 1316 | 0.01504 |
| Head and Neck Squamous cell carcinoma (HNSCC) patients | TBR_1067 | 53 | 0.00009 |
| | TBR_1019 | 3287 | 0.00642 |

Plasma samples from 23 individuals without cancer (healthy controls or chronic HBV carriers) or with various cancers (NPC, HCC, CC, HNSCC) were analyzed by targeted sequencing using the capture probe design as shown in Table 5, provided below. The sequence reads were aligned to the HPV genome and counted. The data show that plasma DNA fragments derived from HPV are detectable in plasma of patients with HPV-related CC or HNSCC but not in any of the other patient groups. The amount of plasma HPV DNA fragments can be expressed in terms of absolute number per volume detected from the amount of sequencing performed or be expressed as a proportion to the amount of other non-HPV derived sequence reads.

As shown in Table 2, the presence of the amount of plasma HPV DNA sequences above a threshold established from healthy individuals or individuals without HPV-related cancers can provide evidence for the presence of the HPV-related cancer. In this analysis, CC and HNSCC are the HPV-related cancers while NPC and HCC are the non-HPV related cancers. In this analysis, a cutoff>0 fragments mapped to HPV or >0% reads mapped to HPV was used. Other methods to establish reference values or cutoffs based on data from individuals without HPV-related cancers, including ROC analysis, >90th percentile, >99th percentile, >2 standard deviations or >3 standard deviations above the mean, for example, can be used.

The difference in range of abundance of plasma HPV DNA sequences in a sample can be reflective of the stage of the HPV-related cancer. Additionally, the difference in the order of magnitude of the plasma HPV DNA sequences can be reflective of cancers of different tissue origin. For example, Table 2 shows that the amounts of plasma HPV DNA sequences are generally higher in samples of CC patients than those of HNSCC patients.

Sequence variants among the plasma HPV DNA sequences can allow one to determine the serotype or genotype of HPV and further provide evidence for the high likelihood of the cancer diagnosis. For example, CC is typically associated with HPV types 16 and HPV type 18.

In a further analysis, Table 3 shows the number of patients with different types of HPV-related malignancies analyzed.

TABLE 3

| Health or disease status | Number of samples |
|---|---|
| Patients with carcinoma of cervix | 11 |
| Patients with HPV-positive head and neck squamous cell carcinoma | 7 |
| Patients with cervical intraepithelial neoplasia | 16 |

FIG. 17 shows the numbers and proportions of reads uniquely mapped to the HPV genome of different HPV serotypes for each clinical case of carcinoma of cervix. For each clinical case, plasma DNA was extracted from 1 mL plasma. Using massively parallel sequencing following target capture, the number of reads uniquely mapped to the HPV genome for each case was derived. The proportion of plasma HPV reads (reads uniquely mapped to the HPV genome) among all mapped reads (i.e. mapping to both human and HPV genomes) after removal of duplicated reads was calculated. All 11 patients with carcinoma of cervix had at least one HPV DNA fragment in their plasma DNA samples. HPV 16 and 18 are two HPV serotypes. Serotypes differ in genetic sequence. Serotypes 16 and 18 are the most common ones associated with cervical cancer.

FIG. 18 shows the numbers and proportions of reads uniquely mapped to the HPV genome of different HPV serotypes for each clinical case of cervical intraepithelial neoplasia (CIN). For each clinical case, plasma DNA was extracted from 1 mL plasma. Using massively parallel sequencing following target capture, the number of reads uniquely mapped to the HPV genome for each case was derived. The proportion of plasma HPV reads (reads uniquely mapped to the HPV genome) among all mapped reads (i.e. mapping to both human and HPV genome) after removal of duplicated reads was calculated. 3 out of 16 patients with CIN had at least one HPV DNA fragment in their plasma DNA samples.

FIG. 19 shows the numbers and proportions of reads uniquely mapped to the HPV genome of different HPV serotypes for each clinical case of HPV positive-head and neck squamous cell carcinoma (HPV+ve HNSCC). The cases were staged according to the 8th Edition of AJCC Cancer Staging Manual. For each clinical case, plasma DNA was extracted from 1 mL plasma. All the 7 patients with HPV+ve HNSCC had at least one HPV DNA fragment in their plasma DNA samples. A higher proportion of patients with HPV+ve HNSCC had HPV DNA fragments in their plasma DNA samples compared to patients with CIN. It may be possibly due to a higher input plasma volume for cases of HPV+ve HNSCC.

270 healthy subjects were analyzed with targeted sequencing by the same capture probe set. 9 of them (3.3%) had at least one HPV DNA fragment in their plasma. FIG. 20 shows the number of plasma HPV fragments and the corresponding HPV serotypes in the plasma samples of the 9 healthy subjects with at least one plasma HPV DNA.

By setting the cutoff in the number of HPV reads for defining 'detectable plasma HPV DNA' at 1, 5 healthy subjects (1.9%) and 2 patients with CIN (12.5%) had detectable (greater than 1) HPV DNA in their plasma. All the 11 patients with carcinoma of cervix and 7 patients with HPV+ve HNSCC remained to have detectable plasma HPV DNA. If the cutoff in the number of HPV reads for defining 'detectable plasma HPV DNA' at 5, only 1 healthy subject (0.3%) had detectable HPV DNA in their plasma. 2 patients with CIN had detectable plasma HPV DNA. All the 11 patients with carcinoma of cervix and 7 patients with HPV+ve HNSCC remained to have detectable plasma HPV DNA. Examples of the cutoff number in the number of HPV reads include but not limited to 1, 2, 3, 4, 5, 10, 15 and 20.

Figure 21:
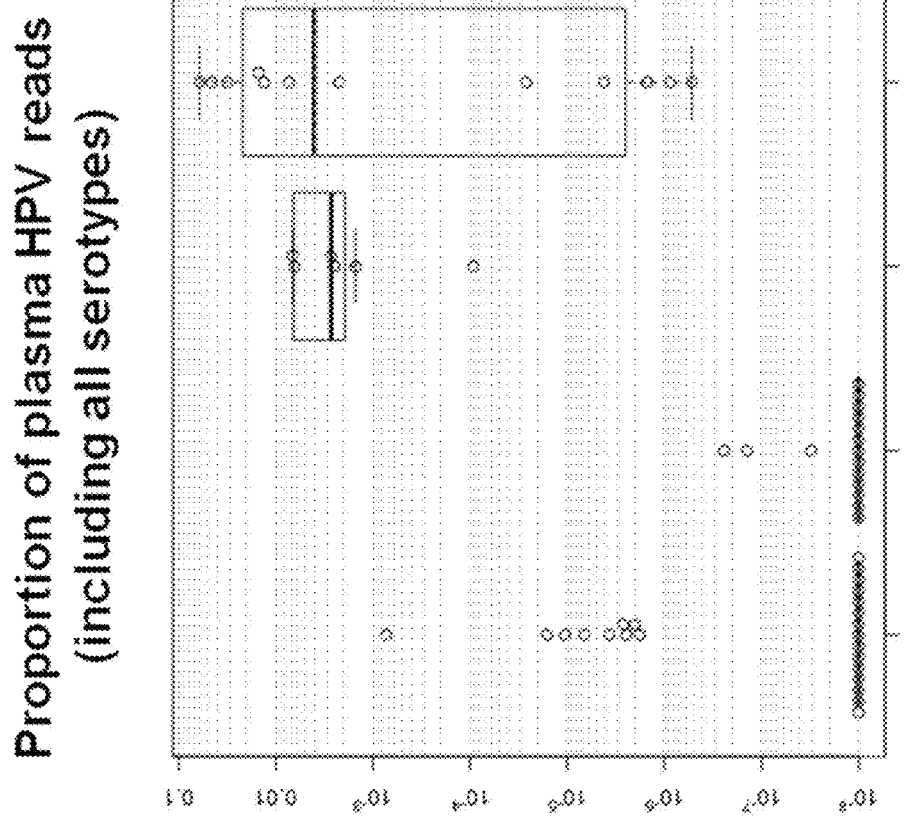
FIG. 21 shows the median proportions of HPV reads (including all serotypes) in the plasma DNA samples of patients with carcinoma of cervix, cervical intraepithelial neoplasia (CIN), HPV positive-head and neck squamous cell carcinoma (HPV+ve HNSCC) and healthy controls.

FIG. 21 shows the median proportions of HPV reads (including all serotypes) in the plasma DNA samples of patients with carcinoma of cervix, cervical intraepithelial neoplasia (CIN), HPV positive-head and neck squamous cell carcinoma (HPV+ve HNSCC) and healthy controls. The median proportion of HPV reads was significantly higher in patients with carcinoma of cervix (0.0048%) than patients with CIN (0%) and healthy controls (0%) ($p<0.0001$, Kruskal-Wallis test). The median proportion of HPV reads was also significantly higher in patients with HPV+ve HNSCC (0.003%) than healthy controls (p<0.0001, Mann-Whitney test)

C. Method

Figure 22:
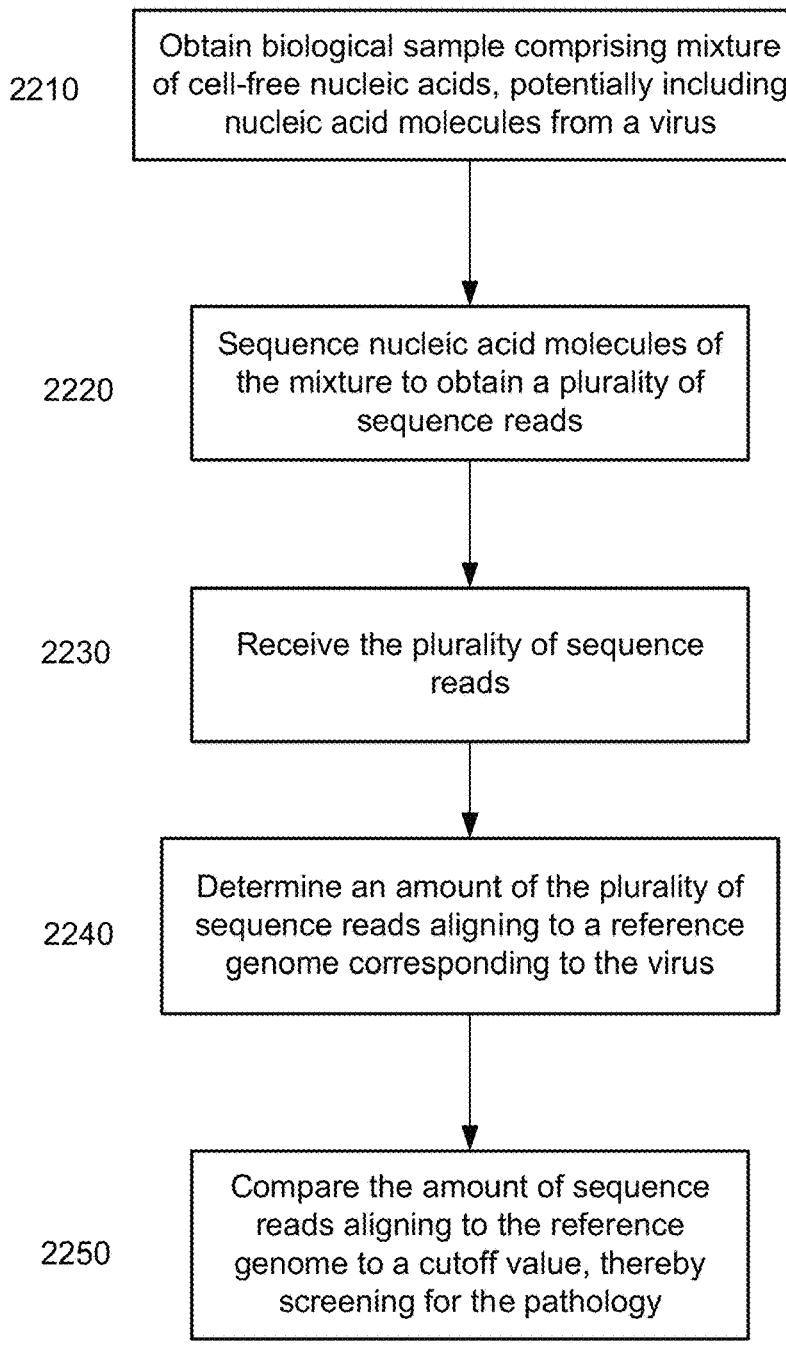
FIG. 22 is a flowchart illustrating a count-based method 2200 using sequence reads of viral nucleic acid fragments in cell-free mixture of a subject to screen for cancer according to embodiments of the present invention.

FIG. 22 is a flowchart illustrating a count-based method 2200 using sequence reads of viral nucleic acid fragments in cell-free mixture of a subject to screen for cancer according to embodiments of the present invention. Aspects of method 2200 can be performed by a computer system, e.g., as described herein.

Method 2200 can be used to screen a biological sample for a pathology, where the biological sample includes a mixture of cell free nucleic acid molecules. The screening can be performed on subjects that are asymptomatic for the pathology (e.g., a type of cancer, CIN, or mononucleosis), and thus identify subjects at an early stage of the pathology. The mixture can include nucleic acid molecules from the subject and potentially nucleic acid molecules from a virus (e.g., EBV, HBV, or HPV).

At block 2210, the biological sample is obtained from the subject. As examples, the biological sample can be blood, plasma, serum, urine, saliva, sweat, tears, and sputum, as well as other examples provided herein. In some embodiments (e.g., for blood), the biological sample can be purified for the mixture of cell-free nucleic acid molecules, e.g., centrifuging blood to obtain plasma.

At block 2220, the mixture of cell-free nucleic acid molecules is sequenced to obtain a plurality of sequence reads. The sequencing may be performed in a variety of ways, e.g., using massively parallel sequencing or next-generation sequencing, using single molecule sequencing, and/or using double- or single-stranded DNA sequencing library preparation protocols. The skilled person will appreciate the variety of sequencing techniques that may be used. As part of the sequencing, it is possible that some of the sequence reads may correspond to cellular nucleic acids.

The sequencing may be targeted sequencing as described herein. For example, biological sample can be enriched for nucleic acid molecules from the virus. The enriching of the biological sample for nucleic acid molecules from the virus can include using capture probes that bind to a portion of, or an entire genome of, the virus. The biological sample can be enriched for nucleic acid molecules from a portion of a human genome, e.g., regions of autosomes. Table 5 provides examples of such capture probes. In other embodiments, the sequencing can include random sequencing.

At block 2230, the plurality of sequence reads that were obtained from the sequencing of the mixture of cell free nucleic acid molecules are received. The sequence reads may be received by a computer system, which may be communicably coupled to a sequencing device that performed the sequencing, e.g., via wired or wireless communications or via a detachable memory device.

At block 2240, an amount of the plurality of sequence reads aligning to a reference genome corresponding to the virus is determined. Examples of aligning the sequence reads to a viral genome are provided herein. The amount can be determined in a variety ways based on the number of sequence reads that align to the reference genome. For example, the number of sequence reads aligned to the reference genome can be normalized. In various embodiments, the normalization may be relative to a volume of the biological sample (or a purified mixture) or relative to a number of sequence reads aligned to a human reference genome.

In some embodiments, the amount of sequence reads aligning to the reference genome includes a proportion of sequence reads aligned to the reference genome relative to a total number of sequence reads. The total number of sequence reads can be a sum of the sequence reads that aligned to the reference genome corresponding to the virus and the sequence reads that aligned to a human genome. In various implementations, any function or derivative of a relative amount (abundance) of the viral nucleic acids to human DNA can be used, where examples of a relative amount include a ratio (e.g., proportion) or a difference between the amounts of the viral nucleic acids and human DNA.

At block 2250, the amount of sequence reads aligning to the reference genome is compared to a cutoff value, thereby screening for the pathology. The screening can include determining a level of the pathology in the subject, e.g., that the subject does or does not have the pathology or has certain levels of the pathology.

The cutoff value can be determined from a set of training samples having a known classification for the pathology, e.g., as described herein. As examples, the cutoff value can be selected using (1) a value below a lowest amount of sequence reads aligning to the reference genome for the training samples classified as having the pathology; (2) a specified number of standard deviations from a mean amount of sequence reads aligning to the reference genome for the training samples classified as having the pathology; or (3) a specificity and a sensitivity for determining a correct classification of the training samples.

In some embodiments, the level of pathology is a level of cancer. In another embodiment, the level of pathology is infectious mononucleosis. As examples, the cancer can be selected from a group consisting of nasopharyngeal cancer, head and neck squamous cell carcinoma, cervical cancer, and hepatocellular carcinoma.

Before the sequencing is performed, a first assay can be used to determine whether a sufficient amount of the virus is detected, and therefore warrants the sequencing to be performed. In some implementations, real-time polymerase chain reaction (PCR) can be performed using the biological sample or a different biological sample obtained from the subject contemporaneously (e.g., same clinical visit) as the biological sample. The real-time PCR can provide a quantity of nucleic acid molecules from the virus using techniques described herein or known to one skilled in the art, e.g., using Ct values. The quantity can be compared to a quantity threshold. When the quantity is above the quantity threshold, the sequencing can be performed, thereby not wasting resources sequencing samples that do not have a sufficient quantity of viral nucleic acids to warrant the more accurate technique. In some embodiments, digital PCR could be used instead of sequencing. The capture probes can be used with corresponding primers in performing the count of sequence reads.

D. Further Details on Determining Cutoff Value

The cutoff value(s) for discriminating between classifications of samples (e.g., whether a subject has a particular cancer associated with a virus) can be determined in various ways. In one embodiment, the cutoff value for the proportion of plasma DNA fragments mapped to the viral genome can be determined as any value below the lowest data point of the cancer patients being analyzed. In other embodiments, the cutoff values can be determined from the mean proportion of the cancer patients minus one standard deviation (SD), mean minus 2 SD, and mean minus 3 SD. In yet other embodiments, the cutoff can be determined after the logarithmic transformation of the proportion of plasma DNA fragments mapped to the viral genome, for example but not limited to mean minus SD, mean minus 2 SD, mean minus 3 SD after the logarithmic transformation of the values of the cancer patients. In yet other embodiments, the cutoff can be determined using Receiver Operator Characteristics (ROC) curves or by nonparametric methods, for example but not limited to including about 100%, about 95%, about 90%, about 85%, or about 80% of the cancer patients being analyzed. In yet another embodiment, to maximize test specificity, the cutoff value could be determined as any value higher than the highest proportion of DNA fragments mapped to the viral genome among non-cancer subjects or the mean plus SD, mean plus 2 SD, mean plus 3 SD with or without logarithmic transformation.

In FIG. 14, by applying a cutoff value of 0.0009% for the proportion of plasma EBV DNA fragments among all the sequenced reads, subjects with NPC and persistently positive plasma EBV DNA from the majority of subjects with transiently positive plasma EBV DNA results were able to be differentiated. In other embodiments (e.g., for other virus/cancer combinations), the cutoff value for proportion of plasma EBV DNA reads among all sequenced reads can be greater than 0.00001%, greater than 0.00005%, greater than 0.0001%, greater than 0.0002%, greater than 0.0003%, greater than 0.0004%, greater than 0.0005%, greater than 0.0006%, greater than 0.0007%, greater than 0.0008%, greater than 0.0009%, greater than 0.001%, greater than 0.002%, greater than 0.003%, greater than 0.004%, greater than 0.005%, greater than 0.01%, greater than 0.1%, or greater than 1%.

III. SIZE-BASED ANALYSIS OF PATHOGEN DNA

We studied and analyzed the differences in the size distributions of plasma viral DNA reads (e.g., EBV, HBV, and HPV) from cancer patients and non-cancer subjects. The size distribution of plasma viral fragments of cancer subjects were statistically longer than the size distribution of viral fragments of non-cancer subjects. At the same time, the size distribution of the plasma viral fragments of cancer subjects were statistically significantly shorter than the plasma human DNA fragments in the same subject.

In some embodiments, sequencing is used to assess size of cell-free viral nucleic acids in a sample. For example, the size of each sequenced plasma DNA molecule can be derived from the start and end coordinates of the sequence, where the coordinates can be determined by mapping (aligning) sequence reads to a viral genome. In various embodiments, the start and end coordinates of a DNA molecule can be determined from two paired-end reads or a single read that covers both ends, as may be achieved in single-molecule sequencing.

A. Differences in Size Distribution

A size distribution can be displayed as a histogram with the size of a nucleic acid fragment on the horizontal axis. The number of nucleic acid fragments at each size (e.g., within 1 bp resolution) can be determined and plotted on the vertical axis, e.g., as a raw number or frequency percentage. The resolution of size can be more than 1 bp (e.g., 2, 3, 4, or 5 bp resolution). The following analysis of size distributions (also referred to as size profiles) shows that the viral DNA fragments in a cell-free mixture from NPC subjects are statistically longer than in subjects with no observable pathology.

Figure 23:
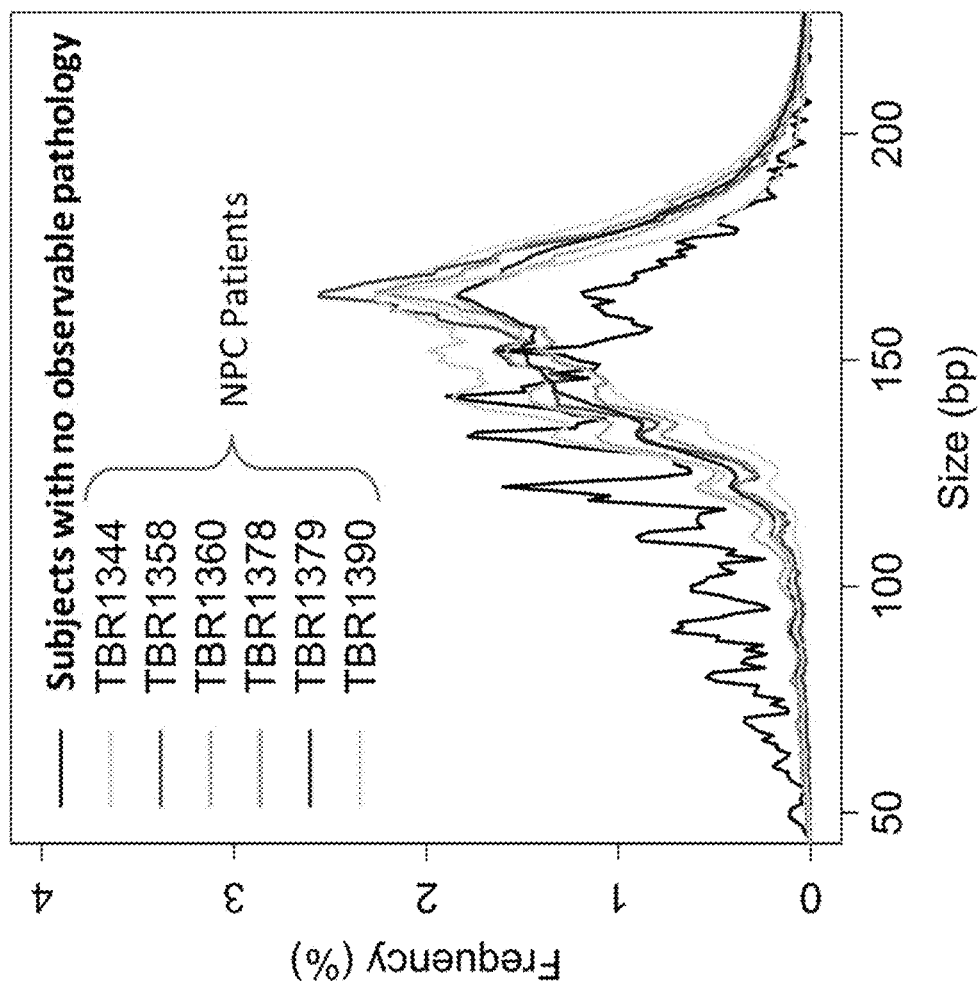
FIG. 23 shows the size distribution of EBV DNA fragments in a pooled sample from normal subjects and 6 subjects having nasopharyngeal cancer (e.g., TBR1344, TBR1358, TBR1360, TBR1378, TBR1379, and TBR1390).

FIG. 23 shows the size distribution of EBV DNA fragments in a normal subject and 6 subjects having NPC (TBR1344, TBR1358, TBR1360, TBR1378, TBR1379, and TBR1390). Using paired-end sequencing, the size of each plasma EBV DNA fragment was deduced based on the coordinates of the outermost nucleotide on each of the two ends of the sequenced EBV DNA fragment. The size profiles of plasma EBV DNA fragments for NPC subjects and those with no observable pathology are shown. The sequenced EBV DNA fragments from all the cases of this group were pooled together to plot an aggregated size profile for these subjects.

The plasma EBV DNA size distribution of the subjects without any observable pathology is on the left side of the size distribution plots of the NPC subjects, indicating that the size distribution of sequenced plasma EBV DNA fragments is shorter in subjects without any observable pathology compared with NPC subjects. These results suggest that the size profile of plasma EBV DNA fragments as measured by sequencing analysis (e.g., massively parallel sequencing) can be used to differentiate subjects with NPC and with false-positive plasma EBV DNA results. In a previous study, it has been shown that plasma EBV DNA are short fragments in NPC subjects (Chan et al. Cancer Res. 2003; 63:2028-32). However, in that previous study, no information was provided regarding the difference in the size distribution of plasma EBV DNA fragments between subjects with NPC and those with false-positive plasma EBV DNA results.

Figure 24:
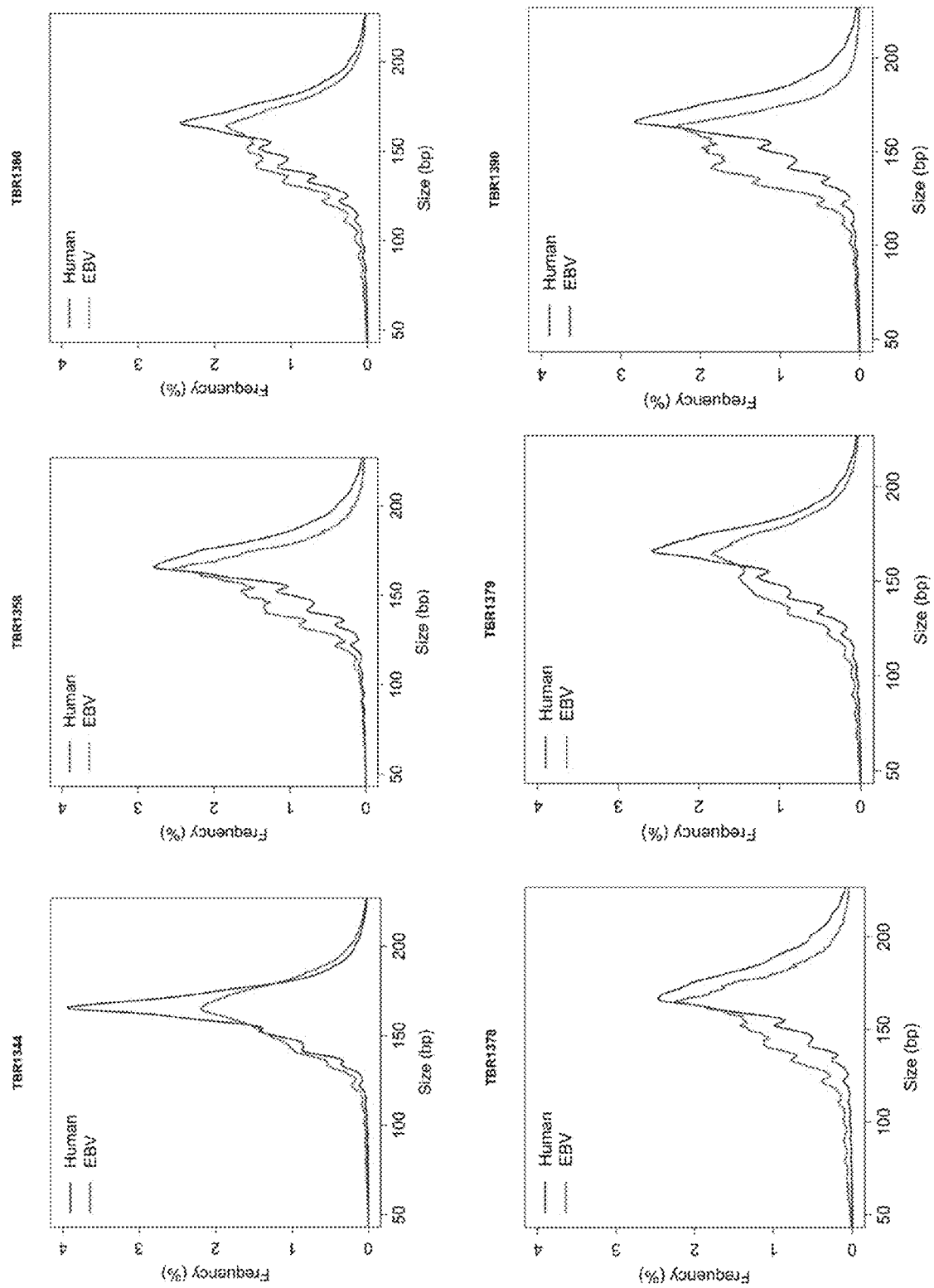
FIG. 24 shows the size distribution of sequenced plasma DNA fragments mapped to the EBV genome and human genome in 6 subjects having nasopharyngeal cancer (NPC) (e.g., TBR1344, TBR1358, TBR1360, TBR1378, TBR1379, and TBR1390).

FIG. 24 shows the size distribution of sequenced plasma DNA fragments mapped to the EBV genome and human genome in 6 subjects having NPC (TBR1344, TBR1358, TBR1360, TBR1378, TBR1379, and TBR1390). For each subject, the size distribution of the plasma EBV DNA fragments is shorter than that of fragments mapped to the human genome. This observation is consistent with the findings of previous reports that the size distribution of plasma DNA derived from tumor cells is shorter that DNA fragments derived from non-tumor cells (Jiang et al. Proc Natl Acad Sci USA. 2015; 112:E1317-25) because the plasma EBV DNA fragments in NPC subjects are derived from the tumor cells (Chan et al. Clin Chem. 2005; 51:2192-5) and the plasma DNA fragments mapped to the human genome are derived from both tumor and non-tumor cells.

Figure 25:
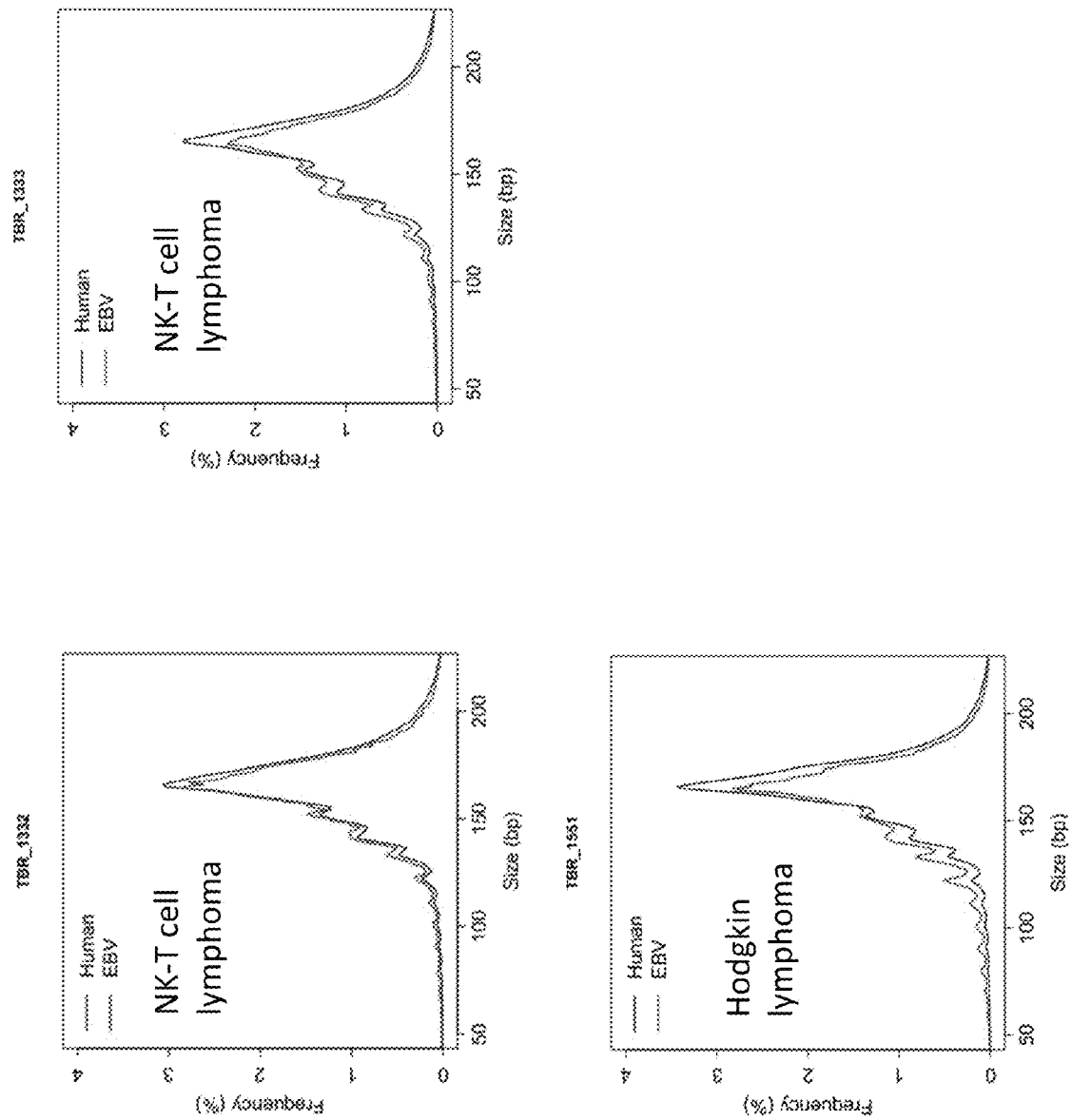
FIG. 25 shows the size distribution of sequenced plasma DNA fragments mapped to the EBV genome and human genome in 3 subjects having lymphoma (TBR1332, TBR1333, and TBR1551).

FIG. 25 shows the size distribution of sequenced plasma DNA fragments mapped to the EBV genome and human genome in 3 subjects having lymphoma (TBR1332, TBR1333, and TBR1551). For each of the three lymphoma subjects, the size distribution of the plasma EBV DNA fragments is shorter than that of fragments mapped to the human genome.

Figure 26:
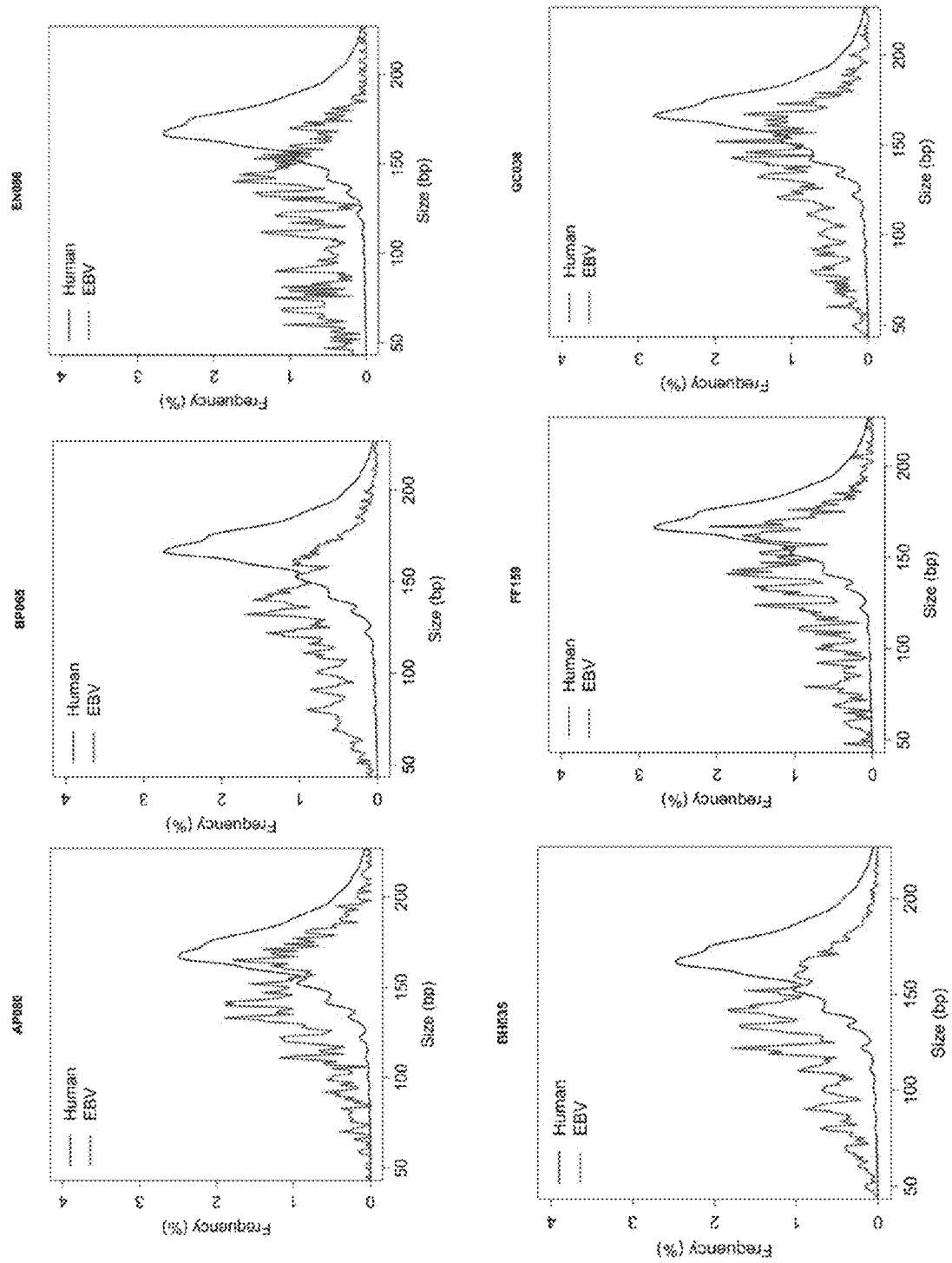
FIG. 26 shows the size distribution of sequenced plasma DNA fragments mapped to the EBV genome and human genome in 6 control subjects (AP080, BP065, EN086, BH035, FF159, and GC038).

FIG. 26 shows the size distribution of sequenced plasma DNA fragments mapped to the EBV genome and human genome in 6 control subjects (AP080, BP065, EN086, BH035, FF159, and GC038). For each of the 14 subjects with false-positive plasma EBV DNA but no observable pathology, the size distribution of the sequenced plasma EBV DNA was shorter than the fragments mapped to the human genome. This observation is surprising as it is generally believed that the EBV DNA fragments in non-cancer subjects are associated with viral particles and high molecular weight fragments are expected to be present in plasma. It is surprising to find the presence of short EBV DNA fragments in this group of subjects.

Figure 27B:
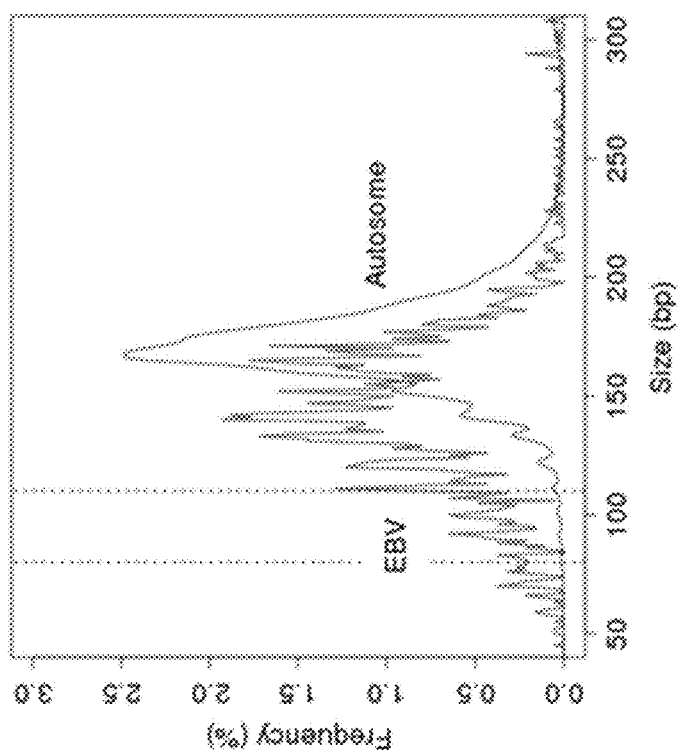
FIGS. 27A and 27B show the size profiles of sequenced plasma DNA fragments in subjects having NPC (FIG. 27A) and subjects that are persistently positive for plasma EBV DNA (FIG. 27B) mapped to the EBV genome and human genome.
Figure 27A:
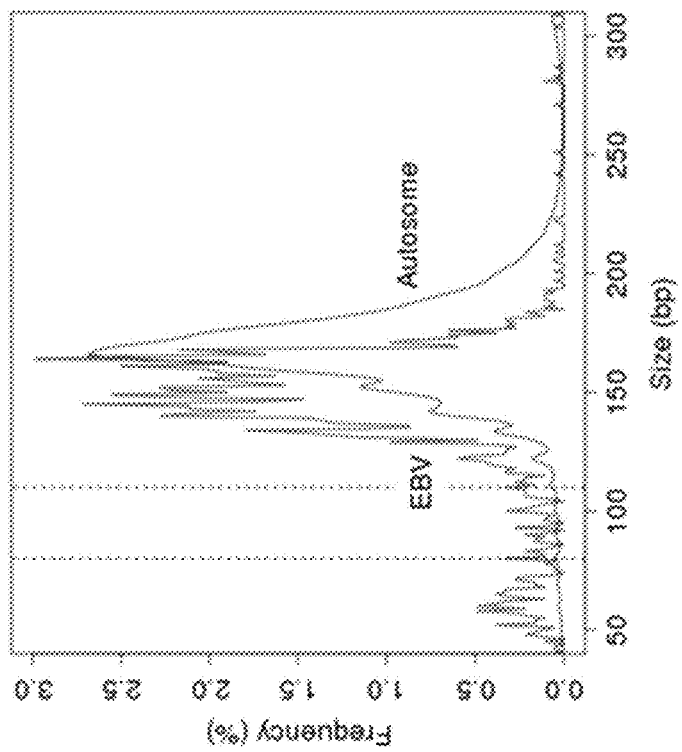

FIGS. 27A and 27B show the size profiles of sequenced plasma DNA fragments in subjects having NPC (26A) and subjects that are persistently positive for plasma EBV DNA (26B) mapped to the EBV genome and human genome. A difference in the size profile pattern of plasma EBV DNA fragments aligned to the EBV genome and those aligned to the autosomal genome (e.g., reference) were observed; those differences were used to differentiate subjects with NPC from subjects with false-positive plasma EBV DNA results.

Figure 28B:
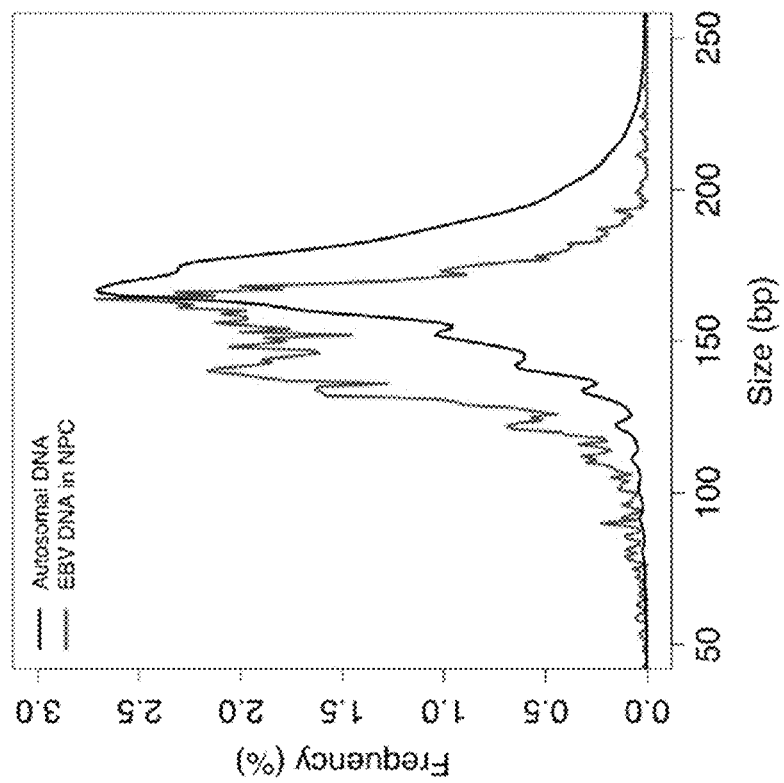
FIG. 28B shows size distributions of EBV DNA (red curve) and human autosomal DNA (black curve) in a non-cancer subject with persistently positive plasma EBV DNA results.
Figure 28A:
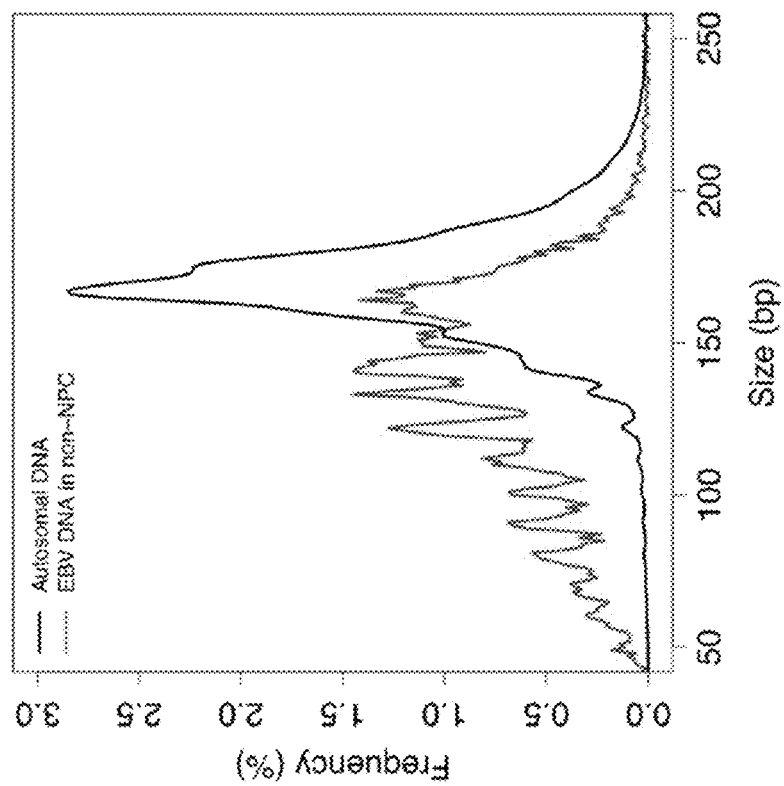
FIG. 28A shows size distributions of EBV DNA (red curve) and autosomal DNA (black curve) in the plasma of a patient with NPC.

FIG. 28A show a size distributions of EBV DNA (red curve) and autosomal DNA (black curve) in the plasma of a patient with NPC. FIG. 28B shows size distributions of EBV DNA (red curve) and human autosomal DNA (black curve) in a non-cancer subject with persistently positive plasma EBV DNA results. We observed that the size profiles of EBV DNA from NPC patients exhibited a reduction in the 166-bp peak, but with a more pronounced peak at around 150 bp when compared with the size profiles of human autosomal DNA (FIG. 28A). The size profiles of EBV DNA from non-cancer subjects showed peaks that were distributed over the shorter fragment sizes (FIG. 28B). Thus, NPC patients had a lower proportion of EBV DNA molecules shorter than 110 bp when compared with that of the non-cancer subjects.

The presence of the characteristic 166-bp peak in the plasma EBV DNA size profile of NPC patients suggested that circulating EBV DNA was nucleosome-bound. The relative prominence of EBV DNA (as circulating tumor DNA) at around 150 bp was concordant with our previous finding that tumor-derived DNA was in general shorter than non-tumor-derived DNA (20).

In contrast to cancer patients, plasma EBV DNA from non-cancer subjects did not exhibit the typical nucleosomal pattern (FIG. 28B). The lack of protection by nucleosome (29) may render those viral sequences more susceptible to DNA degradation resulting in the shorter size distributions of plasma EBV DNA in non-cancer subjects. Therefore, a relatively higher proportion of short EBV DNA fragments was observed in non-NPC subjects than in NPC patients. Virion-associated EBV DNA has been reported to be free of nucleosomes (30). We suspect that the EBV DNA fragments in plasma of the non-NPC subjects may represent degraded viral products or incomplete viral replication products. In fact, the EBV DNA size profiles of the non-cancer subjects (FIG. 28B) showed a series of peaks that were separated by 10-bp.

The characteristic 166-bp peak is also observed in the plasma EBV DNA sequences of the lymphoma patients (FIG. 25). These data indicate that EBV-positive lymphomas and likely other EBV-related malignancies could be distinguished from the non-cancer subjects positive for plasma EBV DNA. Patients with EBV-related malignancies and lymphomas are expected to have higher proportion of long plasma EBV DNA molecules or lower proportion of short plasma EBV DNA molecules than the non-cancer subjects.

B. Size Ratio—Exploration and Validation

The above-mentioned variations in size distributions lead to inter-individual variations in the size profile patterns of sequenced plasma DNA. To compare the proportion of plasma viral DNA reads (e.g., EBV reads) within a certain size range (e.g., between 80 and 110 base pairs) among individuals, the amount of plasma viral DNA fragments can be normalized to the amount of autosomal DNA fragments within the same size range. This metric is denoted as a size ratio. A size ratio can be defined by the proportion of plasma viral DNA fragments within a certain size range divided by the proportion of autosomes (e.g., autosomal DNA fragments) within the corresponding size range. For example, a size ratio of EBV DNA fragments between 80 and 110 base pairs would be:

$$Size_{80\text{-}110bp} ratio = \frac{\text{Proportion of } EBV\ DNA \text{ fragments within 80-110 bp}}{\text{Proportion of autosomal } DNA \text{ fragments within 80-110 bp}}$$

The size ratio can indicate the relative proportion of short DNA fragments within each sample. The lower the EBV DNA size ratio, the lower the proportion of EBV DNA molecules of sizes between 80 and 110 bp.

Figure 29B:
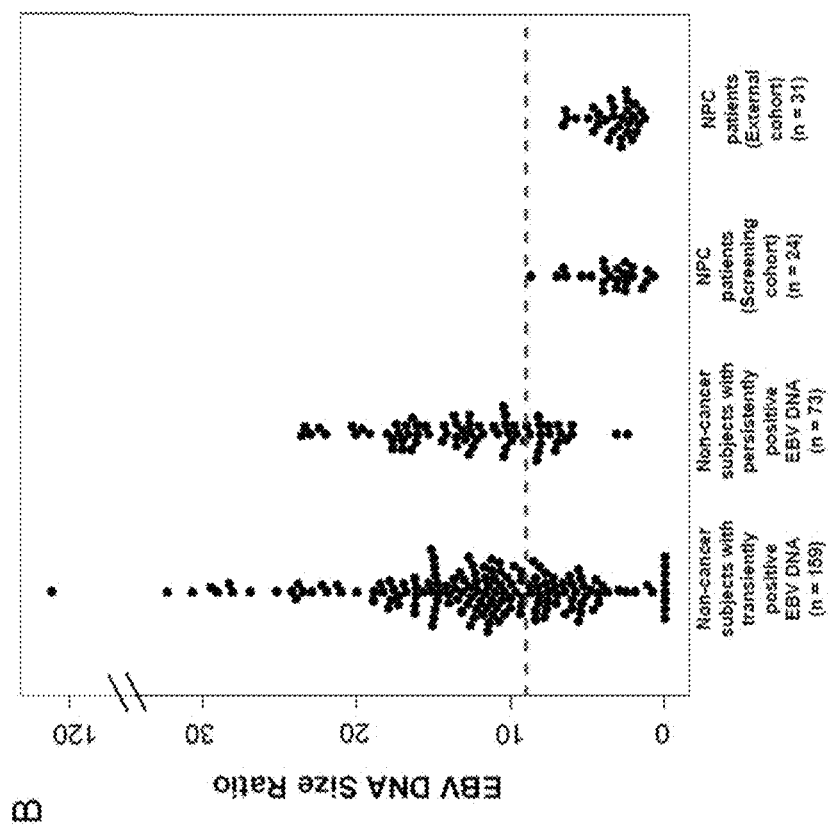
FIG. 29B shows the EBV DNA size ratios of the NPC patients and non-cancer subjects with transiently positive and persistently positive results in the validation sample set also used for FIG. 13B.
Figure 29A:
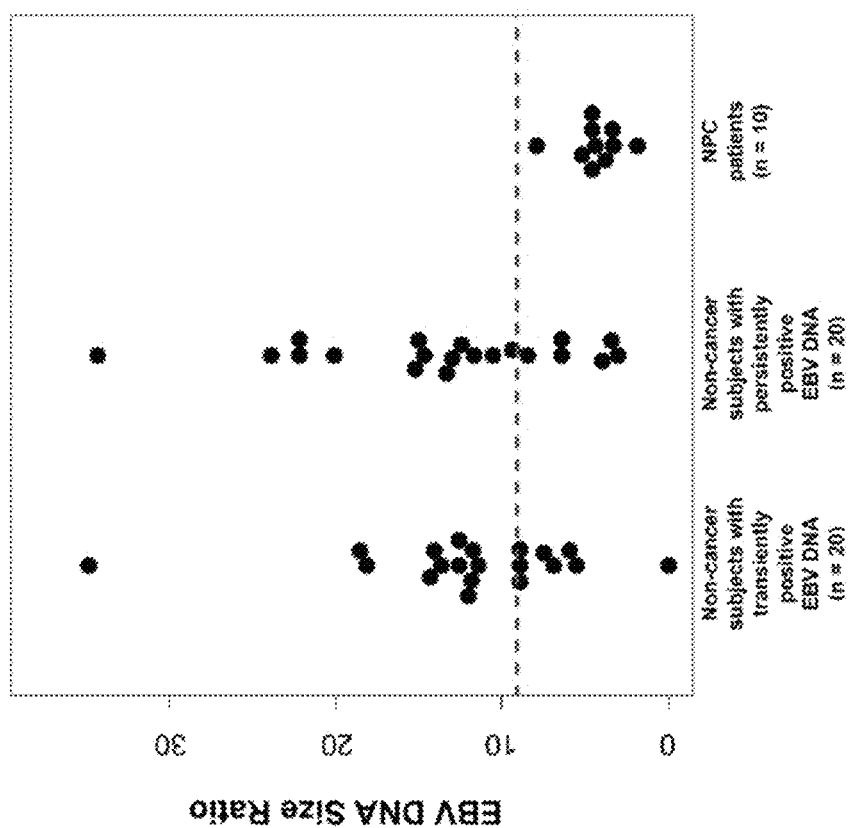
FIG. 29A shows the EBV size ratios of cancer and non-cancer cases in the exploratory sample set also used for FIG. 13A.

FIG. 29A shows the EBV size ratios of cancer and non-cancer cases in the exploratory sample set also used for FIG. 13A. A cutoff value was defined at 3 standard deviations above the mean values of the EBV size ratios of all the 10 cancer patients in the exploratory dataset. The cutoff value of 9.1 is denoted by the red dotted line.

Using this cutoff value, 8 of 20 subjects with transiently positive and 6 of 20 subjects with persistently positive EBV DNA results passed the cutoff in the size-based analysis. The median size ratio from samples of NPC patients (median, 4.5; IQR, 3.5 to 4.6) was significantly lower than the mean ratios from samples of non-cancer subjects with transiently (mean, 11.8; IQR, 8.6 to 13.8, P=0.001, Kruskal-Wallis test) or persistently positive plasma EBV DNA (mean, 12.7; IQR, 8.0 to 16.5, P=0.0005, Kruskal-Wallis test).

FIG. 29B shows the EBV DNA size ratios of the NPC patients and non-cancer subjects with transiently positive and persistently positive results in the validation sample set also used for FIG. 13B. The same cutoff value of 9.1 defined in the exploratory dataset is denoted by the red dotted line.

In FIG. 29B, lower EBV DNA size ratios were observed in samples of NPC patients from both the screening (median, 3.2; IQR, 2.4 to 4.2) and external cohorts (median, 3.0; IQR, 2.4 to 4.3) than samples of non-cancer subjects with transiently positive (median, 11.3; IQR, 7.6 to 15.1; P<0.0001) and persistently positive results (median, 12.7; IQR, 9.0 to 16.5; P<0.0001). These results demonstrated that the finding of a lower proportion of short EBV DNA fragments in patients with NPC from the exploratory dataset was also observed in the external cohort. With the cutoff value of 9.1 defined in the exploratory dataset, all the samples of NPC patients from both cohorts had EBV DNA size ratio smaller than the cutoff value. There were 55 (out of 159) subjects with transiently positive results and 19 (out of 73) subjects with persistently positive results who passed the cutoff in the size-based analysis.

In fact, if we apply these performance characteristics of this size ratio-based approach to the sample cohorts of the prospective screening study of 20,174 asymptomatic subjects, the test would show 97.1% sensitivity, 98.3% specificity and a PPV of 8.9% (Table 4). In other words, determining the plasma EBV DNA size ratio would fare well as a standalone test for differentiating between individuals with and without NPC but with detectable plasma EBV DNA. The plasma EBV DNA size profile assessment test would be able to identify the presence or absence of EBV DNA sequences at the same time when the system or algorithm determines the size profile of any EBV DNA molecules that are found in the sample.

C. Further Results

The analysis above illustrates that a statistical value of a size distribution of sequence reads in a cell-free sample that align to the EBV genome can provide a useful standalone test to screen early stages of NPC. Further results are provided for EBV, HBV, and HPV.

1. EBV

Figure 30:
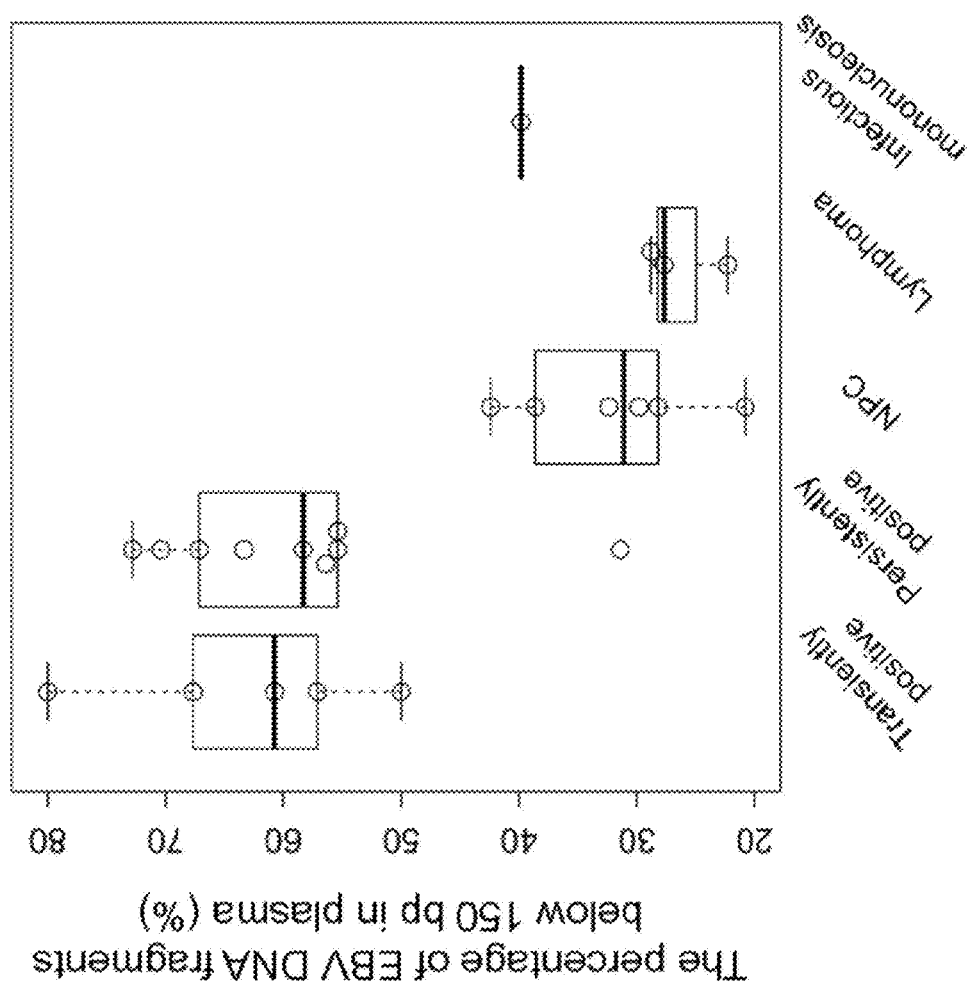
FIG. 30 shows the percentage of sequenced plasma EBV DNA fragments below 150 bp.

FIG. 30 shows the percentage of sequenced plasma EBV DNA fragments below 150 bp. The proportions of EBV DNA fragments below 150 bp were lower in subjects with NPC, lymphoma and infectious mononucleosis when compared with those with transiently positive or persistently detectable plasma EBV DNA but no observable pathology. These results suggest that the analysis of the size of sequenced plasma EBV DNA fragments can be used to differentiate subjects with cancers from those without any observable pathology.

Figure 31:
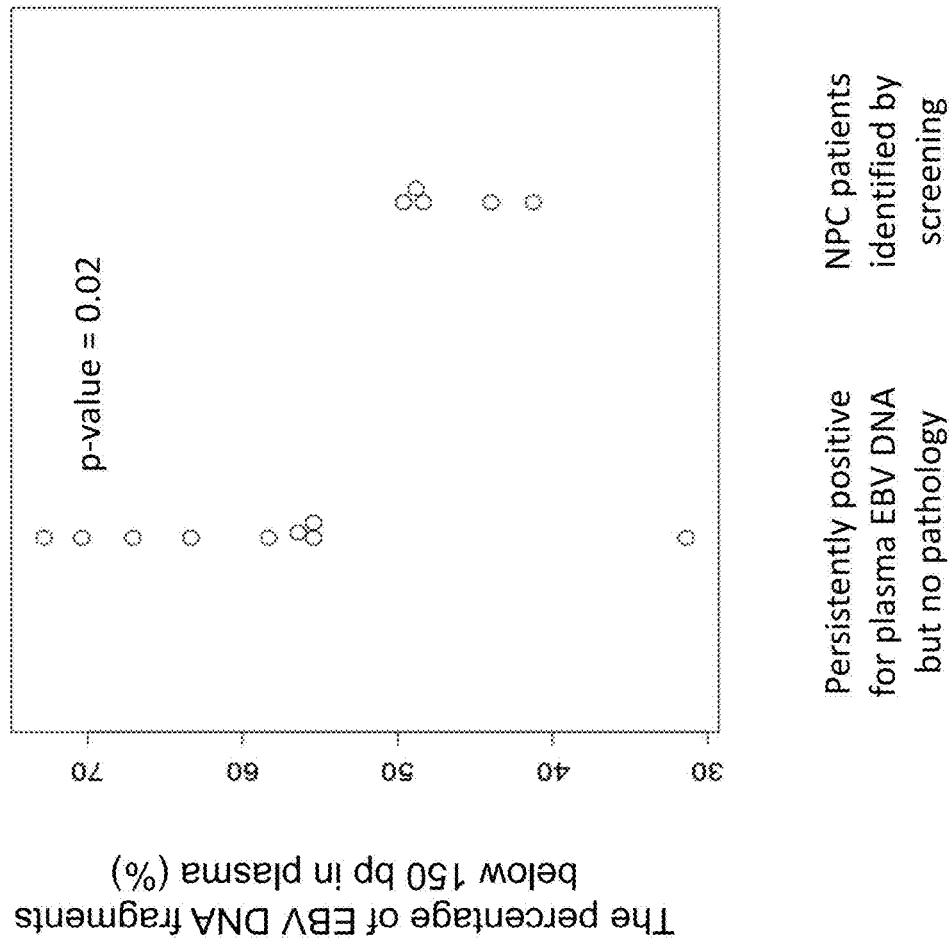
FIG. 31 shows the percentage of EBV DNA fragments below 150 base pairs (bp) in plasma for (left) subjects persistently positive for plasma EBV DNA but having no observable pathology, and (right) early-stage NPC patients identified by screening.

FIG. 31 shows the percentage of EBV DNA fragments below 150 base pairs (bp) in plasma for (left) subjects persistently positive for plasma EBV DNA but having no observable pathology, and (right) NPC subjects. While the proportion of sequenced plasma DNA reads mapped to the EBV genome were not significantly different between the false-positive cases and the cohort 2 NPC cases, the cohort 2 NPC subjects showed significantly lower proportion of short plasma EBV DNA fragments than the subjects with false-positive results (P=0.02, Mann-Whitney test). These results support that the analysis of the size of sequenceable plasma EBV DNA can be used to differentiate NPC subjects from subjects with false-positive plasma EBV DNA results even when the concentrations of plasma EBV DNA for the two groups are similar.

Figure 32:
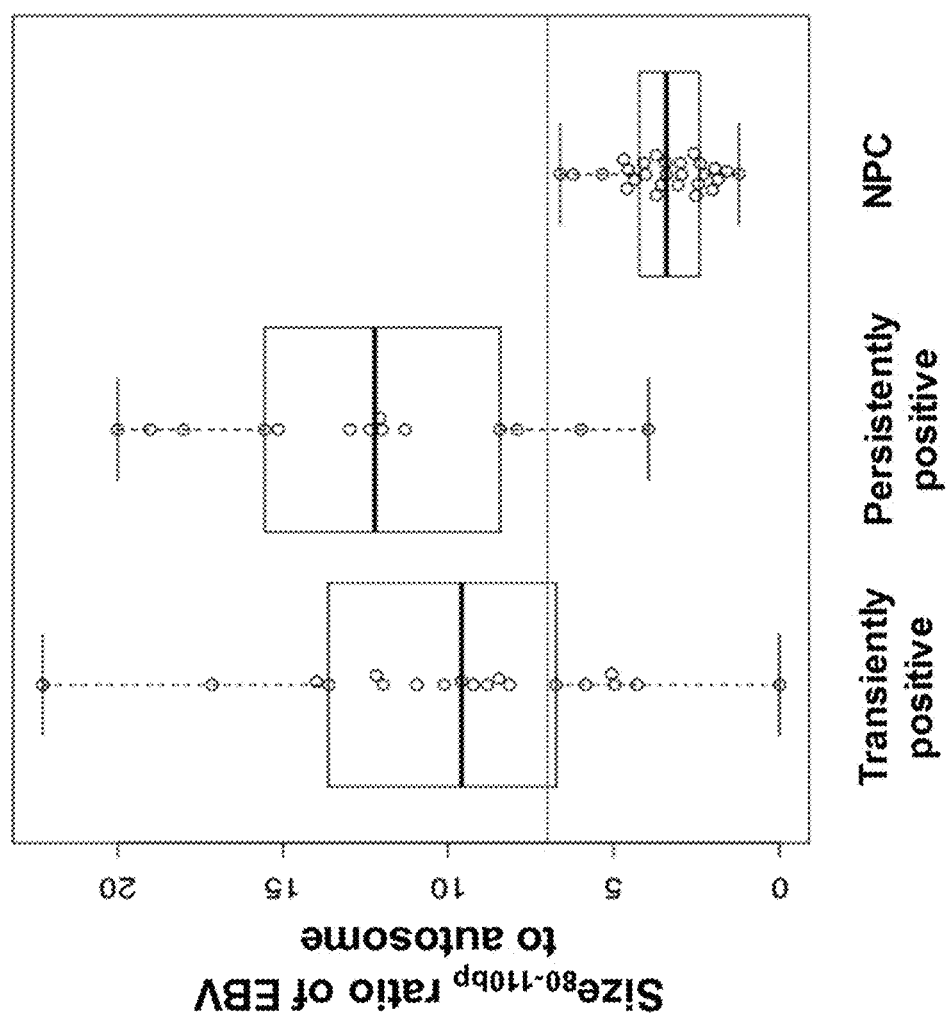
FIG. 32 shows the size ratio of plasma EBV DNA fragments between 80 and 110 base pairs in length to autosomal DNA fragments between 80 and 110 base pairs in length in subjects that are transiently positive or persistently positive for plasma EBV DNA (left or middle, respectively) but have no observable pathology, and subjects identified as having NPC.

FIG. 32 shows the size ratio of plasma EBV DNA fragments between 80 and 110 base pairs in length to autosomal DNA fragments between 80 and 110 base pairs in length in subjects that are transiently positive or persistently positive for plasma EBV DNA (left or middle, respectively) but have no observable pathology, and subjects identified as having NPC. By determining the size ratio (e.g. the proportion of plasma EBV DNA fragments within a certain size range divided by the proportion of autosomal DNA fragments within the corresponding size range) of fragments between 80 and 110 base pairs, we could observe a statistically significant difference between subjects with NPC and subjects with false-positive plasma EBV DNA results (p-value<0.0001; Mann-Whitney U test). Subjects with NPC have a lower size ratio within the size range of 80 to 110 bp than subjects with false-positive plasma EBV DNA results. Accordingly, patients with NPC had a lower proportion of plasma EBV reads within the size range of 80-110 bp among all sequenced EBV reads compared to subjects with transiently positive or persistently positive plasma EBV results.

Figure 33:
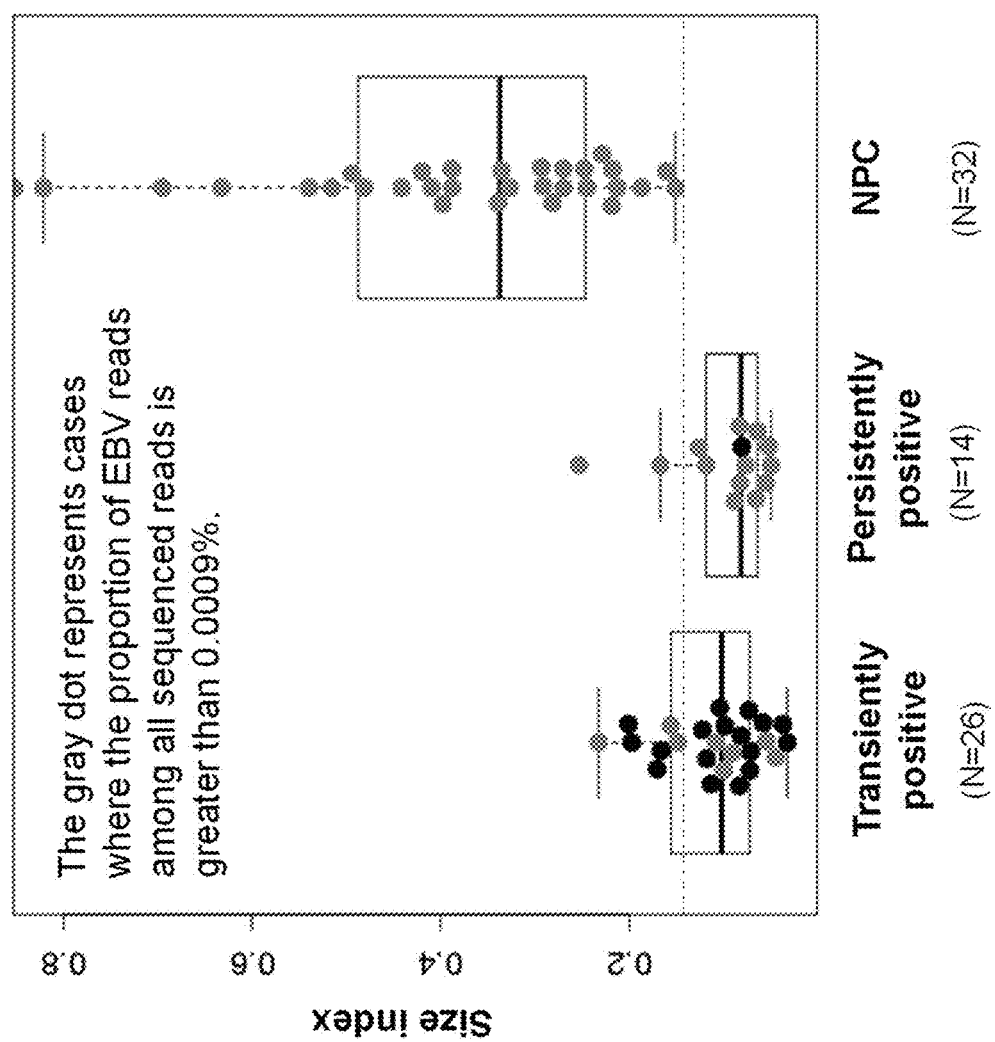
FIG. 33 shows a size index (e.g., an inverse of the size ratio) in subjects that are transiently positive or persistently positive for plasma EBV DNA (left or middle, respectively) but have no observable pathology, and subjects identified as having NPC.

FIG. 33 shows a size index (e.g., an inverse of the size ratio) in subjects that are transiently positive or persistently positive for plasma EBV DNA (left or middle, respectively) but have no observable pathology, and subjects identified as having NPC. A size index can be defined as the inverse of the size ratio, and the size ratio is defined as the proportion of plasma EBV DNA fragments within a certain size range divided by the proportion of autosomal DNA fragments within the corresponding size range. Subjects with NPC were differentiated from subjects with persistently positive plasma EBV DNA based on the difference in the size profile of plasma EBV DNA reads. Using a cutoff value for the size ratio of 7 (e.g., size index greater than 0.14), subjects having NPC were differentiated from the majority of subjects with persistently positive plasma EBV DNA. Gray dots represent cases where the proportion of plasma EBV DNA reads among all sequenced reads were greater than 0.0009% (see, e.g., FIG. 14). Three out of the eight subjects with transiently positive plasma EBV DNA had the size index greater than 0.14. Two out of the thirteen subjects with persistently positive plasma EBV DNA had the size index greater than 0.14. All patients with NPC had the size index greater than 0.14. In some embodiments, a cutoff value for the size index may be used to determine if a subject has a condition (e.g., NPC), is falsely positive for a condition, or does not have a condition.

Figures 34A, 34B:
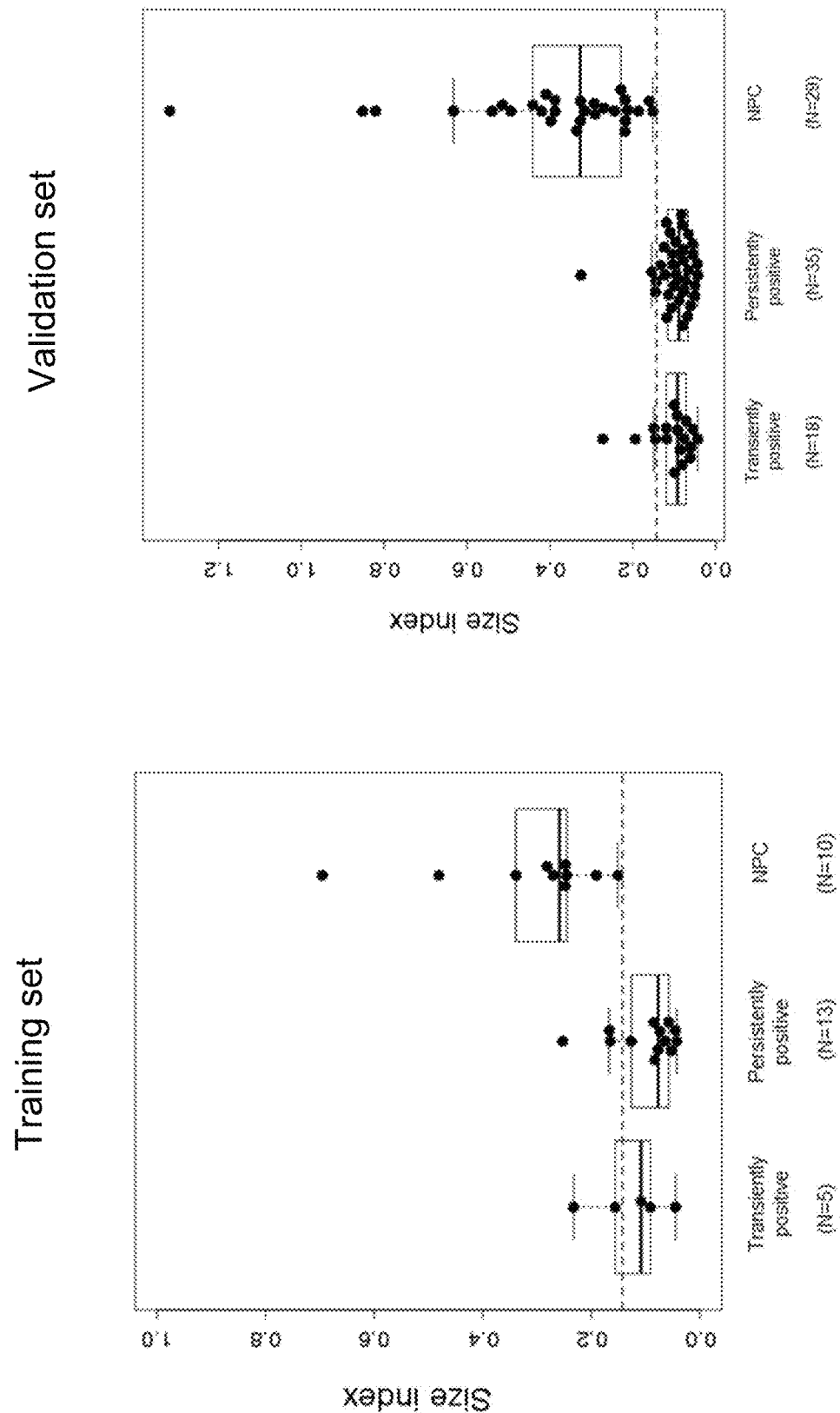
FIG. 34A shows a size index (e.g., an inverse of the size ratio) in subjects that are transiently positive or persistently positive for plasma EBV DNA (left or middle, respectively) but have no observable pathology, and subjects identified as having NPC (right) for a training set.
FIG. 34B shows a size index (e.g., an inverse of the size ratio) in subjects that are transiently positive or persistently positive for plasma EBV DNA (left or middle, respectively) but have no observable pathology, and subjects identified as having NPC (right) for a validation set.

FIG. 34A shows a size index (e.g., an inverse of the size ratio) in subjects that are transiently positive or persistently positive for plasma EBV DNA (left or middle, respectively) but have no observable pathology, and subjects identified as having NPC (right) for a training set. Subjects with NPC were differentiated from subjects with persistently positive plasma EBV DNA based on the difference in the size index of plasma EBV DNA reads.

In one embodiment, the cutoff value for the size index can be determined as any value below lowest proportion of the NPC patients being analyzed. In the current example, a cutoff value of greater than 0.143% (i.e. size ratio of less than 7) can be set to capture all the NPC patients. Using a cutoff value for the size index greater than 0.143, subjects having NPC were differentiated from the majority of subjects with persistently positive plasma EBV DNA. All patients with NPC had the size index greater than 0.143.

FIG. 34B shows a size index (e.g., an inverse of the size ratio) in subjects that are transiently positive or persistently positive for plasma EBV DNA (left or middle, respectively) but have no observable pathology, and subjects identified as having NPC (right) for a validation set. Using a cutoff value for the size index of greater than 0.143, subjects having NPC were differentiated from the majority of subjects with persistently positive plasma EBV DNA. All patients with NPC had the size index greater than 0.143.

2. HBV

Figure 35B:
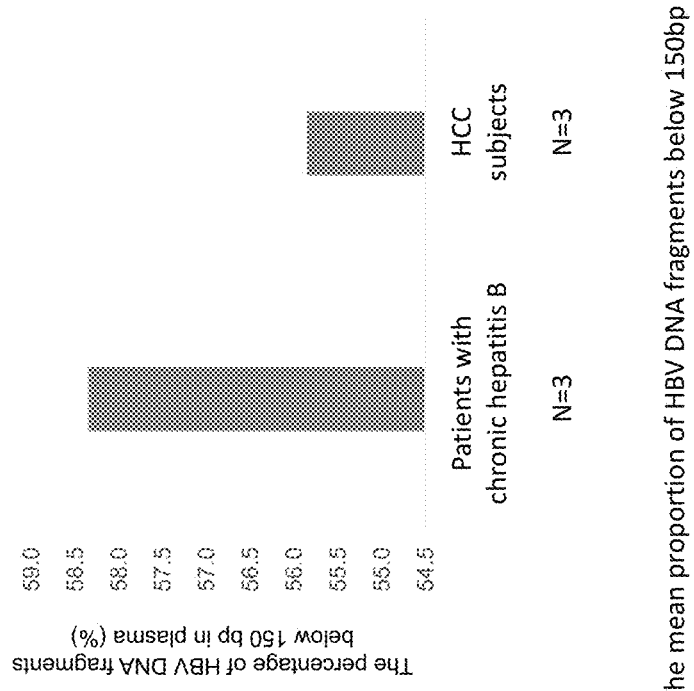
FIG. 35B shows a bar plot of the percentage of HBV DNA fragments below 150 bp in plasma in (left) subjects having chronic hepatitis B and (right) HCC subjects.
Figure 35A:
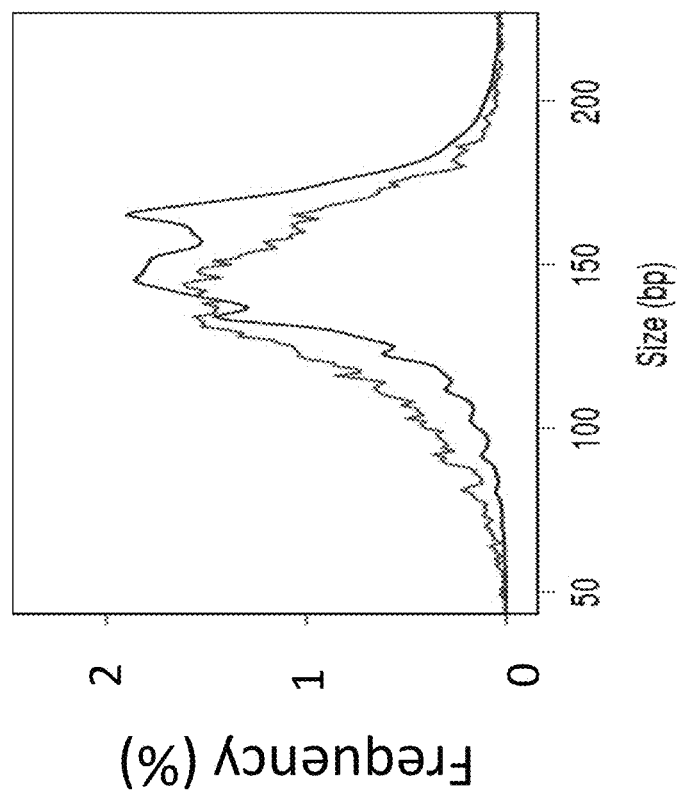
FIG. 35A shows the size distribution of sequenced plasma DNA fragments mapped to the HBV genome and human genome in an HCC subject.

FIG. 35A shows the size distribution of sequenced plasma DNA fragments mapped to the HBV genome and human genome in a HCC subject. Similar to the pattern of the NPC subjects, the size distribution of plasma DNA fragments aligned to the HBV genome was shorter than that of the fragments aligned to the human genome.

FIG. 35B shows a bar plot of the percentage of HBV DNA fragments below 150 bp in plasma in (left) subjects having chronic hepatitis B and (right) HCC subjects. The mean percentage of sequenced plasma HBV DNA of <150 bp was higher in the chronic HBV carriers compared with the HCC subjects. This observation is consistent with the size difference between NPC subjects and those with false-positive plasma EBV DNA results.

3. HPV

The size profile of the plasma HPV DNA sequences can allow one to distinguish those with HPV-related cancer and individuals without cancer but with detectable plasma HPV DNA due to other benign conditions. The size profile of the plasma HPV DNA sequences can further allow one to distinguish between HPV-related cancers of different tissue origin, for example CC and HNSCC.

Figure 36:
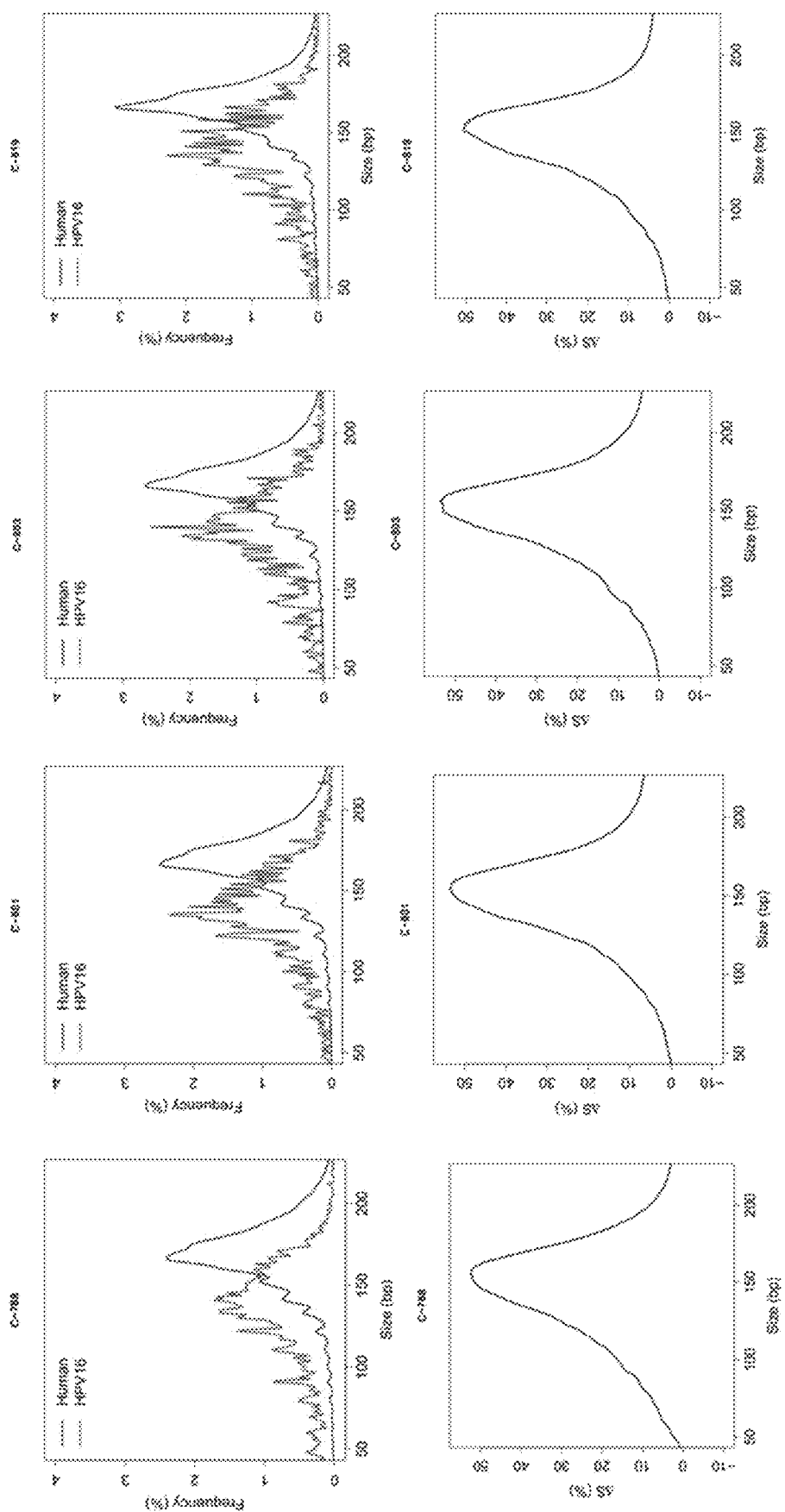
FIGS. 36 and 37 show the size distributions of sequenced plasma HPV DNA fragments and DNA fragments mapped to human genome (autosomal DNA fragments) in 8 subjects having carcinoma of cervix (C-788, C-801, C-803, C-819, C-822, C-877, 3485, 3276).
Figure 37:
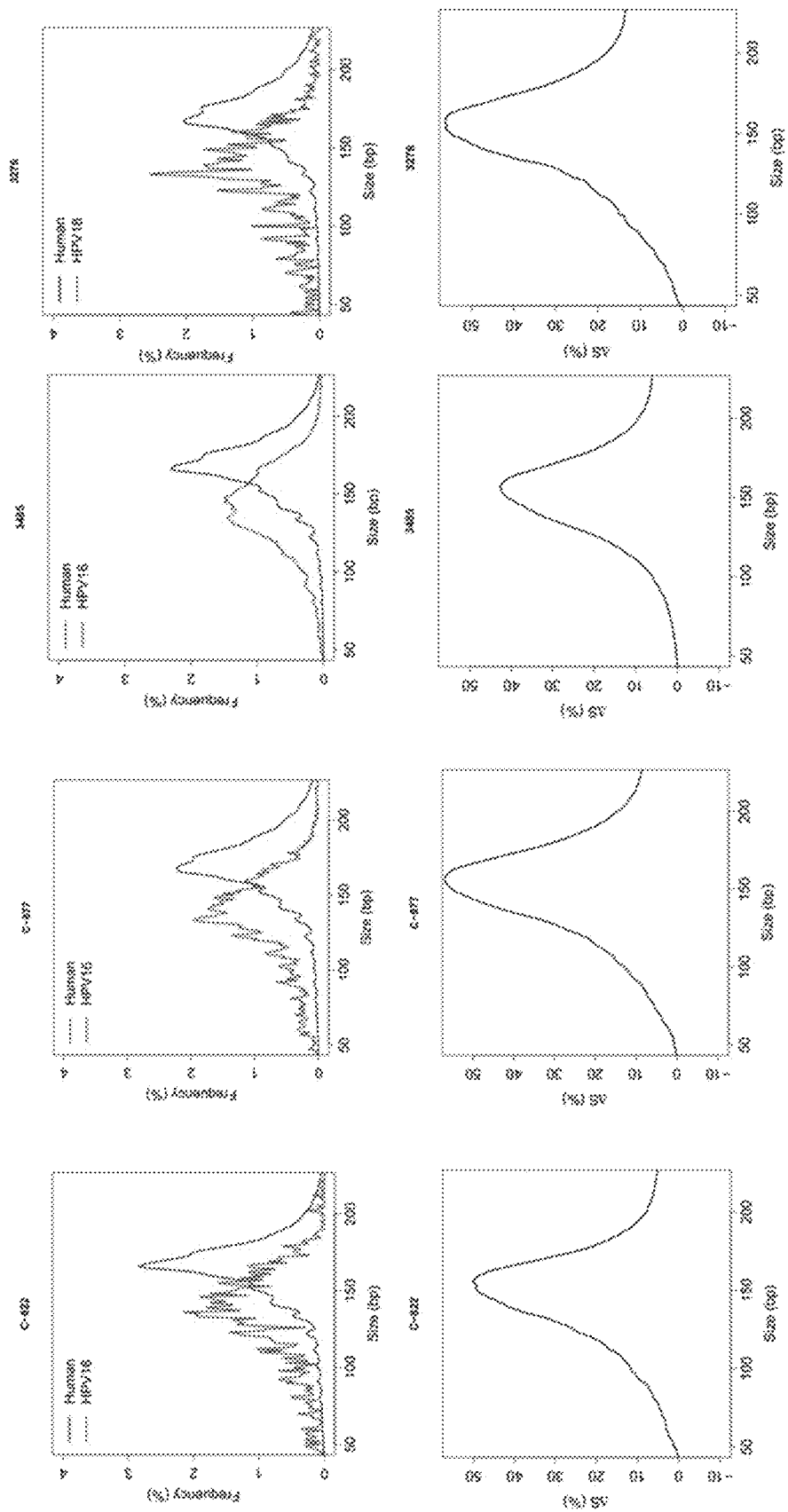

FIGS. 36 and 37 show the size distributions of sequenced plasma HPV DNA fragments and DNA fragments mapped to human genome (autosomal DNA fragments) in 8 subjects having carcinoma of cervix (C-788, C-801, C-803, C-819, C-822, C-877, 3485, 3276). Using paired-end sequencing, the size of each plasma HPV DNA fragment was deduced based on the coordinates of the outermost nucleotide on each of the two ends of the sequenced HPV DNA fragment. For each patient with carcinoma of cervix, the size distribution of plasma HPV fragments is shorter than autosomal DNA fragments. Even for patients with low level of HPV DNA (fewer than 100 HPV DNA reads), a similar cumulative frequency difference (ΔS) curve which peaks at around 150 bp were derived. This suggested that the size profiles of plasma HPV DNA are similar among patients with carcinoma of cervix and could be utilized for size-based diagnostics for HPV-related diseases.

Figure 38:
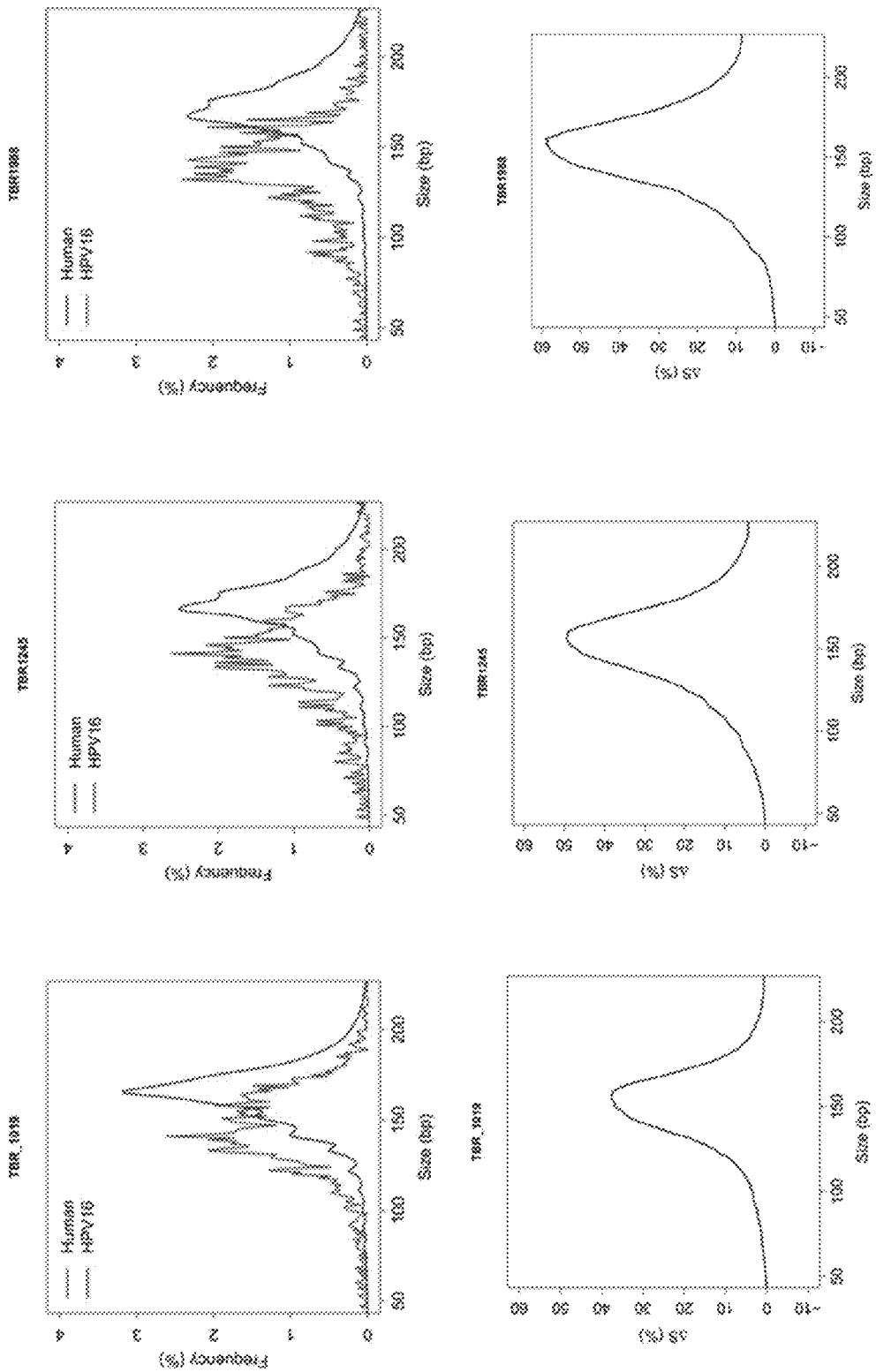
FIGS. 38 and 39 show the size distributions of sequenced plasma HPV DNA fragments and DNA fragments mapped to human genome (autosomal DNA fragments) in 3 subjects having HPV positive head and neck squamous cell carcinoma (HPV+ve HNSCC).
Figure 39:
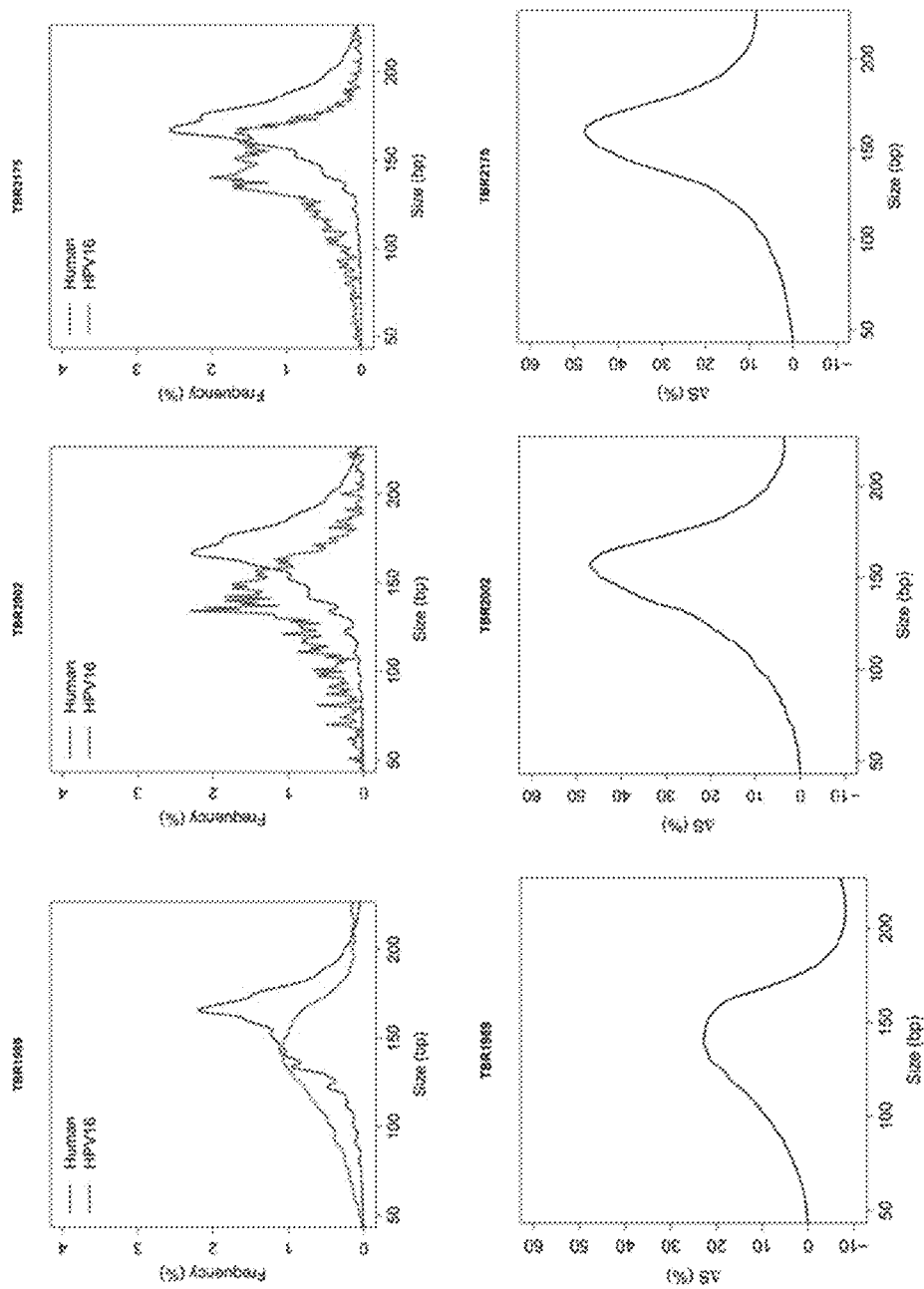

FIGS. 38 and 39 show the size distributions of sequenced plasma HPV DNA fragments and DNA fragments mapped to human genome (autosomal DNA fragments) in 6 subjects having HPV positive head and neck squamous cell carcinoma (HPV+ve HNSCC) (TBR1019, TBR1245, TBR1988, TBR1989, TBR2002 an TBR2175). For each patient with HPV+ve HNSCC, we could observe a similar size distribution curve of plasma HPV fragments. The size distribution of plasma HPV fragments is shorter than autosomal DNA fragments. This suggested that the size profiles of plasma HPV DNA are similar among patients with HPV+ve HNSCC and could be utilized for size-based diagnostics for HPV-related diseases.

D. Various Statistical Values

It should be understood that the size threshold (e.g., 150 bp in FIG. 31) may be any value. The size threshold may be at least about 10 bp, 20 bp, 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp, 105 bp, 110 bp, 115 bp, 120 bp, 125 bp, 130 bp, 135 bp, 140 bp, 145 bp, 150 bp, 155 bp, 160 bp, 165 bp, 170 bp, 175 bp, 180 bp, 185 bp, 190 bp, 195 bp, 200 bp, 210 bp, 220 bp, 230 bp, 240 bp, 250 bp, or greater than 250 bp. For example, the size threshold can be 150 bp. In another example, the size threshold can be 180 bp. In some embodiments, an upper and a lower size threshold may be used (e.g., a range of values). In some embodiments, an upper and a lower size threshold may be used to select nucleic acid fragments having a length between the upper and lower cutoff values. In some embodiments, an upper and a lower cutoff may be used to select nucleic acid fragments having a length greater than the upper cutoff value and less than the lower size threshold.

Various statistical values of a size distribution of nucleic acid fragments can be determined. For example, an average, mode, median, or mean of a size distribution can be used. Other statistical values can be used, e.g., a cumulative frequency for a given size or various ratios of amount of nucleic acid fragments of different sizes. A cumulative frequency can correspond to a proportion (e.g., a percentage) of DNA fragments that are of a given size or smaller, or larger than a given size. The statistical values provide information about the distribution of the sizes of nucleic acid fragments for comparison against one or more cutoffs for determining a level of pathology resulting from a pathogen. The cutoffs can be determined using cohorts of healthy subjects, subjects known to have one or more pathologies, subjects that are false positives for a pathology associated with the pathogen, and other subjects mentioned herein. One skilled in the art will know how to determine such cutoffs based on the description herein, e.g., with reference to a data depicted in FIG. 31.

To perform a size-based analysis, embodiments can calculate a first statistical value of sizes of nucleic acid molecules located in a reference genome of the pathogen (e.g., by aligning a sequence read to the reference genome or using probes). In one embodiment, the first statistical value can be determined from nucleic acid molecules located in one or more particular regions (e.g., regions associated with preferred ending positions) or just the entire reference genome. The first statistical value can be compared to a cutoff to determine a level of pathology.

In some embodiments, the first statistical value of sizes of pathogen fragments can be compared to a reference statistical value of sizes from the human genome. For example, a separation value (e.g. a difference or ratio) can be determined between the first statistical value and a reference statistical value, e.g., determined from other regions in the pathogen reference genome or determined from the human nucleic acids. The separation value can be determined from other values as well. For example, the reference value can be determined from statistical values of multiple regions. The separation value can be compared to a size threshold to obtain a size classification (e.g., whether the DNA fragments are shorter, longer, or the same as a normal region).

Some embodiments can calculate a parameter (separation value), which can be defined as a difference in the proportion of short DNA fragments between the reference pathogen genome and the reference human genome using the following equation:

$$\Delta F = P(\leq 150 \text{ bp})_{test} - P(\leq 150 \text{ bp})_{ref}$$

where $P(\leq 150 \text{ bp})_{test}$ denotes the proportion of sequenced fragments originating from the test tested region with sizes≤150 bp, and $P(\leq 150 \text{ bp})_{ref}$ denotes the proportion of sequenced fragments originating from the reference region with sizes≤150 bp. In other embodiments, other size thresholds can be used, for example but not limited to 100 bp, 110 bp, 120 bp, 130 bp, 140 bp, 160 bp and 166 bp. In other embodiments, the size thresholds can be expressed in bases, or nucleotides, or other units.

A size-based z-score can be calculated using the mean and SD values of ΔF of control subjects.

$$\text{Size-based z-score} = \frac{\Delta F_{sample} - \text{mean } \Delta F_{control}}{SD \; \Delta F_{control}}$$

In some embodiments, a size-based z-score of >3 indicates an increased proportion of short fragments for the pathogen, while a size-based z-score of <−3 indicates a reduced proportion of short fragments for the pathogen. Other size thresholds can be used. Further details of a size-based approach can be found in U.S. Pat. Nos. 8,620,593 and 8,741,811, and U.S. Patent Publication 2013/0237431, all of which are incorporated by reference in its entirety.

To determine a size of a nucleic acid fragment, at least some embodiments can work with any single molecule analysis platform in which the chromosomal origin and the length of the molecule can be analyzed, e.g. electrophoresis, optical methods (e.g. optical mapping and its variants, en.wikipedia.org/wiki/Optical mapping#cite note-Nanocoding-3, and Jo et al. Proc Natl Acad Sci USA 2007; 104: 2673-2678), fluorescence-based method, probe-based methods, digital PCR (microfluidics-based, or emulsion-based, e.g. BEAMing (Dressman et al. Proc Natl Acad Sci USA 2003; 100: 8817-8822), RainDance (www.raindancetech.com/technology/per-genomics-research.asp)), rolling circle amplification, mass spectrometry, melting analysis (or melting curve analysis), molecular sieving, etc. As an example for mass spectrometry, a longer molecule would have a larger mass (an example of a size value).

In one example, nucleic acid molecules can be randomly sequenced using a paired-end sequencing protocol. The two reads at both ends can be mapped (aligned) to a reference genome, which may be repeat-masked (e.g., when aligned to a human genome). The size of the DNA molecule can be determined from the distance between the genomic positions to which the two reads mapped.

Any nucleic acid fragment size or size range may be used to determine the size ratio. In one example, the size ratio can be a ratio of the proportion of viral DNA fragments having a size within 50-75 base pairs in length to the proportion of autosomal DNA fragments having a size within 50-75 base pairs in length. In another example, the size ratio can be a ratio of the proportion of viral DNA fragments having a size within 60-90 base pairs in length to the proportion of autosomal DNA fragments having a size within 60-90 base pairs in length. In another example, the size ratio can be a ratio of the proportion of viral DNA fragments having a size within 70-100 base pairs in length to the proportion of autosomal DNA fragments having a size within 70-100 base pairs in length. In yet another example, the size ratio can be a ratio of the proportion of viral DNA fragments having a size within 90-120 base pairs in length to the proportion of autosomal DNA fragments having a size within 90-120 base pairs in length. In yet another example, the size ratio can be a ratio of the proportion of viral DNA fragments having a size within 120-150 base pairs in length to the proportion of autosomal DNA fragments having a size within 120-150 base pairs in length. In yet another example, the size ratio can be a ratio of the proportion of viral DNA fragments having a size within 150-180 base pairs in length to the proportion of autosomal DNA fragments having a size within 150-180 base pairs in length. In yet another example, the size ratio can be a ratio of the proportion of viral DNA fragments having a size within 180-210 base pairs in length to the proportion of autosomal DNA fragments having a size within 180-210 base pairs in length. In yet another example, the size ratio can be a ratio of the proportion of viral DNA fragments having a size of about 95 base pairs in length to the proportion of autosomal DNA fragments having a size of about 95 base pairs in length. In some embodiments, the size range for viral DNA fragments and the size range for autosomal DNA fragments used to determine the size ratio may be different. For example, the size ratio can be a ratio of the proportion of viral DNA fragments having a size of about 80-110 base pairs in length to the proportion of autosomal DNA fragments having a size of about 120-150 base pairs in length. In another example, the size ratio can be a ratio of the proportion of viral DNA fragments having a size within 80-110 base pairs in length to the proportion of autosomal DNA fragments having a size of about 105 base pairs in length.

E. Method

Figure 40:
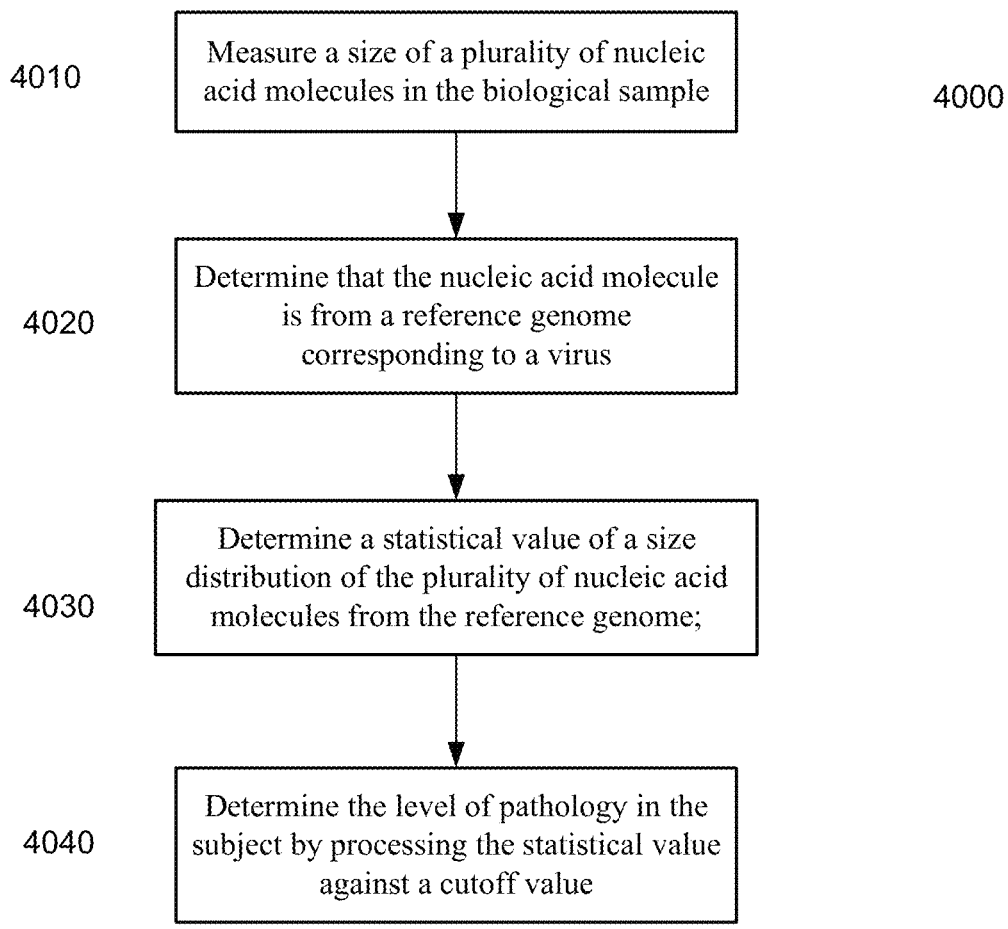
FIG. 40 is a flowchart illustrating a method of using a size distribution of viral DNA fragments to determine a level of cancer according to embodiments of the present invention.

FIG. 40 is a flowchart illustrating a method 4000 of using a size distribution of viral DNA fragments to determine a level of cancer according to embodiments of the present invention. Aspects of method 4000 can be performed in a similar manner as method 2200. At least a portion of the method may be performed by a computer system.

Method 4000 can analyze a biological sample to determine a level of pathology in a subject from which the biological sample is obtained, where the biological sample includes a mixture of cell free nucleic acid molecules. The mixture can include nucleic acid molecules from the subject and potentially nucleic acid molecules from a virus. The analysis can be performed on subjects that are asymptomatic for the pathology (e.g., a type of cancer, CIN, or mononucleosis), and thus identify subjects at an early stage of the pathology.

At block 4010, a size of a plurality of nucleic acid molecules in the biological sample are measured. The size may be measured via any suitable method, for example, methods described above. As examples, the measured size can be a length, a molecular mass, or a measured parameter that is proportional to the length.

In some embodiments, both ends of a nucleic acid molecule can be sequenced and aligned to a genome to determine starting and ending coordinates of the nucleic acid molecule, thereby obtaining a length in bases, which is an example of size. Such sequencing can be targeted sequencing, e.g., involving capture probes as described herein. Other example techniques for determining size include electrophoresis, optical methods, fluorescence-based method, probe-based methods, digital PCR, rolling circle amplification, mass spectrometry, melting analysis (or melting curve analysis), molecular sieving, etc. As an example for mass spectrometry, a longer molecule would have a larger mass (an example of a size value).

At block 4020, it is determined whether a nucleic acid molecule is from a reference genome corresponding to the pathogen. As examples, a location of the nucleic acid molecule in the reference genome can be determined by sequencing and aligning, or using probes corresponding to the reference genome.

In some embodiments, one or more sequence reads that include both ends of the nucleic acid fragment can be received. Thus, a plurality of sequence reads can be obtained from a sequencing of the mixture of cell free nucleic acid molecules. The one or more sequence reads can be aligned to the reference genome to obtain one or more aligned locations. The one or more aligned locations can be used to determine the size of the nucleic acid fragment.

At block 4030, a statistical value of a size distribution of the plurality of nucleic acid molecules from the reference genome is determined. A cumulative frequency of fragments smaller than a size threshold is an example of a statistical value. The statistical value can provide a measure of the overall size distribution, e.g., an amount of small fragments relative to an amount of large fragments. In another embodiment, the statistical value can include a ratio of: (1) a first amount the plurality of nucleic acid molecules in the biological sample from the reference genome that are within a first size range; and (2) a second amount the plurality of nucleic acid molecules in the biological sample from the reference genome that are within a second size range that is different than the first size range. For example, the first range could be fragments below a first size threshold and the second size range could be fragments above a second size threshold. The two ranges can overlap, e.g., when the second size range is all sizes, e.g., as in FIG. 30.

In various embodiments, the statistical value can be an average, mode, median, or mean of the size distribution. In other embodiments, the statistical value can be a percentage of the plurality of nucleic acid molecules in the biological sample from the reference genome that are below a size threshold (e.g., 150 bp). For such a statistical value, the subject can be determined to be positive for the pathology when statistical value is below the cutoff value.

In some embodiments, the statistical value can include a size ratio of (1) a first proportion of sequence reads of nucleic acid molecules that align to the reference genome of the virus with the size within a given range; and (2) a second proportion of sequence reads of nucleic acid molecules that align to a human reference genome with the size within the given range. Such an example is provided in FIG. 32. In various embodiments, the given range can be about 80 to about 110 base pairs, about 50 to about 75 base pairs, about 60 to about 90 base pairs, about 90 to about 120 base pairs, about 120 to about 150 base pairs, or about 150 to about 180 base pairs. In other embodiments, the statistical value can be an inverse of the size ratio, thereby using a size index, e.g., as in FIG. 33.

At block 4040, the level of pathology in the subject is determined by processing the statistical value against one or more cutoff values. For example, the percentage of fragments below a size threshold (e.g., 150) can be compared to a cutoff to determine whether the ratio is below the cutoff. In FIG. 30, a cutoff could be about 45 to discriminate between subjects that are persistently positive for EBV but no pathology (or even transiently positive) and subjects with NPC, lymphoma, or infectious mononucleosis.

In an embodiment where a size ratio is used (e.g., as in FIG. 32), example cutoff values include about 7, about 8, about 9, or about 10. In another embodiment, example cutoff values can be about 0.11, 0.12, 0.13, or 0.14, e.g., when a size index is used.

In various embodiments, the achieved accuracy in discriminating between samples of a set can include: a positive predictive value (PPV) of the determining the level of pathology is at least 6%, 7%, or 8%, wherein a sensitivity of the determining the level of pathology is at least 95%, 96%, or 97%, and/or wherein a specificity of the determining the level of pathology is at least 95%, 96%, 97%, or 98%.

F. Determining Cutoff Value

In some embodiments, a cutoff value for the size ratio may be used to determine if a subject has a condition (e.g., NPC), is falsely positive for a condition, or does not have a condition. For example, subjects with NPC have a lower size ratio within the size range of 80 to 110 bp than subjects with false-positive plasma EBV DNA results. In some embodiments, a cutoff value for a size ratio can be about 0.1, about 0.5, about 1, about 2, about 3, about 4, about 5, about 6, about 7, about 8, about 9, about 10, about 11, about 12, about 13, about 14, about 15, about 16, about 17, about 18, about 19, about 20, about 25, about 50, about 100, or greater than about 100. In some embodiments, a size ratio at and/or below a cutoff value can be indicative of having a condition (e.g., NPC). In some embodiments, a size ratio at and/or above a cutoff value can be indicative of having a condition (e.g., NPC).

In some embodiments, a cutoff value for a size index can be about or least 10, about or least 2, about or least 1, about or least 0.5, about or least 0.333, about or least 0.25, about or least 0.2, about or least 0.167, about or least 0.143, about or least 0.125, about or least 0.111, about or least 0.1, about or least 0.091, about or least 0.083, about or least 0.077, about or least 0.071, about or least 0.067, about or least 0.063, about or least 0.059, about or least 0.056, about or least 0.053, about or least 0.05, about or least 0.04, about or least 0.02, about or least 0.001, or less than about 0.001. In some embodiments, a size index at and/or below a cutoff value can be indicative of having a condition (e.g., NPC). In some embodiments, a size index at and/or above a cutoff value can be indicative of having a condition (e.g., NPC).

In one embodiment, the cutoff value for the size ratio or size index can be determined as any value below lowest proportion of the cancer patients being analyzed. In other embodiments, the cutoff values can be determined for example but not limited to the mean size index of the cancer patients minus one standard deviation (SD), mean minus two SD, and mean minus three SD. In yet other embodiments, the cutoff can be determined after the logarithmic transformation of the proportion of plasma DNA fragments mapped to the viral genome, for example but not limited to mean minus one SD, mean minus two SD, mean minus three SD after the logarithmic transformation of the values of the cancer patients. In yet other embodiments, the cutoff can be determined using Receiver Operator Characteristics (ROC) curves or by nonparametric methods, for example but not limited to including 100%, 95%, 90%, 85%, 80% of the NPC patients being analyzed.

IV. FRAGMENTATION OF PATHOGEN DNA

In this disclosure, we show that there exists a non-random fragmentation process of viral cell-free DNA. Non-random fragmentation process can take place to some extent in various types of biological samples that contain cell-free nucleic acids, e.g. plasma, serum, urine, saliva, cerebrospinal fluid, pleural fluid, amniotic fluid, peritoneal fluid, and ascitic fluid. Cell-free nucleic acids occur naturally in the form of short fragments. Cell-free nucleic acids fragmentation refers to the process whereby high molecular weight nucleic acids (such as DNA in the nucleus of a cell or in a virus) are cleaved, broken, or digested to short fragments when cell-free nucleic acid molecules are generated or released. Discuss of cell-free DNA may equally apply to other cell-free nucleic acids.

Not all cell-free DNA molecules are of the same length. Some molecules are shorter than others. It has been shown that cell-free DNA of a human, such as plasma DNA, is generally shorter and less intact than cellular DNA. Similarly, when a disease process, e.g. cancer, alters the gene expression profile and function of the genome of a cell, the cell-free DNA intact probability profile derived from the cells with disease would be reflective of those cells. The cell-free DNA profile, hence, would provide evidence for or are hallmarks of the presence of the disease. Further, the viral nucleic acids in a cancer cell are affected such that there fragmentation is altered.

Some embodiments further enhance the resolution for studying the profile of cell-free DNA fragmentation. Instead of just summating reads over a stretch of nucleotides to identify regions with higher or lower intact probability or integrity, we studied the actual ending positions or termini of individual cell-free DNA molecules, especially plasma viral nucleic acid molecules. Remarkably, our data reveal that the specific locations of where cell-free viral nucleic acid fragments are cut are non-random. There are certain ending positions of viral nucleic acid fragments that are highly represented within a sample, such as plasma. The number of occurrence or representation of such ending positions is statistically significantly higher than expected by chance alone. We termed these non-random positions of cell-free DNA ending positions as the preferred ending positions or preferred ends. There may also be regions that are non-preferred, e.g., a low level of viral fragments ending at those positions.

A catalog of preferred ends relevant to particular physiological states or pathological states can be identified by comparing the cell-free DNA profiles of preferred ends among individuals with different physiological or pathological states, e.g., cancer compared with non-cancer samples. Another approach is to compare the viral nucleic acid profiles of preferred ends at different time of a physiological (e.g. pregnancy) or pathological (e.g. cancer) process. Examples of such time points include before and after treatment of cancer (e.g. targeted therapy, immunotherapy, chemotherapy, surgery), different time points following the diagnosis of cancer, before and after progression of cancer, before and after development of metastasis, before and after increased severity of disease, or before and after development of complications.

A preferred end can be considered relevant for a physiological or disease state when it has a high likelihood or probability for being detected in that physiological or pathological state. In other embodiments, a preferred end is of a certain probability more likely to be detected in the relevant physiological or pathological state than in other states. Because the probability of detecting a preferred end in a relevant physiological or disease state is higher, such preferred or recurrent ends (or ending positions) would be seen in more than one individual with that same physiological or disease state. The high probability would also render such preferred or recurrent ends to be detectable many times in the same sample or aliquot of the same individual. In some embodiments, a quantitative threshold may be set to limit the inclusion of ends that are detected at least a specified number of times (e.g., 5, 10, 15, 20, etc.) within the same sample or same sample aliquot to be considered as a preferred end.

After a catalog of cell-free DNA preferred ends is established for any physiological or pathological state, targeted or non-targeted methods could be used to detect their presence in cell-free DNA samples, e.g. plasma, or other individuals to determine a classification of the other tested individuals having a similar health, physiologic or disease state. The viral preferred ends could be detected by random non-targeted sequencing. The sequencing depth would need to be considered so that a reasonable probability of identifying all or a portion of the relevant preferred ends could be achieved.

Alternatively, hybridization capture of loci with high density of preferred ends could be performed on the cell-free DNA samples to enrich the sample with cell-free DNA molecules with such preferred ends following but not limited to detection by sequencing, microarray, or the PCR. Yet, alternatively, amplification based approaches could be used to specifically amplify and enrich for the viral nucleic acid fragments with the preferred ends, e.g. inverse PCR, rolling circle amplification. The amplification products could be identified by sequencing, microarray, fluorescent probes, gel electrophoresis and other standard approaches known to those skilled in the art. Further details on targeted sequencing are provided in Materials and Methods section.

In practice, one end position can be the genomic coordinate or the nucleotide identity of the outermost base on one extremity of a cell-free DNA molecule that is detected or determined by an analytical method, such as but not limited to massively parallel sequencing or next-generation sequencing, single molecule sequencing, double- or single-stranded DNA sequencing library preparation protocols, PCR, other enzymatic methods for DNA amplification (e.g. isothermal amplification) or microarray. Such in vitro techniques may alter the true in vivo physical end(s) of the cell-free DNA molecules. Thus, each detectable end may represent the biologically true end or the end is one or more nucleotides inwards or one or more nucleotides extended from the original end of the molecule. For example, the Klenow fragment is used to create blunt-ended double-stranded DNA molecules during DNA sequencing library construction by blunting of the 5' overhangs and filling in of the 3' overhangs. Though such procedures may reveal a cell-free DNA end position that is not identical to the biological end, clinical relevance could still be established. This is because the identification of the preferred being relevant or associated with a particular physiological or pathological state could be based on the same laboratory protocols or methodological principles that would result in consistent and reproducible alterations to the cell-free DNA ends in both the calibration sample(s) and the test sample(s). A number of DNA sequencing protocols use single-stranded DNA libraries (Snyder et al Cell 2016, 164: 57-68). The ends of the sequence reads of single-stranded libraries may be more inward or extended further than the ends of double-stranded DNA libraries.

The genome identity or genomic coordinate of the end position could be derived from results of alignment of sequence reads to a reference genome, e.g. hg19 for a human and a viral reference genome for viral fragments. It could be derived from a catalog of indices or codes that represent the original coordinates of the human genome. While an end is the nucleotide at one or both extremities of a cell-free DNA molecule, the detection of the end could be done through the recognition of other nucleotide or other stretches of nucleotides on the plasma DNA molecule. For example, the positive amplification of a plasma DNA molecule with a preferred end detected via a fluorescent probe that binds to the middle bases of the amplicon. For instance, an end could be identified by the positive hybridization of a fluorescent probe that binds to some bases on a middle section of a plasma DNA molecule, where the fragment size known. In this way, one could determine the genomic identity or genomic coordinate of an end by working out how many bases are external to the fluorescent probe with known sequence and genomic identity. In other words, an end could be identified or detected through the detection of other bases on the same plasma DNA molecule. An end could be a position or nucleotide identity on a cell-free DNA molecule that is read by but not limited to target-specific probes, mini-sequencing, and DNA amplification.

A. Example Quantifying of Fragmentation

Cell-free nucleic acids of the host and viruses that had previously invaded a cell can be subjected to massively parallel sequencing using the Illumina Genome Analyzer platform. Other massively parallel or single molecule sequencers could be used. In some embodiments, paired-end sequencing of the plasma DNA molecules can be performed. For example, each molecule can be sequenced at each end for 50 bp, thus totaling 100 bp per molecule. The two ends of each sequence can be aligned to the reference human genome using the SOAP2 program (Li R et al. Bioinformatics 2009, 25:1966-7). A similar procedure can be used for mapping viral fragments to a reference viral genome.

To reflect the fragmentation patterns, intact probability ($P_I$) can be determined for each nucleotide for the genome based on the sequencing results.

$$P_I = \frac{N_z}{N_T}$$

where $N_z$ is the number of full length sequenced reads covering at least z nucleotides (nt) on both sides (5' and 3') of the target nucleotide; and $N_T$ is the total number of sequenced reads covering the target nucleotide.

The value of $P_I$ can reflect the probability of having an intact DNA molecule centered at a particular position with a length of twice the value of z plus 1 (2z+1). The higher the value of intact probability ($P_I$), the less likely is the plasma DNA being fragmented at the particular nucleotide position. To further illustrate this, the definition of intact probability is illustrated in FIG. 41.

Figure 41:
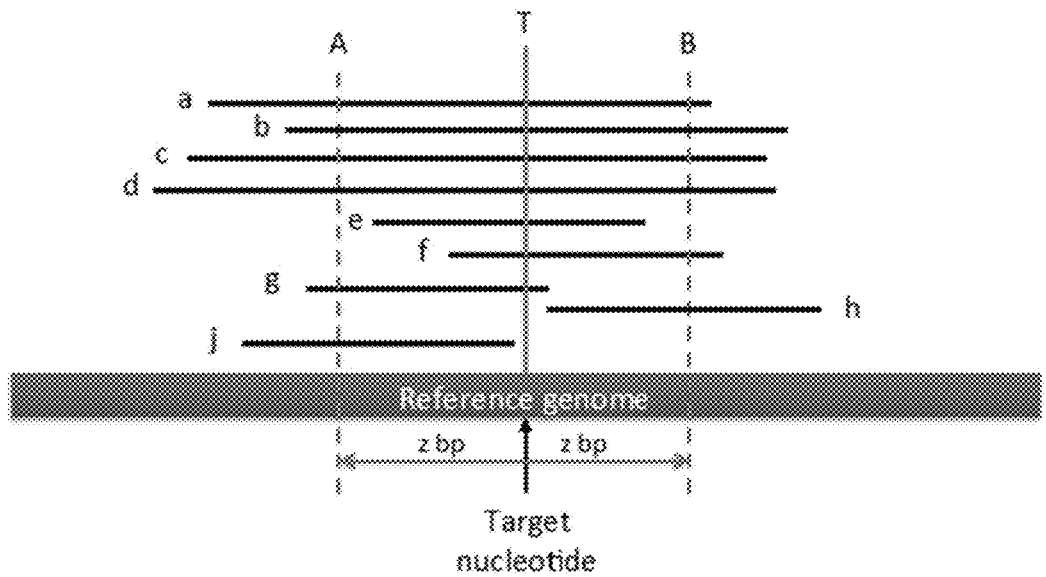
FIG. 41 shows an illustrative example for the definition of intact probability ($P_I$) according to embodiments of the present invention.

FIG. 41 shows an illustrative example for the definition of intact probability ($P_I$). T is the position of the target nucleotide at which $P_I$ is calculated for. A and B are two positions at z nucleotides (nt) upstream (5') and z nt downstream (3') of T, respectively. The black lines labeled from a to j represent sequenced plasma DNA fragments from the maternal plasma. Fragments a to d cover all the three positions A, B and T. Therefore, the number of fragments covering at least z nt on both sides (5' and 3') of the target nucleotide ($N_z$) is 4. In addition, fragments e, f and g also cover the position T, but they do not cover both positions A and B. Therefore, there are a total of 7 fragments covering position T ($N_T$=7). Fragments h and j cover either A or B but not T. These fragments are not counted in $N_z$ or $N_T$. Therefore, the $P_I$ in this particular example is 4/7 (57%).

In one embodiment, $P_I$ can be calculated using 25 as the value of z. Thus, the intact plasma DNA fragments would be defined as fragments covering at least 25 nt upstream of the target position to 25 nt downstream of the target position. In other embodiments, other values of z can be used, for example, but not limited to, 10, 15, 20, 30, 35, 40, 45, 50, 55, 60, 65, 70, 75 and 80.

$P_I$ is an example of a relative abundance of nucleic acid fragments ending within a window of genomic positions. Other metrics can be used, e.g., the reciprocal of $P_I$, which would have an opposite relationship with the probability of having an intact DNA molecule. A higher value of the reciprocal of $P_I$ would indicate a higher probability of being an ending position or an ending window. Other examples are a p-value for a measured number of ending DNA fragments vs. an expected number of ending DNA fragments, a proportion of DNA fragments ending out of all aligned DNA fragments, or a proportion of preferred end termination ratio (PETR), which may be defined in the follow manner.

$$ETR = \frac{\text{No. of DNA fragments end on the nucleotide}}{\text{No. of DNA fragments covering the nucleotide but not end on it}}$$

All such metrics of a relative abundance can measure a rate at which cell-free DNA fragments end within a window, e.g., with a width of 2z+1, where z can be zero, thereby causing the window to be equivalent to a genomic position. Further details on fragmentation and related metrics can be found in PCT Publication WO 2017/012592, which is incorporated by reference in its entirety.

B. Frequency of Ending Positions of Pathogen DNA Fragments

Figure 42:
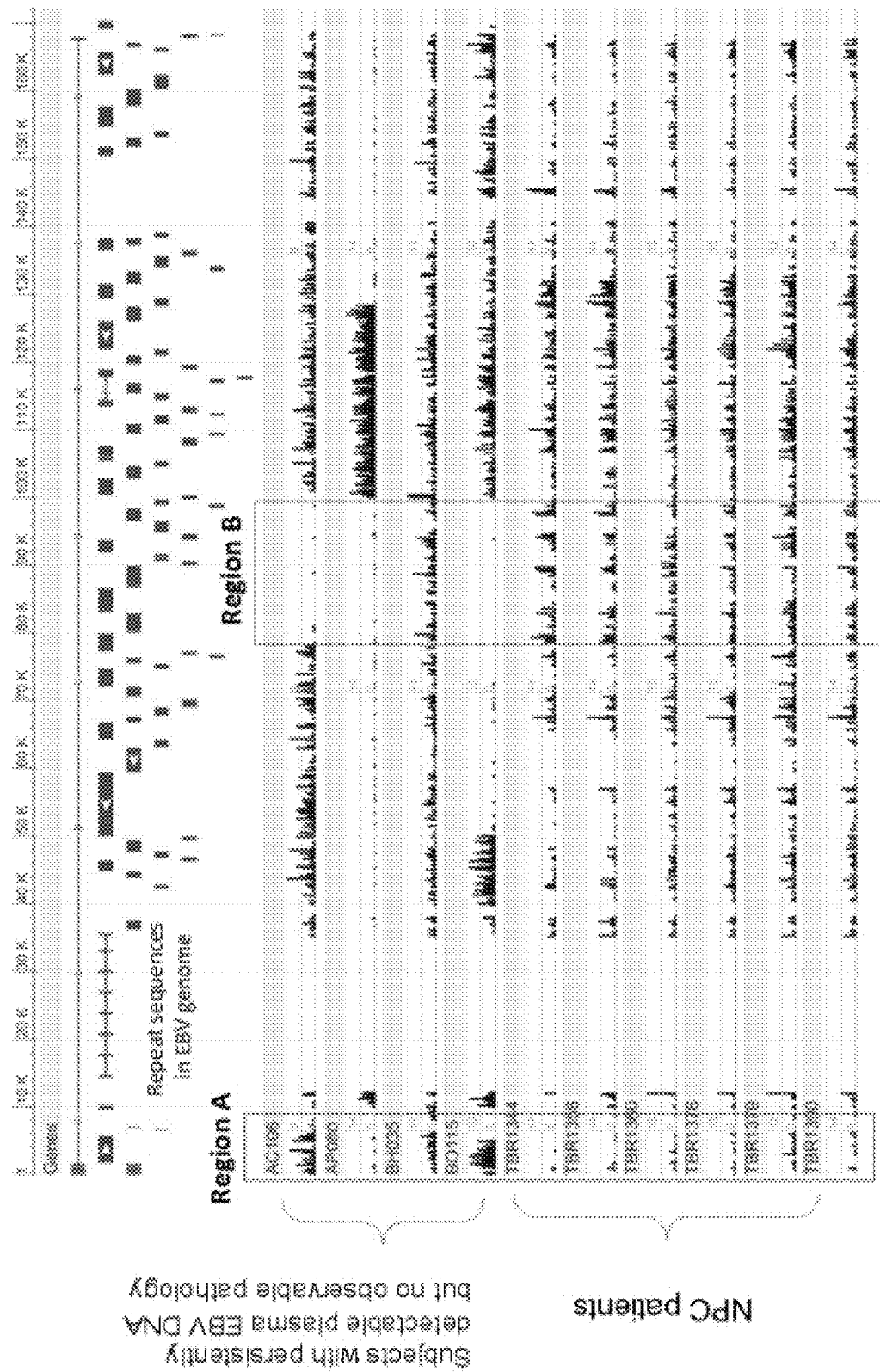
FIG. 42 shows the frequency of plasma EBV DNA fragments ending on each nucleotide in the EBV genome for 4 subjects with persistently false-positive plasma EBV DNA and no observable pathology, and 6 NPC patients.

FIG. 42 shows the frequency of a plasma EBV DNA fragments ending on each nucleotide in the EBV genome for 4 subjects with persistently false-positive plasma EBV DNA and no observable pathology, and 6 NPC subjects. As the numbers of plasma EBV DNA fragments were very small in the subjects with transiently detectable plasma EBV DNA, they are not shown as examples here. The y-axis is the number of plasma EBV DNA fragments ending on a particular nucleotide and the x-axis is the genomic coordinates in the EBV genome.

We observed that the distributions of the ending positions were different between subjects with false-positive results but no observable pathology and NPC subjects. For example, more plasma EBV DNA fragments ended on positions located within Region A in subjects without any pathology whereas more plasma EBV DNA fragments ended on positions located within Region B in NPC subjects. In the region with repeating elements in the EBV genome, the sequenced plasma EBV DNA fragments cannot be mapped to unique locations in the EBV genome. Therefore, there were no uniquely alignable sequenced reads ending within the region with repeats in the EBV genome.

These results suggest that the analysis of the ending positions of the plasma EBV DNA fragments on the EBV genome can be used for differentiating subjects with false-positive results but no pathology from the NPC subjects. The analysis of the ending positions can be performed by but not limited to non-targeted massively parallel sequencing or single molecule sequencing, massively parallel sequencing or single molecule sequencing after target enrichment, amplicon sequencing, real-time PCR, digital PCR, inverse PCR and anchor PCR. For amplicon sequencing, real-time PCR and digital PCR, one embodiment is to have primers or probes covering the specific ending positions.

The analysis could be performed with or without amplification. For amplification based approaches, oligonucleotides complementary to the specific ending positions may be used to enrich for the informative ends (e.g., a nucleic acid fragment having a particular ending-motif). Positive amplification could be interpreted as indicating the presence of such informative ends. Alternatively, the amplified products could be followed by additional steps to identify or confirm the presence of the informative ends. Methods used to detect or confirm the presence of the informative ends could include any one of the following but are not limited to hybridization methods, such as oligonucleotide probes, antibody probes, mini-sequencing, direct sequencing, massively parallel sequencing, single molecule sequencing, mass spectrometry, ligation based assays. Such detection or confirmatory methods could be applied to non-amplification based approaches. Both the amplification and non-amplification based methods for the detection of informative ends could be preceded or followed by hybridization based methods to enrich the sample with viral DNA sequences. Amplification-based methods could be used to enrich the sample with viral DNA sequences.

To demonstrate the association of ending positions with disease conditions, we randomly picked one subject with persistently detectable plasma EBV DNA but no pathology, and one NPC subject for mining the frequent ending positions. We ranked the coordinates of the EBV genome in a descending number of plasma EBV DNA fragments ending on it for the two cases. For such an analysis, the EBV genome coordinate with the largest number of fragments ending on it would be ranked number 1.

For illustration purpose, the coordinates ranking in the top 400 were selected for each of the two cases. In other embodiments, different number of top-ranked coordinates can be selected for the analysis. As examples, the coordinates ranking in the top 100, top 200, top 300, top 500, top 600, top 800 and top 1000 can be selected. In yet another embodiment, the top-ranked coordinates shared by subjects with the same disease status, for example, subjects with NPC, can be selected. In yet another embodiment, the probability of coordinates which have significantly higher probability of being an ending position for plasma EBV DNA in certain disease status can be used. Examples of the thresholds for p-values include but not limited to 0.1, 0.05, 0.01, 0.005, 0.001 and 0.0001. In one embodiment, top-ranked positions shared by a significant proportion of subjects with the same disease status can be used. In yet another embodiment, the top-ranked positions of different subjects with the same disease status can be pulled together. In yet another embodiment, the top-ranked positions shared by a larger proportion of subjects can be given a larger weight and those shared by a smaller proportion of subjects can be given a smaller weight, so that a weighted score can be calculated.

Figure 43:
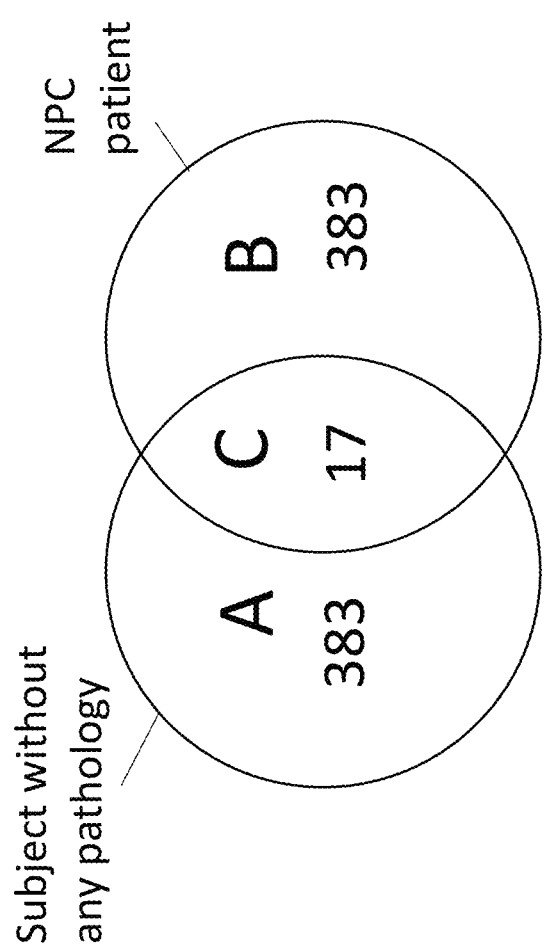
FIG. 43 shows a Venn diagram depicting (A) the number of preferred ending positions specific to subjects not having an observable pathology (383), (B) the number of preferred ending positions specific to subjects having NPC (383), and (C) the preferred ending positions shared by both groups of subjects (17).

FIG. 43 shows a Venn diagram depicting (A) the number of preferred ending positions specific to subjects not having an observable pathology (e.g., 383), (B) the number of preferred ending positions specific to subjects having NPC (e.g., 383), and (C) the preferred ending positions shared by both groups of subjects (e.g., 17). The coordinates within the top 500 rankings in the subject with false-positive EBV DNA but not top-ranked in the NPC subject are denoted as Set A positions. The coordinates within the top 500 rankings in the NPC subject but not top-ranked in the subject with false-positive plasma EBV DNA result are denoted as Set B positions. The coordinates that ranked within the top 400 in both cases are denoted as Set C positions. Only 4.25% of the common ending positions were shared by both cases.

To demonstrate if subjects with the same disease status, for example, with NPC, would share the same preferred ending positions in the EBV genome, we calculated the percentage of fragments ending on the Set A and Set B coordinates for eight subjects with persistently detectable plasma EBV DNA but no pathology and five NPC subjects. The two subjects from whom these coordinates were determined were not included in this analysis.

Figure 44:
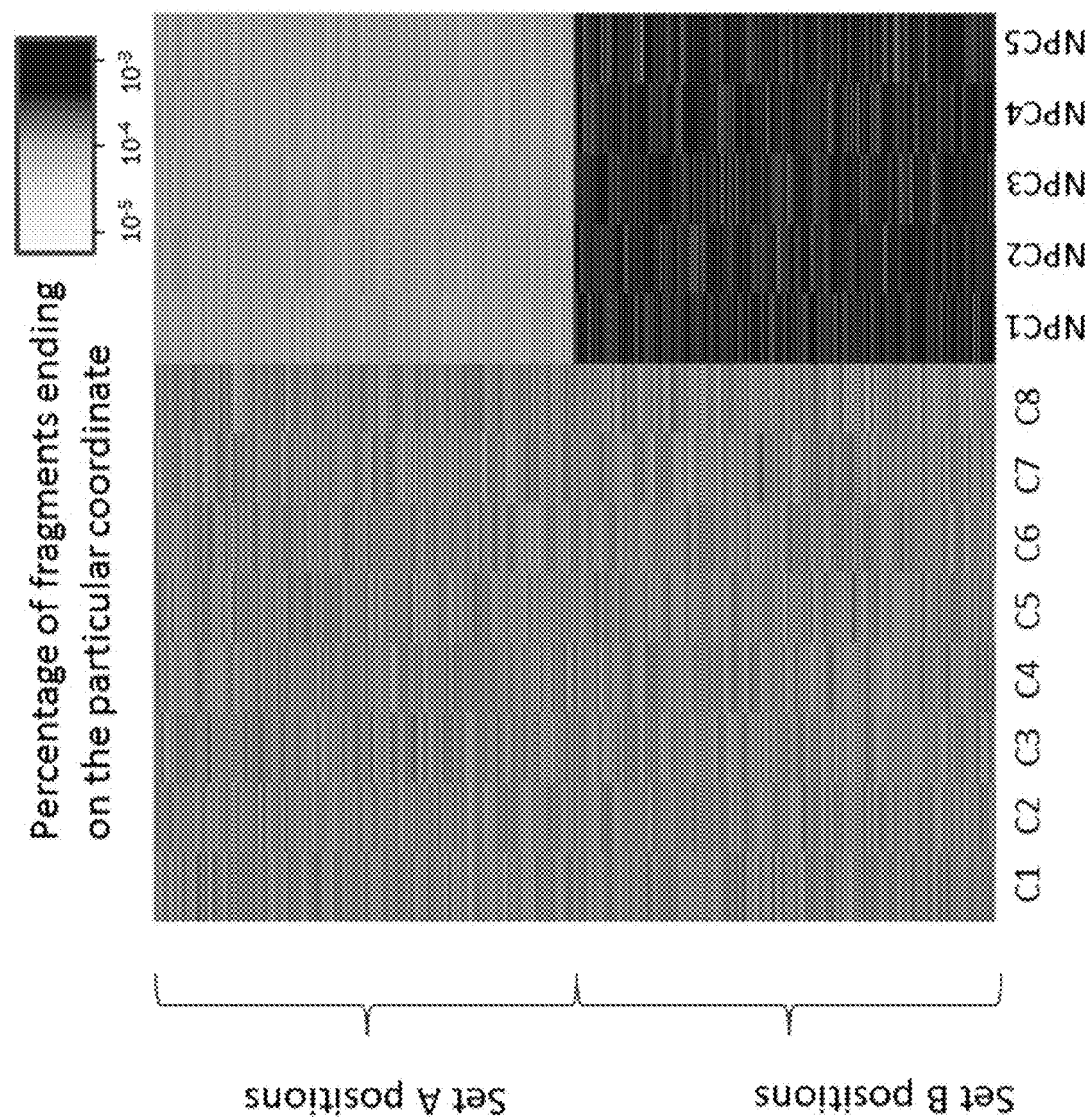
FIG. 44 shows a heat map depicting the percentage of fragments ending on either Set A positions or Set B positions for subjects not having an observable pathology and NPC subjects. A heat map is depicted for 8 subjects not having an observable pathology (left 8 columns; C1-C8) and 5 NPC subjects (right 5 columns; NPC1-NPC5). The nucleic acid fragments in NPC subjects ending on Set A ending positions are relatively less abundant than the nucleic acid fragments in NPC subjects ending on Set B ending positions.

FIG. 44 shows a heat map depicting the percentage of fragments ending on either Set A positions or Set B positions for subjects not having an observable pathology and NPC subjects. A heat map is depicted for 8 subjects not having an observable pathology (left 8 columns; C1-C8) and 5 NPC subjects (right 5 columns; NPC1-NPC5). The nucleic acid fragments in NPC subjects ending on Set A ending positions are relatively less abundant than the nucleic acid fragments in NPC subjects ending on Set B ending positions. Each row represents a particular position and each row represents one subject. Darker color (blue) indicates a higher percentage of EBV DNA fragments ending at the specific position. The five NPC subjects; had higher percentages of plasma EBV DNA fragments ending on the Set B positions (the frequent ending positions from another NPC subject) compared with the subjects without pathology. In contrast, subjects without pathology had higher percentages of plasma EBV DNA fragments ending on the Set A positions (the frequent ending positions from another subject with detectable plasma EBV DNA but no observable pathology) compared with the NPC subjects. These results suggest that the top-ranked ending positions are shared by subjects with the same disease status.

As the top-ranked ending positions were shared by subjects with the same disease status, we investigated the ending positions of plasma EBV DNA in subjects with detectable plasma EBV DNA could be used to indicate the disease status, for example to differentiate NPC subjects from subjects without observable pathology.

To demonstrate the feasibility of this approach, we first determined the number of sequenced plasma EBV DNA fragments ending on Set A and Set B positions. Then we calculated the B/A ratio as:

$$\frac{B}{A}\text{ratio} = \frac{\text{\# of fragments ending on Set } B \text{ positions}}{\text{\# of fragments ending on Set } A \text{ positions}}$$

For the five subjects with transiently positive plasma EBV DNA but no observable pathology, the number of mappable plasma DNA fragments aligned uniquely to the EBV genome were very small. These samples could be completely differentiated from the samples collected from NPC subjects, lymphoma subjects and the subject with infectious mononucleosis. For all the five subjects, the sequenced plasma EBV DNA fragments did not end on any Set A and Set B position.

C. Fragmentation to Determine Level of Pathology

In the NPC subjects, plasma EBV DNA fragments with a terminal nucleotide ending exactly at one or more of the NPC-specific ending positions would be more likely to be derived from the tumor. Based on this assumption, the number of sequenced plasma EBV DNA fragments that ended on the NPC-specific ending positions can be used to indicate the presence or absence of NPC or other cancers having a similar plasma DNA fragmentation pattern. In another embodiment, this parameter can also be used for reflecting the level of cancer, for example but not limited to the size of the tumor, the stage of the cancer, tumor load and the presence of metastasis. Interestingly, in the control subjects, EBV DNA fragments have terminal nucleotides ending at a set of ending positions (e.g., control-specific ending positions) that are unique to control subjects, or at least different from NPC-specific ending positions. As healthy subjects do not have a tumor, the plasma EBV DNA fragments are not derived from a tumor. It is contemplated that the difference in the fragmentation pattern of EBV DNA in control subjects and NPC subjects is related to the specific mechanisms by which DNA fragments. It is contemplated that the NPC-specific fragmentation pattern may be a result of tumor cell apoptosis-induced DNA fragmentation. Additionally, it is contemplated that the control-specific fragmentation pattern may be a result of EBV DNA replication-induced DNA fragmentation.

Both NPC subjects and reference subjects (e.g., healthy subjects, or subjects that are false positive for a disease, such as a tumor) can both have EBV DNA in their blood. However, each population can have a unique EBV DNA fragmentation pattern. By normalizing a first amount of nucleic acids (e.g., than can correspond to a number of EBV DNA fragments from a biological sample from the subject that end at NPC-specific preferred ending locations) with a second amount (e.g., that can correspond to a number of EBV DNA fragments from a reference sample from a healthy subject that end at healthy- or false-positive-specific preferred ending locations), a method of the present disclosure can better distinguish between subjects that are true positive for a condition, and subjects that are false-positive or otherwise healthy.

The identification and application of unique DNA fragmentation patterns for control subjects (e.g., subjects having no observable pathology) and tumor subjects can have tremendous practical value. For example, the abundance of nucleic acid fragments ending on tumor-specific ending positions may not be significantly different in a control subject and a tumor subject. In another example, in tumor subjects having low tumor burden, the EBV DNA abundance may be lower and more difficult to detect, as compared to control subjects, in whom the EBV DNA abundance can be higher, and more easy to detect. In some embodiments, the preferred ending positions for a given subject (e.g., a healthy subject or a tumor subject) can be highly specific (e.g., few of the preferred ending positions for a control subject are also preferred ending positions for a tumor subject).

In some embodiments, an end ratio (e.g., a ratio of a first amount of nucleic acid molecules ending on a first set of genomic positions to a second amount of nucleic acid molecules ending on a second set of genomic positions) can be used to determine a classification of a proportional contribution of a tissue type. In one example, the number of EBV DNA fragments ending on NPC-specific ending positions can be normalized using the number of EBV DNA fragments ending on the control-specific ending positions. In some embodiments, a combination of metrics (e.g., at least two of an end ratio, copy number, and nucleic acid fragment size) may be used to detect a condition (e.g., a tumor) in a subject. For example, as discussed above, NPC subjects can exhibit a higher number of EBV DNA fragments, a higher B/A ratio, and a lower proportion of reads less than 150 base pairs in length, as compared to control subjects.

D. Results

The following data shows that subjects exhibiting a viral load but some with and some without cancer can be differentiated using a relative abundance between viral fragments ending on a first set of positions and viral fragments ending on a second set of positions.

1. EBV

Figure 45:
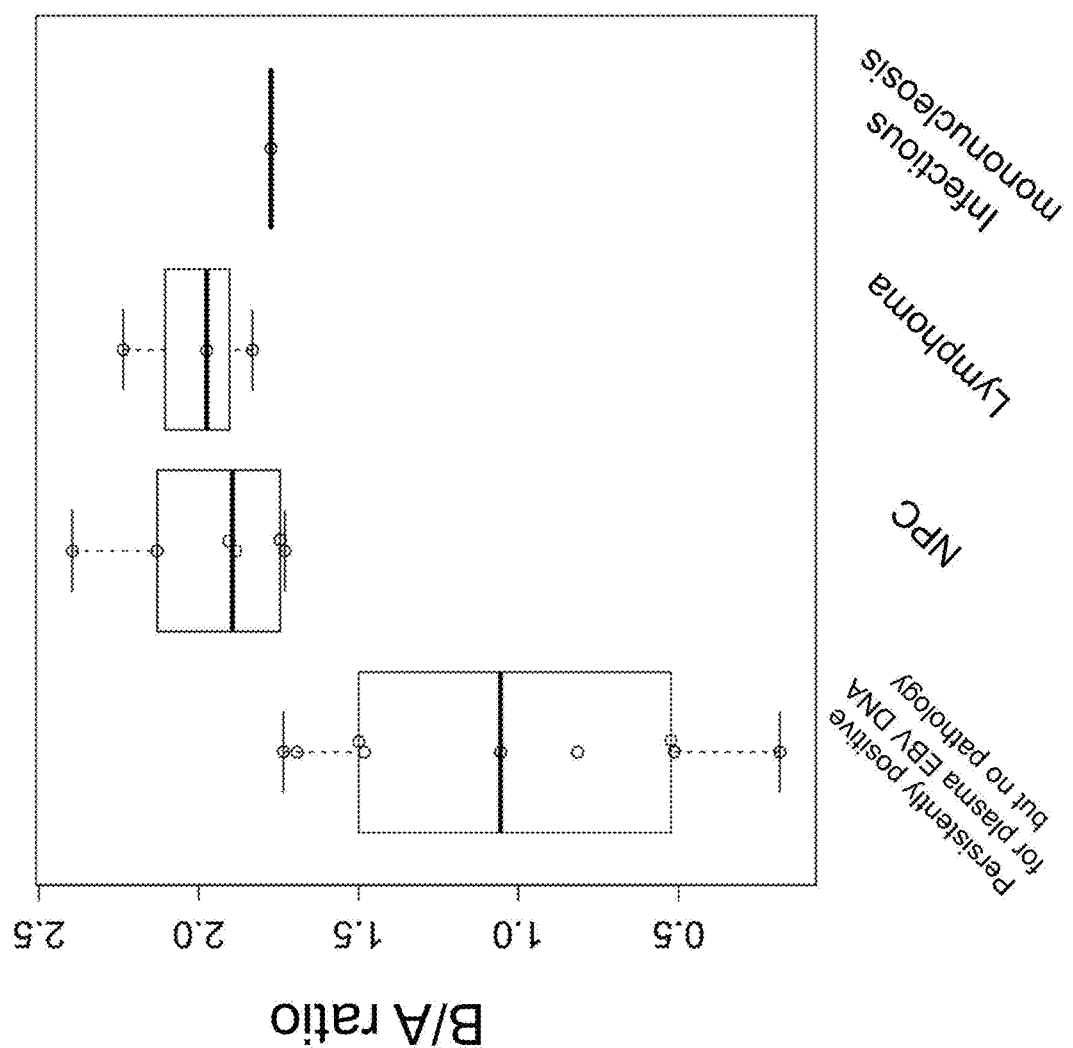
FIG. 45 shows the ratio of the number of fragments ending on Set B positions divided by the number of fragments ending on Set A positions (e.g., B/A ratios) for different groups of subjects.

FIG. 45 shows the ratio of the number of fragments ending on Set B positions divided by the number of fragments ending on Set A positions (e.g., B/A ratios) for different groups of subjects. For subjects with persistently detectable plasma EBV DNA, the B/A ratios of the subjects with no pathology were significantly lower than the NPC subjects (P<0.001, Mann-Whitney test) and the lymphoma subjects (P<0.01, Mann-Whitney test). The B/A ratio of the subject with infectious mononucleosis was higher than all the subjects with persistently detectable plasma EBV DNA but no pathology. These results suggest that the proportion of plasma EBV DNA fragments ending on positions preferentially for different disease can be useful for identifying the disease status of the subject being tested.

In some embodiments, the ending positions of a set (e.g., set A or set B) can be identified when they have a probability higher than expected for random fragmentation. In other embodiments, the most frequently seen ending positions in a pathogen genome (e.g., EBV DNA) in true pathology patients (e.g., NPC) can be identified for set B, and the most frequently seen ending positions for false-positive patients (or other subject without pathology) can be identified as set A. The non-overlapping sets for the respective groups can be used. An amount of fragments at a set of ending positions can be quantified in various ways, with or without normalization.

Figure 46:
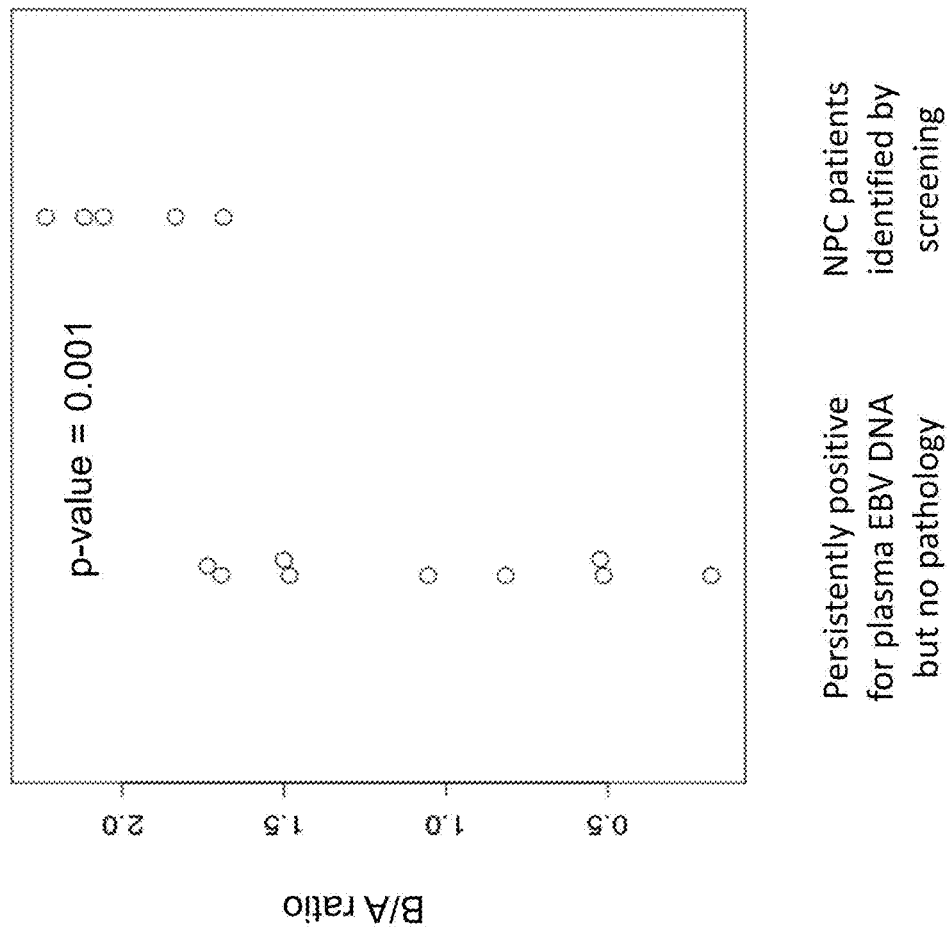
FIG. 46 shows the B/A ratio for (left) subjects persistently positive for plasma EBV DNA but having no observable pathology, and (right) early-stage NPC patients identified by screening.

FIG. 46 shows the B/A ratio for (left) subjects persistently positive for plasma EBV DNA but having no observable pathology, and (right) NPC subjects. The B/A ratio of the two groups were also significantly different (P=0.001, Mann-Whitney test). As the preferred ending positions in the Set B were determined using an independent group of NPC subjects, these results suggest that the preferred ending position are shared between different NPC subjects regardless of the plasma EBV DNA concentration.

Figure 47:
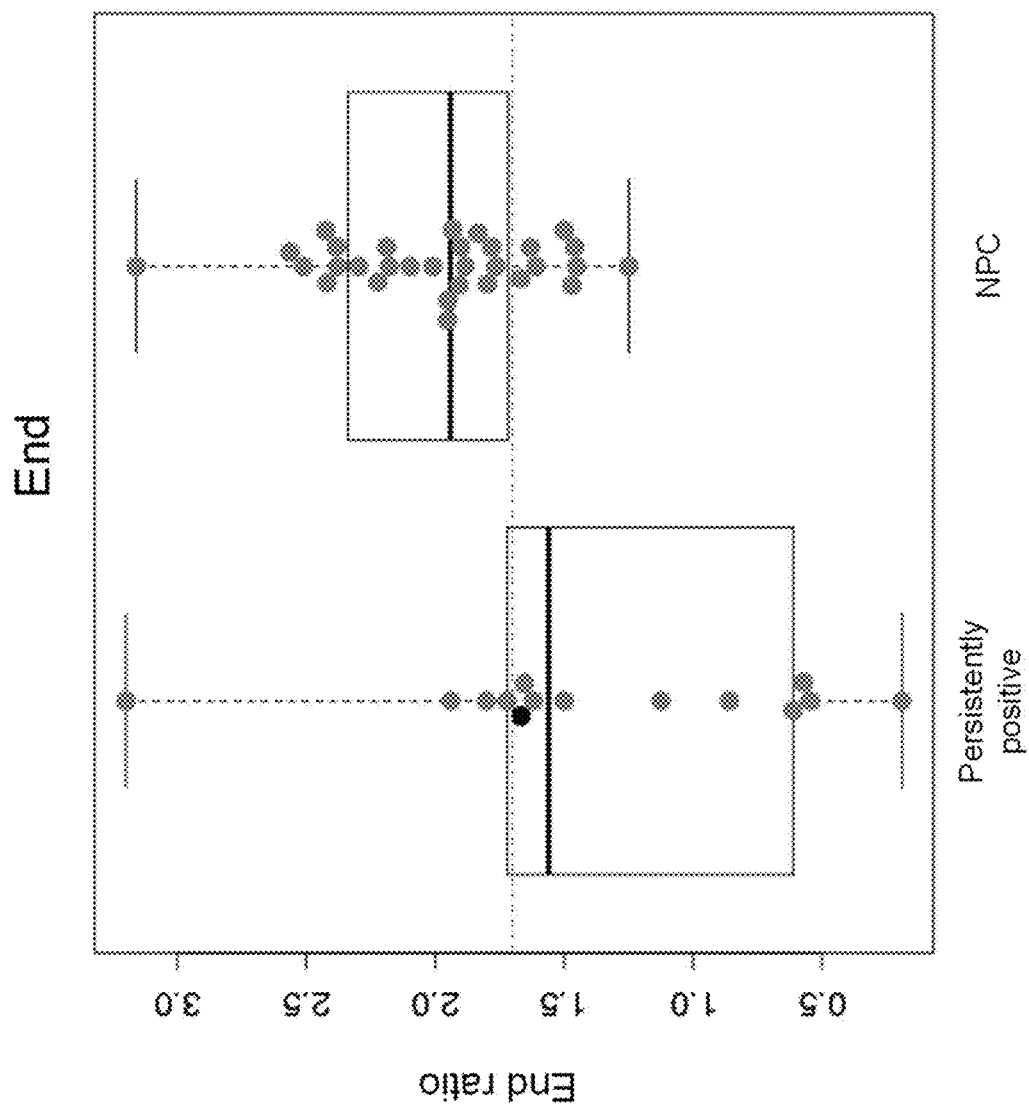
FIG. 47 shows an end ratio (e.g., a ratio of a number of sequenced plasma EBV DNA fragments ending on Set B positions and a number of sequenced plasma EBV DNA fragments ending on Set A positions) in subjects that are persistently positive for plasma EBV DNA (left) but have no observable pathology, and subjects identified as having NPC.

FIG. 47 shows an end ratio (e.g., a ratio of a number of sequenced plasma EBV DNA fragments ending on Set B positions and a number of sequenced plasma EBV DNA fragments ending on Set A positions) in subjects that are persistently positive for plasma EBV DNA (left) but have no observable pathology, and subjects identified as having NPC. For subjects with persistently detectable plasma EBV DNA, the ends ratios of the subjects with no pathology were significantly lower than the end ratios in subjects having NPC (p=0.001; Mann-Whitney test). It is contemplated that the end ratio could serve as a parameter to differentiate subjects with NPC from subjects with persistently positive plasma EBV DNA but without observable pathology.

In other embodiments, the analysis of ending positions can be determined by the number of fragments ending at the preferred positions for the particular condition. For example, the number of fragments ending at the Set B positions can be used to determine the likelihood of a tested subject of having NPC. In another embodiment, the number of fragments ending at such positions can be normalized based on the total number of sequenced fragments or the number of sequenced fragments mapped to the EBV genome or number of sequenced fragments mapped to one or multiple regions of the EBV genome. When a subject is screened for NPC using plasma EBV DNA analysis and shows a positive result. Based on the arrangement used in the study we have performed, we would collect another blood sample in around four weeks and determine if the plasma EBV DNA is persistently positive. Based on the results shown, one alternative arrangement is to analyze the size and the percentage of plasma EBV DNA fragments ending at the NPC-preferred ending positions using B/A ratio. For those cases with high percentage of fragments<150 bp and low B/A ratio, they can be regarded as low risk for NPC whereas those with low percentage of fragments<150 bp and high B/A ratio can be referred for further investigations. This arrangement can improve the logistics of the tests and obviate the need for asking the subjects to come back for further blood collection.

Apart from NPC, the analysis of the size of viral DNA fragments and their ending positions in plasma can also be used for the detection of other cancers associated with viral infection. In this regard, we analyzed three HCC subjects and three subjects with chronic hepatitis B infection but without HCC. In China and Southeast Asia, a large proportion of HCC are associated with HBV infection. The plasma DNA samples of these subjects were sequenced after target enrichment using the protocol described above.

2. HBV

One HCC subject was randomly selected for the analysis of preferred ending positions. The coordinates of the HBV genome were ranked in descending order of the number of plasma DNA fragments ending on these positions in this particular HCC subject. For illustration purpose, the top 800 positions were identified. These positions are denoted as the HCC-preferred positions. In other embodiments, other numbers of positions can be used, for example, but not limited to 100, 200, 400, 600, 1000, or 1500. For illustration purpose, another 2000 positions were randomly selected for normalizing the number of plasma DNA fragments aligning to the HBV genome. Other numbers can be used for this normalization process, for example, but not limited to 200, 400, 600, 800, 1000, 1500 and 2500. In other embodiments, the normalization with the total DNA in the plasma sample or the total number of sequenced reads or total number of reads aligned to the HBV genome can be used.

Figure 48:
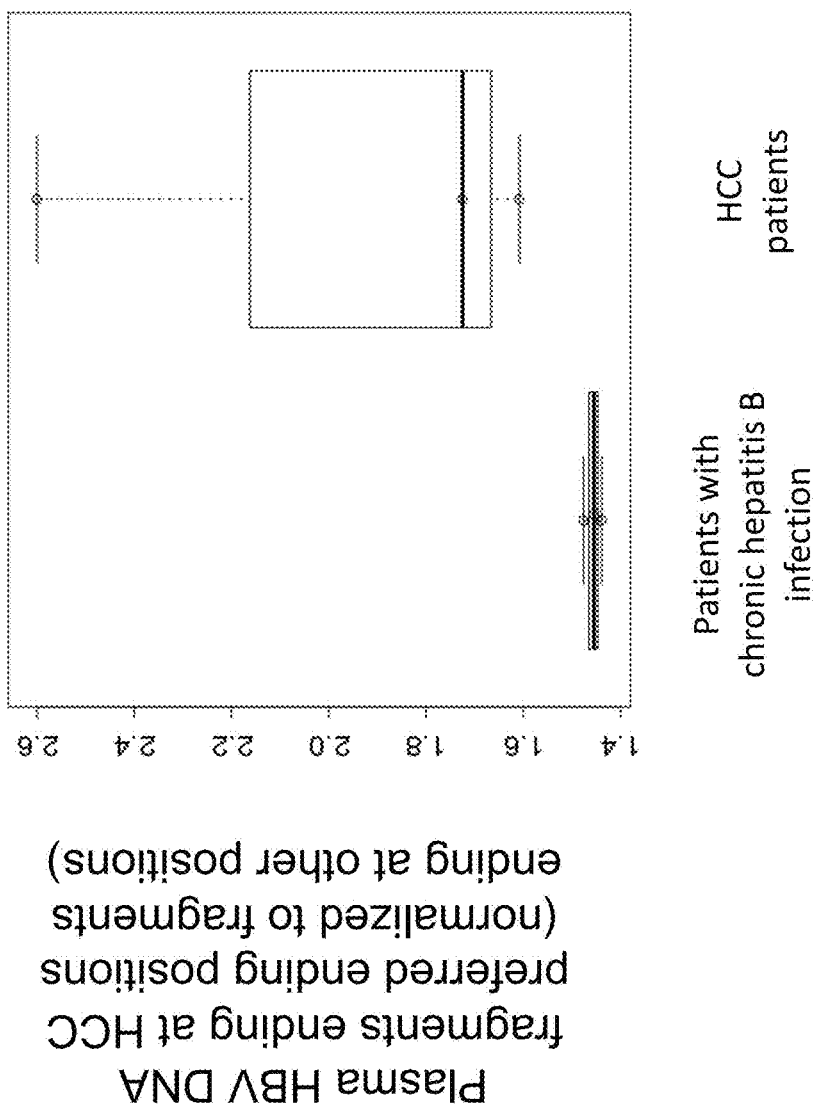
FIG. 48 shows a box and whiskers plot of the number of plasma HBV DNA fragments ending at HCC preferred ending positions normalized to fragments ending at other positions in (left) subjects having chronic hepatitis B and (right) HCC subjects.

FIG. 48 shows a box and whiskers plot of the number of plasma HBV DNA fragments ending at HCC preferred ending positions normalized to fragments ending at other positions in (left) subjects having chronic hepatitis B and (right) HCC subjects. The number of plasma HBV DNA fragments ending at the HCC-preferred positions were higher in the HCC subjects compared with the subjects with chronic HBV infection but without HCC. These results suggest that the number of fragments ending at the HCC-preferred positions can be used to distinguish HCC subjects from chronic HBV carriers without HCC.

It should be understood that, when normalizing the number of plasma DNA fragments ending at preferred ending positions to fragments ending at 'other positions', the 'other positions' may be one or more of any other position of a gene or genome. While the 'other positions' can correspond to preferred ending positions (e.g., the preferred ending positions of nucleic acid fragments aligned to a reference genome), it is not necessary that the 'other positions' be preferred ending positions. In one embodiment, the 'other positions' may correspond to the least preferred ending positions for a plurality of nucleic acids. In another embodiment, the 'other positions' may correspond to a random set of positions.

For the HBV and HPV (below) work, some embodiments identified the most frequently seen (e.g. top 1,000) ends in the HCC or cervical cancer cases, respectively, and identified the least frequent ends (e.g. bottom 1,000) in the same case, where the latter is used for normalization. The data shown in FIG. 49 shows a quantification of the most frequent HCC ends expressed as a ratio of other ends (e.g., the least frequent or any random ends).

3. HPV

The analysis of the fragmentation pattern of viral DNA in plasma can be generalized to other cancers associated with viral infection. As an illustrative example, we analyzed the plasma of a subject with a head and neck squamous cell carcinoma. This cancer has a close association with HPV infection. The plasma DNA was sequenced after target enrichment as described above. The plasma DNA fragments uniquely aligned to the HPV were analyzed.

Figure 49A:
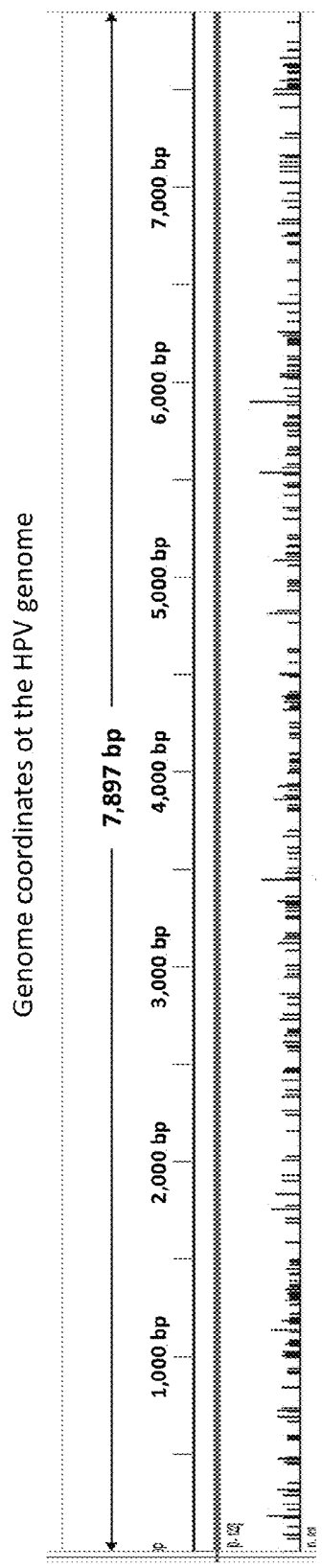
FIGS. 49A and 49B shows the number of plasma HPV DNA fragments ending at different positions of the HPV genome.
Figure 49B:
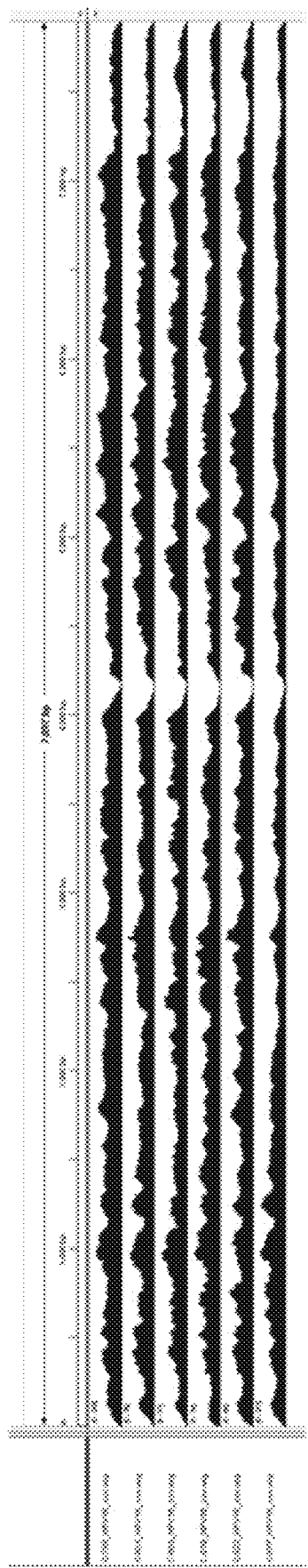

FIGS. 49A and 49B shows the number of plasma HPV DNA fragments ending at different positions of the HPV genome. Similar to the patterns observed in the NPC subjects and the HCC subjects, there were positions in the HPV genome that were more likely to be the ending positions of the plasma DNA of the head and neck squamous cell carcinoma subject (FIG. 49A). These positions can be applied for detecting this type of cancer. Our data also suggest that a similar approach can be used for detecting cervical cancer associated with HPV infection. The six cervical cancer cases shown in FIG. 49B are the same as the first size cases shown in FIG. 17. In one embodiment, the preferred ending positions for cervical cancers can be determined. Then, any subjects with a positive plasma HPV DNA result can be tested if those plasma HPV DNA would end on the cervical cancer-preferred ending positions. Those subjects with plasma HPV DNA ending on such positions are more likely to have cervical cancers whereas those with plasma HPV DNA ending on other positions are more likely to have false-positive results.

As shown in FIG. 49B, the fragmentation patterns of the plasma HPV DNA sequences can allow one to distinguish those with HPV-related cancer and individuals without cancer but with detectable plasma HPV DNA due to other benign conditions. The size profile and fragmentation patterns of the plasma HPV DNA sequences can further allow one to distinguish between HPV-related cancers of different tissue origin, for example CC (FIG. 49B) and HNSCC (FIG. 49A).

Figure 50:
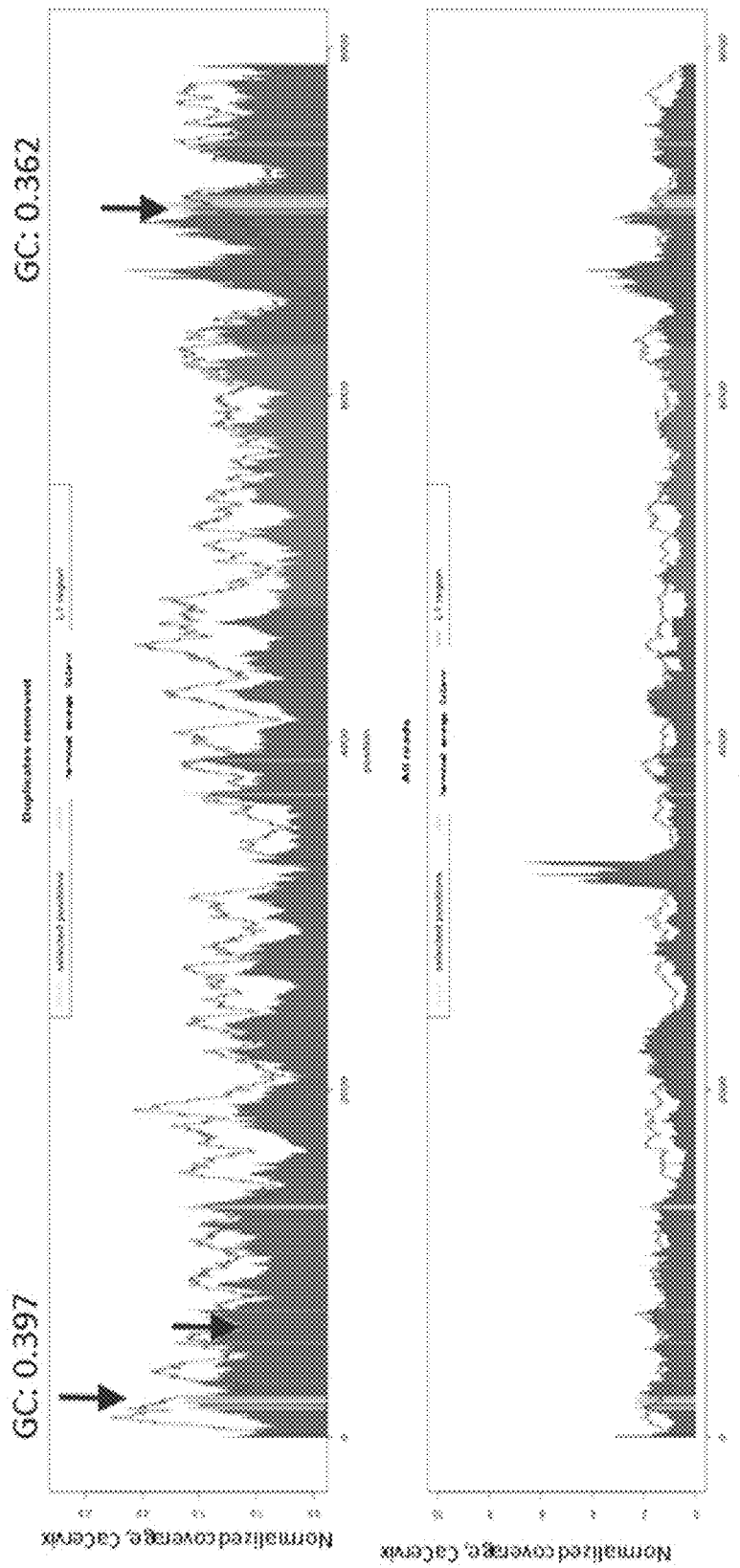
FIG. 50 shows that the coverage of HPV DNA molecules in plasma are uneven across the whole HPV genomes.

FIG. 50 shows that the coverage of HPV DNA molecules in plasma are uneven across the whole HPV genomes, suggesting the fragmentation patterns would be different across HPV genomes. The unevenness can be seen in data before and after removing the PCR duplication according to mapped genomic coordinates in HPV genome. Such unevenness of coverage might be correlated with GC content.

Figure 51:
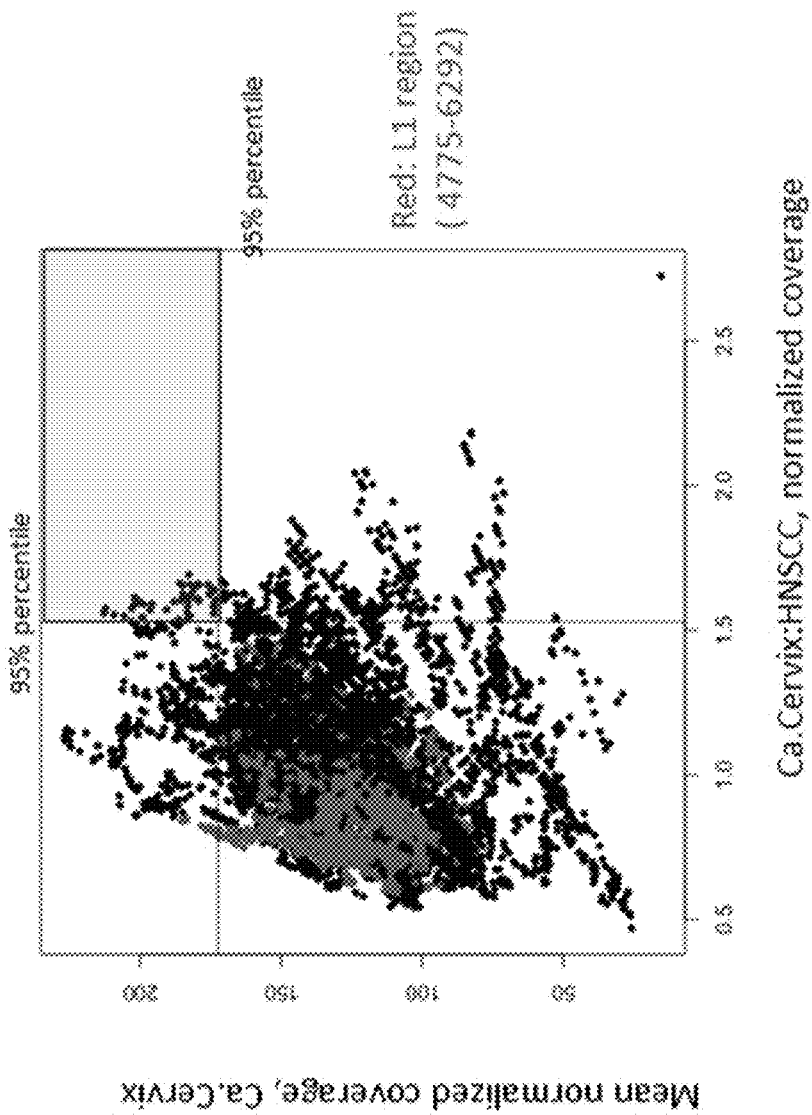
FIG. 51 shows that the differential fragmentation patterns can be determined by comparing the HPV fragment coverages between subjects with cervical cancer (CC) and head and neck squamous cell carcinoma (HSNCC).

FIG. 51 shows that the differential fragmentation patterns can be determined by comparing the HPV fragment coverages between subjects with cervical cancer and head and neck squamous cell carcinoma (HSNCC). X-axis is the ratio of HPV fragment coverages in a subject of cervical cancer to HSNCC. Y-axis is the coverage of HPV fragments in a subject of cervical cancer. The area in red indicated differential fragmentation patterns which had more abundant fragments present in the subject of cervical cancer and at the same time had 1.5× fold more fragments in a subject of cervical cancer than HSNCC. These data suggested the viral DNA fragmentation patterns could be used to inform different types of cancers.

Figure 52:
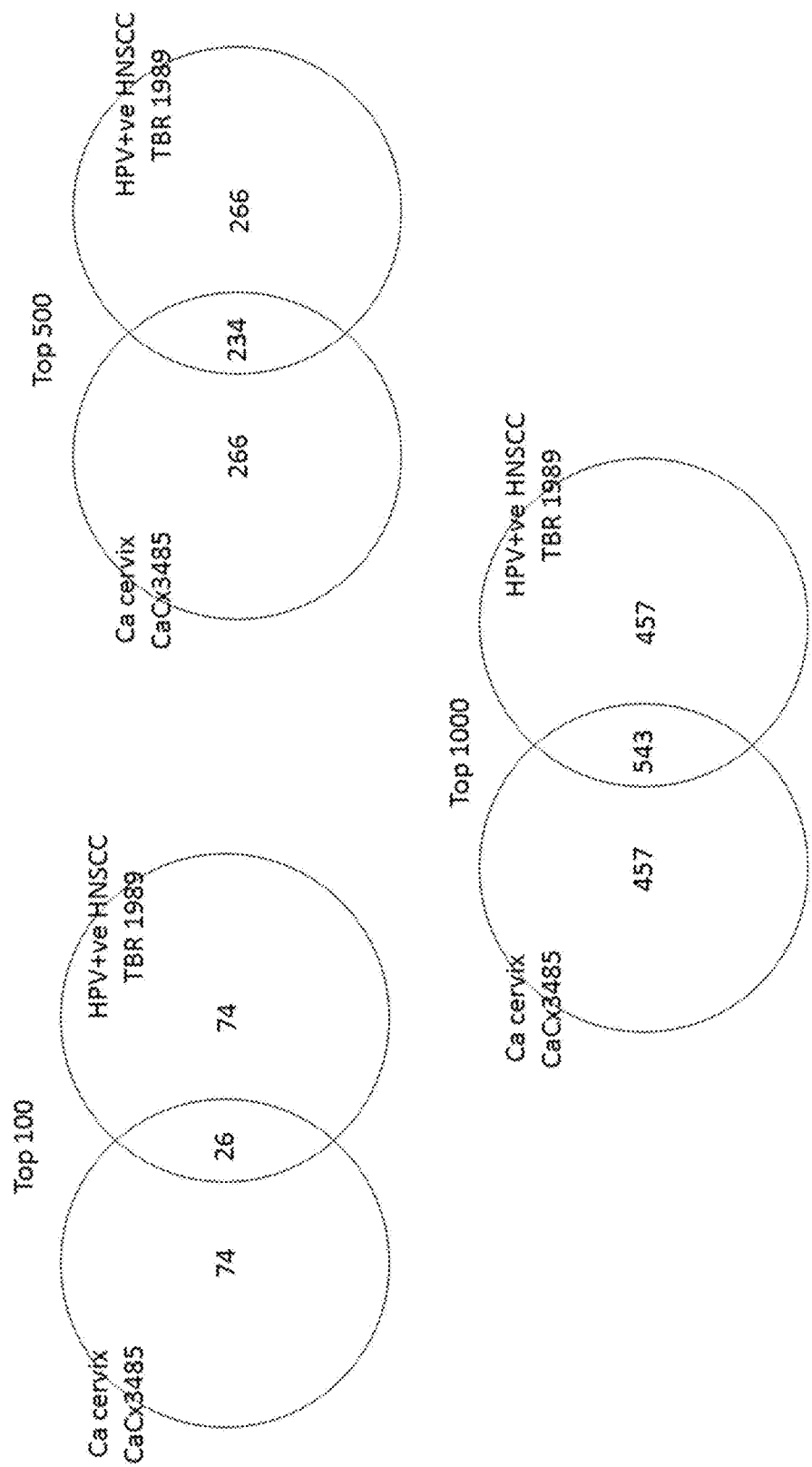
FIG. 52 shows Venn diagrams for an analysis of preferred ending positions of plasma HPV DNA reads by sequencing.

FIG. 52 shows Venn diagrams for an analysis of preferred ending positions of plasma HPV DNA reads by sequencing. We investigated if the plasma HPV DNA fragments would have preferred ending positions at the HPV genome. We hypothesized that the preferred positions for plasma HPV DNA fragments would be different between subjects with different HPV-related malignancies. To demonstrate the association of ending positions with disease conditions, we randomly picked one patient with carcinoma of cervix (CaCx3485) and one patient with HPV positive head and neck squamous cell carcinoma (HPV+ve HNSCC) (TBR1989) for mining of the frequent ending positions. We ranked the coordinates of the HPV genome in a descending number of plasma HPV DNA fragments ending on it for the two cases. In such arrangement, the HPV genome coordinate with the largest number of fragments ending on it would rank 1.

For illustration purpose, the coordinates ranking at the top 100, top 500 and top 1000 were selected for each of the two cases. In other embodiments, different number of top-ranked coordinates can be selected for the analysis.

FIG. 52 shows the 100, 500 and 1000 most common ending positions in the EBV genome for a patient with carcinoma of cervix and a patient with HPV+ve HNSCC. For the 100 most common ending positions, 26 (26%) of the common ending positions were shared by both cases. For the 500 most common ending positions, 234 (46.8%) of the common ending positions were shared by both cases. For the 1000 most common ending positions, 543 (54.3%) of the common ending positions were shared by both cases.

E. Method

Figure 53:
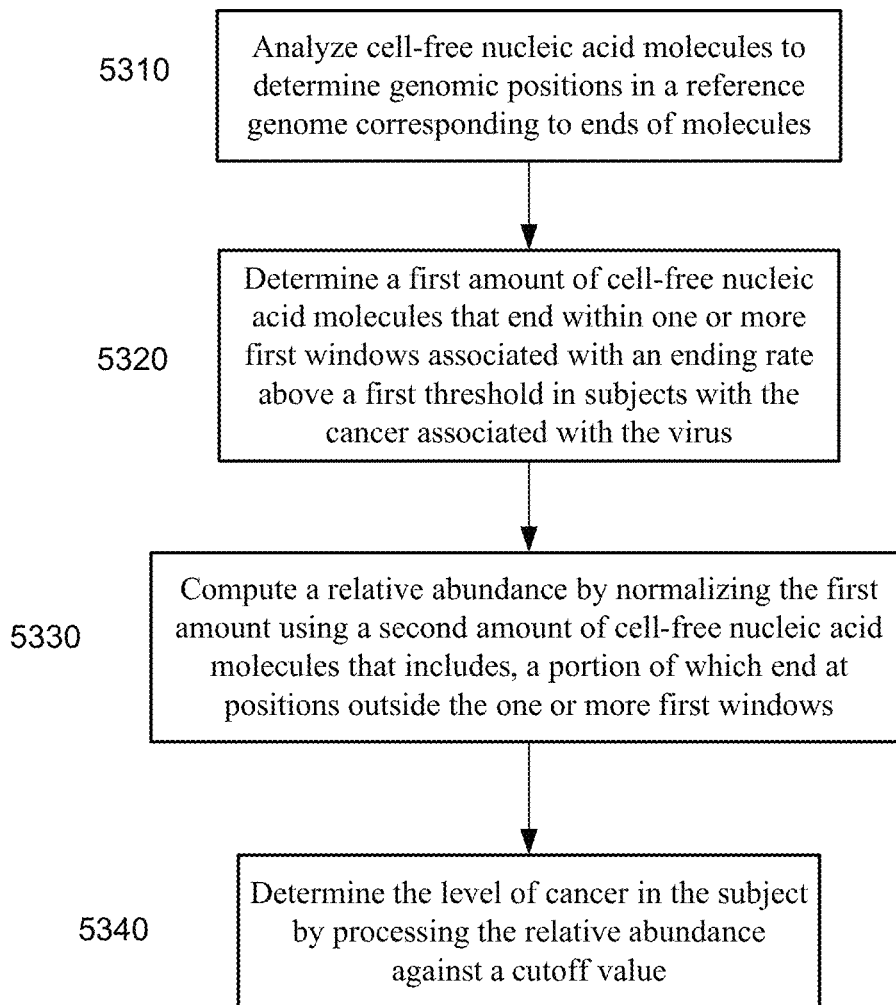
FIG. 53 is a flowchart illustrating a method for determining a level of cancer in a subject based on fragmentation patterns of nucleic acid molecules from a virus according to embodiments of the present invention.

FIG. 53 is a flowchart illustrating a method 5300 for determining a level of cancer in a subject based on fragmentation patterns of nucleic acid molecules from a virus according to embodiments of the present invention. Aspects of method 4000 can be performed in a similar manner as method 2200. At least a portion of the method may be performed by a computer system.

At block 5310, a first plurality of cell-free nucleic acid molecules from a biological sample of the subject are analyzed. The analyzing of a cell-free nucleic acid comprises determining a genomic position in a reference genome corresponding to at least one end of the cell-free nucleic acid molecule, where the reference genome corresponds to the virus. Both genomic positions corresponding to both ends of the cell-free nucleic acid molecule can be determined.

At block 5320, a first amount of the first plurality of cell-free nucleic acid molecules that end within one of first windows is determined. Each first window comprises at least one of a first set of genomic positions at which ends of cell-free nucleic acid molecules are present at a rate above a first threshold in subjects with the cancer associated with the virus.

The second set of genomic positions can be identified by analyzing the cell-free nucleic acid molecules of a reference sample from a reference subject (e.g., a healthy subject) that does not have the cancer. In one embodiment, the second set of genomic positions comprises all genomic positions corresponding to an end of at least one of the first plurality of cell-free nucleic acid molecules.

The first set of genomic positions can be identified by analyzing a second plurality of cell-free nucleic acid molecules from at least one first additional sample to identify ending positions of the second plurality of cell-free nucleic acid molecules. The at least one first additional sample can be known to have the cancer associated with the virus and be of a same sample type as the biological sample. For each genomic window of a plurality of genomic windows, a corresponding number of the second plurality of cell-free nucleic acid molecules ending on the genomic window can be computed and compared a reference value to determine whether the rate of cell-free nucleic acid molecules ending on one or more genomic positions within the genomic window is above the first threshold. The at least one first additional sample can be from the subject and be obtained at a different time than the biological sample. Each of the first set of genomic positions can have at least a specified number of cell-free nucleic acid molecules of the second plurality of cell-free nucleic acid molecules ending on the genomic position.

At block 5330, a relative abundance of the first plurality of cell-free nucleic acid molecules ending within one of the first windows is computed by normalizing the first amount using a second amount of the first plurality of cell-free nucleic acid molecules from the biological sample. The second amount of cell-free nucleic acid molecules can include cell-free nucleic acid molecules ending at a second set of genomic positions outside of the first windows including the first set of genomic positions. The first and second sets may or may not overlap. Normalizing the first amount includes computing the relative abundance using the first amount and the second amount.

The relative abundance can comprise a ratio of the first amount and the second amount. As an example, the relative abundance can be the B/A ratio.

At block 5340, the level of pathology in the subject is determined by processing the relative abundance against one or more cutoff values. For example, it can be determined whether the relative abundance is greater than the cutoff value. For example, the B/A ratio can be compared to a cutoff to determine whether the ratio is above the cutoff. In FIG. 45, a cutoff could be about 1.7 to discriminate between subjects that are persistently positive for EBV but no pathology and subjects with NPC, lymphoma, or infectious mononucleosis.

F. Determination of Ending Position

When sequencing nucleic acids (e.g., DNA or RNA), there are various possibilities of the ending patterns of fragments. For example, there are generally four configurations of ends for plasma DNA: (A) A double stranded DNA molecule with two flushed ends; (B) A double strand DNA molecule with one flushed end, and one non-flushed end (showing each of the two scenarios, as either one of the two strands can protrude out); (C) A double strand DNA molecule with two non-flushed end, with different combinations of protruding ends; and (D) A single stranded DNA molecule.

For the configurations with non-flushed ends, there are different patterns depending on whether the 5' or the 3' end of the DNA molecule is protruded. For (B), the double-stranded DNA molecules has one flushed end and one non-flushed end. In an example B1, the 5' end is protruded and in an example B2, the 3' end is protruded. For (C), there are three possible patterns when both ends are non-flushed. In (C1), 5' end protrudes on both sides. In (C2), 3' end protrudes on both sides. In (C3), 5' end protrudes on one side and 3' end protrudes on the other side.

For sequencing, paired-end sequencing protocols commonly sequence one end of each of the stands. They are therefore considered double-stranded DNA sequencing protocols. When the two ends are not flushed, protocols can either cut nucleotides off or add nucleotides to the end to make them flushed. The Klenow fragment is an enzyme that can carry out such operations. Other protocols in the field use single-stranded DNA sequencing protocols.

Regardless of the specific technique used (including use of probes), as long as the ending positions are repeatable and show correlation, as is shown here, whether a true end of a DNA fragment is obtained in sequencing does not affect the results, as any offset is repeatable, and thus cancel out. Further, certain techniques can be used for identifying an ending position, as is described in the Terms section.

G. Identification of Preferred Ending Positions

Various embodiments described above identify preferred ending positions for viral fragments, where some of the preferred ending positions can be contiguous, thereby forming a preferred ending window. Different metrics can be used to identify rates of occurrence of cell-free viral fragments at genomic windows (e.g., a genomic position for the smallest window).

In yet other examples, a difference in sets of high rate ending positions (e.g., rate above a threshold) for samples having and not having a condition (e.g., cancer, possibly of a particular type) can be used to identify preferred ending sites for a particular tissue type associated with the condition, e.g., as described with the use of Venn diagrams. As yet other examples, a significantly higher rate in one sample with a condition than with another sample not having the condition can provide preferred ending sites of a particular virus. In various embodiments, some or all of such example techniques can be used together. The rate can be measured by any metric of relative abundance.

In some embodiments of above methods, a first set of genomic positions at which ends of cell-free viral nucleic acid molecules occur at a rate above a threshold can be identified in the following manner. A calibration sample can be analyzed in a similar manner as the test sample, where the two samples of a same type (e.g., plasma, serum, urine, etc.) and the calibration sample is known to include a first tissue type (e.g., tumor tissue of the liver for an HCC patient). A number of viral fragments ending in a genomic window (e.g., of width one or more) can be compared to a reference value to determine whether a rate of ending positions is above a threshold for that position. In some embodiments, if the rate exceeds the reference value, each of the genomic positions within the first genomic window can be identified as having the rate be above the threshold when the corresponding number exceeds the reference value. Such a process can identify preferred ending windows, which include preferred ending positions.

The reference value can be such that only the top N genomic windows have a rate above the threshold. For example, the first set of genomic positions can have the highest N values for the corresponding numbers. As examples, N can be at least 10, at least 100, at least 1,000, at least 2,500, at least 5,000, at least 10,000, at least 50,000, at least 100,000, at least 500,000, at least 1,000,000, or at least 5,000,000.

As another example, the reference value can be an expected number of viral fragments ending within the genomic window according to a probability distribution and an average length of cell-free DNA molecules in a sample.

A p-value can be determined using the corresponding number and the expected number, wherein the threshold corresponds to a cutoff p-value (e.g., 0.01). The p-value being less than the cutoff p-value indicates that the rate is above the threshold.

As yet another example, the reference value can include a measured number of cell-free DNA molecules ending within the genomic window from a sample identified as not having cancer. To compare to the reference value, a first ratio can be taken of the corresponding number ending at a position and a third number of the third plurality of cell-free nucleic acid molecules covering the genomic window. For this comparison, the reference value can include a reference ratio of the measured number of reads ending within the genomic window and a fourth number of the third plurality of cell-free nucleic acid molecules covering the genomic window and not ending within the genomic window. In one implementation, the third number of cell-free nucleic acid molecules do not end within the genomic window. It can be determined whether the first ratio is greater than a multiplicative factor times the reference ratio.

In some embodiments, a null hypothesis is that all fragments would be fragmented randomly so that each genomic position would have an equal probability of being the end of a fragments. The fragments can be assumed to be a specified size (e.g., 166 bp) on average. The p-value was calculated as $$p\text{-value}=\text{Poisson}(N_{actual}, N_{predict})$$

where Poisson ( ) is the Poisson probability function; $N_{actual}$ is the actual number of reads ending at the particular nucleotide; and $$N_{predict} = \frac{\text{Total number of reads}}{\text{nucleotides in genome}}.$$

The p-value can be adjusted using the Benjamini and Hochberg correction (Bejamini et al. Journal of the Royal Statistical Society, 1995; 57:289-300) so as to achieve an expected false-discovery rate (FDR), e.g., <1%. Accordingly, determining whether the rate is above the first threshold can comprise determining a corresponding p-value using the corresponding number and the expected number, where the first threshold corresponds to a cutoff p-value. The corresponding p-value being less than the cutoff p-value indicating that the rate of cell-free nucleic acid molecules ending within the genomic window is above the first threshold.

In some embodiments, the genomic positions whose rate of the second plurality of cell-free nucleic acid molecules ending on the genomic position is above the first threshold comprises a first superset. Identifying the first set of genomic positions can further comprises analyzing a third plurality of cell-free nucleic acid molecules from at least one second additional sample identified as not having the cancer to identify a second superset of the third plurality of cell-free nucleic acid molecules ending on the genomic position is above the first threshold. The first set of genomic positions can comprise the genomic positions that are in the first superset and that are not in the second superset.

H. Relative Abundance

Various examples of relative abundance values are provided herein, e.g., intact probability ($P_I$), p-value described in previous section, and the PETR value determined using a genomic window or a genomic position when the window is of width one. For PETR for a genomic position (window of width one), a corresponding number of viral nucleic acid fragments ending on the genomic position can be computed for each genomic position of the first set of genomic positions. This can be done as part of determining that the first number (e.g., numerator) of the first plurality of viral fragments end on any one of the first set of genomic positions. A third number (e.g., denominator) of cell-free DNA molecules covering the genomic position and not ending on the genomic position can be computed as part of determining the second number of viral molecules. A first ratio of the corresponding number and the third number can be determined, and a mean of the first ratios can be used as the relative abundance.

In some embodiments, a window-based PETR (w-PETR) ratio between the numbers of fragments ending within Window A and those ending within Window B can be determined. For w-PETR, a corresponding number of cell-free DNA molecules ending within a first window including the genomic position can be computed for each genomic position of the first set of genomic positions. A third number of cell-free DNA molecules ending within a second window including the genomic position can be computed. The second window can be larger than the first window. In some cases, first ratios of the corresponding numbers and the third numbers can be used as the relative abundance, or a mean of the first ratios used as the relative abundance.

Another examples of a relative abundance value is a proportion of viral fragments ending on a genomic window, e.g., measured as a proportion of sequenced DNA fragments ending on a preferred ending position. Thus, the second set of genomic positions can include all genomic positions corresponding to an end of at least one of the first plurality of viral fragments.

V. COMBINED TECHNIQUES

The discussion above focused on each of the tests as standalone techniques. In various embodiments, the different techniques can be combined. A few examples of combinations are provided below, along with some results. The combination of techniques can be performed at a same time, e.g., using the same portion or different portions of a sample or using different samples taken during a same clinical visit.

A. Combined Count and Size

The count-based analysis and the size-base analysis can be combined to achieve increased accuracy in discriminating between subjects with a pathology and those without.

1. EBV

Figure 54:
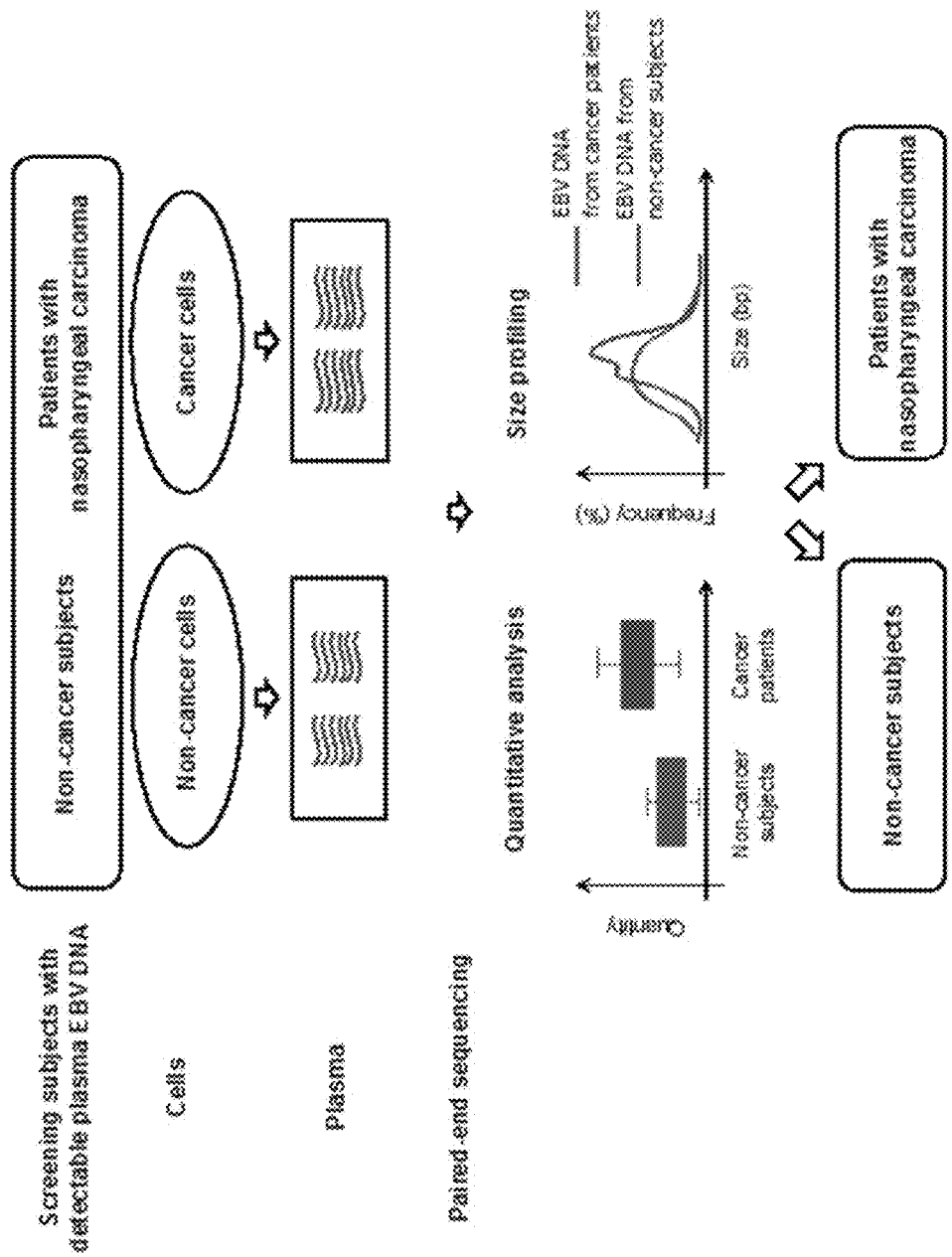
FIG. 54 illustrates a quantitative and size profile analysis of plasma EBV DNA in patients with nasopharyngeal carcinoma and non-cancer subjects.

FIG. 54 illustrates a quantitative and size profile analysis of plasma EBV DNA in patients with nasopharyngeal carcinoma and non-cancer subjects. We performed target-capture sequencing of plasma EBV DNA and identified differences in the abundance and size profiles of EBV DNA molecules within plasma of NPC and non-NPC subjects, as described in sections on the standalone techniques.

Using combined count- and size-based analysis of plasma EBV DNA, screening of nasopharyngeal carcinoma could be performed with a single time-point testing at an enhanced positive predictive value. NPC patients had significantly higher amounts of plasma EBV DNA having longer fragment lengths. Cutoff values were established from an exploratory dataset and tested in a validation sample set.

Figure 55:
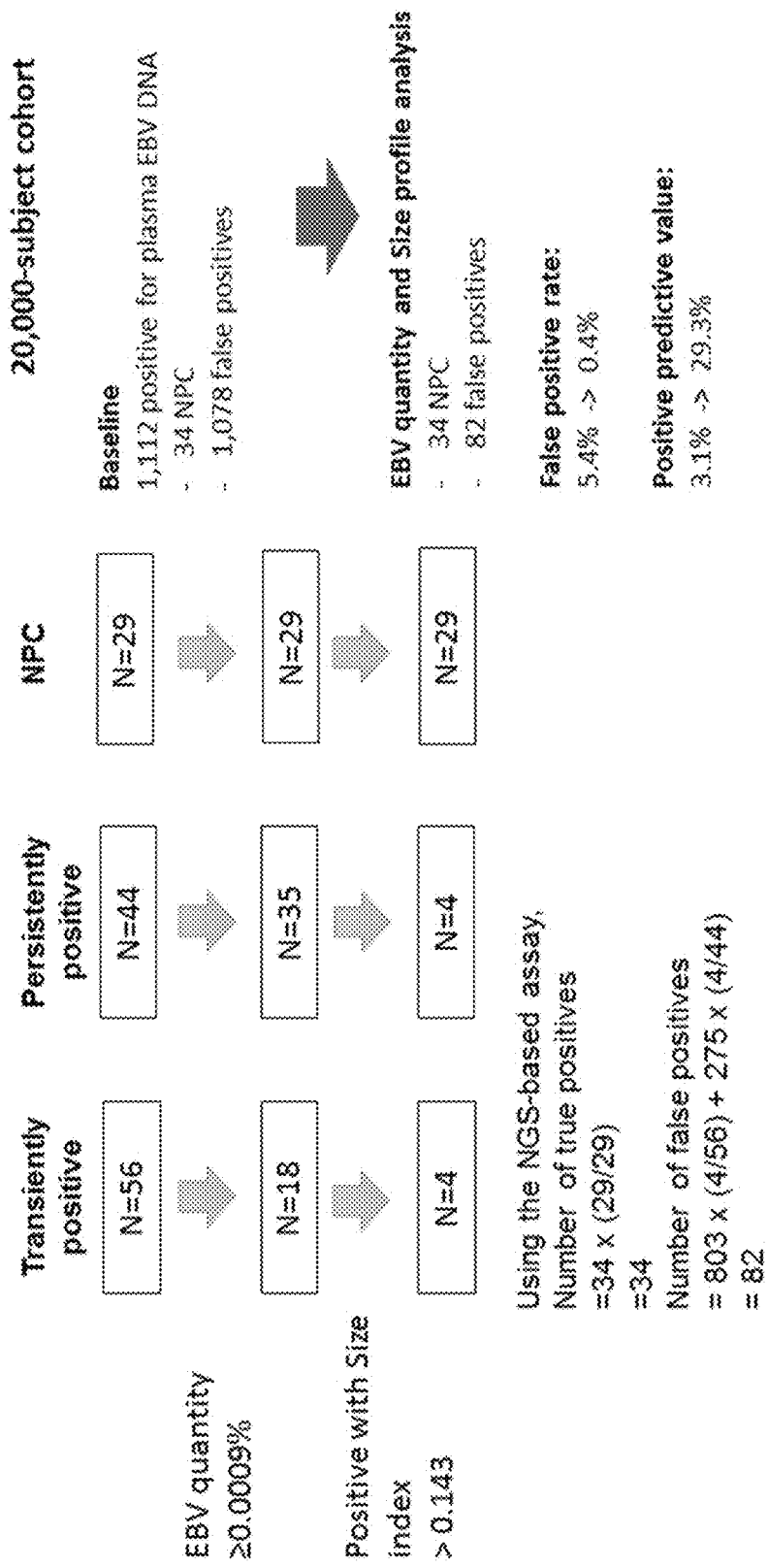
FIG. 55 shows the number of subjects identified as being transiently positive or persistently positive for plasma EBV DNA but have no observable pathology, and subjects identified as having NPC following a first analysis using a proportion of sequenced plasma DNA fragments mapped to the EBV genome and a subsequent second analysis using a size ratio.

FIG. 55 shows an overview of an analysis of one validation set. The analysis started with a validation set that included 56 transiently positive samples; 44 persistently positive samples, and 29 confirmed NPC samples. Setting a cutoff value for the proportion of plasma DNA fragments mapped to the EBV genome in subjects at 0.0009%, 18 of the transitively positive samples were above the threshold; 35 of the persistently positive samples were above the threshold; and 29 of the NPC samples were above the threshold. Using a size index cutoff of greater than 0.143, 4 of the transiently positive were above the cutoff, 4 of the persistently positive were above the cutoff, and 29 of the NPC were above the cutoff Starting with an over 20,000-subject cohort, 1,112 subjects were positive for plasma EBV DNA. 34 of those subjects had NPC; 1,078 were false positives. Using the next generation sequencing based assay for EBV quantity and size profile analysis, the number of false positives was estimated to be reduced to 82 (803 transitively positive samples×(4/56)+275 persistently positive×(4/44) gives an estimate of 82 false positives). The false positive rate of the initial assay was 5.4% (1078/(20174-34)*100%). Using the next generation sequencing assays for EBV quantity and size profile analysis can reduce the false positive rate to 0.4% (82 false positives/(20,174−34) total*100%). The positive predictive value of the initial assay was 3.1% (34/1112*100%). Using the next generation sequencing assays for EBV quantity and size profile analysis can increase the positive predictive value to 29.3%. (34 true positives/(34 true positives+82 false positives) *100%=29.3%). An improved false positive and positive predictive value is provided, without comprising sensitivity, all based on an initial blood sample. FIG. 54 illustrates that a next-generation sequencing assay performed on an initial samples positive for plasma EBV DNA can reduce a false positive rate and increase a positive predictive value.

In another embodiment, subjects identified as having NPC following a first analysis using a proportion of sequenced plasma DNA fragments mapped to the EBV genome (e.g., greater than or equal to 0.0009%) and a subsequent second analysis using a size ratio (e.g., less than or equal to 7%). Using a combination of the plasma EBV quantity analysis (e.g., a proportion of EBV DNA reads among all sequenced reads) and the size ratio, the NPC detection rate, false positive rate and positive predictive value in the cohort of 72 subjects was calculated. The NPC detection rate was 100%. The false positive rate is 13.5% and the positive predictive value is 86.5%. In contrast, using only real-time PCR analysis to screen for subjects having NPC, the false positive rate was 30.4% and the positive predictive value was 69.6%. Therefore, we could observe an almost three-fold reduction in the false positive rate using a combined analysis of EBV DNA quantity and size analysis from targeted capture sequencing with the above cutoffs of 0.0009% and 7%.

Adopting a model that required a sample to concurrently pass cutoffs for EBV DNA counting and size measurements, NPCs were detected at a positive predictive value (PPV) of 19.6%. Accordingly, a plasma sample was deemed to be positive and identified as NPC if its sequencing data concurrently passed the cutoffs in both the count- and size-based analyses. This represented superior performance when compared with the PPV of 11.0% in the prospective screening study that required participants with an initially detectable plasma EBV DNA result to be retested within 4 weeks.

We performed the combined count- and size-based analysis for all samples in the validation sample set. By applying the same cutoff values defined in the exploratory dataset, all the samples of NPC patients from both the screening and external cohorts could be captured.

Figure 56B:
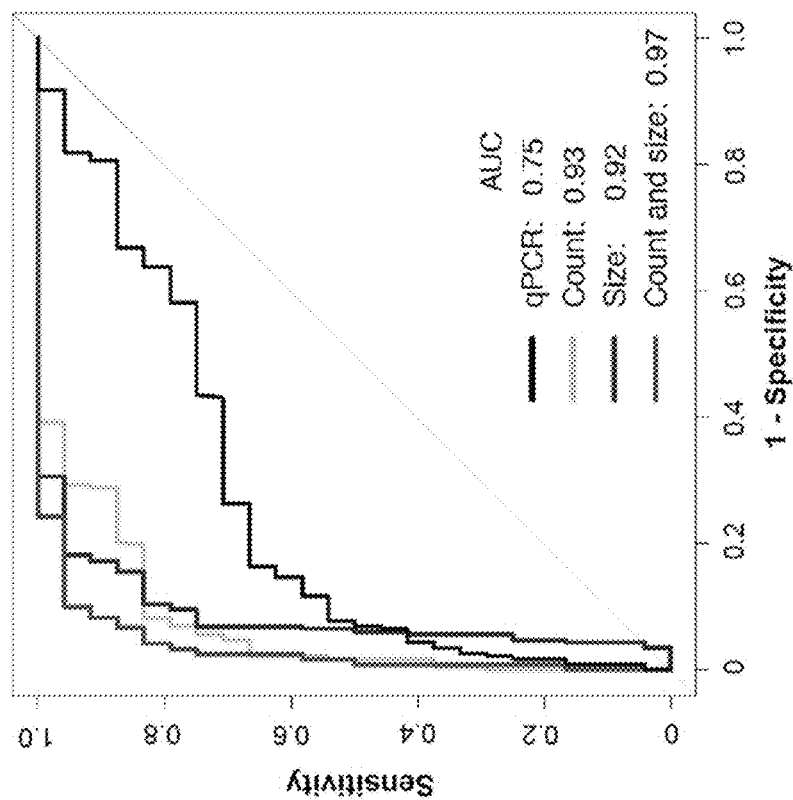
FIG. 56B shows the receiver operating characteristic (ROC) curves for the count-based analysis, size-based analysis, combined sequencing analysis, and real-time PCR analysis.
Figure 56A:
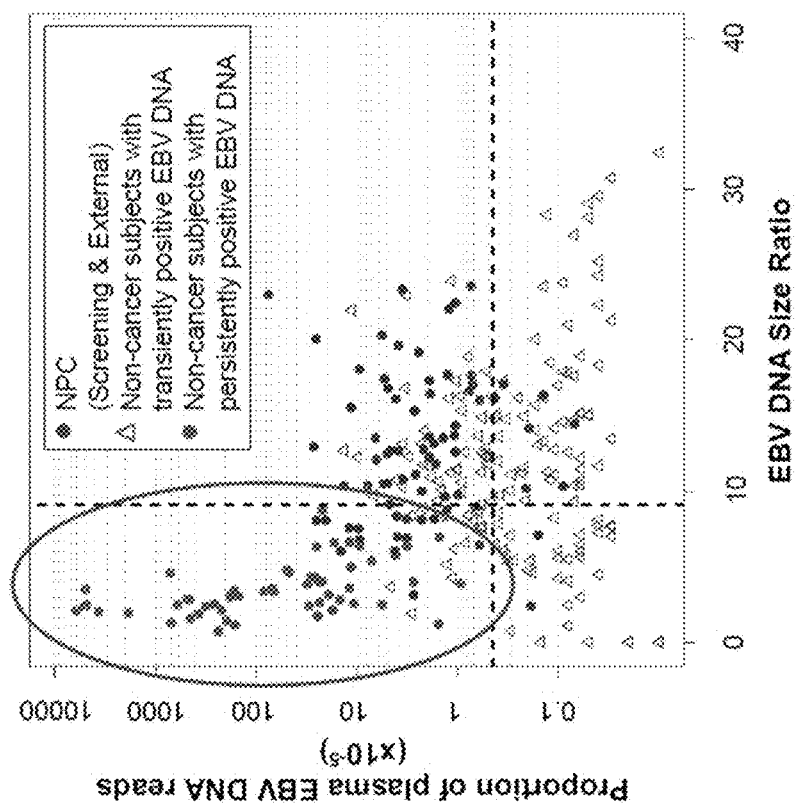
FIG. 56A shows a plot of the relationship between the proportions of plasma EBV reads and corresponding size ratio values for all the cases in the validation sample set.

FIG. 56A shows a plot of the relationship between the proportions of plasma EBV reads and corresponding size ratio values for all the cases in the validation sample set. The same cutoff values in the count- and size-based analyses defined in the exploratory sample set are denoted by the grey dotted lines. The red oval highlights the quadrant with cases which passed the cutoffs in the combined count- and size-based analysis. There were 15 (out of 159) subjects with transiently positive results and 17 (out of 73) subjects with persistently positively results who passed both the cutoffs in the count- and size-based analyses.

We compared the diagnostic performances of the count-based, size-based and combined count- and size-based analyses as well as real-time PCR in differentiating NPC patients from non-cancer subjects in the validation sample set using receiver operating characteristic (ROC) curve analysis.

FIG. 56B shows the receiver operating characteristic (ROC) curves for the count-based analysis, size-based analysis, combined sequencing analysis, and real-time PCR quantitative analysis. The real-time PCR performance is based on quantitative plasma EBV DNA values determined by the real-time PCR assay to arbitrate between the NPC and non-NPC cases. The area under the curve (AUC) values are shown. Area under the curve values for the count-based, size-based and combined analyses were 0.93, 0.92 and 0.97, respectively, and were significantly higher than that of PCR-based analysis (0.75) (P=0.0071, P=0.0143, P=0.0008 respectively, Bootstrap test). These data show that the count-based analysis alone, the size-based analysis alone or the combined count- and size-based analysis all performed better than using real-time PCR for plasma EBV DNA quantification.

Since the combined count- and size-based analysis achieved the best diagnostic performance, we proposed a new NPC screening protocol with incorporation of the combined analysis of plasma EBV DNA after baseline real-time PCR-based analysis. Target-capture sequencing would be performed on baseline plasma samples with EBV DNA detectable by real-time PCR. In this new protocol, subjects are defined as 'screen-positive' if their plasma samples pass the cutoffs in both the count-based and the size-based analyses. Subjects are defined as 'screen-negative' if the plasma samples do not pass the cutoff in either the count-based or size-based analysis.

FIG. 57 shows modeling the performance of count-based analysis and size-based analysis of plasma EBV DNA in the entire 20,174-subject screening cohort using the cutoffs from FIG. 56A. The estimated sensitivity, specificity, positive predictive value and false positive rates are stated. CI denotes that 95% confidence intervals.

Based on the performance of the combined analysis in the validation sample set, we have estimated the sensitivity, specificity, positive predictive value and false positive rate in the entire 20,174-subject cohort of the prospective screening trial assuming the new screening protocol were adopted. In the validation cohort, 15 out of 159 (9.4%) subjects with transiently positive EBV DNA results, 17 out of 73 (23.3%) subjects with persistently positive results and all the 24 patients with NPC (100%) passed the cutoffs in the count- and size-based analyses. They were all considered as 'screen-positive' according to the new protocol. In the screening study, one subject with undetectable plasma EBV DNA by real-time PCR analysis developed NPC within one year (7). Since all the cancer cases tested positive in the screening study could be captured, the projected sensitivity of this new protocol would be 97.1% (95% confidence interval (CI), 95.5 to 98.7%), which would be the same as for the previous two time-point screening protocol. The estimated number of subjects with false 'screen-positive' results was 140 (9.4% of the 'transiently positive' group and 23.3% of the 'persistently group' in the screening cohort). The estimated specificity would be 99.3% (95% CI, 99.2% to 99.4%). The PPV and false positive rate were estimated to be 19.6% (95% CI, 13.7% to 25.5%) and 0.70% (95% CI, 0.58% to 0.8%), respectively. The projected performance of the count-based and size-based analyses in the 20,174-subject cohort is shown in Table 4.

TABLE 4

Projected diagnostic performance of the count-based, size-based and combined analyses in the 20,174-subject cohort.

| | 20,174-subject cohort | | |
|---|---|---|---|
| | Sensitivity (%) | Specificity (%) | PPV (%) |
| Count-based analysis | 97.1 | 97.4 | 6.1 |
| Size-based analysis | 97.1 | 98.3 | 8.9 |
| Combined analysis | 97.1 | 99.3 | 19.6 |

By uncovering the differences in abundance and size profiles of plasma EBV DNA among subjects with or without NPC, more specific identification of NPC could be achieved. The cutoff values determined for the sequencing analyses were based on the goal to maintain the sensitivity achieved with real-time PCR testing in the prospective screening study (7). Thus, the key differentiator for the performance of the sequencing-based test rooted in the improved specificity that it offered. The data from the prospective screening study showed that real-time PCR had a false-positive rate of 5.4% when testing was performance on a single baseline blood sample. This was associated with a PPV of 3.1%. In this study, the sequencing analyses were performed on the baseline blood samples. Using the count-based sequencing approach, the false-positive rate was 2.6% and the PPV was 6.0% (Table 4). The size-based approach when used independently has a false-positive rate of 1.7% and PPV of 8.9%. To further enhance the test performance, we proposed an approach that required a sample to concurrently pass both the count- and size-based cutoffs in order to be deemed as tested positive. Using such a combined approach, we achieved a false-positive rate of just 0.7% and PPV of 19.6%. These data represent a significant improvement over that of real-time PCR even when considering the two time-point protocol that had a PPV of 11.0%.

The sequencing-based analyses allows the identification of the presence of plasma EBV DNA at the same time as quantifying (count-based analysis) or measuring the DNA size profile (size-based analysis) and thus could be used as tests independent of prescreening by other tests. On the other hand, the projected performance shown in Table 4 also suggests that the sequencing-based test could be used as a second tier test subsequent to testing by real-time PCR. Real-time PCR is used to determine the presence or absence of plasma EBV DNA in a subject. If the real-time PCR test is positive, one could then perform just the count-based sequencing analysis, just the size-based sequencing analysis, or the combined count- and size-based sequencing analysis to distinguish the cancer true positives from the false-positive cases (positive for EBV DNA but without NPC). Such an arrangement would render the NPC screening program most cost effective because every screened individual is tested by the real-time PCR test, which is of lower costs than sequencing. Only those tested positive for plasma EBV DNA by real-time PCR (about 5% of the population) would proceed to the sequencing test. The sequencing test could be performed on the same plasma DNA extraction as the real-time PCR test, sample from the same blood draw but a different aliquot, or a different blood draw. However, should sequencing costs fall or deemed economical enough, all first line screening could be based on sequencing (count-based alone, size-based alone or combined count- and size-based). It may offer practical advantage to the laboratory for maintaining one test than two platforms for the one program, namely real-time PCR and sequencing.

2. Determining Cutoffs

We have adopted modelling approaches to develop algorithms for the use of EBV DNA count and size ratio analyses in differentiating NPC patients from non-NPC subjects with transiently and persistently positive plasma EBV DNA. In one embodiment, we have used the classification and regression trees (CART) analysis. One aim of the CART analysis is to achieve the largest separation among the different groups (or the highest detection rate of each group). This is achieved by developing the algorithm for the EBV DNA count and size analyses and finding an optimal cutoff value in the two parameters (EBV DNA count and size ratios). Using the CART analysis, we have developed the algorithm: analysis of EBV DNA size ratios first, then the EBV DNA count. The three numbers in each set represent the number of non-NPC subjects with transiently positive plasma EBV DNA, non-NPC subjects with persistently positive plasma EBV DNA and NPC patients, respectively.

Figure 58:
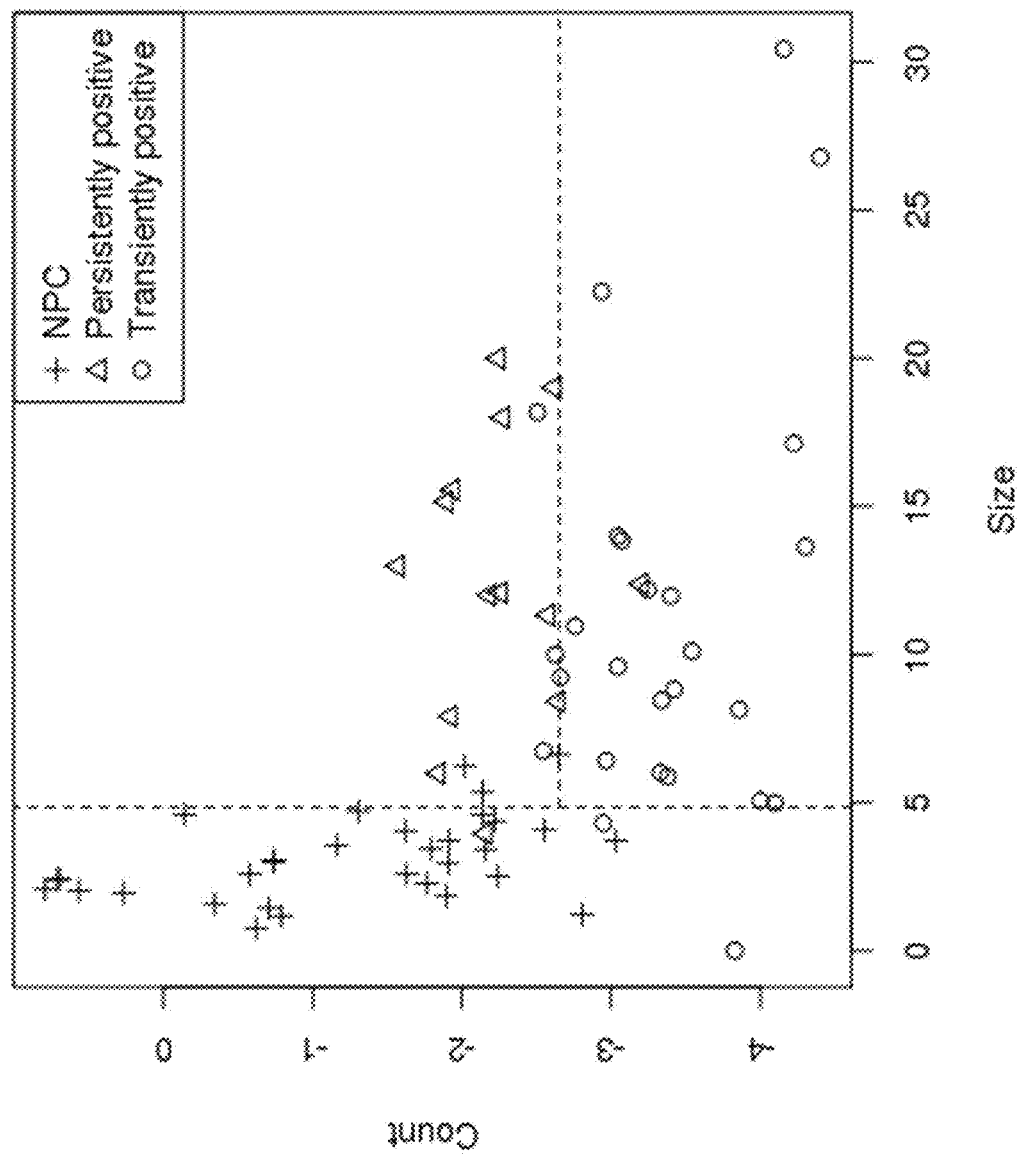
FIGS. 58 and 59 show the results of a classification and regression tree (CART) analysis to determine optimal cutoff values in various parameters for distinguishing between subjects that are transiently positive or persistently positive for plasma EBV DNA but have no observable pathology, or subjects identified as having NPC.
Figure 59:
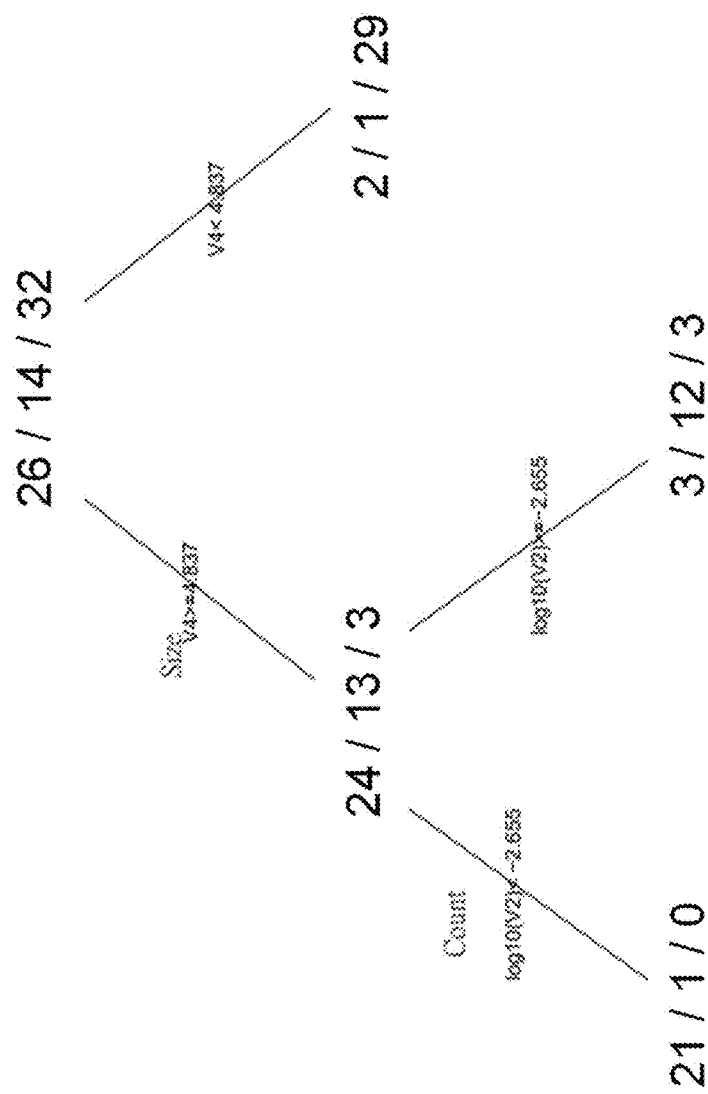

FIGS. 58 and 59 show the results of a classification and regression tree (CART) analysis to determine optimal cutoff values in various parameters for distinguishing between subjects that are transiently positive or persistently positive for plasma EBV DNA but have no observable pathology, or subjects identified as having NPC. A person having ordinary skill in the art will appreciate that a variety of methods may be used to determine the cutoff values used to distinguish between different groups within the cohort or population. A non-limiting example of such a method is CART analysis. In the CART analysis, the goal is to find an optimal cutoff value in the parameters to achieve the largest separation among the different groups (or the highest detection rate of each group).

This CART analysis yielded that the size ratio cut-off value=4.837, and the log (EBV count) cut-off value=−2.655. Using these cutoff values, the NPC detection rate was 90.6% and the positive predictive value is 90.6%. With the EBV DNA size ratio analysis and the cutoff value set at 4.837, 24 non-NPC subjects with transiently positive, 13 non-NPC subjects with persistently positive plasma EBV DNA and 3 NPC patients were classified into one group (EBV DNA size ratio greater than or equal to 4.837), and 2 non-NPC subjects with transiently positive, 1 non-NPC subjects with persistently positive plasma EBV DNA and 29 NPC patients were classified into another group (EBV DNA size ratio less than 4.837).

The group with EBV DNA size ratio greater than or equal to 4.837 were further classified with the EBV DNA count analysis. With the EBV count analysis and the cutoff value of log (EBV count) set at −2.655, 21 non-NPC subjects with transiently positive, 1 non-NPC subjects with persistently positive plasma EBV DNA and 0 NPC patients were classified into one group (log (EBV count) less than −2.655), and 3 non-NPC subjects with transiently positive, 12 non-NPC subjects with persistently positive plasma EBV DNA and 3 NPC patients were classified into another group (log (EBV count) greater than or equal to −2.655). With these cutoff values, the NPC detection rate is 90.6% and the positive predictive value is 90.6%. Other decision tree types could also be used, including but not limited to boosted trees and bootstrap aggregated decision trees.

3. Method

Figure 60:
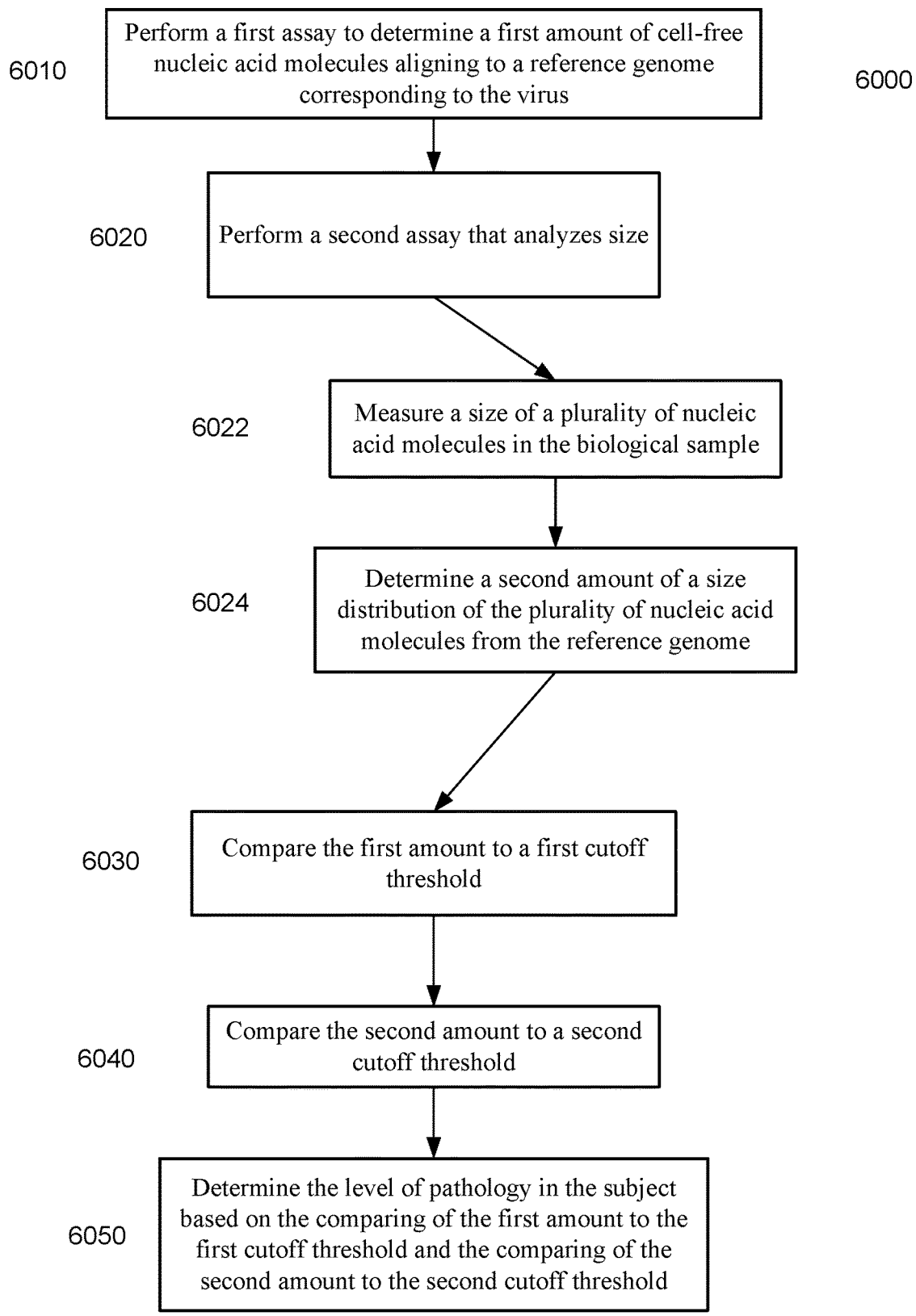
FIG. 60 is a flowchart for a method that combined a count-based and a size-based analysis of viral nucleic acid fragments to determine a level of pathology according to embodiments of the present invention.

FIG. 60 is a flowchart for a method that combined a count-based and a size-based analysis of viral nucleic acid fragments to determine a level of pathology according to embodiments of the present invention. Aspects of method 6000 can be performed in a similar manner as methods 2200 and 4000. At least a portion of the method may be performed by a computer system.

Method 6000 can analyze a biological sample to determine a level of pathology in a subject from which the biological sample is obtained, where the biological sample includes a mixture of cell free nucleic acid molecules. The mixture can include nucleic acid molecules from the subject and potentially nucleic acid molecules from a virus. The analysis can be performed on subjects that are asymptomatic for the pathology (e.g., a type of cancer, CIN, or mononucleosis), and thus identify subjects at an early stage of the pathology.

At block 6010, a first assay is performed. The first assay can analyze a plurality of cell-free nucleic acid molecules from a first biological sample of the subject to determine a first amount of the plurality of cell-free nucleic acid molecules aligning to a reference genome corresponding to the virus. As examples, the first assay can include real-time polymerase chain reaction (PCR) or sequencing, e.g., as performed in method 2200.

At block 6020, a second assay is performed using a size-based analysis. Blocks 6022 and 6024 can be performed as part of performing the second assay. The second assay can be performed on a second biological sample, which may be the same or different than the first biological sample. The first biological sample and the second biological sample can be from a same blood sample (e.g., different plasma/serum portions). In some embodiments, the second assay is only performed when the first amount is above the first cutoff. The second assay can be performed in a similar manner as described in for method 4000, e.g., via electrophoresis or sequencing both ends of a nucleic acid fragment and alignment. Such sequencing can be targeted sequencing, e.g., involving capture probes as described herein At block 6022, a size of each of the plurality of nucleic acid molecules in a second biological sample is measured. Block 6022 can be performed in a similar manner as block 4010 of FIG. 40.

At block 6024, a second amount of a size distribution of the plurality of nucleic acid molecules from the reference genome is determined. Block 6024 can be performed in a similar manner as block 4030 of FIG. 40. In some embodiments, the second amount is of nucleic acid molecules having a size within a given range and aligning to the reference genome. Such a second amount can be normalized using a third amount of cell-free nucleic acid molecules having a size within a different range and aligning to the reference genome (e.g., as in FIG. 31). As another example, second amount can be normalized using a third amount of cell-free nucleic acid molecules having a size within the given range and aligning to an autosomal genome. (e.g., as in FIG. 32).

At block 6030, the first amount is compared to a first cutoff. It can be determined whether the first amount exceeds the first cutoff (e.g., above). An extent that the first amount exceeds the first cutoff can be determined, e.g., so as to inform the final determination of the level of pathology.

At block 6040, the second amount is compared to a second cutoff. It can be determined whether the first amount exceeds the first cutoff (e.g., above or below, depending on how the second amount is defined). An extent that the second amount exceeds the second cutoff can be determined, e.g., so as to inform the final determination of the level of pathology.

At block 6050, the level of pathology in the subject is determined based on the comparing of the first amount to the first cutoff and the comparing of the second amount to the second cutoff. In some embodiments, the subject is determined to have the pathology only if the first amount exceeds the first cutoff and the second amount exceeds the second cutoff In various embodiments, the positive predictive value of determining the level of cancer can be at least 15%, at least 17%, or at least 19%, a sensitivity of determining the level of cancer is at least 95%, at least 96%, or at least 97%, and/or a specificity of determining the level of cancer is at least 95%, at least 96%, at least 97%, at least 98%, or at least 99%.

B. Combined Fragments and Size

As another example, the fragmentation and size analyses can be combined.

Figure 61:
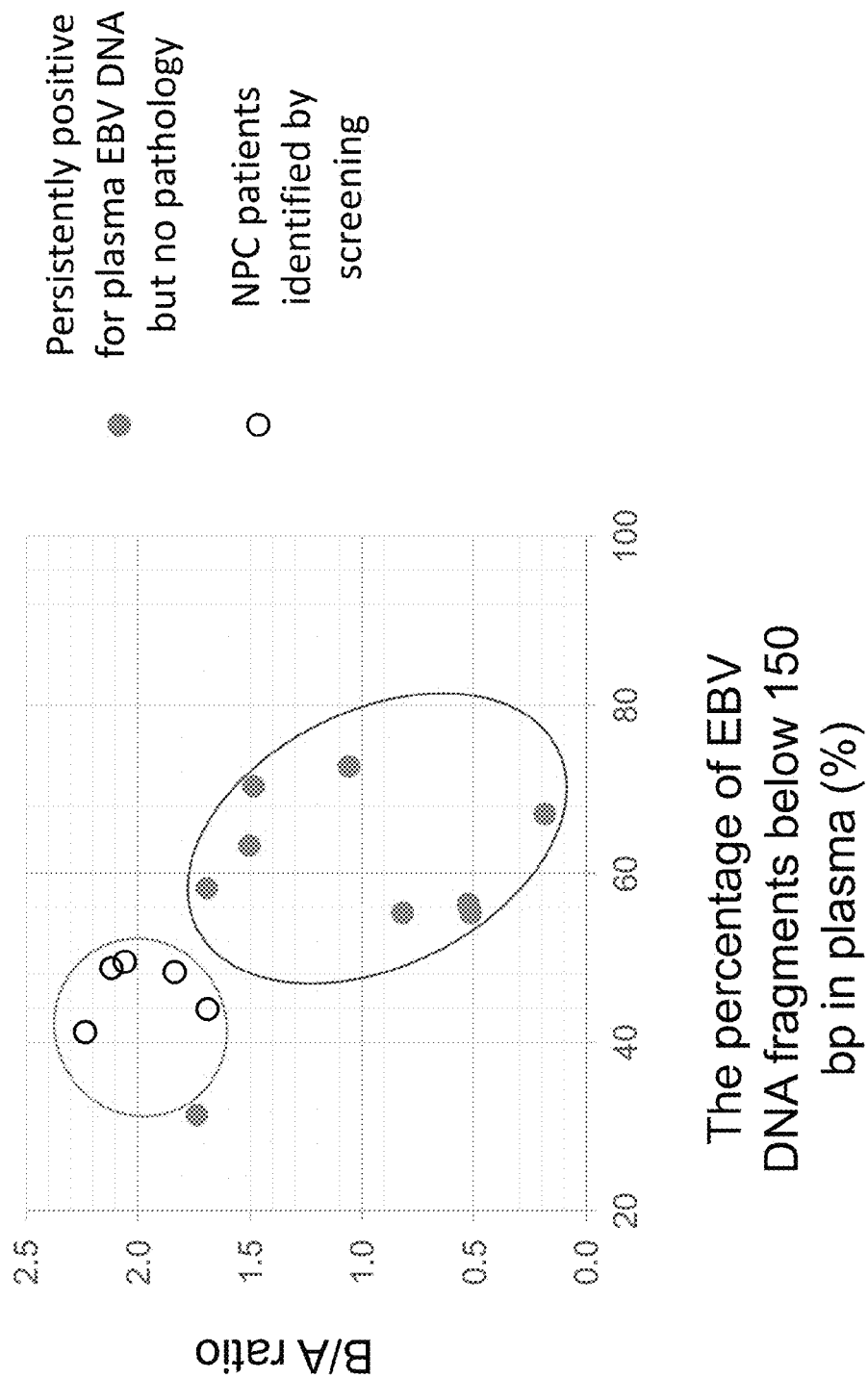
FIG. 61 shows a scatter plot of the B/A ratio vs the percentage of EBV DNA fragments below 150 bp in plasma for (closed circle) subjects persistently positive for plasma EBV DNA but having no observable pathology, and (open circle) early-stage NPC patients identified by screening.

FIG. 61 shows a scatter plot of the B/A ratio vs the percentage of EBV DNA fragments below 150 bp in plasma for (closed circle) subjects persistently positive for plasma EBV DNA but having no observable pathology, and (open circle) NPC subjects. Based on the percentage of sequenced plasma EBV DNA fragments of <150 bp and the B/A ratio, NPC subjects could be differentiated from those with false-positive plasma EBV DNA results. Only one subject with a false-positive result was clustered with the NPC subjects using these two parameters.

VI. BENEFITS OF IMPROVEMENTS

From the public health point of view, any improvement in the PPV would have a substantial impact. Guangdong is one of the provinces in China with the highest incidence rates of NPC (33). According to the China Statistical Yearbook 2016, there are about 20 million men aged between 40 to 65 years old in the Guangdong province. If a universal NPC screening program is adopted for all men within this age range who have the highest age-specific incidence, the new protocol would lead to a reduction in the number of false positives by 50%, that is, 140,000 subjects. Such a large number would imply a substantial reduction in the medical expenditures initially spent on follow-up tests and confirmatory investigations including endoscopy and magnetic resonance imaging (MRI).

A benefit of some embodiments is that high PPV could be achieved from blood sampling of just a single time-point. By overcoming the need for testing at two time-points, our new protocol has significant advantages over the previous protocol requiring two time-point testing. Previous studies on other cancer screening programs have shown that a substantial proportion of participants with abnormal screening test results reported anxiety and distress (34). Hence, for two time-point testing, subjects with detectable EBV DNA at baseline could only obtain their final screening status after the follow-up tests. These subjects may experience anxiety while waiting for the follow-up tests. In addition, the requirement to test two time-points presents much logistical challenges. There are direct costs associated with recalling subjects initially tested positive for second testing. Compliance may become an issue when the protocol is adopted in the clinical context. Reduction in compliance would result in reduction in the sensitivity of the NPC screening program.

In contrast, the new sequencing-based protocol obviates the need for a second blood sample to define a person having been 'screened positive'. This new protocol is thus more clinically and logistically practical, and may be more easily accepted by the general public.

The data in our current study showed that target sequencing analysis of plasma EBV DNA could achieve high PPV for NPC screening. In this study, the performance of the sequencing test is modeled against the cases assessed by real-time PCR in the prospective screening study. Therefore, the performance data are representative of a two-staged test that combines the use of real-time PCR and sequencing analysis of plasma EBV DNA. For example, real-time PCR assessment of plasma EBV DNA is performed as the first line test. 5.5% of tested subjects (comprising true NPC and false-positives) would have detectable levels of plasma EBV DNA. These samples would then be additionally analyzed by the sequencing test. This would represent a much more cost-effective approach because ~95% of the population could be screened negative by the real-time PCR test.

Our work has highlighted the value of studying the fragmentation patterns of viral nucleic acids in human plasma. The clinical significance of the presence of EBV DNA in plasma of subjects without NPC is currently unknown. By showing the differences in the molecular nature of these molecules from those found in plasma of NPC patients offer some level of reassurance that they are less likely to represent a predisposition to NPC. Nonetheless, we are currently following up these individuals on an annual basis to assess their clinical outcome in the future. On the other hand, it would be worthwhile to explore the fragmentation patterns of plasma EBV DNA in different EBV-associated diseases or cancers, for examples, infectious mononucleosis, Hodgkin lymphoma, Burkitt's lymphoma and post-transplant lymphoproliferative disorder. Such work would be useful for establishing disease-specific molecular signatures of plasma EBV DNA and understanding the pathophysiology of EBV in different diseases. In future studies, the fragmentation patterns of circulating DNA molecules of other viral species associated with cancers (35) could also be analyzed. For examples, circulating hepatitis B virus DNA in patients with hepatocellular carcinoma and circulating human papillomavirus DNA in patients with cervical cancer could be studied.

In summary, we have developed a second generation approach for screening of NPC. This approach is based on the differentiating quantitative and size-based characteristics of plasma EBV DNA between NPC patients and non-cancer subjects. Such an approach not only demonstrates a more superior performance in reduction of false positives but also allows a single time-point testing without the need of a follow-up blood sample. We believe that this more clinically practical protocol would greatly streamline testing and facilitate the implementation on a population scale. It is envisioned that the mortality rate from NPC would potentially be reduced as a result of mass screening in endemic regions. This study has also shed light on avenues of future developments for plasma DNA-based screening for other cancer types.

Some embodiments can comprise providing a therapeutic intervention based on the classification or performing imaging of the subject based on the classification.

VII. MATERIALS AND METHODS

Various example techniques are described below, which may be implemented in various embodiments.

Regarding blood sample collection and plasma DNA extraction, peripheral blood samples can be collected into EDTA-containing tubes and immediately stored at 4° C. The blood sample can be centrifuged to separate plasma from remaining blood components (e.g., red blood cells, white blood cells, and platelets). For example, the blood samples can be first centrifuged at 1,600 g for 10 min at 4° C. and the plasma portion re-centrifuged at 16,000 g for 10 min at 4° C. to remove the residual blood cells. Centrifugation for 15 minutes at 2,000×g depletes platelets in the plasma sample. Plasma samples can be stored at 2-8° C. until further analysis. Plasma DNA was extracted from 4 mL of plasma. DNA from plasma was extracted using the QIAamp DSP DNA Blood Mini Kit (Qiagen).

Regarding DNA library construction, indexed plasma DNA libraries can be constructed using the KAPA Library Preparation Kit (Kapa Biosystems) according to the manufacturer's protocol. The adaptor-ligated DNA was amplified with 13 cycles of PCR using the KAPA HiFi HotStart ReadyMix PCR Kit (KAPA Biosystems).

Regarding sequencing of DNA libraries, the multiplexed DNA libraries can be sequenced using either the NextSeq 500 or the HiSeq 2500 Sequencing platforms (Illumina). A paired-end sequencing protocol was used, with 75 nucleotides being sequenced from each end.

Regarding alignment of sequencing data, the paired-end sequencing data can be analyzed by means of the SOAP2 (36) in the paired-end mode. The paired-end reads were aligned to the combined reference genomes including reference human genome (hg19) and EBV genome (AJ507799.2). Up to two nucleotide mismatches were allowed for the alignment of each end. Only paired-end reads with both ends uniquely aligned to the same chromosome with the correct orientation, spanning an insert size within 600 bp, were used for downstream analysis.

In some embodiments, sequencing data analysis was performed by bioinformatics programs written in Perl and R languages. The Kruskal-Wallis test was used to compare the plasma EBV DNA concentrations among the NPC patients, non-cancer subjects with transiently positive EBV DNA and non-cancer subjects with persistently positive EBV DNA in the whole screening cohort and in the exploratory and validation datasets. The Kruskal-Wallis test was also used to compare the proportion of EBV DNA reads in the three groups in the exploratory and validation datasets. A P value of <0.05 was considered as statistically significant.

A. Targeted Enrichment

The specificity of detecting tumor-derived nucleic acids can be proportional with the concentration of tumor-derived nucleic acids in the sample. Accordingly, target-specific enrichment can be used to increase the concentration of tumor-derived nucleic acids in the sample. For example, a DNA probe having a sequence complementary to, and capable of binding, BamHI sequence (5'-GGATCC-3') in EBV DNA can be used to perform targeted enrichment of the EBV DNA fragments in the sample. The DNA probe is also labeled with a high affinity tag (e.g., biotin), which allows the target-bound probe to be recovered. Following recovery of the target-bound probe, the EBV DNA is dissociated and separated from the probe. Subsequently, the enriched sample can be analyzed according the methods described herein.

For enrichment of viral DNA molecules from the plasma DNA samples for subsequent sequencing analysis, target enrichment with EBV capture probes was performed. The EBV capture probes which covered the entire EBV genome were ordered from Roche NimbleGen (SeqCap EZ Developer, Roche NimbleGen Inc). DNA libraries from 5 samples were multiplexed in one capture reaction. Equal amounts of DNA libraries for each sample were used. We had also included probes to cover human autosomal regions for reference. Since EBV DNA is the minority in the plasma DNA pool, an ~100× more excess of EBV probes relative to the autosomal DNA probes were used in each capture reaction. After the capture reaction, the captured DNA libraries were re-amplified with 14 cycles of PCR.

In some embodiments, targeted capture can be performed using capture probes designed to bind to any portion of the EBV genome. In some embodiments, capture probes can be biotinylated, and magnetic beads (e.g., streptavidin coated beads) are used to pull down or enrich the capture probes hybridized to a nucleic acid target (e.g., an EBV genome fragment) after library preparation. In some embodiments, the panel of capture probes used can also target a portion of the human genome. For example, capture probes may be designed to hybridize to at least a portion of one or more chromosomes (e.g., either copy of chromosomes 1, 8, and/or 13). In some embodiments, at least about 1 mb, at least 5 mb, at least 10 mb, at least 20 mb, at least 30 mb, at least 40 mb, at least 50 mb, at least 60 mb, at least 70 mb, at least 80 mb, at least 90 mb, or at least 100 mb of the human genome is targeted using capture probes in the panel. In some embodiments, the capture probe panel can pull down about 285 sequence reads corresponding to the EBV. In some embodiments, the capture probe panel can pull down about 40 million sequence reads corresponding to the human genome.

To analyze the cell-free human papilloma virus (HPV) DNA in plasma, targeted sequencing with capture enrichment by specifically designed capture probes can be used. These capture probes can cover the whole HPV genome, the whole hepatitis B virus (HBV) genome, the whole EBV genome and multiple genomic regions in the human genome (including regions on chr1, chr2, chr3, chr5, chr8, chr15, chr22). For each plasma sample analyzed, DNA was extracted from 1-4 mL plasma using the QIAamp Circulating Nucleic Acid kit. For each case, all extracted DNA was used for the preparation of the sequencing library using the TruSeq Nano library preparation kit. Twelve cycles of PCR amplification was performed on the sequencing library using the Illumina TruSeq Nano PCR amplification kit. The amplification products were captured using the SEQCAP-EZ kit (Nimblegen) using the custom-designed probes covering the viral and human genomic regions stated above. After target capturing, 14 cycles of PCR amplification were performed and the products were sequenced using the Illumina NextSeq platform. For each sequencing run, four to five samples with unique sample barcodes were sequenced using the paired-end mode. Each DNA fragments would be sequenced 75 nucleotides from each of the two ends. After sequencing, the sequenced reads would be mapped to an artificially combined reference sequence which consists of the whole human genome (hg19), the whole HPV genome, the whole HBV genome and the whole EBV genomes. Sequenced reads mapping to unique position in the combined genomic sequence would be used for downstream analysis.

For example, capture probes may be designed to cover the whole EBV genome, the whole hepatitis B virus (HBV) genome, the whole human papillomavirus (HPV) genome and/or multiple genomic regions in the human genome (including regions on chr1, chr2, chr3, chr5, chr8, chr15 and chr22). To efficiently capture viral DNA fragments from plasma, more probes hybridizing to viral genomes than human autosomal regions of interest may be used. In one embodiment, for whole viral genomes, on average 100 hybridizing probes covering each region with ~200 bp in size (e.g., 100× tiling capturing probes). For the regions of interest of human genome, we designed on average 2 hybridizing probes covering each region with ~200 bp in size (e.g., 2× tiling capturing probes). The capture probes may be designed according to Table 5.

TABLE 5

Design of capture probes for targeted sequencing

|  |  | Length (bp) | Targeted capture design |
|---|---|---|---|
| Autosomes | chr1 | 29,382,851 | 2× tiling capturing probes |
|  | chr2 | 819,161 |  |
|  | chr3 | 25,981,149 |  |
|  | chr5 | 2,339,138 |  |
|  | chr8 | 21,438,698 |  |
|  | chr15 | 767,847 |  |
|  | chr22 | 327,728 |  |
| Viral targets | EBV | 170,771 | 100× tiling capturing probes |
|  | HBV | 3,216 |  |
|  | HPV16 | 7,855 |  |
|  | HPV18 | 7,789 |  |
|  | HPV31 | 7,791 |  |
|  | HPV33 | 7,744 |  |
|  | HPV35 | 7,813 |  |
|  | HPV39 | 7,734 |  |
|  | HPV45 | 7,784 |  |
|  | HPV51 | 7,674 |  |
|  | HPV52 | 7,820 |  |
|  | HPV56 | 7,814 |  |
|  | HPV58 | 7,705 |  |
|  | HPV66 | 7,806 |  |
|  | HPV68 | 7,751 |  |
|  | HPV70 | 7,884 |  |

There were a total of 2.1M probes for human DNA, EBV HPV and HBV. 188,342 probes were for EBV DNA capture. The ratio of EBV sequence to be captured to human DNA sequence to be captured was 0.0021.

B. Amplification Free Analysis

The analysis of the cell-free DNA molecules can be amplification free. When using PCR, the sequencing depth (i.e. the number of sequence reads covering a particular nucleotide or ending on the particular nucleotide in a reference genome) does not directly reflect how many plasma DNA molecules covering that particular nucleotide are analyzed. This is because one plasma DNA molecule can generate multiple replicates during the PCR process, and multiple sequence reads can originate from a single plasma DNA molecule. This duplication problem would become more important with: i) a higher number of PCR cycles for amplifying the sequencing library; ii) an increased sequencing depth, and iii) a smaller number of DNA molecules in the original plasma sample (e.g. a smaller volume of plasma).

Accordingly, some embodiments can include obtaining template DNA molecules from the biological sample to be analyzed; preparing a sequencing library of analyzable DNA molecules using the template DNA molecules, the preparation of the sequencing library of analyzable DNA molecules not including an operation of DNA amplification of the template DNA molecules; sequencing the sequencing library of analyzable DNA molecules to obtain a plurality of sequence reads corresponding to the first plurality of cell-free DNA molecules. Analyzing the first plurality of cell-free DNA molecules can include receiving, at the computer system, the plurality of sequence reads and aligning, by the computer system, the plurality of sequence reads to the reference genome to determine genomic positions for the plurality of sequence reads.

VIII. SUBJECTS

Where relevant in the description herein, a subject can have any type of cancer or tumor. In an example, a subject can have nasopharyngeal cancer, or cancer of the nasal cavity. In another example, a subject can have oropharyngeal cancer, or cancer of the oral cavity. Non-limiting examples of cancer can include, but are not limited to, adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, hepatocellular carcinoma, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The term 'lymphoma' generally refers to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' generally refers to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, the patient may have a cancer that is not breast cancer.

Examples of cancer include cancers that cause solid tumors as well as cancers that do not cause solid tumors. Furthermore, any of the cancers mentioned herein may be a primary cancer (e.g., a cancer that is named after the part of the body where it first started to grow) or a secondary or metastatic cancer (e.g., a cancer that has originated from another part of the body).

A subject at risk of cancer may be at risk because of a particular condition such as a pre-cancerous condition. Pre-cancerous conditions include but are not limited to actinic keratosis, Barrett's esophagus, atrophic gastritis, ductal carcinoma in situ, dyskeratosis congenita, sideropenic dysphagia, lichen planus, oral submucous fibrosis, solar elastosis, cervical dysplasia, leukoplakia, and erythroplakia). In some cases, a patient may be at risk of cancer because of cell or tissue dysplasia (e.g., an abnormal change in cell number, abnormal change in cell shape, abnormal change in cell size, or abnormal change in cell pigmentation). A subject that is at risk of cancer may be a patient that was exposed to a carcinogenic agent. Such patients may include patients with exposure to known or probable carcinogens (e.g., acetyaldehyde, asbestos, or tobacco products), or patients exposed to ionizing radiation (e.g., gamma radiation, beta-radiation, X-radiation, or ultraviolet radiation). In some cases, a patient at risk of cancer is at risk because of a family history of cancer.

In some embodiments, a method of the present disclosure may detect a tumor or cancer in a subject, wherein the tumor or cancer has a geographic pattern of disease. In an example, a subject may have an EBV-related cancer (e.g., nasopharyngeal cancer), which is prevalent in South China (e.g., Hong Kong SAR). In another example, subject may have an HPV-related cancer (e.g., oropharyngeal cancer), which is prevalent in the United States and Western Europe. In yet another example, a subject can have a Human T-lymphotrophic virus-1 (HTLV-1)-related cancer (e.g., adult T-cell leukemia/lymphoma), which is prevalent in southern Japan, the Caribbean, central Africa, parts of South America, and in some immigrant groups in the southeastern United States.

Both DNA and RNA viruses have been shown to be capable of causing cancer in humans. In some embodiments, a subject may have a cancer caused by a virus (e.g., an oncovirus). In some embodiments, a subject may have a cancer, and the cancer may be detectable using viral DNA. For example, viral DNA may have a unique fragmentation pattern in healthy subjects as compared to a subject having a cancer or tumor. In some aspects, a particular viral-DNA fragmentation pattern (e.g., the viral-DNA fragmentation pattern in a control subject or a tumor subject) may be detectable using one or more specific nucleotides at which the viral DNA fragments, the size (e.g., length or mass) of the resulting fragmented viral DNA, the copy number of the viral DNA fragments, or any other characteristic of the viral DNA fragments (e.g., methylation signature, sequence, GC content, or binding affinity) In some embodiments, a subject may have cancer, and the cancer may be detectable using tumor-derived viral DNA. In some embodiments, a subject may have a cancer, and the cancer may be detectable using tumor-derived viral DNA, or a fragment thereof, in cell-free sample obtained from the subject (e.g., a blood sample, a plasma sample, or a serum sample). A person having skill in the art will appreciate that a virus may have multiple viral strains (e.g., related viruses that may differ in their genetic makeup), which are included within the scope of the embodiments of the present application. For example, a subject can have oral, oropharyngeal, cervical cancer, penile, anal, vaginal, or vulvar cancer caused by (or associated with) infection by a HPV, which can include more than 150 related viruses. Infection with EBV can also increase a subject's risk of developing nasal cancer, nasopharyngeal cancer, lymphomas (e.g., Burkitt lymphoma or Hodgkin lymphoma), or stomach cancer. In yet another example, infection with the Hepatitis B virus (HBV) or Hepatitis C virus can cause chronic infections, which can increase a subject's chance of developing liver cancer. Non-limiting examples of viruses that may cause, or be associated with, cancer in a subject include HPV, EBV, HBV, hepatitis C virus (HCV), Human immunodeficiency virus (e.g., associated with Kaposi sarcoma, cervical cancer, non-Hodgkin lymphoma, anal cancer, Hodgkin disease, lung cancer, oral cancer, oropharyngeal cancer, skin cancer, and liver cancer), human herpes virus 8 (e.g., associated with Kaposi sarcoma, blood cancer, primary effusion lymphoma, and Castleman disease), Human T-lymphotrophic virus-1 (e.g., associated with lymphocytic leukemia, non-Hodgkin lymphoma, and adult T-cell leukemia/lymphoma), and Merkel cell polyomavirus (e.g., associated with skin cancers such as Merkel cell carcinoma). In some embodiments, a non-human subject (e.g., a primate) may have cancer, and the cancer may be detectable using tumor-derived viral DNA. For example, infection with Simian virus 40 (SV40) can increase a subject's risk of developing mesothelioma, brain tumor, bone cancer, and lymphoma.

A subject as described herein may be of any age and may be an adult, infant or child. In some cases, the patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of patients that may benefit is patients over the age of 40. Another particular class of patients that may benefit is pediatric patients, who may be at higher risk of chronic heart symptoms. Furthermore, a patient treated by any of the methods or compositions described herein may be male or female.

Any of the methods disclosed herein may also be performed on a non-human subject, such as a laboratory or farm animal, or a cellular sample derived from an organism disclosed herein. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

IX. EXAMPLE SYSTEMS

Figure 62:
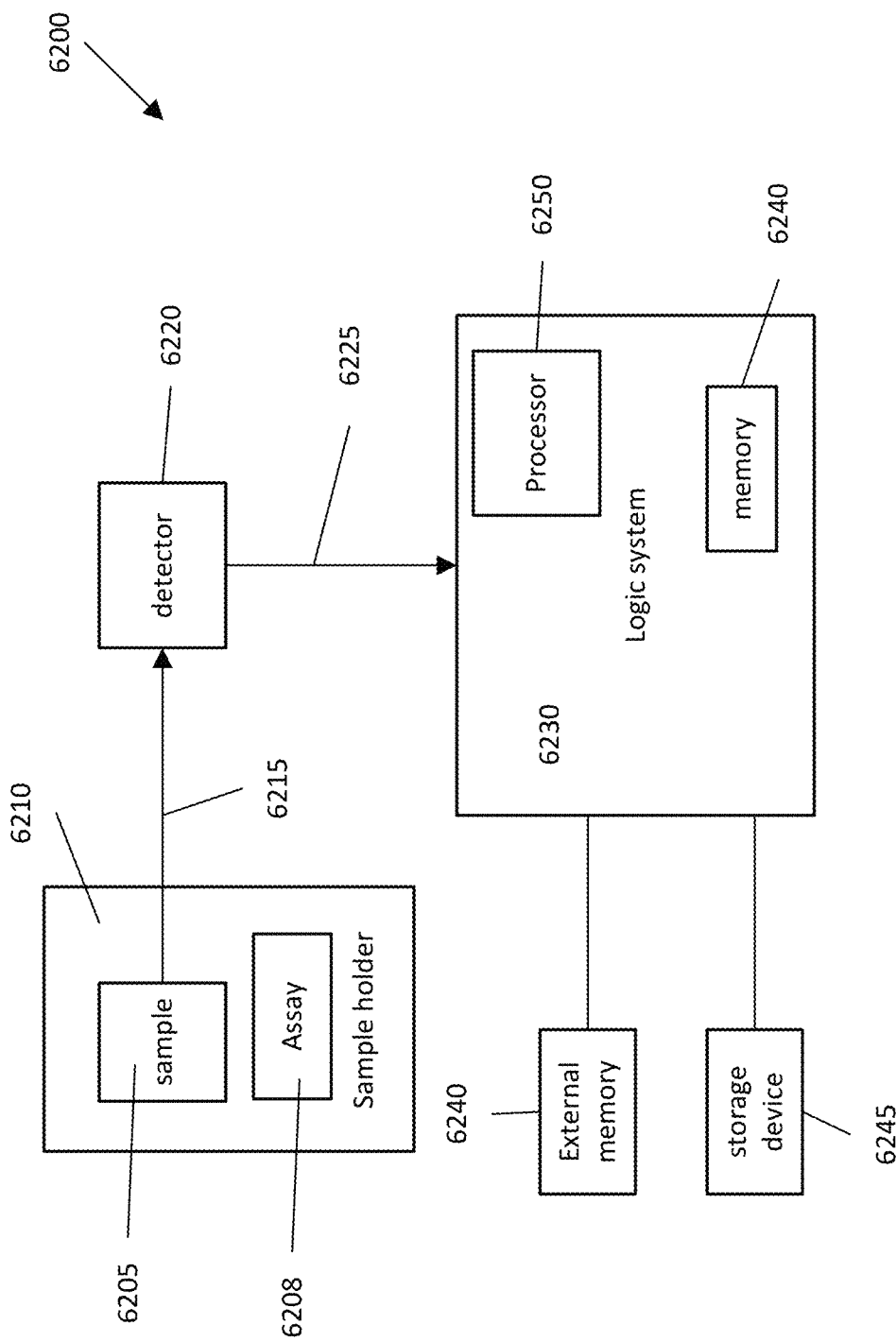
FIG. 62 illustrates a system 5900 according to an embodiment of the present invention.

FIG. 62 illustrates a system 6200 according to an embodiment of the present invention. The system as shown includes a sample 6205, such as cell-free DNA molecules within a sample holder 6210, where sample 6205 can be contacted with an assay 6208 to provide a signal of a physical characteristic 6215. An example of a sample holder can be a flow cell that includes probes and/or primers of an assay or a tube through which a droplet moves (with the droplet including the assay). Physical characteristic 6215, such as a fluorescence intensity value, from the sample is detected by detector 6220. Detector can take a measurement at intervals (e.g., periodic intervals) to obtain data points that make up a data signal. In one embodiment, an analog to digital converter converts an analog signal from the detector into digital form at a plurality of times. A data signal 6225 is sent from detector 6220 to logic system 6230. Data signal 6225 may be stored in a local memory 6235, an external memory 6240, or a storage device 6245.

Logic system 6230 may be, or may include, a computer system, ASIC, microprocessor, etc. It may also include or be coupled with a display (e.g., monitor, LED display, etc.) and a user input device (e.g., mouse, keyboard, buttons, etc.). Logic system 6230 and the other components may be part of a stand-alone or network connected computer system, or they may be directly attached to or incorporated in a thermal cycler device. Logic system 6230 may also include optimization software that executes in a processor 6250.

Figure 63:
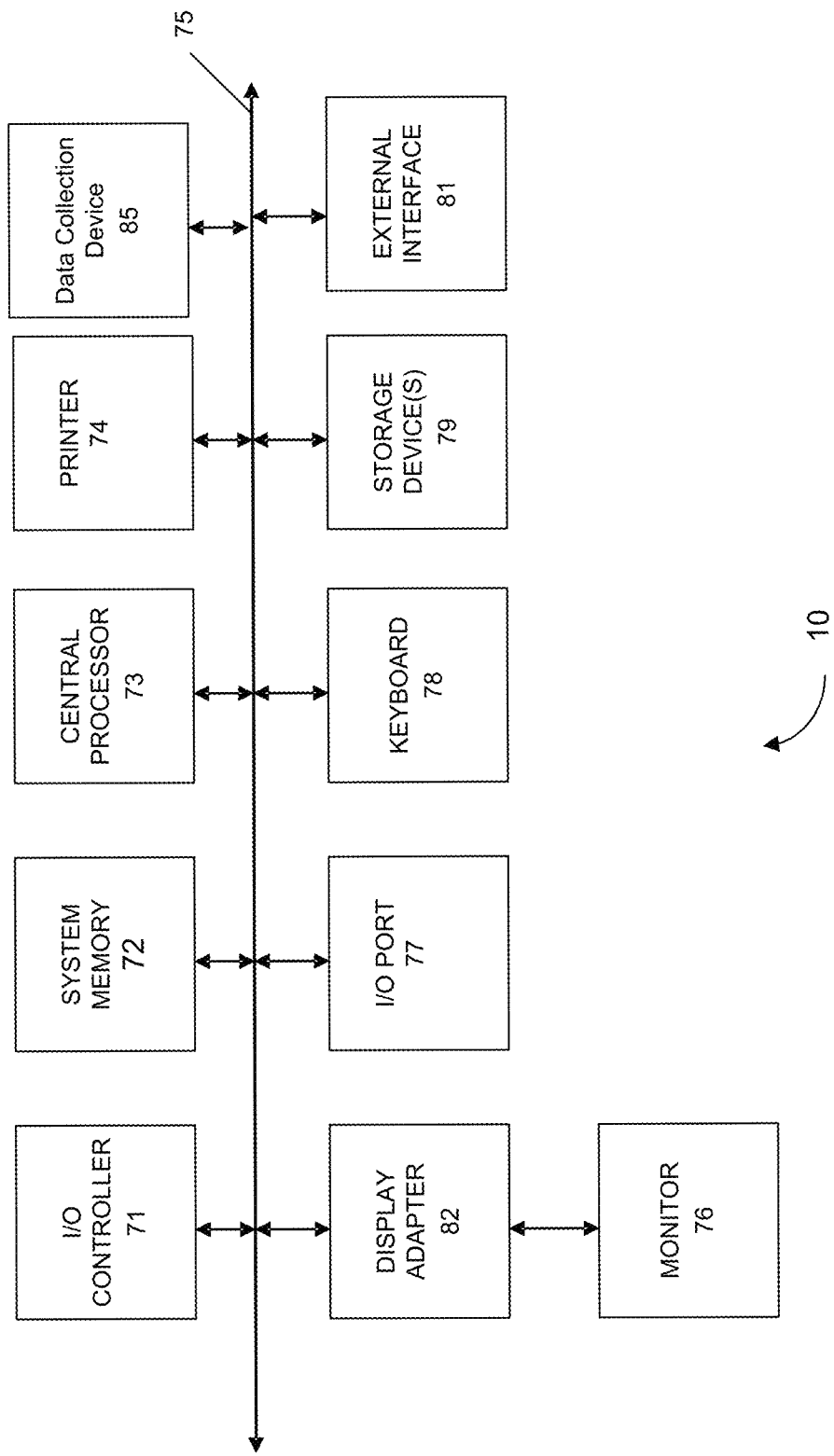
FIG. 63 shows a block diagram of an example computer system 10 usable with system and methods according to embodiments of the present invention.

Any of the computer systems mentioned herein may utilize any suitable number of subsystems. Examples of such subsystems are shown in FIG. 63 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 63 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of connections known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the operations. Thus, embodiments can be directed to computer systems configured to perform the operations of any of the methods described herein, potentially with different components performing a respective operations or a respective group of operations. Although presented as numbered operations, operations of methods herein can be performed at a same time or in a different order. Additionally, portions of these operations may be used with portions of other operations from other methods. Also, all or portions of an operation may be optional. Additionally, any of the operations of any of the methods can be performed with modules, units, circuits, or other approaches for performing these operations.

The section headings used herein are for organizational purposes only and are not to be construed as limiting the subject matter described.

It is to be understood that the methods described herein are not limited to the particular methodology, protocols, subjects, and sequencing techniques described herein and as such may vary. It is also to be understood that the terminology used herein is for the purpose of describing particular embodiments only, and is not intended to limit the scope of the methods and compositions described herein, which will be limited only by the appended claims. While some embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

While some embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

All patents, patent applications, publications, and descriptions mentioned herein are incorporated by reference in their entirety for all purposes. None is admitted to be prior art.

X. REFERENCES

1. S.-J. Dawson, D. W. Y. Tsui, M. Murtaza, H. Biggs, O. M. Rueda, S.-F. Chin, M. J. Dunning, D. Gale, T. Forshew, B. Mahler-Araujo, S. Rajan, S. Humphray, J. Becq, D. Halsall, M. Wallis, D. Bentley, C. Caldas, N. Rosenfeld, Analysis of circulating tumor DNA to monitor metastatic breast cancer. *N Engl. J. Med.* 368, 1199-1209 (2013).
2. A. R. Thierry, F. Mouliere, S. El Messaoudi, C. Mollevi, E. Lopez-Crapez, F. Rolet, B. Gillet, C. Gongora, P. Dechelotte, B. Robert, M. Del Rio, P.-J. Lamy, F. Bibeau, M. Nouaille, V. Loriot, A.-S. Jarrousse, F. Molina, M. Mathonnet, D. Pezet, M. Ychou, Clinical validation of the detection of KRAS and BRAF mutations from circulating tumor DNA. *Nat. Med.* 20, 430-435 (2014).
3. T. Forshew, M. Murtaza, C. Parkinson, D. Gale, D. W. Y. Tsui, F. Kaper, S.-J. Dawson, A. M. Piskorz, M. Jimenez-Linan, D. Bentley, J. Hadfield, A. P. May, C. Caldas, J. D. Brenton, N. Rosenfeld, Noninvasive identification and monitoring of cancer mutations by targeted deep sequencing of plasma DNA. *Sci. Transl. Med.* 4, 136ra68-136ra68 (2012).
4. J. Tie, Y. Wang, C. Tomasetti, L. Li, S. Springer, I. Kinde, N. Silliman, M. Tacey, H. L. Wong, M. Christie, S. Kosmider, I. Skinner, R. Wong, M. Steel, B. Tran, J. Desai, I. Jones, A. Haydon, T. Hayes, T. J. Price, R. L. Strausberg, L. A. Diaz, N. Papadopoulos, K. W. Kinzler, B. Vogelstein, P. Gibbs, Circulating tumor DNA analysis detects minimal residual disease and predicts recurrence in patients with stage II colon cancer. *Sci. Transl. Med.* 8, 346ra92-346ra92 (2016).
5. T. Reinert, L. V Scholer, R. Thomsen, H. Tobiasen, S. Vang, I. Nordentoft, P. Lamy, A. S. Kannerup, F. V Mortensen, K. Stribolt, S. Hamilton-Dutoit, H. J. Nielsen, S. Laurberg, N. Pallisgaard, J. S. Pedersen, T. F. Orntoft, C. L. Andersen, Analysis of circulating tumour DNA to monitor disease burden following colorectal cancer surgery. *Gut* 65, 625-634 (2016).
6. L. A. Diaz Jr, R. T. Williams, J. Wu, I. Kinde, J. R. Hecht, J. Berlin, B. Allen, I. Bozic, J. G. Reiter, M. A. Nowak, K. W. Kinzler, K. S. Oliner, B. Vogelstein, The molecular evolution of acquired resistance to targeted EGFR blockade in colorectal cancers. *Nature* 486, 537-540 (2012).

7. K. C. A. Chan, J. K. S. Woo, A. King, B. C. Y. Zee, W. K. J. Lam, S. L. Chan, S. W. I. Chu, C. Mak, I. O. L. Tse, S. Y. M. Leung, G. Chan, E. P. Hui, B. B. Y. Ma, R. W. K. Chiu, S. F. Leung, A. C. van Hasselt, A. T. C. Chan, Y. M. D. Lo, Analysis of plasma Epsteing Barr virus DNA to screen for nasopharyngeal cancer. N Engl. I Med. 377, 513-522 (2017).
8. Y. M. D. Lo, L. Y. Chan, K. W. Lo, S. F. Leung, J. Zhang, A. T. Chan, J. C. Lee, N. M. Hjelm, P. J. Johnson, D. P. Huang, Quantitative analysis of cell-free Epstein-Barr virus DNA in plasma of patients with nasopharyngeal carcinoma. Cancer Res 59, 1188-1191 (1999).
9. J. A. Kanakry, H. Li, L. L. Gellert, M. V. Lemas, W. S. Hsieh, F. Hong, K. L. Tan, R. D. Gascoyne, L. I. Gordon, R. I. Fisher, N. L. Bartlett, P. Stiff, B. D. Cheson, R. Advani, T. P. Miller, B. S. Kahl, S. J. Horning, R. F. Ambinder, Plasma Epstein-Barr virus DNA predicts outcome in advanced Hodgkin lymphoma: Correlative analysis from a large North American cooperative group trial. Blood 121, 3547-3553 (2013).
10. J. A. Kanakry, A. M. Hegde, C. M. Durand, A. B. Massie, A. E. Greer, R. F. Ambinder, A. Valsamakis, The clinical significance of EBV DNA in the plasma and peripheral blood mononuclear cells of patients with or without EBV diseases. Blood 127, 2007-2017 (2016).
11. Y. M. D. Lo, L. Y. Chan, A. T. Chan, S. F. Leung, K. W. Lo, J. Zhang, J. C. Lee, N. M. Hjelm, P. J. Johnson, D. P. Huang, Quantitative and temporal correlation between circulating cell-free Epstein-Barr virus DNA and tumor recurrence in nasopharyngeal carcinoma. Cancer Res 59, 5452-5455 (1999).
12. S. F. Leung, K. C. A. Chan, B. B. Ma, E. P. Hui, F. Mo, K. C. K. Chow, L. Leung, K. W. Chu, B. Zee, Y. M. D. Lo, A. T. C. Chan, Plasma Epstein-Barr viral DNA load at midpoint of radiotherapy course predicts outcome in advanced-stage nasopharyngeal carcinoma. Ann. Oncol. 25, 1204-1208 (2014).
13. Hong Kong Cancer Registry, Nasopharyngeal Cancer in 2015, (2015) (available at http://www3.ha.org.hk/cancereg/statistics.html).
14. J. Kanakry, R. Ambinder, The biology and clinical utility of EBV monitoring in blood. Curr Top Microbiol Immunol 391, 475-499 (2015).
15. K. C. A. Chan, E. C. W. Hung, J. K. S. Woo, P. K. S. Chan, S. F. Leung, F. P. T. Lai, A. S. M. Cheng, S. W. Yeung, Y. W. Chan, T. K. C. Tsui, J. S. S. Kwok, A. D. King, A. T. C. Chan, A. C. Van Hasselt, Y. M. D. Lo, Early detection of nasopharyngeal carcinoma by plasma Epstein-Barr virus DNA analysis in a surveillance program. Cancer 119, 1838-1844 (2013).
16. H. Y. Wang, C. H. Hsieh, C. N. Wen, Y. H. Wen, C. H. Chen, J. J. Lu, Cancers screening in an asymptomatic population by using multiple tumour markers. PLoS One 11, e0158285 (2016).
17. K. C. A. Chan, J. Zhang, A. T. C. Chan, K. I. K. Lei, S. F. Leung, L. Y. S. Chan, K. C. K. Chow, Y. M. D. Lo, Molecular characterization of circulating EBV DNA in the plasma of nasopharyngeal carcinoma and lymphoma patients. Cancer Res. 63, 2028-2032 (2003).
18. K. C. A. Chan, A. T. C. Chan, S. F. Leung, J. C. S. Pang, A. Y. M. Wang, J. H. M. Tong, K. F. To, L. Y. S. Chan, L. L. S. Tam, N. Y. F. Chung, J. Zhang, K. W. Lo, D. P. Huang, Y. M. D. Lo, Investigation into the origin and tumoral mass correlation of plasma Epstein-Barr virus DNA in nasopharyngeal carcinoma. Clin. Chem. 51, 2192-2195 (2005).
19. Y. M. D. Lo, K. C. A. Chan, H. Sun, E. Z. Chen, P. Jiang, F. M. F. Lun, Y. W. Zheng, T. Y. Leung, T. K. Lau, C. R. Cantor, R. W. K. Chiu, Maternal plasma DNA sequencing reveals the genome-wide genetic and mutational profile of the fetus. Sci. Transl. Med. 2, 61ra91-61ra91 (2010).
20. P. Jiang, C. W. M. Chan, K. C. A. Chan, S. H. Cheng, J. Wong, V. W.-S. Wong, G. L. H. Wong, S. L. Chan, T. S. K. Mok, H. L. Y. Chan, P. B. S. Lai, R. W. K. Chiu, Y. M. D. Lo, Lengthening and shortening of plasma DNA in hepatocellular carcinoma patients. Proc. Natl. Acad. Sci. U.S.A. 112, E1317-E1325 (2015).
21. M. W. Snyder, M. Kircher, A. J. Hill, R. M. Daza, J. Shendure, Cell-free DNA comprises an in vivo nucleosome footprint that informs its tissues-of-origin. Cell 164, 57-68 (2016).
22. K. Sun, P. Jiang, K. C. A. Chan, J. Wong, Y. K. Y. Cheng, R. H. S. Liang, W. Chan, E. S. K. Ma, S. L. Chan, S. H. Cheng, R. W. Y. Chan, Y. K. Tong, S. S. M. Ng, R. S. M. Wong, D. S. C. Hui, T. N. Leung, T. Y. Leung, P. B. S. Lai, R. W. K. Chiu, Y. M. D. Lo, Plasma DNA tissue mapping by genome-wide methylation sequencing for noninvasive prenatal, cancer, and transplantation assessments, Proc. Natl. Acad. Sci. U.S.A. 112, E5503-E5512 (2015).
23. F. Mouliere, N. Rosenfeld, Circulating tumor-derived DNA is shorter than somatic DNA in plasma. Proc. Natl. Acad. Sci. U.S.A. 112, 3178-3179 (2015).
24. F. Mouliere, B. Robert, E. Peyrotte, M. Del Rio, M. Ychou, F. Molina, C. Gongora, A. R. Thierry, High fragmentation characterizes tumour-derived circulating DNA. PLoS One 6 (2011), doi:10.1371/journal.pone.0023418.
25. H. R. Underhill, J. O. Kitzman, S. Hellwig, N. C. Welker, R. Daza, D. N. Baker, K. M. Gligorich, R. C. Rostomily, M. P. Bronner, J. Shendure, Fragment length of circulating tumor DNA. PLoS Genet. 12, 1-24 (2016).
26. D. Chandrananda, N. P. Thome, M. Bahlo, High-resolution characterization of sequence signatures due to non-random cleavage of cell-free DNA. BMC Med. Genomics 8, 29 (2015).
27. S. C. Y. Yu, K. C. A. Chan, Y. W. L. Zheng, P. Jiang, G. J. W. Liao, H. Sun, R. Akolekar, T. Y. Leung, A. T. J. I. Go, J. M. G. van Vugt, R. Minekawa, C. B. M. Oudejans, K. H. Nicolaides, R. W. K. Chiu, Y. M. D. Lo, Size-based molecular diagnostics using plasma DNA for noninvasive prenatal testing. Proc. Natl. Acad. Sci. U.S.A. 111, 8583-8588 (2014).
28. K. C. A. Chan, J. Zhang, A. B. Y. Hui, N. Wong, T. K. Lau, T. N. Leung, K. W. Lo, D. W. S. Huang, Y. M. D. Lo, Size distributions of maternal and fetal DNA in maternal plasma. Clin. Chem. 50, 88-92 (2004).
29. J. E. Shaw, L. F. Levinger, C. W. Carter, Nucleosomal structure of Epstein-Barr virus DNA in transformed cell lines. J. Virol. 29, 657-665 (1979).
30. R. F. Ambinder, Plasma Epstein-Barr virus DNA for screening. N Engl. J. Med. 377, 584-585 (2017).
31. D. J. Gaffney, G. McVicker, A. A. Pai, Y. N. Fondufe-Mittendorf, N. Lewellen, K. Michelini, J. Widom, Y. Gilad, J. K. Pritchard, Controls of nucleosome positioning in the human genome. PLoS Genet. 8, 1-13 (2012).
32. J. Zhong, K. Luo, P. S. Winter, G. E. Crawford, E. S. Iversen, A. J. Hartemink, Mapping nucleosome positions using DNase-seq, Genome Res. 26, 351-364 (2016).
33. S. M. Cao, M. J. Simons, C. N. Qian, The prevalence and prevention of nasopharyngeal carcinoma in China. Chin. J. Cancer 30, 114-119 (2011).
34. L. Sharp, L. Tilson, S. Whyte, A. O. Ceilleachair, C. Walsh, C. Usher, P. Tappenden, J. Chilcott, A. Staines, M.

Barry, H. Comber, Using resource modelling to inform decision making and service planning: the case of colorectal cancer screening in Ireland. *BMC Health Serv. Res.* 13, 105 (2013).

35. E. A. Mesri, M. A. Feitelson, K. Munger, Human viral oncogenesis: A cancer hallmarks analysis. *Cell Host Microbe* 15, 266-282 (2014).

36. R. Li, C. Yu, Y. Li, T. W. Lam, S. M. Yiu, K. Kristiansen, J. Wang, SOAP2: An improved ultrafast tool for short read alignment, *Bioinformatics* 25, 1966-1967 (2009).

What is claimed is:

1. A method of analyzing a biological sample, including a mixture of cell-free nucleic acid molecules, to determine a level of pathology in a subject from which the biological sample is obtained, the mixture including nucleic acid molecules from the subject and potentially nucleic acid molecules from a virus, the method comprising:
for each of a plurality of nucleic acid molecules in the biological sample:
measuring a size of the nucleic acid molecule, wherein the plurality of nucleic acid molecules includes at least 10,000 nucleic acid molecules;
determining whether the nucleic acid molecule is from a reference genome, thereby determining a set of nucleic acid molecules from the reference genome, the reference genome corresponding to the virus;
determining a statistical value of a size distribution of the set of nucleic acid molecules from the reference genome, the size distribution spanning a range of different sizes; and
determining the level of pathology in the subject by processing the statistical value against a cutoff value, wherein the statistical value being above the cutoff value indicates a different level of pathology than the statistical value being below the cutoff value.

2. The method of claim 1, wherein the statistical value is an average, mode, median, or mean of the size distribution.

3. The method of claim 1, wherein the statistical value is a percentage of the plurality of nucleic acid molecules in the biological sample from the reference genome that are below a size threshold.

4. The method of claim 1, wherein the statistical value includes a ratio of:
a first amount the plurality of nucleic acid molecules in the biological sample from the reference genome that are within a first size range; and
a second amount the plurality of nucleic acid molecules in the biological sample from the reference genome that are within a second size range that is different than the first size range.

5. The method of claim 1, wherein the statistical value includes a ratio of:
a first proportion of sequence reads of nucleic acid molecules that align to the reference genome of the virus with the size within a given range; and
a second proportion of sequence reads of nucleic acid molecules that align to a human reference genome with the size within the given range.

6. The method of claim 5, wherein the given range is about 80 to about 110 base pairs, about 50 to about 75 base pairs, about 60 to about 90 base pairs, about 90 to about 120 base pairs, about 120 to about 150 base pairs, or about 150 to about 180 base pairs.

7. The method of claim 5, wherein the statistical value is an inverse of the ratio.

8. The method of claim 1, wherein measuring the size of the nucleic acid molecule and determining that the nucleic acid molecule is from the reference genome includes:
receiving one or more sequence reads that include both ends of the nucleic acid molecule, thereby obtaining a plurality of sequence reads from a sequencing of the mixture of cell free nucleic acid molecules;
aligning the one or more sequence reads to the reference genome to obtain one or more aligned locations; and
using the one or more aligned locations to determine the size of the nucleic acid molecule.

9. The method of claim 8, further comprising:
performing the sequencing of the mixture of cell-free nucleic acid molecules to obtain the plurality of sequence reads.

10. The method of claim 9, further comprising:
performing real-time polymerase chain reaction (PCR) of the biological sample or a different biological sample obtained from the subject contemporaneously as the biological sample, thereby determining a quantity of nucleic acid molecules from the virus;
comparing the quantity to a quantity threshold; and
when the quantity is above the quantity threshold, performing the sequencing of the mixture of cell-free nucleic acid molecules.

11. The method of claim 9, wherein the sequencing includes random sequencing.

12. The method of claim 1, further comprising enriching the biological sample for nucleic acid molecules from the virus.

13. The method of claim 12, wherein the enriching the biological sample for nucleic acid molecules from the virus includes using capture probes that bind to a portion of, or an entire genome of, the virus.

14. The method of claim 12, further comprising:
enriching the biological sample for nucleic acid molecules from a portion of a human genome.

15. The method of claim 1, wherein a positive predictive value (PPV) of the determining the level of pathology is at least 6%, 7%, or 8%, wherein a sensitivity of the determining the level of pathology is at least 95%, 96%, or 97%, and/or wherein a specificity of the determining the level of pathology is at least 95%, 96%, 97%, or 98%.

16. The method of claim 1, wherein the level of pathology is a level of cancer.

17. The method of claim 16, wherein the cancer is selected from a group consisting of nasopharyngeal cancer, head and neck squamous cell carcinoma, cervical cancer, and hepatocellular carcinoma.

18. The method of claim 16, wherein the level of cancer is selected from a group consisting of: an amount of tumor tissue in the subject, a size of a tumor in the subject, a stage of the tumor in the subject, a tumor load in the subject, and presence of tumor metastasis in the subject.

19. The method of claim 1, wherein the virus comprises EBV DNA, HPV DNA, HBV DNA, HCV nucleic acids, or fragments thereof.

20. The method of claim 1, further comprising providing a therapeutic intervention based on the level of pathology or performing imaging of the subject based on the level of pathology.

21. A method of screening a biological sample, including a mixture of cell-free nucleic acid molecules, for a pathology, the biological sample obtained from a subject that is asymptomatic for the pathology, the mixture including nucleic acid molecules from the subject and potentially nucleic acid molecules from a virus, the method comprising:

receiving a plurality of sequence reads obtained from a sequencing of the mixture of cell-free nucleic acid molecules, wherein the plurality of sequence reads includes at least 10,000 sequence reads;

determining an amount of the plurality of sequence reads aligning to a reference genome, the reference genome corresponding to the virus; and determining a level of pathology by comparing the amount of sequence reads aligning to the reference genome to a cutoff value, wherein the amount of sequence reads being above the cutoff value indicates a different level of pathology than the amount of sequence reads being below the cutoff value.

22. The method of claim 21, further comprising:
determining a level of the pathology in the subject based on the comparing of the amount of sequence reads to the cutoff value.

23. The method of claim 22, wherein the amount of sequence reads being above the cutoff value indicates a different level of the pathology than the amount of sequence reads being below the cutoff value.

24. The method of claim 22, wherein the level of the pathology is a level of cancer.

25. The method of claim 24, wherein the cancer is selected from a group consisting of nasopharyngeal cancer, head and neck squamous cell carcinoma, cervical cancer, and hepatocellular carcinoma.

26. The method of claim 24, wherein the level of cancer is selected from a group consisting of: an amount of tumor tissue in the subject, a size of a tumor in the subject, a stage of the tumor in the subject, a tumor load in the subject, and presence of tumor metastasis in the subject.

27. The method of claim 21, wherein the amount of sequence reads aligning to the reference genome includes a proportion of sequence reads aligned to the reference genome relative to a total number of sequence reads.

28. The method of claim 27, wherein the total number of sequence reads is a sum of the sequence reads that aligned to the reference genome corresponding to the virus and the sequence reads that aligned to a human genome.

29. The method of claim 21, wherein the amount of sequence reads aligning to the reference genome includes a number of sequence reads aligned to the reference genome per volume of the biological sample analyzed.

30. The method of claim 21, wherein the cutoff value is determined from training samples having a known classification for the pathology.

31. The method of claim 30, wherein the cutoff value is selected using (1) a value below a lowest amount of sequence reads aligning to the reference genome for the training samples classified as having the pathology; (2) a specified number of standard deviations from a mean amount of sequence reads aligning to the reference genome for the training samples classified as having the pathology; or (3) a specificity and a sensitivity for determining a correct classification of the training samples.

32. The method of claim 21, further comprising:
performing the sequencing of the mixture of cell-free nucleic acid molecules to obtain the plurality of sequence reads.

33. The method of claim 32, further comprising:
performing real-time polymerase chain reaction (PCR) of the biological sample or a different biological sample obtained from the subject contemporaneously as the biological sample, thereby determining a quantity of nucleic acid molecules from the virus;

comparing the quantity to a quantity threshold; and
when the quantity is above the quantity threshold, performing the sequencing of the mixture of cell-free nucleic acid molecules.

34. The method of claim 32, wherein the sequencing includes random sequencing.

35. The method of claim 21, further comprising enriching the biological sample for nucleic acid molecules from the virus.

36. The method of claim 35, wherein the enriching the biological sample for nucleic acid molecules from the virus includes using capture probes that bind to a portion of, or an entire genome of, the virus.

37. The method of claim 35, further comprising: enriching the biological sample for nucleic acid molecules from a portion of a human genome.

38. The method of claim 21, wherein the virus comprises EBV DNA, HPV DNA, HBV DNA, HCV nucleic acids, or fragments thereof.

39. A method of analyzing a biological sample, including a mixture of cell-free nucleic acid molecules, to determine a level of pathology in a subject from which the biological sample is obtained, the mixture including nucleic acid molecules from the subject and potentially nucleic acid molecules from a virus, the method comprising:

performing a first assay, wherein the first assay comprises analyzing a first plurality of cell-free nucleic acid molecules from a first biological sample of the subject to determine a first amount of the first plurality of cell-free nucleic acid molecules aligning to a reference genome, the reference genome corresponding to the virus; and performing a second assay, wherein the second assay comprises:
measuring a size of each of a second plurality of cell-free nucleic acid molecules in a second biological sample, the second plurality of cell-free nucleic acid molecules including at least 10,000 nucleic acid molecules; and
determining a second amount of a size distribution of the second plurality of cell-free nucleic acid molecules from the reference genome, the size distribution spanning a range of different sizes;

comparing the first amount to a first cutoff;
comparing the second amount to a second cutoff; and
determining the level of pathology in the subject based on the comparing of the first amount to the first cutoff and the comparing of the second amount to the second cutoff, wherein the first amount being above the first cutoff and the second amount being above the second cutoff indicates a different level of pathology than the first amount being below the first cutoff and the second amount being below the second cutoff.

40. The method of claim 39, wherein the second assay is performed when the first amount is above the first cutoff.

41. The method of claim 39, wherein the subject is determined to have the pathology only if the first amount exceeds the first cutoff and the second amount exceeds the second cutoff.

42. The method of claim 39, wherein the second amount is of nucleic acid molecules having a size within a given range and aligning to the reference genome.

43. The method of claim 42, further comprising normalizing the second amount using a third amount of cell-free nucleic acid molecules having a size within a different range and aligning to the reference genome.

44. The method of claim 42, further comprising normalizing the second amount using a third amount of cell-free nucleic acid molecules having a size within the given range and aligning to an autosomal genome.

45. The method of claim 39, wherein the first biological sample and the second biological sample are from a same blood sample.

46. The method of claim 39, wherein the first biological sample and the second biological sample are the same sample, and wherein the second plurality of cell-free nucleic acid molecules is the first plurality of cell-free nucleic acid molecules.

47. A method of analyzing a biological sample, including a mixture of cell-free nucleic acid molecules, to determine a level of cancer in a subject from which the biological sample is obtained, the mixture including nucleic acid molecules from the subject and potentially nucleic acid molecules from a virus, the method comprising:
  analyzing at least 10,000 nucleic acid molecules, including a first plurality of cell-free nucleic acid molecules from the biological sample of the subject, wherein the analyzing a cell-free nucleic acid comprises determining a genomic position in a reference genome corresponding to at least one end of the cell-free nucleic acid molecule, the reference genome corresponding to the virus;
  determining a first amount of the first plurality of cell-free nucleic acid molecules that end within one or more first windows, each first window comprising at least one of a first set of genomic positions at which ends of cell-free nucleic acid molecules are present at a rate above a first threshold in subjects with the cancer associated with the virus;
  computing a relative abundance of the first plurality of cell-free nucleic acid molecules ending within one of the first windows by normalizing the first amount using a second amount of the first plurality of cell-free nucleic acid molecules from the biological sample, wherein the second amount of the first plurality of cell-free nucleic acid molecules includes cell-free nucleic acid molecules ending at a second set of genomic positions outside of the one or more first windows including the first set of genomic positions; and
  determining the level of cancer in the subject by processing the relative abundance against a cutoff value, wherein the relative abundance being above the cutoff value indicates a different level of cancer than the relative abundance being below the cutoff value.

48. The method of claim 47, further comprising:
  determining the second amount of the first plurality of cell-free nucleic acid molecules that end within one of second windows, each second window comprising at least one of a second set of genomic positions at which ends of cell-free nucleic acid molecules are present at a rate above a second threshold in subjects without the cancer resulting from the virus,
  wherein normalizing the first amount includes computing the relative abundance using the first amount and the second amount.

49. The method of claim 48, further comprising identifying the second set of genomic positions, wherein the identifying comprises:
  analyzing the cell-free nucleic acid molecules of a reference sample from a reference subject that does not have the cancer, wherein analyzing each of the cell-free nucleic acid molecules of the reference sample comprises:
  determining the genomic position in the reference genome corresponding to at least one end of the cell-free nucleic acid molecule.

50. The method of claim 47, further comprising identifying the first set of genomic positions at which ends of cell-free nucleic acid molecules occur at the rate above the first threshold.

51. The method of claim 50, wherein identifying the first set of genomic positions comprises:
  analyzing a second plurality of cell-free nucleic acid molecules from at least one first additional sample to identify ending positions of the second plurality of cell-free nucleic acid molecules, wherein the at least one first additional sample is known to have the cancer associated with the virus and is of a same sample type as the biological sample;
  for each genomic window of a plurality of genomic windows:
    computing a corresponding number of the second plurality of cell-free nucleic acid molecules ending on the genomic window; and
    comparing the corresponding number to a reference value to determine whether the rate of cell-free nucleic acid molecules ending on one or more genomic positions within the genomic window is above the first threshold.

* * * * *